US012740776B2

(12) United States Patent
Amanatullah et al.

(10) Patent No.: US 12,740,776 B2
(45) Date of Patent: Sep. 22, 2026

(54) METHODS AND APPARATUSES FOR PERFORMING A KNEE ARTHROPLASTY

(71) Applicant: Knimble Designs, Inc., Menlo Park, CA (US)

(72) Inventors: Derek F. Amanatullah, Menlo Park, CA (US); Thomas Jefferson Blumenfeld, Davis, CA (US); Richard David Komistek, Knoxville, TN (US); Michael LaCour, Knoxville, TN (US)

(73) Assignee: Knimble Designs, Inc., Menlo Park, CA (US)

(*) Notice: Subject to any disclaimer, the term of this patent is extended or adjusted under 35 U.S.C. 154(b) by 0 days.

(21) Appl. No.: 19/264,495

(22) Filed: Jul. 9, 2025

(65) Prior Publication Data

US 2025/0339137 A1 Nov. 6, 2025

Related U.S. Application Data

(63) Continuation of application No. 19/170,618, filed on Apr. 4, 2025.

(Continued)

(51) Int. Cl.

*A61B 17/02* (2006.01)
*A61B 17/15* (2006.01)
*A61B 17/17* (2006.01)
*A61B 17/56* (2006.01)
*A61B 90/00* (2016.01)
*A61B 17/00* (2006.01)

(52) U.S. Cl.

CPC .......... *A61B 17/025* (2013.01); *A61B 17/157* (2013.01); *A61B 17/1767* (2013.01); *A61B 17/56* (2013.01); *A61B 90/03* (2016.02); *A61B 90/08* (2016.02); *A61B 2017/00367* (2013.01); *A61B 2017/00477* (2013.01); *A61B 2017/0268* (2013.01); *A61B 2017/564* (2013.01); *A61B 2090/034* (2016.02); *A61B 2090/0807* (2016.02)

(58) Field of Classification Search

CPC ............................ A61B 17/1764; A61F 2/461
See application file for complete search history.

(56) References Cited

U.S. PATENT DOCUMENTS 5,630,820 A 5/1997 Todd
5,688,280 A 11/1997 Booth, Jr. et al.

(Continued)

FOREIGN PATENT DOCUMENTS

WO PCT/US2025/023209 9/2025

*Primary Examiner* — Sameh R Boles
(74) *Attorney, Agent, or Firm* — Dorton & Willis LLP; Ryan Willis

(57) ABSTRACT

Methods and devices are disclosed for soft tissue balancing of a knee joint during an arthroplasty procedure that include balancing the knee joint at or near mid-flexion, while maintaining the rotational position of the femur with respect to the tibia that replicates proper kinematic placement of these bones. Also disclosed are methods and devices for soft tissue balancing of a knee joint during an arthroplasty procedure that include balancing the knee joint at or near mid-flexion using one or more expansion devices that are not actively requiring monitoring and/or recording of forces applied by the bodily tissues, but instead uses incremental changes in actual length/height of the expansion device to determine whether the joint is properly tensioned or too lax.

26 Claims, 95 Drawing Sheets

Related U.S. Application Data

(60) Provisional application No. 63/672,332, filed on Jul. 17, 2024, provisional application No. 63/575,092, filed on Apr. 5, 2024.

(56) References Cited

U.S. PATENT DOCUMENTS

| | | | | |
|---|---|---|---|---|
| 5,800,438 | A | 9/1998 | Tuke et al. | |
| 7,367,984 | B2 | 5/2008 | Kulcinski et al. | |
| 11,701,097 | B2 | 7/2023 | Capote et al. | |
| 11,786,261 | B2 | 10/2023 | Nielsen et al. | |
| 11,786,262 | B1 * | 10/2023 | Komistek | A61B 5/4585 606/96 |
| 11,812,978 | B2 | 11/2023 | Trabish et al. | |
| 11,911,050 | B2 | 2/2024 | Amanatullah et al. | |
| 2019/0358056 | A1 | 11/2019 | Lerat et al. | |
| 2020/0085420 | A1 | 3/2020 | Capote et al. | |
| 2020/0305942 | A1 * | 10/2020 | Oden | A61B 17/154 |
| 2022/0354512 | A1 | 11/2022 | Rock et al. | |
| 2023/0172600 | A1 * | 6/2023 | Dumpe | A61B 34/20 606/90 |
| 2024/0342036 | A1 | 10/2024 | Walkington et al. | |

* cited by examiner

LATERAL SIDE 1320
1296
1270
1350
1334
1308
1372
1324
1298
1264
1340
1206
1364
1322
1338
1360
1364
1376
1324
1210
1204
1202
1204

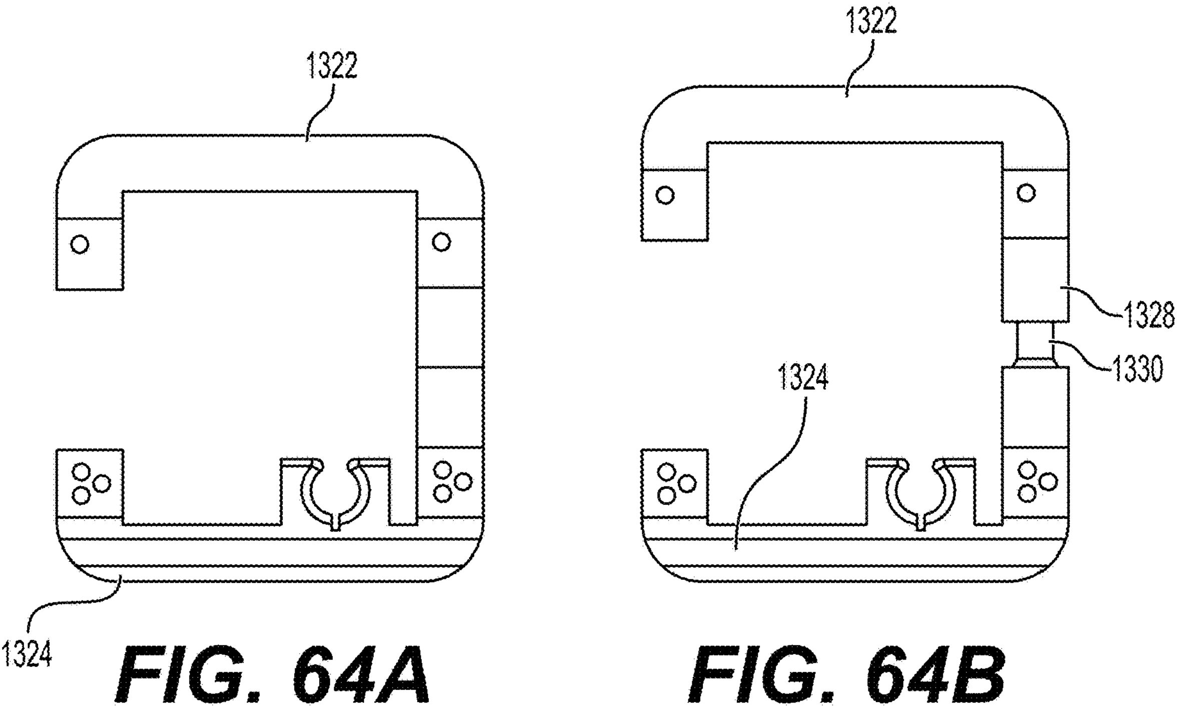
FIG. 64A
FIG. 64B
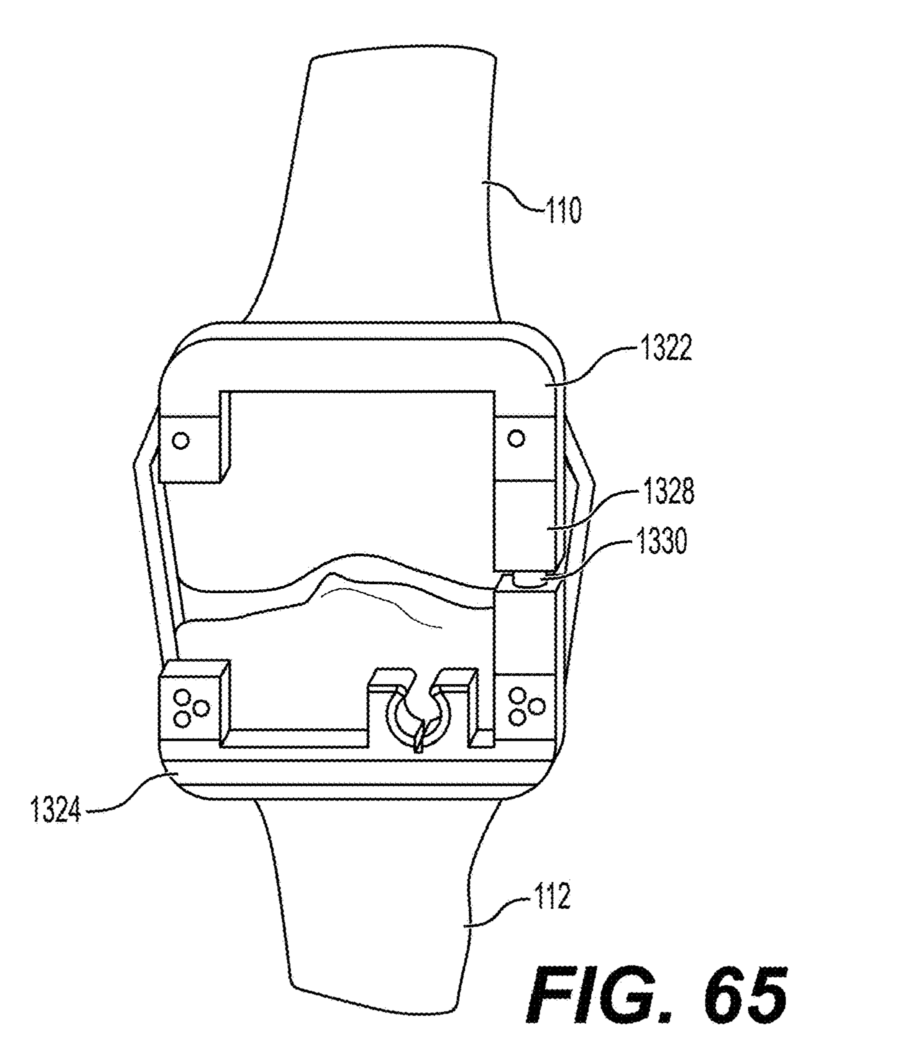
FIG. 65

METHODS AND APPARATUSES FOR PERFORMING A KNEE ARTHROPLASTY

CROSS-REFERENCE TO RELATED APPLICATIONS

The present application is a continuation of U.S. Non-provisional patent application Ser. No. 19/170,618, filed Apr. 4, 2025 and titled "METHODS AND APPARATUSES FOR PERFORMING A KNEE ARTHROPLASTY," which claims the benefit of U.S. Provisional Patent Application No. 63/575,092, filed on Apr. 5, 2024 and titled "METHODS AND APPARATUSES FOR PERFORMING A KNEE ARTHROPLASTY, and U.S. Provisional Patent Application No. 63/672,332, filed on Jul. 17, 2024 and titled "METHODS AND APPARATUSES FOR PERFORMING A KNEE ARTHROPLASTY, the disclosures of each of which are hereby incorporated by reference in their entirety.

INTRODUCTION TO THE INVENTION

The present disclosure is directed to surgical equipment and methods and, more specifically, to surgical equipment for use in knee arthroplasty and associated methods for balancing a knee joint.

Referencing FIG. 1, the present disclosure contemplates that, at full extension, a normal human knee joint includes the lateral and medial femoral condyles predominantly contacting the tibia plateau anterior of the anteroposterior midline, with the lateral femoral condyle contact being more anterior than the medial femoral condyle contact. As the knee joint is repositioned from full extension toward full flexion (approximately 160 degrees, which varies depending upon anatomical constraints and a person's ability to flex his/her knee), the lateral femoral condyle contact with the tibial plateau moves posteriorly in a progressive manner until reaching approximately 120 degrees of flexion. After this amount of flexion is reached, the lateral femoral condyle rolls off of the tibia plateau and moves down the posterior aspect of the tibia a small amount. In contrast, the medial femoral condyle initially moves posteriorly from full extension to mid-flexion (ranging from 60-80 degrees), followed by moving anteriorly as the knee progressively flexes to full knee flexion. Accordingly, compared to the lateral femoral condyle, the medial femoral condyle remains more central on the tibial plateau throughout knee flexion, mainly due to the medial collateral ligament (MCL) as it resists too much posterior medial condyle motion. The present disclosure contemplates that, at times, some total knee arthroplasty (TKA) designs try to induce too much medial condyle rollback leading to the MCL becoming too tight and resisting weight-bearing knee flexion. The contact patterns exhibited by the medial and lateral femoral condyles of a normal knee lead to a fan-like motion pattern, where the lateral femoral condyle rotates around the medial femoral condyle in a non-pivoting pattern. As is indicative of the motion patterns of FIG. 1, movement of both medial and lateral femoral condyles across the flexion range of motion in a healthy knee joint is progressive in nature and omits directional changes that are sudden and "jerky." Sudden or jerky motion within a knee joint reflects unhealthy or unnatural kinematics, which may result from an unhealthy natural knee joint or be the byproduct of an orthopedic knee joint exhibiting excessive wear and/or improper anatomical positioning.

The present disclosure contemplates that when structural changes occur in the contact surfaces of the knee joint, due to arthritis or degeneration (including formation of osteophytes), that the body cannot adequately repair, it may be time for a patient to consider total or partial knee arthroplasty. Knee arthroplasty involves a surgical procedure where contact surfaces of the knee joint are replaced with orthopedic implants, with partial knee arthroplasty replacing a portion of the contact surfaces, while total knee arthroplasty replaces all contact surfaces. Time honored concepts of total knee arthroplasty have yielded excellent survivorship outcomes at greater than 10-year follow-up both in single surgeon, institutional, and in large registry data. These concepts may include coronal alignment, resection of the distal femur and proximal tibia, and balancing of the soft tissues comprising the soft tissue envelope of the knee joint, including, but not limited to, the medial and lateral collateral ligaments (and optionally the posterior collateral ligament (PCL) when a PCL retaining orthopedic implant is selected).

With regards to FIGS. 2A and 2B, the present disclosure contemplates that once the anterior cruciate ligament (ACL) is resected for posterior cruciate retaining (PCR) TKA surgery, the femoral condyle experiences very abnormal or paradoxical motion patterns where the kinematics are often opposite of the normal knee and the knee often experiences sliding with progressive knee flexion rather than rollback. FIG. 2A shows the lateral condyle motion pattern for five subjects with a PCR TKA and FIG. 2B shows the medial condyle motion for these same subjects. These subjects are experiencing very erratic motion patterns opposite of the normal knee motion pattern. In a PCR TKA, the ACL is sacrificed while the PCL is left intact. Without the ACL, the PCL no longer has a counter-balancing force to ensure a smooth motion pattern. In a posterior stabilized (PS) TKA and posterior cruciate sacrificing (PCS) TKA, the ACL and PCL are both sacrificed. With the cruciate ligaments in a PS and PCS TKA, and the ACL sacrificed in a PCR TKA, the femoral condyles can slide and move in abnormal manners with respect to the proximal tibia.

The present disclosure contemplates that TKA knee joints often exhibit motion of the femoral condyles that is opposite of the normal knee, where one or both femoral condyle contact surfaces can slide anteriorly prior to reaching mid-flexion. The motion patterns of TKA femoral condyles reflected in FIGS. 2A and 2B can be "jerky" or oscillating and include abrupt changes of direction in proximity to mid-flexion, which a patient can perceive as instability of the knee joint and feeling insecure during normal daily activities.

The present disclosure contemplates that, unlike TKA knee joint, the lateral femoral condyle contact area of a normal knee joint at full extension is centered around 5 to 10 millimeters anterior the anteroposterior midline and progressively moves posteriorly until reaching full flexion around 10 to 20 millimeters posterior of the anteroposterior midline.

The present disclosure contemplates that using in vivo fluoroscopy in three-dimensions, many studies conducted on TKA patients document very different kinematic knee joint motion patterns compared to the normal knee. It is presumed that these joint motion pattern differences are due to the loss of the ACL in a PCR TKA and the loss of both cruciate ligaments in a PS TKA, along with improper balancing of retained soft tissues around the knee (i.e., the soft tissue envelope). Unlike the normal knee where the lateral femoral condyle contact area progressively moves in the posterior direction with increasing knee flexion up until approximately 75 degrees of flexion, TKA patients often demonstrate significant anterior motion (the opposite of normal knee kinematics) during early flexion. In the normal knee, the medial femoral condyle contact area is centered at around 0-5 millimeters anterior of the anteroposterior midline at full extension and remains very stable with increasing knee flexion. In TKA patients, the medial femoral condyle often exhibits abnormal motion that reverses direction in between full extension and mid-flexion, thus leading to mid-flexion instability.

The present disclosure contemplates that the abnormal locations of the medial and lateral femoral condyle contact areas, especially near mid-flexion, often result in patients noticing the abnormal motion and having stability concerns. During fluoroscopy it has been seen that patients have to hold onto railings or gain support from other people while flexing their orthopedic knee joint because of this unnatural sliding motion, causing them to feel unstable. In the normal knee, the femoral condyle contact area at full extension is anterior on the tibia with respect to the anterior-posterior midline and progressively moves posteriorly through mid-flexion, but with TKA knee joints, the contact areas can be quite variable and often lead to sudden directional changes that a patient feels due the femoral condyles sliding on the tibial tray. Therefore, when a TKA patient bends his/her knee joint, the femur slides forward rather than rolling back. Also, during chair rise and step-up maneuvers, the femoral condyles slide posteriorly rather than rolling forward. In the normal knee, rolling feels stable to a person, but in a TKA knee joint, abnormal sliding and directional changes translate into a patient feeling mid-flexion instability.

The present disclosure contemplates that during knee replacement surgery, the knee joint is typically balanced at full extension and/or at 90 degrees of flexion. As used herein, joint balancing generally refers to putting the bones of a joint in positions that emulate appropriate soft tissue tensions that mimic normal or another desired tension. Therefore, even though mid-flexion is the area when a patient experiences significant abnormal motion, the knee joint is not balanced by the surgeon at this flexion degree or proximate this degree of flexion. And even if a surgeon performed a soft tissue balance at mid-flexion, such a balance would be after principal bone cuts were made to the distal femur and to the proximal tibia. Therefore, during the transition range of motion (e.g., mid-flexion) from full extension to 90 degrees of flexion, the absence of balancing (or balancing after distal femur and proximal tibia bone cuts were completed) within this range of motion may lead to soft tissues not being properly balanced throughout the knee joint range of motion. This absence of balancing or improper balancing may lead to a knee joint that becomes progressively too tight as the orthopedic knee moves from full extension to 90 degrees of flexion or a knee joint that progressively becomes too loose. The present disclosure contemplates that no balancing or improper balancing drives a surgeon's determination of where to principally cut the distal femur and proximal tibia. Accordingly, if the balancing is absent or improper, the resulting bone cuts on the distal femur and proximal tibia may be erroneous. And this may result in an orthopedic implant position on the femur and tibia that is non-optimal for replicating natural knee kinematics.

The present disclosure contemplates that, regardless of the orthopedic implants chosen, soft tissue balancing should originate at mid-flexion and occur before any principal bone cuts to the distal femur and proximal tibia are preformed (excluding removal of osteophytes from the proximal tibia and distal femur). When soft tissue balancing of the knee joint originates and is conducted at or near mid-flexion, a number of advantages are apparent. For example, at or near mid-flexion, the primary contact areas of the lateral femoral condyle and the medial femoral condyle are generally parallel to the anterior-posterior midline of the proximal tibia. What this means is that axial rotation of the femur with respect to the tibia is neutral or can said to approximate zero degrees. Namely, when balancing a knee joint at full extension, the position of the condyle contact areas (see FIG. 1) is not generally parallel to the anterior-posterior midline because the lateral condyle contact area is considerably more anterior than the medial condyle contact area, which means the femur is axially rotated a positive set of degrees (e.g., 9 degrees). In contrast, when balancing a knee joint at 90 degrees of flexion, the position of the condyle contact areas (see FIG. 1) is again not generally parallel to the anterior-posterior midline because the lateral condyle contact area is considerably more posterior than the medial condyle contact area, which means the femur is axially rotated a negative set of degrees (e.g., −12 degrees). In other words, a normal knee exhibits approximately 21 degrees of axial rotation of the femur with respect to the tibia between full extension and 90 degrees of flexion. But by choosing to balance the soft tissues at or near mid-flexion, the impact of the axial rotation of the femur with respect to the tibia on the soft tissues is minimized because this flexion approximates a neutral soft tissue state.

Understanding soft tissue balancing proximate mid-flexion, may result in knowledge about soft tissues including, but not limited to, ligament lengths, strain, and forces for improved balancing of a knee arthroplasty joint. Unfortunately, the balancing of the knee at full extension and/or 90 degrees of flexion is often done by feel and in a passive environment. Therefore, load is not applied to the bearing surface and the ligaments are not in tension. This form of knee balancing could be a primary reason for knee instability and patients feeling abnormal slipping occurring with their knees.

Accordingly, there is a need in the art to soft tissue balance a knee arthroplasty joint that includes balancing at least proximate mid-flexion of the joint prior to making principal cuts on the distal femur and proximal tibia. In some example embodiments according to at least some aspects of the present disclosure, mid-flexion may include angles such as about 30 degrees to about 70 degrees given that mid-flexion instability for TKA knees does readily appear at other flexion angles, between full extension (zero degrees) and 90 degrees away from full extension. In this manner, balancing of a TKA knee at a mid-flexion angle takes place proximate where the majority of abnormal motion would otherwise be present if balancing of the knee arthroplasty joint was not undertaken or improperly taken after principal bone cuts are made to the proximal tibia and distal femur.

There is also a need in the art for surgical tools and equipment specifically directed to facilitate soft tissue balancing of a knee arthroplasty joint at mid-flexion angles between full extension and 90 degrees from full extension, and specifically encompassing angles between about 30 and about 70 degrees from full extension.

It is a first aspect of the present invention to provide a joint distractor comprising: (i) a primary housing to which is mounted a first paddle that extends anteriorly therefrom; (ii) a second paddle selectively repositionable with respect to the primary housing and extending anteriorly therefrom, the second paddle being vertically repositionable with respect to the first paddle; and, (iii) a repositionable catch operatively coupled to the second paddle and configured to move between a first position that locks the relative position of the second paddle with respect to the first paddle, and a second position that allows the relative position of the second paddle with respect to the first paddle to change.

In a more detailed embodiment of the first aspect, the second paddle is configured to be permanently constrained with respect to the primary housing in an anterior-to-posterior direction and a medial-to-lateral direction, where the anterior-to-posterior direction is perpendicular to the medial-to-lateral direction, and the first paddle is configured to be permanently constrained with respect to the primary housing in the anterior-to-posterior direction, the medial-to-lateral direction, and a vertical direction, where the anterior-to-posterior direction and the medial-to-lateral direction are each perpendicular to the vertical direction. In yet another more detailed embodiment, the joint distractor further includes a rack, where the primary housing defines a first cavity, the rack is configured to be at least partially seated within the first cavity, the rack is operatively coupled to the second paddle, and the rack is selectively repositionable in the vertical direction with respect to the primary housing. In a further detailed embodiment, the rack includes an elongated cuboid shape, the first cavity comprises an elongated cuboid cavity and the rack includes indicia on at least one side thereof. In still a further detailed embodiment, the joint distractor further includes a handle repositionably mounted to the primary housing and operatively coupled to the rack, where the handle is repositionable between a first position that retards motion of the rack with respect to the primary housing, and a second position that allows motion of the rack with respect to the primary housing. In a more detailed embodiment, the handle is biased toward the first position. In a more detailed embodiment, the handle is pivotally mounted to the primary housing and a spring interposes the primary housing and the handle to bias the handle toward the first position. In another more detailed embodiment, the primary housing includes an adapter configured to engage a surgical drill guide, where the surgical drill guide includes a plurality of predrilled guide holes that are vertically spaced apart in predetermined increments. In yet another more detailed embodiment, the adapter comprises at least one of a projection and a projection receiver. In still another more detailed embodiment, an interface between the adapter and the surgical drill guide is configured to inhibit motion between the primary housing and the surgical drill guide in a medial-to-lateral direction and a vertical direction perpendicular to the medial-to-lateral direction.

In yet another more detailed embodiment of the first aspect, at least a portion of the surgical drill guide is repositionable with respect to the primary housing in a medial-to-lateral direction and is constrained in a vertical direction perpendicular to the medial-to-lateral direction. In yet another more detailed embodiment, the first and second paddles each have an engagement section configured to be inserted between opposing bones of a joint. In a further detailed embodiment, the engagement section of the first paddle includes an arcuate profile including an anterior-to-posterior curvature, and the engagement section of the second paddle includes an arcuate profile including an anterior-to-posterior curvature. In still a further detailed embodiment, the engagement section of the first paddle includes a first finger separated laterally from a second finger, and the engagement section of the second paddle includes a third finger. In a more detailed embodiment, a lateral profile of the first finger and the second finger are identical, and a lateral profile of the third finger is identical to the first finger. In a more detailed embodiment, the first paddle includes a first base mounted to the primary housing, where the first base includes a first guide for a spring, the second paddle includes a second base repositionably coupled to the primary housing, where the second base includes a second guide for the spring, and the spring interposes the first base and the second base. In another more detailed embodiment, the joint distractor further includes a rack, where the primary housing defines a first cavity, the rack is at least partially seated within the first cavity and repositionable with respect to the primary housing, and the rack is operatively coupled to the second paddle. In yet another more detailed embodiment, the primary housing includes at least one wall that inhibits motion of the rack in at least one of the anterior-to-posterior direction and the medial-to-lateral direction, but allows motion in the vertical direction, where the anterior-to-posterior direction, the medial-to-lateral direction, and the vertical direction are each perpendicular with respect to one another. In still another more detailed embodiment, the joint distractor further includes a stopper, where the rack includes a plurality of teeth vertically distributed therealong, the stopper is repositionable with respect to the primary housing between an engaged position and a disengaged position, the stopper includes at least one catch configured to retardedly engage at least one of the plurality of teeth when the stopper is in the engaged position, and the at least one catch is configured not to retardedly engage at least one of the plurality of teeth when the stopper is in the disengaged position.

In a more detailed embodiment of the first aspect, when the stopper is in the engaged position, the second paddle has a fixed vertical position with respect to the first paddle and the primary housing, and when the stopper is in the disengaged position, the second paddle has a variable vertical position with respect to the first paddle and the primary housing. In yet another more detailed embodiment, the joint distractor further includes a handle repositionably mounted to the primary housing and operatively coupled to the stopper, where the handle is repositionable between a first position that corresponds with the stopper in its retardedly engaged position, and a second position that corresponds with the stopper in its non-retardedly engaged position. In a further detailed embodiment, the rack is configured to extend through an opening at a top of the primary housing, and the rack includes indicia on at least one side thereof. In still a further detailed embodiment, the rack is configured to extend through an opening at a bottom of the primary housing, and the rack includes indicia on at least one side thereof. In a more detailed embodiment, the indicia allows one to immediately determine an amount of vertical separation between the second paddle and the first paddle. In a more detailed embodiment, the rack includes a through hole configured to face the tibia and act as a drill bit guide. In another more detailed embodiment, the plurality of predrilled guide holes of the surgical drill guide includes a hole pattern that is repeated and spaced apart in at least one of the medial-to-lateral direction and the vertical direction, perpendicular to the medial-to-lateral direction.

In a more detailed embodiment of the first aspect, the hole pattern that is repeated and spaced apart in the medial-to-lateral direction, and the hole pattern includes at least two holes having longitudinal centers that do not lie along a common straight vertical line. In yet another more detailed embodiment, the hole pattern that is repeated and spaced apart in the medial-to-lateral direction and the vertical direction perpendicular to the medial-to-lateral direction, and the hole pattern includes at least two holes having longitudinal centers that do not lie along a common straight vertical line. In a further detailed embodiment, a spacing between repeated hole pattern is at least one of fixed and variable. In still a further detailed embodiment, the joint distractor further includes a surgical guide comprising a trajectory guide and at least two pin guides, where the trajectory guide includes at least one of: (i) an elongated through opening configured to receive at least two surgical pins; and (ii) a pair of through openings, each of the pair of through openings configured to receive a separate surgical pin, and each of the at least two pin guides includes a plurality of through holes, where at least two of the plurality of through holes include longitudinal centers that do not lie along a common straight vertical line. In a more detailed embodiment, the plurality of through holes extending through each of the at least two pin guides have a mirrored pattern, and the mirrored patterns position the plurality of through holes in incrementally vertically spaced positions. In a more detailed embodiment, the mirrored patterns comprise at least two rows of through holes, and the through holes of each of the at least two rows have longitudinal centers that lie along a common straight line. In another more detailed embodiment, each of the at least two pin guides is repositionable with respect to the trajectory guide in a medial-to-lateral direction. In yet another more detailed embodiment, each of the at least two pin guides is not repositionable with respect to the trajectory guide in a proximal-to-distal direction, each of the at least two pin guides is not repositionable with respect to the trajectory guide in a vertical direction, and each of the proximal-to-distal direction and the vertical direction is perpendicular to the medial-to-lateral direction. In still another more detailed embodiment, the trajectory guide and each of the at least two pin guides includes a key and keyway interface to facilitate repositioning of each of the at least two pin guides in the medial-to-lateral direction with respect to the trajectory guide.

In yet another more detailed embodiment of the first aspect, the trajectory guide includes the key, the key embodies a dovetail shape, each of the at least two pin guides includes the keyway, and the keyway embodies a dovetail cavity. In yet another more detailed embodiment, the joint distractor further includes a surgical cutting guide, where the surgical cutting guide includes at least one of: (i) an elongated through opening configured to receive at least two surgical pins; and (ii) a pair of through openings, each of the pair of through openings configured to receive a separate surgical pin, and the surgical cutting guide also including at least one of: (a) a top planar surface; and (b) an elongated through hole configured to provide a guide for a surgical cutting blade to facilitate a planar cut. In a further detailed embodiment, the surgical cutting guide includes the elongated through opening configured to receive at least two surgical pins, and the surgical cutting guide includes the top planar surface. In still a further detailed embodiment, the joint distractor further includes a surgical cutting guide, where the surgical cutting guide includes the pair of through openings, and the surgical cutting guide includes the elongated through hole configured to provide the guide for the surgical cutting blade. In a more detailed embodiment, the surgical cutting guide includes the elongated through opening configured to receive at least two surgical pins, and the surgical cutting guide includes the elongated through hole configured to provide the guide for the surgical cutting blade. In a more detailed embodiment, the joint distractor further includes a surgical cutting guide, where the surgical cutting guide includes the pair of through openings, and the surgical cutting guide includes the top planar surface.

It is a second aspect of the present invention to provide a joint distractor comprising: (i) a first paddle extending anteriorly from a primary housing, the first paddle configured to fit between bones of a joint; (ii) a second paddle extending anteriorly from the primary housing, the second paddle configured to fit between the bones of the joint; (iii) a first spring applied to at least one of the first paddle and the second paddle to increase a vertical spacing between the first and second paddles until reaching a predetermined resistance to further vertical spacing; and, (iv) a measurement tool to discern the vertical spacing between the first paddle and the second paddle upon reaching the predetermined resistance.

In a more detailed embodiment of the second aspect, the joint distractor further includes a repositionable lock having a first position where the vertical spacing between the first paddle and the second paddle is fixed, and a second position where the vertical spacing between the first paddle and the second paddle is variable. In yet another more detailed embodiment, the first paddle and the second paddle are configured to automatically increase a vertical spacing therebetween when the repositionable lock is in the second position. In a further detailed embodiment, the predetermined resistance is supplied by soft tissues proximate the exposed bones of the joint. In still a further detailed embodiment, the first spring comprises a coil spring. In a more detailed embodiment, the coil spring includes a plurality of coil springs, with the plurality of coil springs having differing spring rates, and at least one of the plurality of coil springs is not biasing the first and second paddles at a given time. In a more detailed embodiment, the first spring comprises an inflatable bladder. In another more detailed embodiment, the inflatable bladder includes a plurality of inflatable bladders, with the plurality of inflatable bladders having differing spring rates when inflated, and at least one of the plurality of inflatable bladders is not biasing the first and second paddles at a given time. In yet another more detailed embodiment, the joint distractor further includes a constraint fixing a medial-to-lateral position of the first paddle with respect to the second paddle in a medial-to-lateral direction, where the constraint allows the first paddle to be vertically repositionable with respect to the second paddle in a vertical direction, the vertical direction being perpendicular to the medial-to-lateral direction. In still another more detailed embodiment, the second paddle is configured to be permanently constrained with respect to the primary housing in an anterior-to-posterior direction and a medial-to-lateral direction, where the anterior-to-posterior direction is perpendicular to the medial-to-lateral direction, and the first paddle is configured to be permanently constrained with respect to the primary housing in the anterior-to-posterior direction, the medial-to-lateral direction, and a vertical direction, where the anterior-to-posterior direction and the medial-to-lateral direction are each perpendicular to the vertical direction.

In yet another more detailed embodiment of the second aspect, the joint distractor further includes a rack, where the primary housing defines a first cavity, the rack is configured to be at least partially seated within the first cavity, the rack is operatively coupled to the second paddle, and the rack is selectively repositionable in the vertical direction with respect to the primary housing. In yet another more detailed embodiment, the rack includes an elongated cuboid shape, the first cavity comprises an elongated cuboid cavity, the rack includes indicia on at least one side thereof, and the rack comprises the measurement tool. In a further detailed embodiment, the joint distractor further includes a handle repositionably mounted to the primary housing and operatively coupled to the repositionable lock, wherein the handle is repositionable between a first posture coinciding with the first position of the repositionable lock, and a second posture coinciding with the second position of the repositionable lock. In still a further detailed embodiment, the handle is biased toward the first posture. In a more detailed embodiment, the handle is pivotally mounted to the primary housing and a spring interposes the primary housing and the handle to bias the handle toward the first posture. In a more detailed embodiment, the primary housing includes an adapter configured to engage a surgical drill guide, where the surgical drill guide includes a plurality of predrilled guide holes that are vertically spaced apart in predetermined increments. In another more detailed embodiment, the adapter comprises at least one of a projection and a projection receiver. In yet another more detailed embodiment, an interface between the adapter and the surgical drill guide is configured to inhibit motion between the primary housing and the surgical drill guide in a medial-to-lateral direction and a vertical direction perpendicular to the medial-to-lateral direction. In still another more detailed embodiment, at least a portion of the surgical drill guide is repositionable with respect to the primary housing in a medial-to-lateral direction and is constrained in a vertical direction perpendicular to the medial-to-lateral direction.

In a more detailed embodiment of the second aspect, the first and second paddles each have an engagement section configured to be inserted between the bones of the joint. In yet another more detailed embodiment, the engagement section of the first paddle includes an arcuate profile including an anterior-to-posterior curvature, and the engagement section of the second paddle includes an arcuate profile including an anterior-to-posterior curvature. In a further detailed embodiment, the engagement section of the first paddle includes a first finger separated laterally from a second finger, and the engagement section of the second paddle includes a third finger. In still a further detailed embodiment, a lateral profile of the first finger and the second finger are identical, and a lateral profile of the third finger is identical to the first finger. In a more detailed embodiment, the first paddle includes a first base mounted to the primary housing, where the first base includes a first guide for the first spring, the second paddle includes a second base repositionably coupled to the primary housing, where the second base includes a second guide for the first spring, and the first spring interposes the first base and the second base. In a more detailed embodiment, the primary housing includes at least one wall that inhibits motion of the rack in at least one of the anterior-to-posterior direction and the medial-to-lateral direction, but allows motion in the vertical direction, where the anterior-to-posterior direction, the medial-to-lateral direction, and the vertical direction are each perpendicular with respect to one another. In another more detailed embodiment, the rack includes a plurality of teeth vertically distributed therealong, the repositionable lock includes at least one catch configured to retardedly engage at least one of the plurality of teeth when the repositionable lock is in the first position, and the at least one catch is configured not to retardedly engage at least one of the plurality of teeth when the repositionable lock is in the second position.

In a more detailed embodiment of the second aspect, the joint distractor further includes a handle repositionably mounted to the primary housing and operatively coupled to the repositionable lock, wherein the handle is repositionable between a first posture that corresponds with the repositionable lock in its first position, and a second posture that corresponds with the repositionable lock in its second position. In yet another more detailed embodiment, the rack is configured to extend through an opening at a top of the primary housing, and the rack comprises the measurement tool and includes indicia on at least one side thereof. In a further detailed embodiment, the rack is configured to extend through an opening at a bottom of the primary housing, and the rack comprises the measurement tool and includes indicia on at least one side thereof. In still a further detailed embodiment, the rack includes a through hole configured to face the tibia and act as a drill bit guide. In a more detailed embodiment, the plurality of predrilled guide holes of the surgical drill guide includes a hole pattern that is repeated and spaced apart in at least one of the medial-to-lateral direction and the vertical direction, perpendicular to the medial-to-lateral direction. In a more detailed embodiment, the hole pattern that is repeated and spaced apart in the medial-to-lateral direction, and the hole pattern includes at least two holes having longitudinal centers that do not lie along a common straight vertical line. In another more detailed embodiment, the hole pattern that is repeated and spaced apart in the medial-to-lateral direction and the vertical direction perpendicular to the medial-to-lateral direction, and the hole pattern includes at least two holes having longitudinal centers that do not lie along a common straight vertical line. In yet another more detailed embodiment, a spacing between repeated hole pattern is at least one of fixed and variable. In still another more detailed embodiment, the joint distractor further includes a surgical guide comprising a trajectory guide and at least two pin guides, where the trajectory guide includes at least one of: (i) an elongated through opening configured to receive at least two surgical pins; and (ii) a pair of through openings, each of the pair of through openings configured to receive a separate surgical pin, and each of the at least two pin guides includes a plurality of through holes, where at least two of the plurality of through holes include longitudinal centers that do not lie along a common straight vertical line.

In yet another more detailed embodiment of the second aspect, the plurality of through holes extending through each of the at least two pin guides have a mirrored pattern, and the mirrored patterns position the plurality of through holes in incrementally vertically spaced positions. In yet another more detailed embodiment, the mirrored patterns comprise at least two rows of through holes, and the through holes of each of the at least two rows have longitudinal centers that lie along a common straight line. In a further detailed embodiment, each of the at least two pin guides is repositionable with respect to the trajectory guide in a medial-to-lateral direction. In still a further detailed embodiment, each of the at least two pin guides is not repositionable with respect to the trajectory guide in a proximal-to-distal direction, each of the at least two pin guides is not repositionable with respect to the trajectory guide in a vertical direction, and each of the proximal-to-distal direction and the vertical direction is perpendicular to the medial-to-lateral direction. In a more detailed embodiment, the trajectory guide and each of the at least two pin guides includes a key and keyway interface to facilitate repositioning of each of the at least two pin guides in the medial-to-lateral direction with respect to the trajectory guide. In a more detailed embodiment, the trajectory guide includes the key, the key embodies a dovetail shape, each of the at least two pin guides includes the keyway, and the keyway embodies a dovetail cavity. In another more detailed embodiment, the joint distractor further includes a surgical cutting guide, where the surgical cutting guide includes at least one of: (i) an elongated through opening configured to receive at least two surgical pins; and (ii) a pair of through openings, each of the pair of through openings configured to receive a separate surgical pin, and the surgical cutting guide also including at least one of: (a) a top planar surface; and (b) an elongated through hole configured to provide a guide for a surgical cutting blade to facilitate a planar cut. In yet another more detailed embodiment, the surgical cutting guide includes the elongated through opening configured to receive at least two surgical pins, and the surgical cutting guide includes the top planar surface. In still another more detailed embodiment, the surgical cutting guide includes the pair of through openings, and the surgical cutting guide includes the elongated through hole configured to provide the guide for the surgical cutting blade.

In a more detailed embodiment of the second aspect, the surgical cutting guide includes the elongated through opening configured to receive at least two surgical pins, and the surgical cutting guide includes the elongated through hole configured to provide the guide for the surgical cutting blade. In yet another more detailed embodiment, the surgical cutting guide includes the pair of through openings, and the surgical cutting guide includes the top planar surface.

It is a third aspect of the present invention to provide a method of resecting a tibia, the method comprising: (i) inserting a first distractor between a distal femur condyle and a proximal tibia condyle receiver while a femur and a tibia are in mid-flexion; (ii) tensioning soft tissue proximate a joint of the tibia and the femur and using the first distractor to identify a gap between the distal femur condyle and the proximal tibia condyle receiver in mid-flexion when the soft tissue is tensioned; (iii) mounting a surgical pin to the tibia responsive to identifying the gap and establishing a necessary gap to accommodate an orthopedic implant; (iv) positioning a cutting guide with respect to the tibia using the surgical pin; and, (v) resecting the tibia using the cutting guide.

In a more detailed embodiment of the third aspect, inserting the first distractor between the distal femur condyle and the proximal tibia condyle receiver includes inserting paddles of the first distractor between the distal femur condyle and the proximal tibia condyle receiver, where at least one of the paddles is repositionable with respect to a second of the paddles. In yet another more detailed embodiment, inserting paddles of the first distractor between the distal femur condyle and the proximal tibia condyle receiver includes medially-to-laterally centering the paddles with respect to the distal femur condyle and the proximal tibia condyle receiver. In a further detailed embodiment, medially-to-laterally centering the paddles with respect to the distal femur condyle and the proximal tibia condyle receiver includes orienting the paddles to overlap a dwell location on at least one of the distal femur condyle and the proximal tibia condyle receiver. In still a further detailed embodiment, using the first distractor to identify the gap between the distal femur condyle and the proximal tibia condyle receiver includes repositioning at least one of a plurality of paddles of the first distractor that are positioned between the distal femur condyle and the proximal tibia condyle receiver, and measuring a distance traveled by the at least one paddle. In a more detailed embodiment, measuring the distance traveled by the at least one paddle includes reading a gauge associated with the first distractor. In a more detailed embodiment, the gauge reflects a straight line distance traveled by the at least one paddle. In another more detailed embodiment, the gauge comprises a vertical support that is operatively coupled to the at least one paddle and repositionable with respect to a housing of the first distractor. In yet another more detailed embodiment, the vertical support is constrained by the housing to inhibit straight line motion in the medial-to-lateral direction and the proximal-to-distal direction, and rotational motion, so the only degree of freedom available to the vertical support is in the vertical direction that is perpendicular to the medial-to-lateral direction and the proximal-to-distal direction. In still another more detailed embodiment, tensioning the soft tissue proximate the joint of the tibia and the femur includes monitoring rate of change in strain as a function of stress to tension the soft tissue, where tensioning is achieved when the rate of change in strain has markedly decreased, but the stress has not markedly decreased.

In yet another more detailed embodiment of the third aspect, using the first distractor to identify the gap between the distal femur condyle and the proximal tibia condyle receiver includes releasing a stopper of the first distractor to allow paddles of the first distractor to reposition away from one another until reaching an equilibrium. In yet another more detailed embodiment, when the paddles reach the equilibrium, engaging the stopper to lock the relative positions of the paddles with respect to one another and thereafter identifying the gap. In a further detailed embodiment, the paddles are biased away from one another using at least one spring comprising part of the first distractor. In still a further detailed embodiment, releasing the stopper of the first distractor includes repositioning a handle repositionably mounted to a housing of the first distractor, which repositions the stopper with respect to at least one of the paddles. In a more detailed embodiment, the method further includes operatively coupling a drill guide to the first distractor, where the drill guide includes a plurality of through openings facing at least one of the femur and the tibia, and drilling two parallel holes into at least one of the femur and the tibia by repetitively inserting a drill bit into the drill guide. In a more detailed embodiment, operatively coupling the drill guide to the first distractor includes operatively coupling a ball with respect to a receiver having a partially spherical cavity, and where the ball is associated with one of the drill guide and the first distractor, while the receiver is associated with the other of the drill guide and the first distractor. In another more detailed embodiment, operatively coupling the drill guide to the first distractor includes operatively coupling a projection with respect to a receiver having a cavity configured to receive the projection, and where the projection is associated with one of the drill guide and the first distractor, while the receiver is associated with the other of the drill guide and the first distractor. In yet another more detailed embodiment, operatively coupling the drill guide to the first distractor includes limiting at least one of vertical repositioning and lateral repositioning of the drill guide with respect to the first distractor. In still another more detailed embodiment, operatively coupling the drill guide to the first distractor includes allowing rotational repositioning of the drill guide with respect to the first distractor about an axis in parallel with a longitudinal axis of at least one of the through openings.

In a more detailed embodiment of the third aspect, drilling two parallel holes includes drilling two parallel holes into the proximal tibia by inserting the drill bit through a first of the plurality of through openings and inserting the drill bit through a second of the plurality of through openings, and mounting the surgical pin to the proximal tibia includes inserting a separate surgical pin into each of the two parallel holes. In yet another more detailed embodiment, mounting the surgical pin to the tibia includes mounting a pair of surgical pins to the tibia, and positioning the cutting guide with respect to the tibia using the surgical pin includes sliding the cutting guide over the pair of surgical pins so that a top of the cutting guide establishes a plane parallel to a plane of the eventual resected tibia. In a further detailed embodiment, mounting the surgical pin to the tibia includes mounting a pair of surgical pins to the tibia, and positioning the cutting guide with respect to the tibia using the surgical pin includes sliding the cutting guide over the pair of surgical pins so that an elongated through slot of the cutting guide establishes a trajectory parallel to a plane of the eventual resected tibia. In still a further detailed embodiment, the method further includes using the cutting guide to drill a hole into the tibia, and mounting an individual surgical pin to the tibia, where the individual surgical pin and the pair of surgical pins, when mounted to the tibia, are orientated in a triangular arrangement, where positioning the cutting guide with respect to the tibia using the surgical pin includes sliding the cutting guide over the pair of surgical pins and the individual surgical pin so that rotation of the cutting guide with respect to the tibia is precluded.

It is a fourth aspect of the present invention to provide a method of resecting a tibia, the method comprising: (i) inserting a first distractor between a distal femur condyle and a proximal tibia condyle receiver while a distal femur and a proximal tibia are in mid-flexion; (ii) using the first distractor to identify a gap between the distal femur condyle and the proximal tibia condyle receiver in mid-flexion when soft tissue proximate the proximal tibia and distal femur are tensioned; (iii) calculating an implant gap necessary to accommodate an orthopedic implant inserted between the distal femur and the proximal tibia; (iv) mounting a surgical pin to the proximal tibia responsive to calculating the implant gap; (v) positioning and orienting a cutting guide with respect to the proximal tibia by using the surgical pin; and, (vi) resecting the proximal tibia using the cutting guide, where an anterior-to-posterior slope of a proximal tibia resection is fixed by an anterior-to-posterior slope of the cutting guide.

In a more detailed embodiment of the fourth aspect, inserting the first distractor between the distal femur condyle and the proximal tibia condyle receiver includes inserting the first distractor between a distal femur medial condyle and a proximal tibia medial condyle receiver. In yet another more detailed embodiment, inserting the first distractor between the distal femur condyle and the proximal tibia condyle receiver includes inserting the first distractor between a distal femur lateral condyle and a proximal tibia lateral condyle receiver. In a further detailed embodiment, the method further includes inserting a second distractor between a distal femur medial condyle and a proximal tibia medial condyle receiver while the distal femur and the proximal tibia are at mid-flexion, and where inserting the first distractor between the distal femur condyle and the proximal tibia condyle receiver includes inserting the first distractor between a distal femur lateral condyle and a proximal tibia lateral condyle receiver. In still a further detailed embodiment, the first distractor includes a first femoral paddle and a first tibial paddle, the second distractor includes a second femoral paddle and a second tibial paddle, inserting the second distractor between the distal femur medial condyle and the proximal tibia medial condyle receiver includes initially inserting the second femoral paddle and the second tibial paddle in between the distal femur medial condyle and the proximal tibia medial condyle receiver and, thereafter, repositioning at least one of the second femoral paddle and the second tibial paddle to span a medial gap between the distal femur medial condyle and the proximal tibia medial condyle receiver as soft tissue proximate the proximal tibia and distal femur are tensioned, and inserting the first distractor between the distal femur lateral condyle and the proximal tibia lateral condyle receiver includes initially inserting the first femoral paddle and the first tibial paddle in between the distal femur lateral condyle and the proximal tibia lateral condyle receiver and, thereafter, repositioning at least one of the first femoral paddle and the first tibial paddle to span a lateral gap between the distal femur lateral condyle and the proximal tibia lateral condyle receiver as the soft tissue proximate the proximal tibia and distal femur are tensioned. In a more detailed embodiment, the method further includes using the second distractor to identify a medial gap between the distal femur medial condyle and the proximal tibia medial condyle receiver at mid-flexion when the soft tissue proximate the proximal tibia and distal femur are tensioned, wherein using the first distractor to identify the gap between the distal femur condyle and the proximal tibia condyle receiver at mid-flexion includes using the first distractor to identify a lateral gap between the distal femur lateral condyle and a proximal tibia lateral condyle receiver. In a more detailed embodiment, the method further includes concurrently engaging the first and second distractor by a positioning device to provide a uniform anterior-to-posterior slope of that portion of each of the first and second distractors positioned between the distal femur and the proximal tibia. In another more detailed embodiment, concurrently engaging the first and second distractor by the positioning device includes: (a) operatively coupling the positioning device to the first distractor using a first device that limits anterior-to-posterior and medial-to-lateral travel therebetween, and a second device that inhibits vertical travel therebetween, and (b) operatively coupling the positioning device to the second distractor using a third device that limits anterior-to-posterior and medial-to-lateral travel therebetween, and a fourth device that inhibits vertical travel therebetween. In yet another more detailed embodiment, using the second distractor to identify the medial gap includes reading a repositionable scale associated with the second distractor to discern the spacing between the distal femur medial condyle and the proximal tibia medial condyle receiver, and using the first distractor to identify the lateral gap includes reading a repositionable scale associated with the first distractor to discern the spacing between the distal femur lateral condyle and the proximal tibia lateral condyle receiver. In still another more detailed embodiment, the distal femur includes at least one of a native femoral bone, a native femoral bone including a chamfer cut, a femoral orthopedic trial, and a femoral orthopedic implant.

It is a fifth aspect of the present invention to provide a method of using a surgical robot to carry out at least one bone resection cut on at least one of a tibia and a femur, the method comprising: (i) using at least one position tracker to track the three dimensional position of at least one of a femur and a tibia; (ii) relaying tracking information as to the three dimensional position of at least one of the femur and the tibia to a controller controlling position and motion of a surgical robot; and, (iii) using the surgical robot to make at least one bone resection cut on at least one of the femur and the tibia, after a posterior chamfer cut is made to the femur, using registration with the posterior chamfer cut.

In a more detailed embodiment of the fifth aspect, using the surgical robot to make at least one bone cut includes making a bone cut on the tibia and the femur. In yet another more detailed embodiment, the posterior chamfer cut is a first bone resection cut made to the femur. In a further detailed embodiment, the surgical robot includes: (a) a multi-axis robotic arm, (b) a tool carrier with a series of surgical tools selectively coupled to the multi-axis robotic arm, and (c) a robot controller configured to identify a position of the femur and the tibia relative to at least one of the multi-axis robotic arm and one of the series of surgical tools mounted to the multi-axis robotic arm. In still a further detailed embodiment, using registration with the posterior chamfer cut includes not using pre-operative or intra-operative imaging to register the position of at least one of the femur and the tibia with respect to the surgical robot.

BRIEF DESCRIPTION OF THE DRAWINGS

FIG. 64A is a front view of frame members of a surgical guide in a first configuration in accordance with the instant disclosure.

FIG. 64B is a front view of frame members of a surgical guide in a second configuration in accordance with the instant disclosure.

FIG. 65 is a front view of a knee joint showing the relative position of the frame members of a surgical guide in a given configuration in accordance with the instant disclosure.

DETAILED DESCRIPTION

Figure 1:
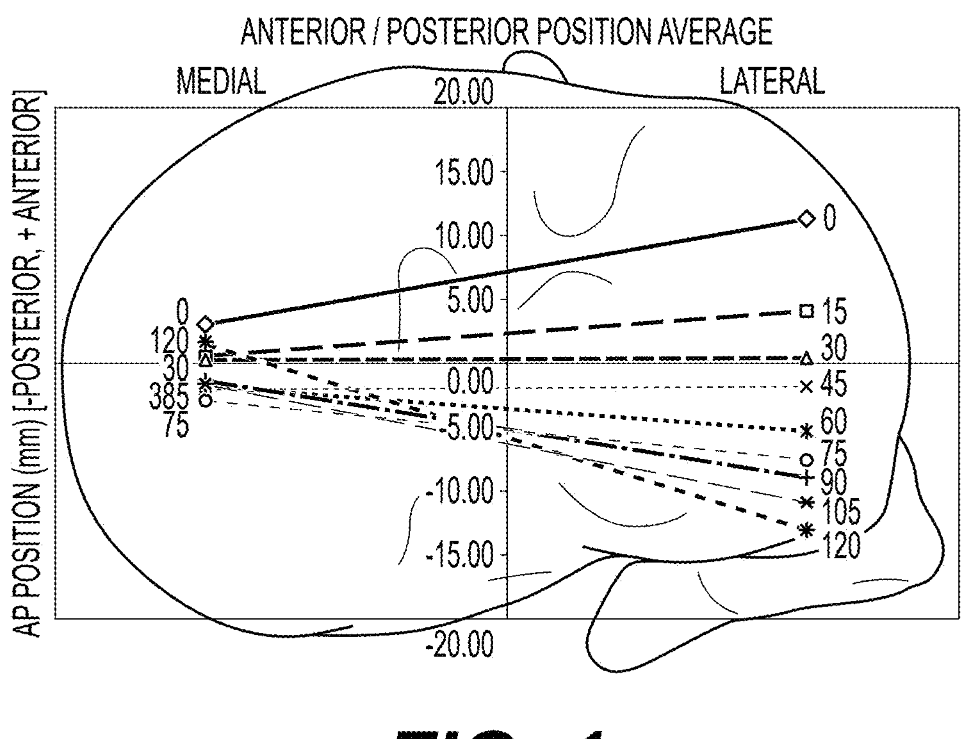
FIG. 1 is a plot of a motion pattern for a normal knee joint showing the anterior-posterior positions of the medial and lateral condyles at various degrees of flexion.
Figure 2:
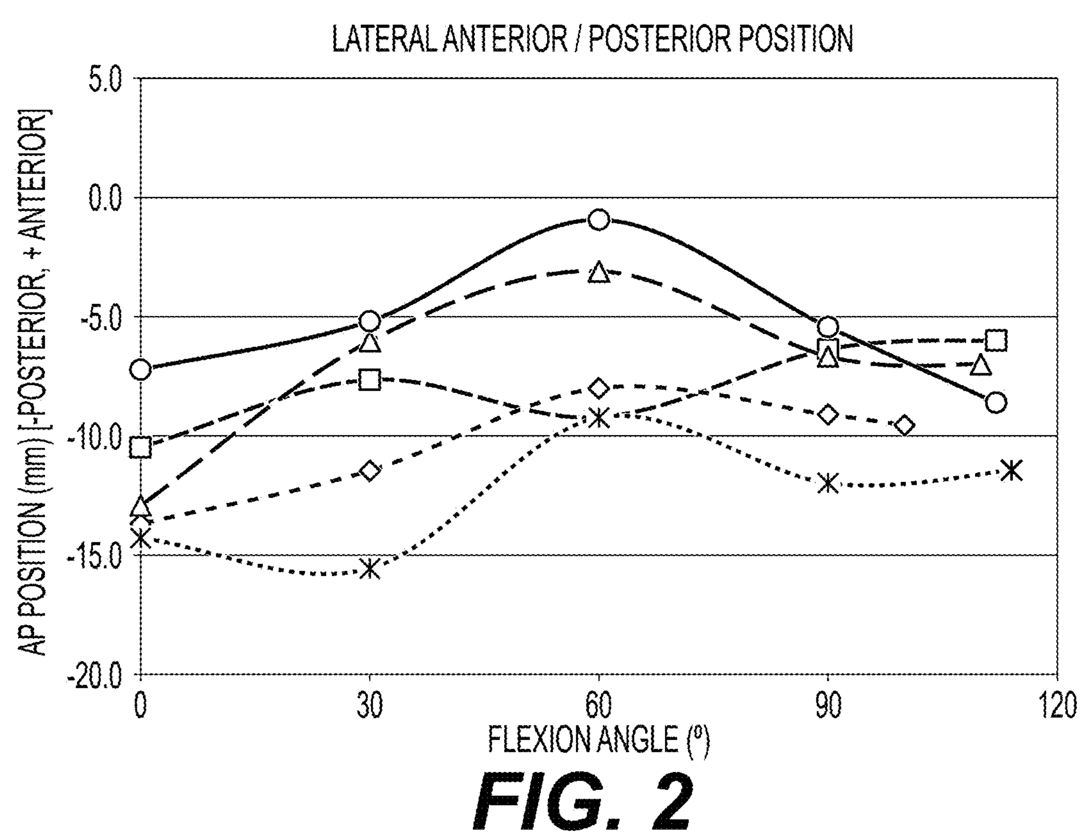
FIG. 2 is a plot of the anterior-posterior position of the lateral condyle as a function of flexion angle for five subjects implanted with a posterior cruciate ligament retaining total knee arthroplasty.

The exemplary embodiments of the present disclosure are described and illustrated below to encompass surgical equipment and associated methods for performing a knee arthroplasty procedure. It should be noted that while the discussion hereafter may refer to total knee arthroplasty (TKA), it should be understood that for purposes of explanation herein, TKA is also intended to encompass partial knee arthroplasty (PKA), unicompartmental knee arthroplasty (UKA), and revision knee arthroplasty (RKA). To the extent any surgical equipment and techniques described herein are unique to PKA, UKA, or RKA, an associated discussion will be included. Otherwise, any reference to TKA is intended to encompass PKA, UKA, and RKA. In addition, any reference herein to "patient" includes live and dead humans, as well as any live or dead non-human mammal. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

The present disclosure contemplates that to achieve alignment and component position of femoral and tibial components as part of a TKA procedure, there are two predominant methodologies for performing a knee replacement. In a first methodology, commonly known as the "Gap Balanced" technique, the patient's knee joint is distracted either in extension or 90 degrees of flexion first, with the implication that the soft tissues, including the collateral ligaments, are "balanced" in tension, and thereafter a resection of the distal femur and proximal tibia is performed. Traditional concepts of bone distance removal of 9 millimeters from the non-deficient distal femoral condyle, and 4 millimeters off the deficient tibial condyle receiver, may be used, with the cuts made in varus and valgus on both the femur and tibia to achieve a neutral mechanical axis (i.e., when the bone ends are placed together the leg is "straight"). Depending upon whether one resects the proximal tibia or distal femur first has implications for the subsequent ligament balance obtained thereafter. With the Gap Balanced technique, the assumption is that a rectangle or near rectangle of known distance is created between the cut bone ends of the tibia and femur, where this distance is the same in full extension and at 90 degrees of flexion.

The present disclosure contemplates that, in contrast, the second most common methodology, referred to as the "Measured Resection" technique, requires a surgeon to take measured amounts of bone from the distal femur and proximal tibia (similar to that for the Gap Balanced technique), and then perform releases, if necessary, to create a rectangle of known distance. By removing an equal amount of bone from the posterior femur and the distal femur, and performing any releases, the assumption is that a rectangle of known (and equal) distance is created. The present disclosure contemplates that this assumption as to the desirability of rectangularity in either method, as well as where this rectangle should be placed, may be a faulty premise in some circumstances.

The present disclosure contemplates that the desirability of rectangularity and the location of the rectangle may be based on at least four inherent and poorly defined assumptions: 1) that a rectangle of constant distance is created in extension and in 90 degrees of flexion; 2) the rectangle does not change in width over a 90 degree arc of motion (from extension to 90 degrees of flexion); 3) that the balanced ligaments are equidistant in the positions of extension and 90 degrees of flexion; and, 4) that the surgeon can define the rectangle placement in three planes by making cuts at two distinct angles (distal femur and proximal tibia) without any knowledge of the accuracy of the planes created on the distal femur and proximal tibia.

The present disclosure contemplates that in a study of 101 computer navigated TKA knees, it was discovered that after initial creation of "mechanical neutral" proximal tibial and distal femoral resections and subsequent anterior-posterior (AP) femoral cuts, an average of two "releases" were required for placement of trial components to achieve a balanced knee (balance defined as equal "force" medially and laterally obtained via a tibial sensor when the "heel push test" was performed throughout a range of motion). While of interest, the bone cuts were performed separately, and the total force applied was only alluded to (120-145 Newtons per manuscript). Of note, increasing the tibial insert thickness 2 millimeters increased the total force by approximately 70%, thus tending to prove that one can create a sense of stability. In most manufacturing processes for orthopedic implant components, an inaccuracy of this level would lead to a process redesign; in TKA, such inaccuracy may lead to mid-flexion and flexion laxity, and patient dissatisfaction. The present disclosure contemplates that using either the Gap Balancing or Measured Resection technique may result in inherent inaccuracy.

The present disclosure contemplates that an underlying issue in soft tissue balancing is not just in achieving some relationship between the medial and lateral collateral ligaments, it is in agreeing on where this relationship should occur as a function of knee flexion and axial rotation between the femur and tibia. Studies undertaken of the medial and lateral collateral ligaments divided these ligaments into three portions (anterior, middle, and posterior) and examined the in vivo changes in ligament length during flexion. In general, over the range of motion from full extension to at least 90 degrees flexion, the anterior fibers increased in length, the middle fibers did not change, and the posterior fibers reduced in length. Applying these observations to the Gap Balancing technique reveals mechanical conflicts in soft tissue balancing driven by the technique itself. From the understanding of ligament length, particularly of the medial collateral ligament (MCL), and the range of length change seen from extension to 90 degrees of flexion, balancing in flexion and extension results in a lax MCL in mid-flexion.

The present disclosure contemplates that Gap Balancing can be reduced to the simple imposition of a defined distance between two bone ends (one of which must be cut first) if, after the proximal tibial resection is made, the knee is held in flexion and the soft tissues are balanced and the posterior resection cuts are being marked. However, a resection made without reference (except anteriorly) to the prior cut may create a larger or smaller gap posteriorly. The same issue arises in extension when making the distal femoral resection. While the amount of anterior bone to be resected is planned based on the distance identified in flexion, the execution often times fails to keep the flexion extension axis constant. Accordingly, resections/cuts that are not linked in plane are divergent from anterior to posterior. Therefore, a Gap Balanced knee may keep a constant anterior distance between the anterior aspect of the femoral resection(s) and the proximal tibial resection, but not a constant posterior distance. Empirical evidence suggests that creation of a constant rectangle is almost never achieved when using the Gap Balanced technique, which is one of the causes of flexion laxity. In addition, the MCL and lateral collateral ligament (LCL) vary in length between full extension and 90 degrees of flexion and beyond. Thus, if the Gap Balancing technique is predicated on flexion balancing first, the identified "gap" in flexion results in over resecting the distal femur, again leading to mid-flexion laxity. And if the distal femur is cut after the proximal tibia, and thereafter the posterior femoral resection is made, this often results in over resection of the posterior femur. These same issues occur using the Measured Resection technique.

The present disclosure contemplates that despite the technical appearance of a well-done TKA (full range of motion, varus valgus and anterior posterior stability, and radiographic confirmation of appropriate placement of the components), at least 25% of patients report dissatisfaction with their reconstructed knee joint. Typical problems include, but are not limited to, ongoing pain, a feeling of instability, quadriceps soreness, and swelling. Essentially, what is occurring is anterior translation of the tibial component relative to the femoral component, which is equivalent to an anterior cruciate deficient knee. The clinical diagnosis of what is causing this can be broken down into two possibilities (or both) based on where the knee appears to be lax to stress: (a) mid-flexion, defined as increased varus valgus opening to stress at 30 to 60 degrees of flexion; or, (b) flexion, defined as increased anterior laxity at 90 degrees of flexion. Generally, for these conditions to exist, the knee is stable (i.e., no opening to varus/valgus stress) in full extension.

The present disclosure contemplates that flexion laxity at 90 degrees of flexion is often easier to diagnose than mid-flexion laxity. While it is generally accepted that the clinical finding of flexion laxity is greater than 5 mm of anterior-posterior (AP) laxity at 90 degrees of flexion, there may be several caveats. For any midpoint sagittal axis defined by the femoral component, the tibial component is either directly under (neutral), anterior to, or posterior to, this axis. The knee should be pushed posteriorly to a maximal position defined by either the post of the posteriorly stabilized component hitting the femoral cam, or where the posterior translation is stopped by the posterior cruciate ligament. From this position with the leg hanging (note that performance of this test with the patient lying down results in the weight of the thigh, and the conformity of the tibial liner, potentially influencing the findings) the knee is drawered forward and the laxity graded as either less than 5 mm, 5 to 10 mm, or greater than 10 mm. The lax side can be assessed as well by stressing the knee into varus and valgus and noting where femoral rotation begins to be seen. The "hanging clunk" sign has been defined and represents the reduction of the tibia to the posterior femur. This clunk can be identified either by testing for a deep tendon reflex, or asking the patient to rapidly extend the knee from 90 degrees of flexion and noting the superior translation of the tibia prior to the leg extending. It is assumed that at this level of laxity there is mid-flexion laxity as well.

The present disclosure contemplates that mid-flexion laxity is harder to diagnose. Testing of the varus/valgus stability at 30 degrees of flexion may suggest laxity of one of the collateral ligaments, or both.

The present disclosure contemplates that the current state of preparation and procedure for performing a TKA neither addresses nor evaluates the laxity seen when femoral and tibial cuts are performed without planar reference to each other (linked), or suggests where within a soft tissue envelope the orthopedic implants should be placed. In simplest terms, the imposition of a constant rectangle of known width from extension to 90 degrees of flexion is not achieved with accuracy using current TKA techniques and surgical equipment. From a kinematic standpoint, as the knee starts to flex, if the rectangular distance is not a constant, the increased distance results in anterior translation of the tibia. This may be counteracted by quadriceps contraction. Over the first 90 degrees of motion, the tibial component, rather than maintaining a constant relationship in distance to the femoral component, oscillates anteriorly, and then reduces with quadriceps force, and then oscillates, creating a sinusoidal curve over the first 90 degrees of flexion.

The present disclosure contemplates that a main concern for gap balancing is that the determination of tension or spacing on each side is not exact. If a surgeon attempts to gap balance and hopes to achieve 50% tension of the ligaments on the lateral side and 50% tension of the ligaments on the medial side or 50% compression of each condyle, but is not exact, the patients may have 60-80% of the tension or compression on one side and 20-40% on the other side. This would lead to an imbalance and could result in the abnormal kinematics discussed earlier. Having greater tension on one side (medial or lateral) or greater compression on one slide could lead to excessive abnormal sliding of one condyle leading to abnormal or reverse axial rotation of the femur with respect to the tibia during knee flexion.

Figure 4:
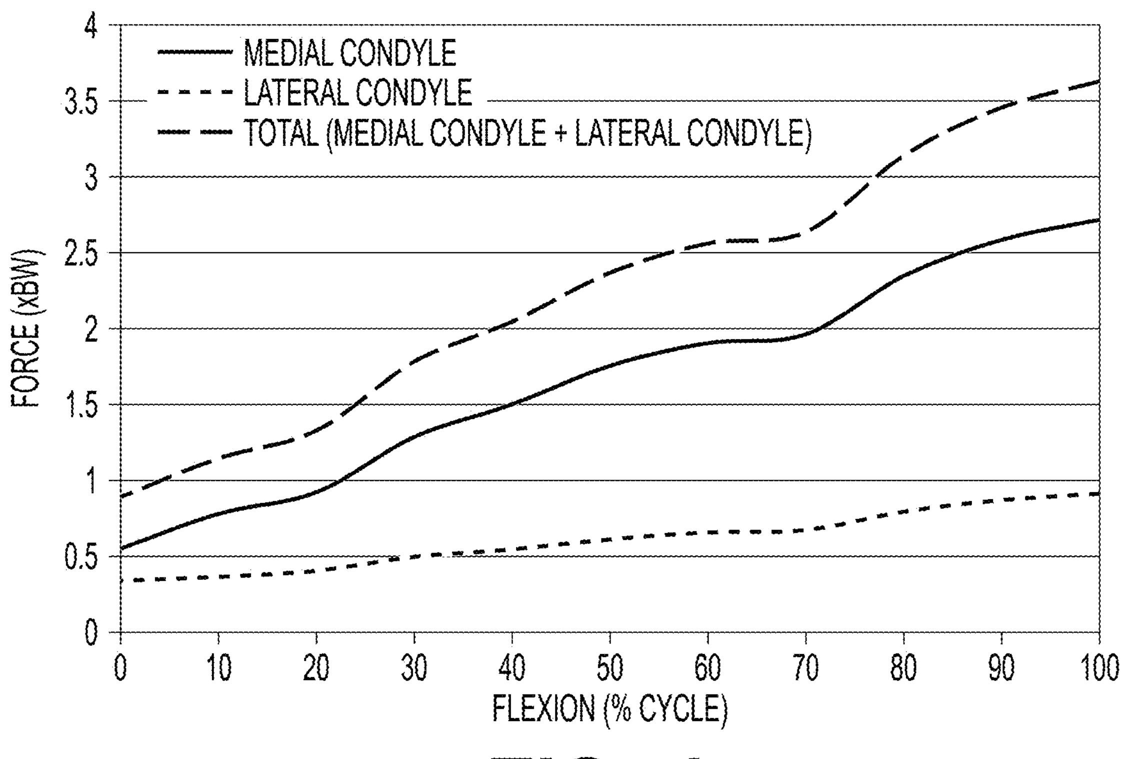
FIG. 4 is a plot of force as a function of flexion for the medial and lateral condyles of a normal knee.
Figure 5:
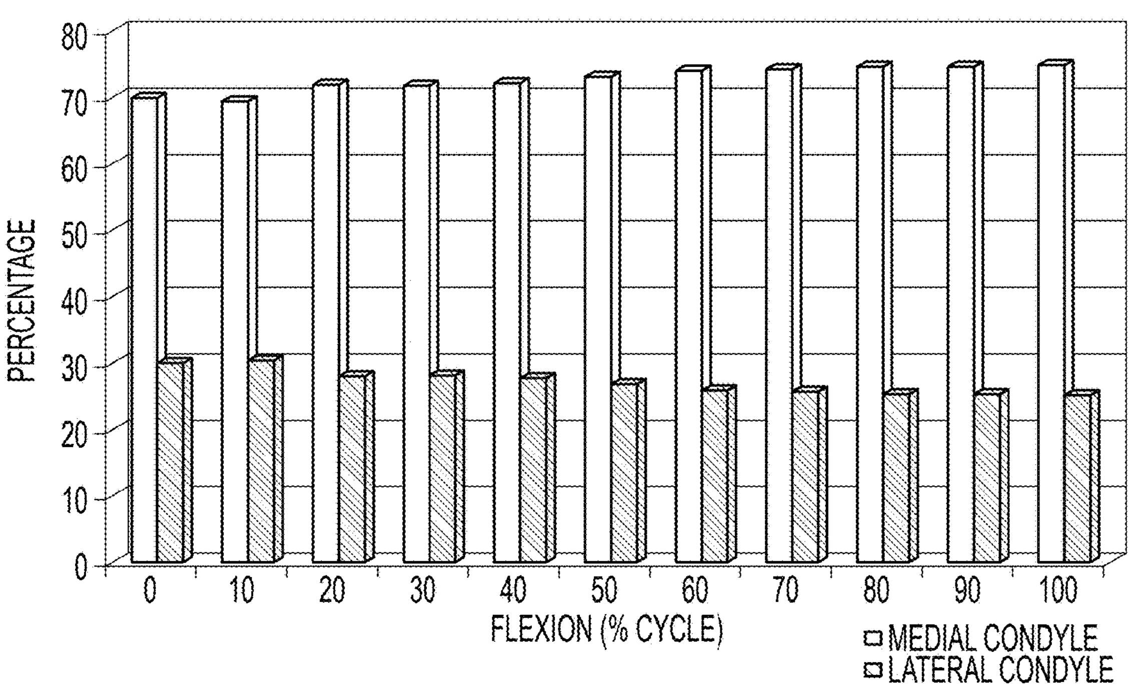
FIG. 5 is a bar graph showing the percentage of the total force that is imposed on each of the medial and lateral condyles at various flexion angles.

FIG. 4 is a plot of force as a function of flexion for the medial and lateral condyles of a normal knee, and FIG. 5 is a bar graph showing the percentage of the total force that is imposed on each of the medial and lateral condyles at various flexion angles. Referring to FIGS. 4 and 5, the present disclosure contemplates that, in a normal knee joint, the femorotibial forces interacting at the medial femoral condyle are higher than those forces interacting at the lateral femoral condyle. The femorotibial force passing through the medial femoral condyle are routinely about 60-70% of the overall force, while the lateral femoral condyle exhibits 30-40% of the overall knee force. In extreme cases, the femorotibial forces passing through the medial femoral condyle can be more than 2.5× that of the forces passing through the lateral femoral condyle.

The present disclosure contemplates that although the forces are not symmetrical in the normal knee, surgeons may attempt to gap balance the knee desiring to have equal forces for the medial and lateral condyles. Unfortunately, this may be done under passive conditions and not using reliable instrumentation to ensure the goal is equal to the outcome. Further, despite the pre-surgical asymmetrical loading, the TKA surgery may be intentionally performed to yield symmetrical loading. This could be a reason why the axial rotation of implanted knees is much less than the axial rotation of the normal knee.

Figure 3:
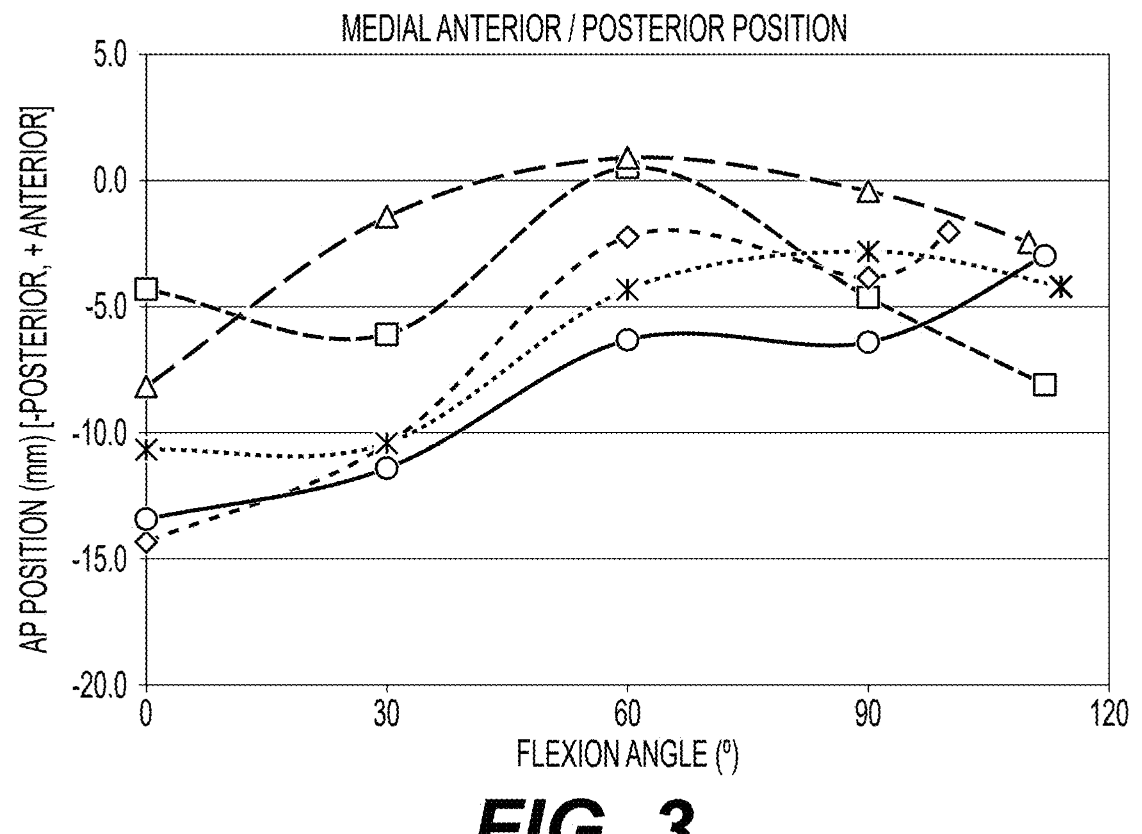
FIG. 3 is a plot of the anterior-posterior position of the medial condyle as a function of flexion angle for five subjects implanted with a posterior cruciate ligament retaining total knee arthroplasty.

The present disclosure contemplates that the differences in forces applied to a normal knee joint results in more rollback of the lateral femoral condyle during knee flexion and axial rotation of the femur with respect to the tibia being reflected in greater anterior-posterior travel of the lateral femoral condyle with respect to the medial femoral condyle, allowing the medial femoral condyle to remain more central and the lateral femoral condyle. In addition, in the normal knee, the femoral condyles are asymmetric in shape, as well as ligament balancing and soft-tissue forces being asymmetric. When a surgeon attempts to Gap Balance a TKA and equate the forces in the medial and lateral aspects, the surgeon is changing the knee balance and can foster a hinge-like motion pattern where both condyles move symmetrically and exhibit much less axial rotation. In the normal knee, on average, the knee experiences about 27 degrees of axial rotation (see FIG. 3), while in an average TKA joint, abnormal axial rotation patterns are exhibited with substantially less axial rotation (on the order of less than 3 degrees). If a surgeon attempts to balance the knee with equal gaps and tension, the result is often a TKA knee experiencing minimal or no axial rotation, or even reverse axial rotation.

Figure 6:
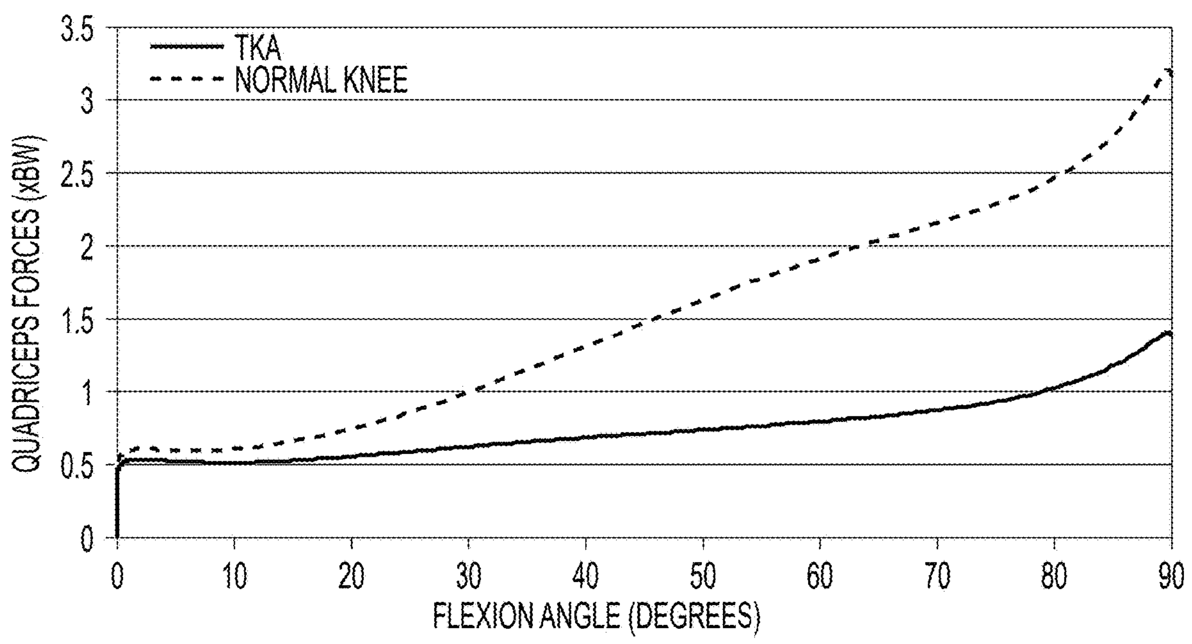
FIG. 6 is a plot of quadriceps force as a function of flexion angle for a normal knee and an implanted knee.

FIG. 6 is a plot of quadriceps force as a function of flexion angle for a normal knee and an implanted knee. Referencing FIG. 6, the present disclosure contemplates that if a TKA joint is improperly balanced (e.g., not balanced at mid-flexion), sliding of the femoral component may lead to a reaction by the quadriceps muscles and cause the force to be much greater than the amount necessary. Quadriceps muscle forces may be firing much earlier for a TKA knee than for a normal knee, thus leading to higher quadriceps forces in deeper flexion. There is only so much force that the quadriceps can apply to drive knee motion and when the maximum amount is utilized, the implanted knee can no longer flex any further. It has been shown that implanted knee motion is statistically less than the normal knee. This sliding motion of the femoral component induces the quadriceps muscle to apply greater forces in an attempt to stabilize the knee joint. Unfortunately, since the quadriceps muscle is only able to provide a maximum amount of force, and this force is necessary to stabilize the TKA joint in early flexion, some patients can reach flexion limits around 70-90 degrees of flexion due to the fact that their quadriceps muscle becomes too tight and exceeds their maximum allowable force too early. FIG. 6 reflects data obtained during in vivo studies measuring the quadriceps force applied as a function of flexion angle for a normal knee joint and a TKA joint during weight-bearing activities. In the normal knee joint, quadriceps force increases from full extension and are on the order of a 3× increase upon reaching 90 degrees flexion. In contrast, for a TKA joint, quadriceps force increases rather dramatically from full extension and are on the order of a 6.5× increase upon reaching 90 degrees flexion. And these higher quadriceps forces lead to abnormal knee mechanics and less than desired weight-bearing flexion in a TKA joint.

In accordance with the instant disclosure, it has been discovered that carrying out a soft tissue balance at or proximate to mid-flexion prior to making principal cuts on the distal femur and proximal tibia obviates most, if not all, of the foregoing issues exhibited when otherwise balancing a TKA joint at full extension (0 degrees flexion) or beyond 90 degrees flexion. Specifically, balancing a patient's joint at mid-flexion may keep the knee joint more stable while performing weight-bearing activities, allowing muscle forces (such as the quadriceps) to be less and allowing for greater range of motion during weight-bearing knee joint flexion.

The present disclosure contemplates that balancing of the soft tissues at mid-flexion may create the potential for a rectangle to be imposed on two bony surfaces (distal femur, proximal tibia). Some exemplary techniques in accordance with the instant disclosure may differ from other techniques by imposing a rectangle for symmetric balancing or a trapezoid for asymmetric balancing in six degrees of freedom wherein each cut plane on the femur and tibia (varus-valgus, anterior-posterior, and rotational) is intimately related and parallel to the corresponding cut plane (e.g., after equilateral ligament balancing the varus-valgus of the tibial cut results in the varus-valgus of the femoral cut, with cut resection levels based on known TKA principles).

The present disclosure contemplates that if a surgeon balances a knee at full extension and/or 90 degrees of knee flexion under passive conditions, the soft tissues, such as the ligaments, aren't loaded and as the knee flexes or extends away from the point of balancing, the ligaments may not remain balanced at different degrees of flexion and/or extension. The present disclosure contemplates that the instance of greatest instability or laxity in the knee may occur during mid-flexion, which may lead to abnormal knee kinematics and excessive sliding. Patients may feel this sense of sliding, leading to them not feeling confident as the knee doesn't feel stable.

Generally, some example methods according to at least some aspects of the present disclosure include measurement of knee ligament tension and gaps at (or near) the angle corresponding to the femoral chamfer angle (which generally corresponds to knee mid-flexion) prior to planar cuts being made to the proximal tibia and distal femur. Once the knee is positioned at that angle, medial collateral and lateral collateral ligament and compartment information is derived and recorded. The first cut is the femoral chamfer cut. Then, the proximal tibial cut is made with respect to the femoral chamfer cut. Alternatively, the first cut may be the proximal tibial cut, and then the femoral chamfer cut may be made with respect to the tibial cut. The knee may again be measured at this orientation so ligament lengths and tension and distances between the cuts are maintained and recorded. Then, knee is reoriented to full extension and ligament lengths and tension and compartment gaps may be properly positioned and referenced with respect to the information gained and recorded at the knee chamfer angle. Then, the femoral extension cut is made. By way of example, the femoral component chamfer cut may be the same distance from the proximal tibial cut (at mid-flexion) as the femoral extension cut is from the proximal tibial cut (at full extension). Also, the ligament tensions and lengths when measured between the chamfer cut to the tibial cut (at mid-flexion) may be the same as when measured between the extension cut to the tibial cut (at full extension).

FIGS. 7A-7H are sequential, simplified lateral section views of a knee joint ultimately undergoing distal femoral and proximal tibial resections in connection with the exemplary TKA procedures discussed hereafter, all according to at least some aspects of the present disclosure. The following description referencing FIGS. 7A-7H is intended to provide an overview and context for the methods and apparatuses described in detail below.

Figure 7A:
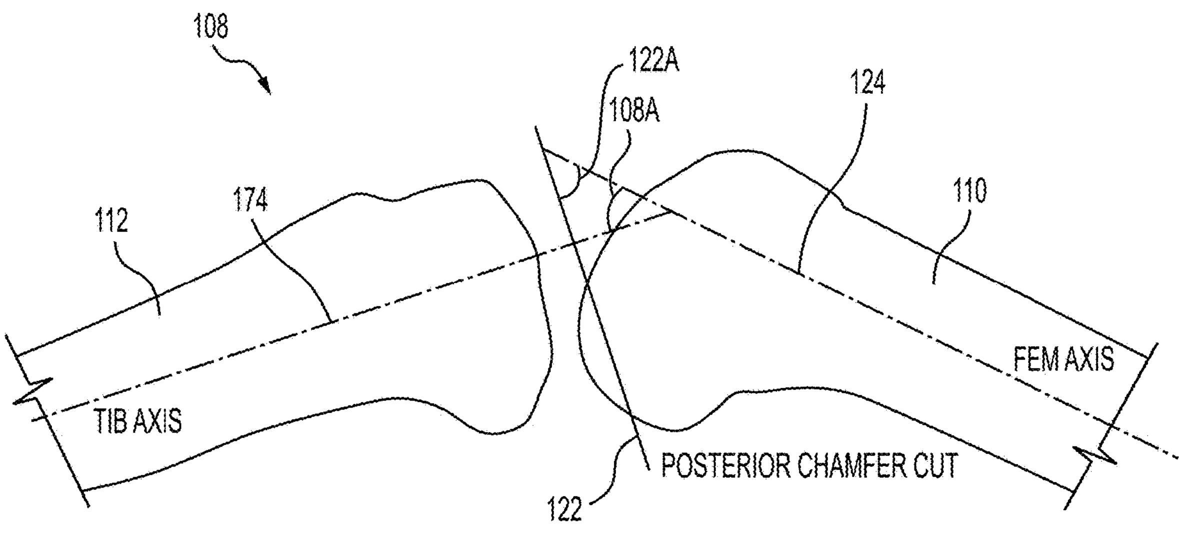
FIGS. 7A-7H are sequential, simplified lateral section views of a knee joint undergoing femoral and tibial resections in connection with a total knee arthroplasty procedure.

Turning to FIG. 7A, a knee joint 108 is positioned at a desired degree of flexion. For example, the knee joint 108 is positioned so that a flexion angle 108A between a femur 110 (e.g., femoral canal axis 124) and a tibia 112 (e.g., tibial longitudinal axis 174) is at a desired mid-flexion angle, such as about 45 degrees. In some example embodiments, balancing a TKA joint in accordance with the instant disclosure is performed at or proximate mid-flexion of the femur 110 with respect to the tibia 112. In exemplary form, the posterior chamfer angle 122A of a TKA may coincide with the mid-flexion angle of the knee joint 108 (e.g., approximately 45 degrees between the femur 110 and tibia 112). By way of example, the posterior chamfer cut 122 may be angled approximately 45 degrees from the femoral canal axis 124. Determination of the posterior chamfer angle 122A with respect to a fixed axis (such as the femoral canal axis 124, also known as the femoral intramedullary canal) allows a surgeon to know the angle that the distal femur 110 should be orientated with respect to the proximal tibia 112 so that the posterior chamfer cut 122 may made first before cuts to the proximal tibia and distal femur (beyond removal of osteophytes). If, for instance, the posterior chamfer angle is 45 degrees, then the distal femur 110 may be repositioned by the surgeon to be angled at approximately 45 degrees with respect to the proximal tibia 112. In this fashion, some example TKA procedures according to at least some aspects of the present disclosure may involve making a posterior chamfer cut 122 as the first resection cut to the femur 110.

Figure 7B:
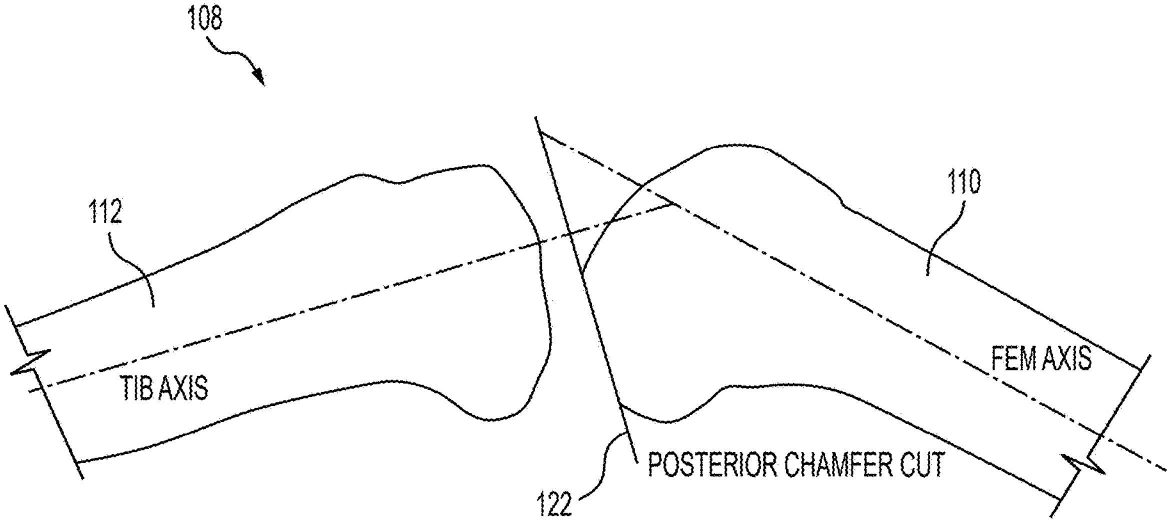
Figure 7C:
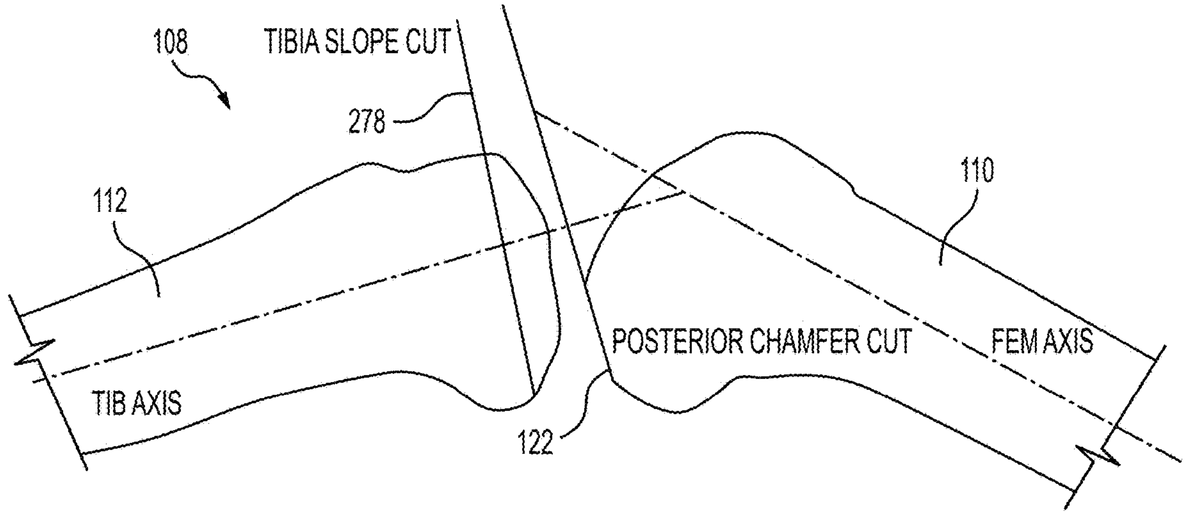
Figure 7D:
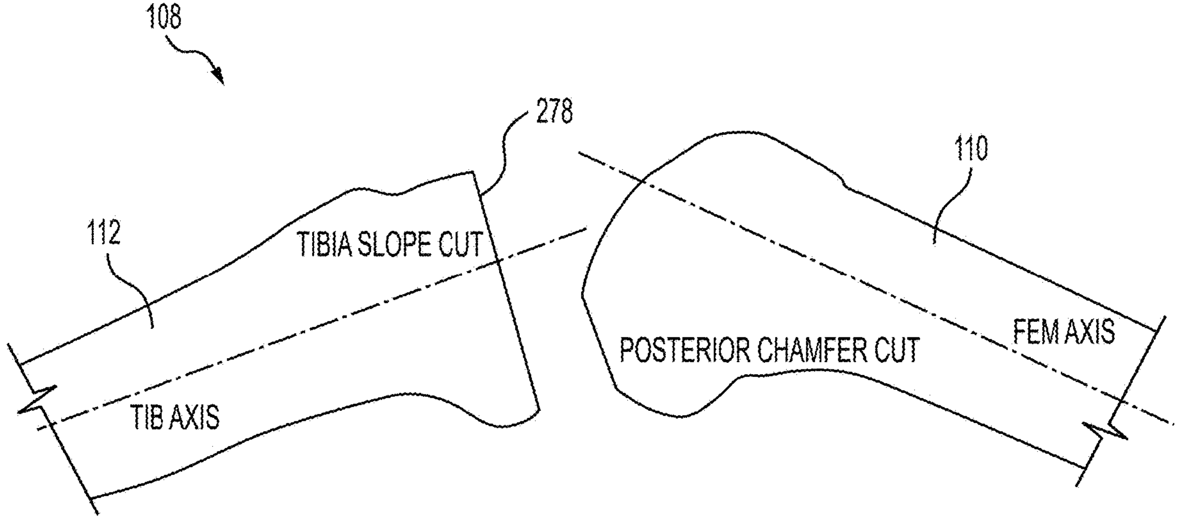
Figure 7E:
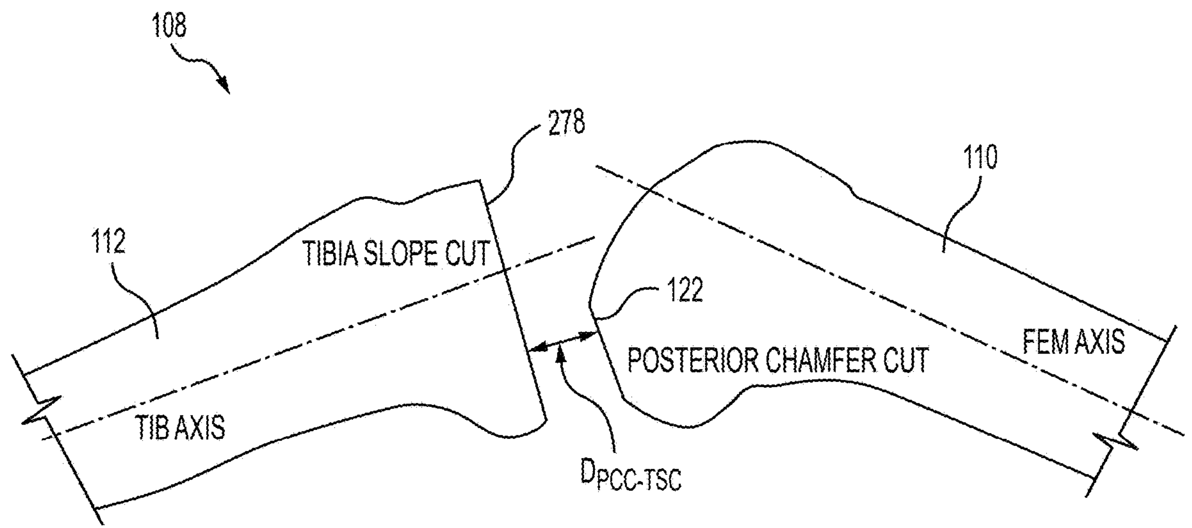

Referring to FIG. 7B, after the knee 108 is soft tissue balanced, as discussed in more detail hereafter, at or near the desired mid-flexion angle, the posterior chamfer cut 122 is made. Referring to FIG. 7C, the location and orientation of tibial plateau cut 278 is determined, resulting from soft tissue balancing the knee 108 at or near mid-flexion. Referring to FIG. 7D, the tibial plateau cut 278 is performed. Referring to FIG. 7E, a distance between the posterior chamfer cut 122 and the tibial plateau cut 278 is measured to verify the distance the surgeon determined is appropriate for the orthopedic implant based upon the soft tissue balance performed at or near mid-flexion.

In some alternative methods, the tibial plateau cut 278 may be made first before any cuts are made to the femur, including the posterior chamfer cut 122. However, it is preferred, but not required, that the knee 108 be soft tissue balanced at or near mid-flexion prior to the tibial plateau cut 278 and the posterior chamfer cut 122. Presuming the tibial plateau cut 278 occurs first, the posterior chamfer cut 122 may be made second. It should be noted that soft tissue balancing of the knee 108 can occur at or near mid-flexion after the tibial plateau cut 278 and the posterior chamfer cut 122 are complete to verify the soft tissue balance determinations previously undertaken at or near mid-flexion before these bone cuts were initiated. In this manner, the surgeon is able to revise one or both of the tibial plateau cut 278 and the posterior chamfer cut 122 if the soft tissues are not balanced post bone cuts. In some such methods, although the posterior chamfer cut 122 may be made after the tibial plateau cut 278, the posterior chamfer cut 122 may be the first cut on the femur 110.

Figure 7F:
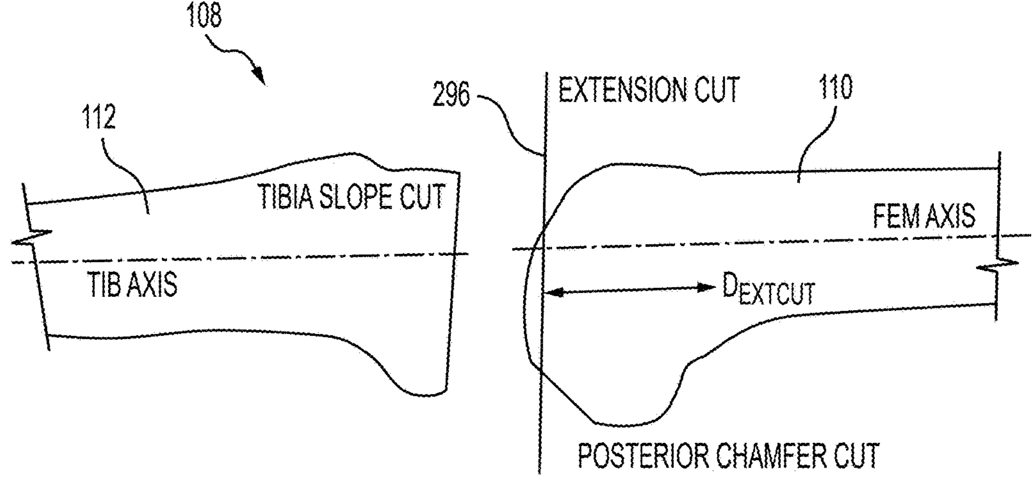
Figure 7G:
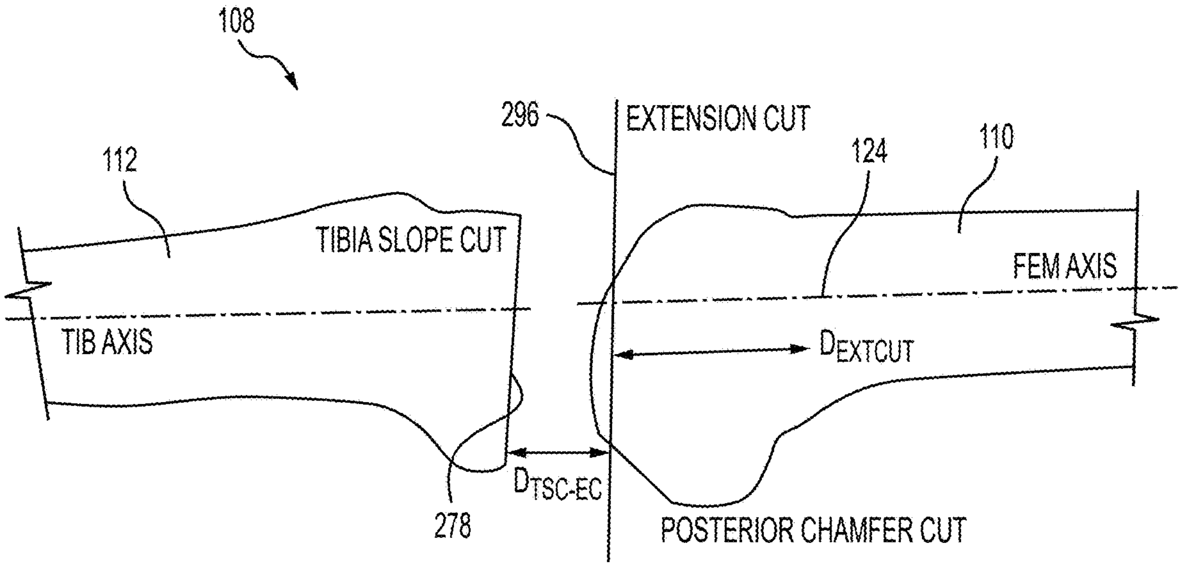
Figure 7H:
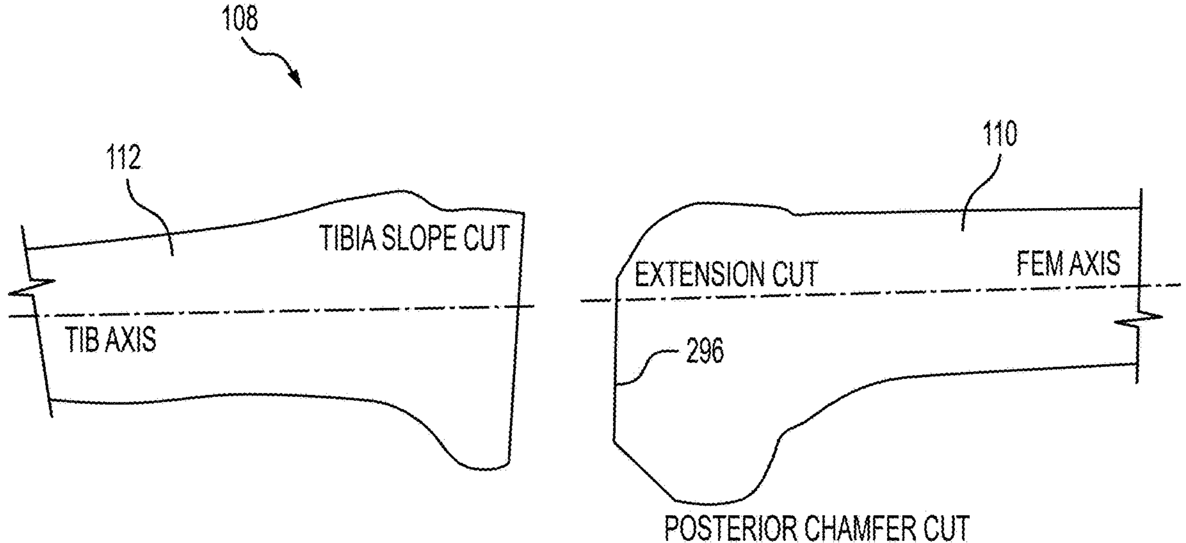

Referring to FIG. 7F, the knee 108 is positioned in full extension after making the tibial plateau cut 278 and the posterior chamfer cut 122. The location and orientation of a femoral extension cut 296 is thereafter determined. Referring to FIG. 7G, the distance between the tibial plateau cut 278 and the femoral extension cut 296 may be matched to the distance between the posterior chamfer cut 122 and the tibial plateau cut 278 (FIG. 7E), such as by selecting the location of the femoral extension cut 296 along the femoral canal axis 124 that yields the desired geometry. As will be discussed in more detail hereafter, this desired geometry in part is based upon the orthopedic implant chosen by the surgeon, as well as the dimensions determined from the soft tissue balancing near mid-flexion. Referring to FIG. 7H, the femoral extension cut 296 is performed. In various example methods, additional measurements, balancing, and/or cuts may be performed to prepare the knee 108 to receive the implant trials and orthopedic implants. These additional cuts may include cuts to the femur including, without limitation, an anterior femur cut, a posterior femur cut, and an anterior chamfer cut.

Figure 8:
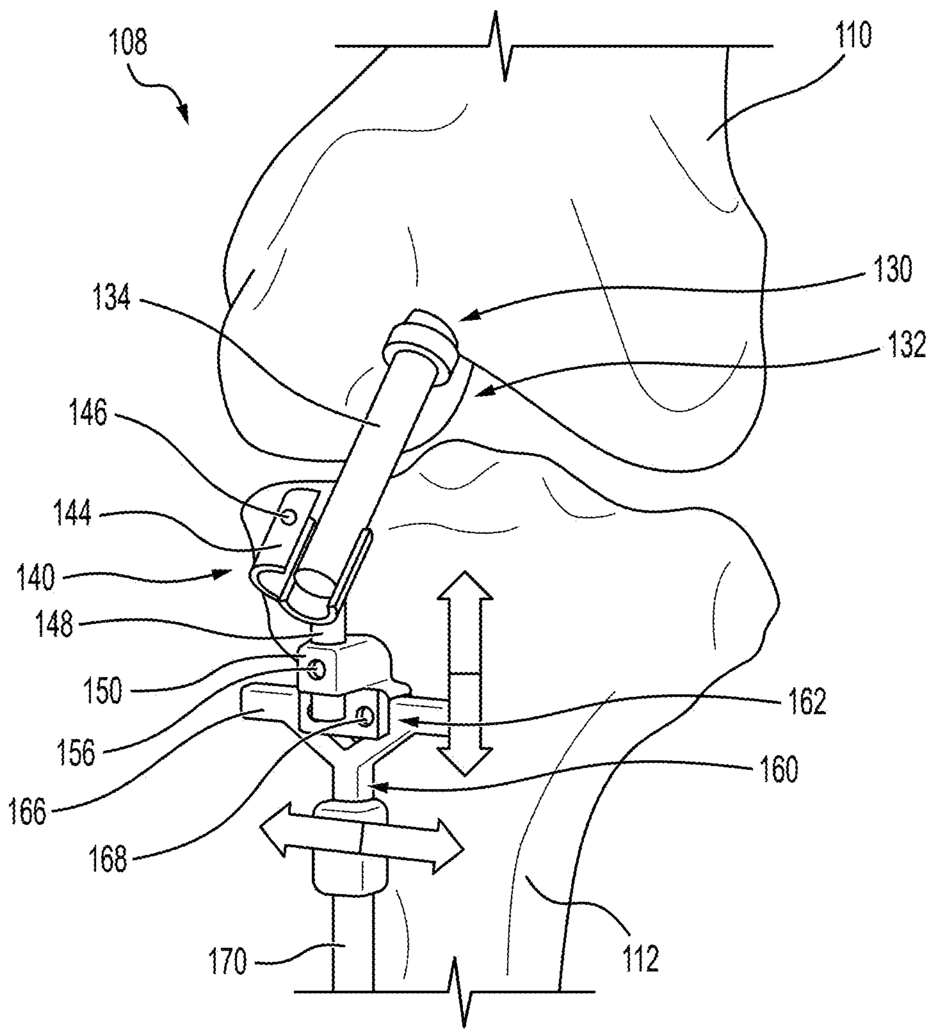
FIG. 8 is a perspective view of a femoral intramedullary rod mated with a receiving device of an example knee balancing jig.
Figure 9:
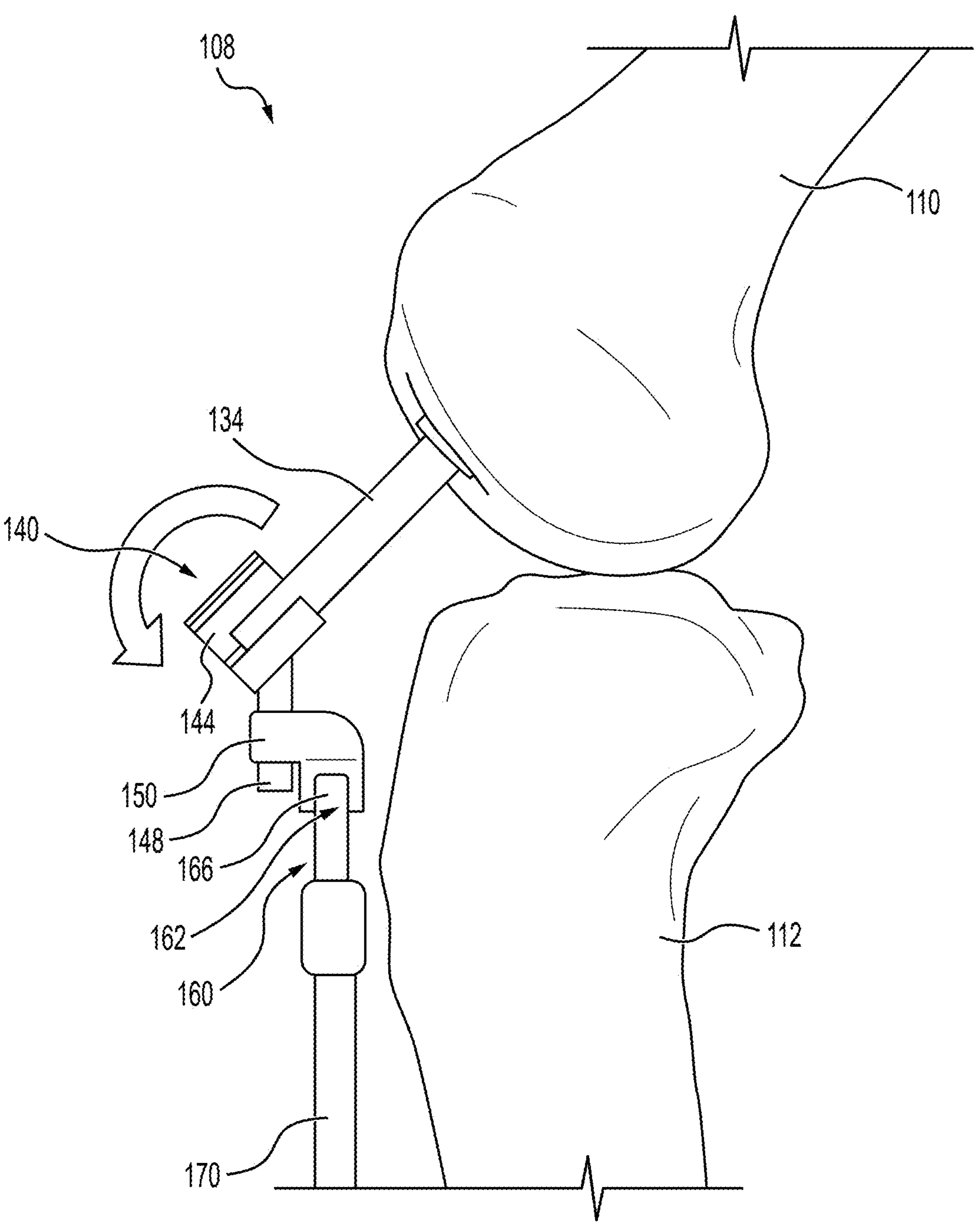
FIG. 9 is a lateral view of the femoral intramedullary rod mated with the receiving device of the knee balancing jig.

FIG. 8 is a perspective view of a femoral intramedullary rod mated with a receiving device of an example knee balancing jig, and FIG. 9 is a lateral view of the femoral intramedullary rod mated with the receiving device of the knee balancing jig, all according to at least some aspects of the present disclosure. Referring to FIGS. 7A, 7B, 8, and 9, making the posterior chamfer cut 122 can be accomplished in a number of ways. By way of example, an opening 130 is drilled into the distal femur 110 just above the top of the femoral intercondylar notch 132 so that a drill bit (not shown) performing the bone removal to create the opening is coaxial with the femoral canal axis 124 in both coronal (anterior view) and sagittal planes (lateral view). After the opening 130 is drilled, an intramedullary rod 134 is inserted into the opening 130 and seated to be secured within the opening, with a portion of the intramedullary rod 134 extending linearly and distally from the femur 110. In exemplary form, the intramedullary rod 134 includes a straight longitudinal shape with a circular cross-section normal to the straight shape.

In various example embodiments, the intramedullary rod 134 may have a cross-section that is round, oval, square, rectangular or any shape suitable for mating with other components as described below. The intramedullary rod 134 may include a stop device 131 (such as an enlarged collar) that will come flush with the femoral bone on the outer surface of the intramedullary canal so that the whole rod 134 doesn't sink into the intramedullary canal. Therefore, when this stop device 131 comes flush with the bone, a portion of the intramedullary rod will protrude outward. In some alternative example embodiments, an extramedullary rod may be substituted for the intramedullary rod 134.

A femoral placement guide 140 engages the intramedullary rod 134 and may be used to properly locate various components throughout the remainder of the TKA procedure. In exemplary form, the placement guide 140 may include a receiving device comprising a cylindrical collar 144, which may be in the form of a hinged, catcher's-mitt-like receiver, or may be any shape that can receive the intramedullary rod 134 at a prescribed flexion angle or range of angles. The collar 144 includes a cylindrical through bore sized to accommodate throughput of at least a portion of the intramedullary rod 134 distally extending from the femur 110 and is arranged to receive the rod 134 at the prescribed angle or range of angles. By way of further example, the through bore is dimensioned with relatively tight internal circumference tolerances with respect to the outside circumference of the intramedullary rod 134 so that the rod freely slides with respect to the collar 144, but does not have enough play so that travel of the collar occurs along an axis angled greater than five degrees with respect to a longitudinal axis of the intramedullary rod. In exemplary form, the collar 144 may include a set screw 146 or other retainer to fix the longitudinal motion of the collar with respect to the intramedullary rod 134 when the desired position is reached. In alternative embodiments, the receiving device or catcher's mitt may have any suitable shape that mates with the intramedullary rod. The receiving device 144 may have the same diametrical or dimensional shape as the intramedullary rod 134 or may be larger, allowing for some relative movement, if needed. For purposes of explanation, the motion of the collar 144 with respect to the intramedullary rod 134 will be described as angular motion along two axes, a Z-axis and a Y-axis perpendicular to the Z-axis.

In some alternative embodiments, one or more external femoral components may be utilized in place of or in addition to the intramedullary rod 134. For example, an extramedullary rod and/or an external clamping or positioning component may be used as an external femoral component.

Extending from the collar 144 is a shaft 148. In this exemplary embodiment, the shaft 148 may be repositionably or rigidly mounted to an exterior circumference of the collar 144 and may be angled with respect to the collar incorporating a predetermined angle. This shaft 148, if not rigidly mounted, may be rotatable along one or three directions and/or translate around one or three directions. In the illustrated embodiment, the predetermined angle may be between 35 and 55 degrees (e.g., about 45 degrees), for example, again depending on the implant and the implant chamfer angle. Other similar embodiments may be associated with other predetermined angles as described elsewhere herein, such as mid-flexion angles generally between 30 and 70 degrees of flexion. In any event, the shaft 148 is generally straight and incorporates a shape that allows the shaft to traverse along a follower 150 in at least one of a linear manner and a rotational manner. In exemplary form, the shaft 148 may include a constant circular or rectangular cross-section, or include any other constant cross-sectional shapes that facilitate at least one of linear and rotational motion along a single axis.

By way of example, the follower 150 may include a first shaped opening sized to accommodate throughput of at least a portion of the shaft 148. By way of further example, the opening may be dimensioned with relatively tight internal tolerances with respect to the outside tolerances of the shaft 148 so that the shaft freely slides with respect to the follower 150, but does not have enough play so that travel of the shaft occurs along an axis angled greater than five degrees with respect to a longitudinal axis of the shaft. In this fashion, interaction between the shaft 148 and follower 150 provides linear and/or rotational adjustment in only one of three axes. For purposes of explanation, the vertical motion of the shaft 148 with respect to the follower 150 will be described as motion along the Y-axis. In a case where the shaft 148 is rectangular in cross-section, the first shaped opening of the follower 150 may be correspondingly rectangular in cross-section or otherwise bounded on the periphery to constrain motion of the shaft to occur along only a single axis. In some example embodiments, these components (shaft 148, follower 150) allow for linear motion and rotation around one or more axis and then, once positioned correctly, could be locked to achieve the proper angle.

In exemplary form, the follower 150 may include a set screw 156 or other retainer to fix the vertical and/or rotational motion of the follower with respect to the shaft 148 when the desired vertical and/or rotational position and/or orientation is reached. As will be discussed in more detail hereafter, the relative position of the femoral placement guide 140, the follower 150, and a tibial placement guide 160 are fixed relative to one another after achieving balancing of the knee joint at or proximate mid-flexion.

In this exemplary embodiment, the follower 150 also includes a second shaped opening 162 sized to accommodate throughput of at least a portion of a beam 166 of the tibial placement guide 160. By way of further example, the opening 162 is dimensioned with relatively tight internal tolerances with respect to the outside tolerances of the beam 166 so that the follower 150 freely slides with respect to the beam, but does not have enough play so that travel of the follower occurs along an axis angled greater than five degrees with respect to a longitudinal axis of the beam. In this fashion, interaction between the beam 166 and follower 150 provides adjustment in only one of three axes. For purposes of explanation, the horizonal motion of the follower 150 with respect to the beam 166 will be described as motion along an X-axis, where the X-axis is perpendicular to the Y-axis and concurrently perpendicular to the Z-axis. In other words, the motion of the follower 150 along the beam 166 occurs along an axis that is perpendicular to an axis along which the shaft 148 traverses with respect to the follower 150. In exemplary form, the X-axis cross-section of the beam 166 may be circular, oblong, triangular, rectangular, or any other shape that allows traversal of the follower 150. In a case where the beam 166 is rectangular in cross-section, the second shaped opening 162 may be correspondingly rectangular in cross-section or otherwise bounded on the periphery to constrain motion of the beam to occur only along a single axis, the X-axis. Likewise in a case where the beam 166 is circular or oblong in cross-section, the second shaped opening 162 may be correspondingly circular or oblong in cross-section or otherwise bounded on the periphery to constrain motion of the beam to occur only along a single axis, the X-axis.

In exemplary form, in addition to the beam 166, the tibial placement guide 160 may be disposed on a tibial reference, such as a cylindrical rod 170, which may include an extramedullary tibial rod, extending generally perpendicularly from the beam. In the illustrated embodiment, the tibial placement guide 160 is mounted to the rod 170 generally anterior to the knee 108 so that the beam 166 is oriented generally in a medial-lateral orientation. When the tibial placement guide 160 is properly aligned, the cylindrical rod 170 may extend substantially parallel to the tibial longitudinal axis 174 and/or may be secured to the patient's lower leg using conventional extramedullary fasteners.

The adjustability of the receiving device 144 relative to the tibial rod 170 may allow for translation, rotation, and orientation changes so that the retrieving device can properly mate with the femoral rod 134. As shown in the figures, various components may be installed on and removed from the tibial placement guide 160 as needed throughout an example TKA procedure. Additionally, it should be understood that, for clarity and ease of view, some of the figures herein may not include components that may remain in place from step to step in some example procedures.

In practice, prior to the opening 130 being drilled into the distal femur 110, a surgeon may use a surgical saw or other surgical equipment to remove osteophytes present in or around the medial and lateral condyles of the femur, as well as the medial and lateral condyle receivers of the tibia. Likewise, depending upon the orthopedic implant chosen, the surgeon may also resect one or both of the anterior cruciate ligament (ACL) and the posterior cruciate ligament (PCL) prior to or after the opening 130 being drilled. In any event, the opening 130 is drilled while the medial collateral ligament (MCL) and the lateral collateral ligament (LCL) remain intact. Thereafter, the intramedullary rod 134 is inserted into the opening 130.

After the opening 130 is drilled into the distal femur 110 and the intramedullary rod 134 is inserted therein, a portion of the intramedullary rod extends distally from the femur. Thereafter, the femur is positioned relative to the tibia at or near mid-flexion (between about 30 degrees and about 75 degrees of knee flexion, preferably closer to 45 degrees). But, as depicted in FIG. 1, the centers of contact area of the femoral condyles with respect to the tibial condyle receivers change rotationally as a function of knee flexion angle. Namely, on the lateral side, the center of contact area for the lateral femoral condyle at full extension (approximately zero degrees of flexion) is well anterior of the anterior-posterior centerline of the tibia. As the knee begins to flex and continues to flex approaching 120 degrees, the lateral femoral condyle progressively moves posteriorly. And on the medial side, the center of contact area of the medial femoral condyle at full extension (approximately zero degrees of flexion) is slightly anterior of the anterior-posterior centerline and progresses posteriorly until reaching 75 degrees of flexion. But unlike the lateral condyle, the medial condyle begins moving in the opposite direction (i.e., anteriorly) and the center of contact area actually crosses the anterior-posterior midline at flexion angles approaching 120 degrees. As will be discussed in more detail hereafter, what the foregoing means is that soft tissue balancing the knee at different degrees of flexion also needs to account for the kinematically correct rotational position of the femur with respect to the tibia.

Current soft tissue balancing inaccurately maintains a single rotational position of the femur relative to the tibia, regardless of the degree of knee flexion. Yet FIG. 1 shows that this inconsistent with the actual kinematics of a healthy knee. Instead, to correctly soft tissue balance, one needs to ensure that the rotational position of the femur relative to the tibia changes as the angle of flexion changes. What this means is that when one attempts to soft tissue balance at zero degrees, the femur should be rotated so that the lateral condyle is more anterior than the medial condyle. And soft tissue balancing at mid-flexion should rotate the femur so that the lateral condyle and the medial condyle are parallel to the tibia anterior-posterior midline. Moreover, soft tissue balancing at 90 degrees of flexion should rotate the femur so that the medial condyle is more anterior than the lateral condyle, with both condyles being positioned posterior to the tibial anterior-posterior midline. Failing to rotate the femur correctly at a given flexion angle for soft tissue balancing will result in soft tissue constraints resembling a simple hinge joint with no rotation of the femur with respect to the tibia. Accordingly, the instant disclosure teaches performing a soft tissue balance at mid-flexion (not necessarily to the exclusion of soft tissue balancing at other degrees of flexion or at full extension), as well as rotationally positioning the femur relative to the tibia to replicate natural kinematic positioning of the bones and soft tissues while performing the soft tissue balancing.

Turning back to FIGS. 8 and 9, the femoral placement guide 140 is then repositioned so that the collar 144 traverses along the intramedullary rod 134. Thereafter, during, or before placing the collar 144 around the intramedullary rod 134, the follower 150 is positioned to traverse along the shaft 148, in addition to the follower engaging and traversing along the beam 166. In exemplary form, the component parts of the femoral placement guide 140 and the tibial placement guide 160 allow for repositioning of the component parts so that the cylindrical rod 170 is positioned adjacent the tibial tubercle and parallel to the tibial longitudinal axis 174, while the collar 144 circumscribes the intramedullary rod 134. After reaching this arrangement, the component parts are secured to one another so that the collar 144 is fixed in position with respect to the intramedullary rod 134 (such as by tightening the set screw 146), and the follower 150 is fixed in position with respect to the shaped shaft 148 (such as by tightening the set screw 156). By securing in fixed position the femoral placement guide 140 with respect to the intramedullary rod 134, motion of the femoral placement guide 140 along the Z-axis is in inhibited. Likewise, by securing in fixed position the femoral placement guide 140 with respect to the follower 150, motion of the follower along the Y-axis is inhibited. The follower 150 is secured with respect to the beam 166 using one or more set screws 168, for example.

Figure 10A:
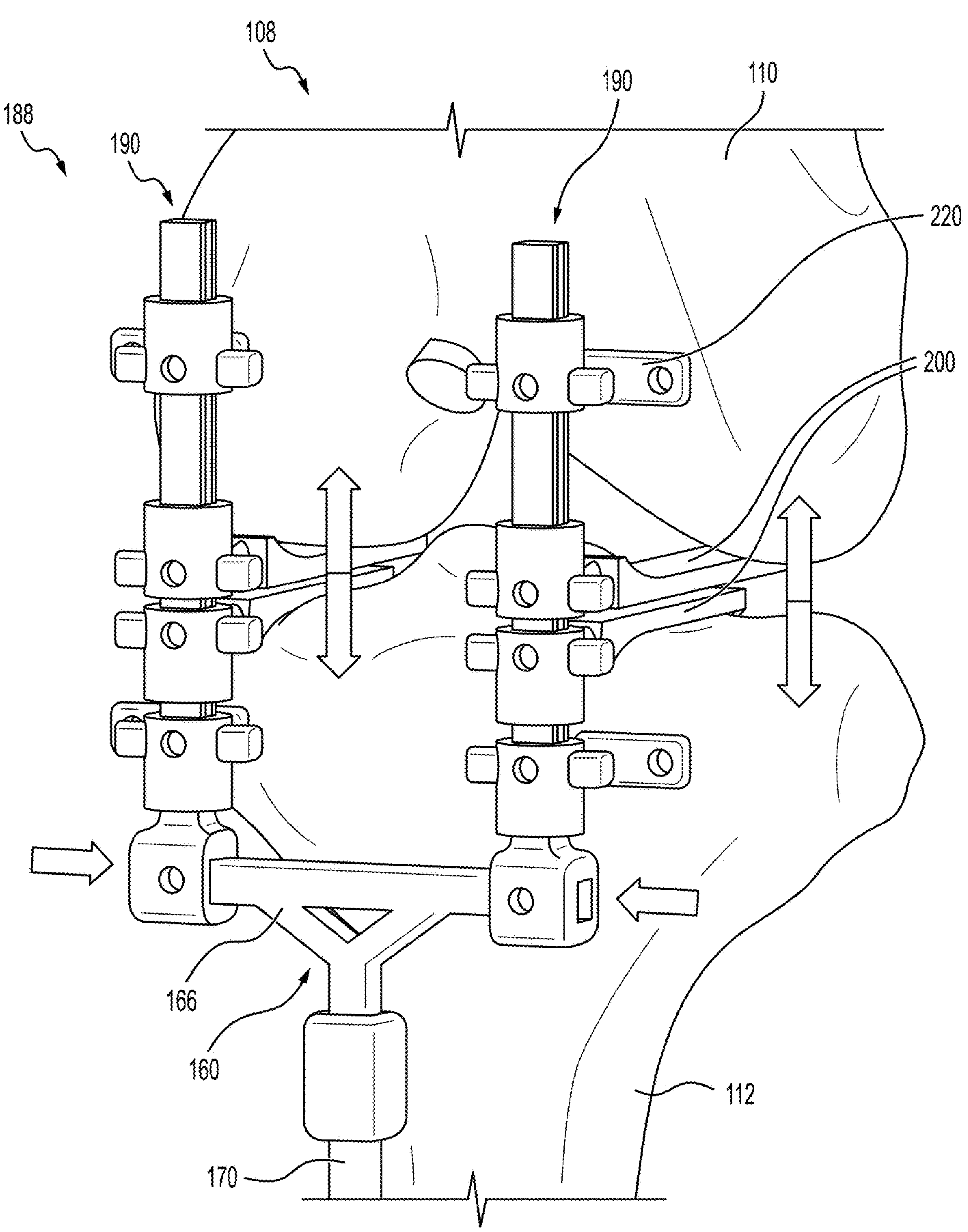
FIG. 10A is a perspective view of the example knee balancing jig with balancing assemblies installed in use on a knee joint.
Figure 10B:
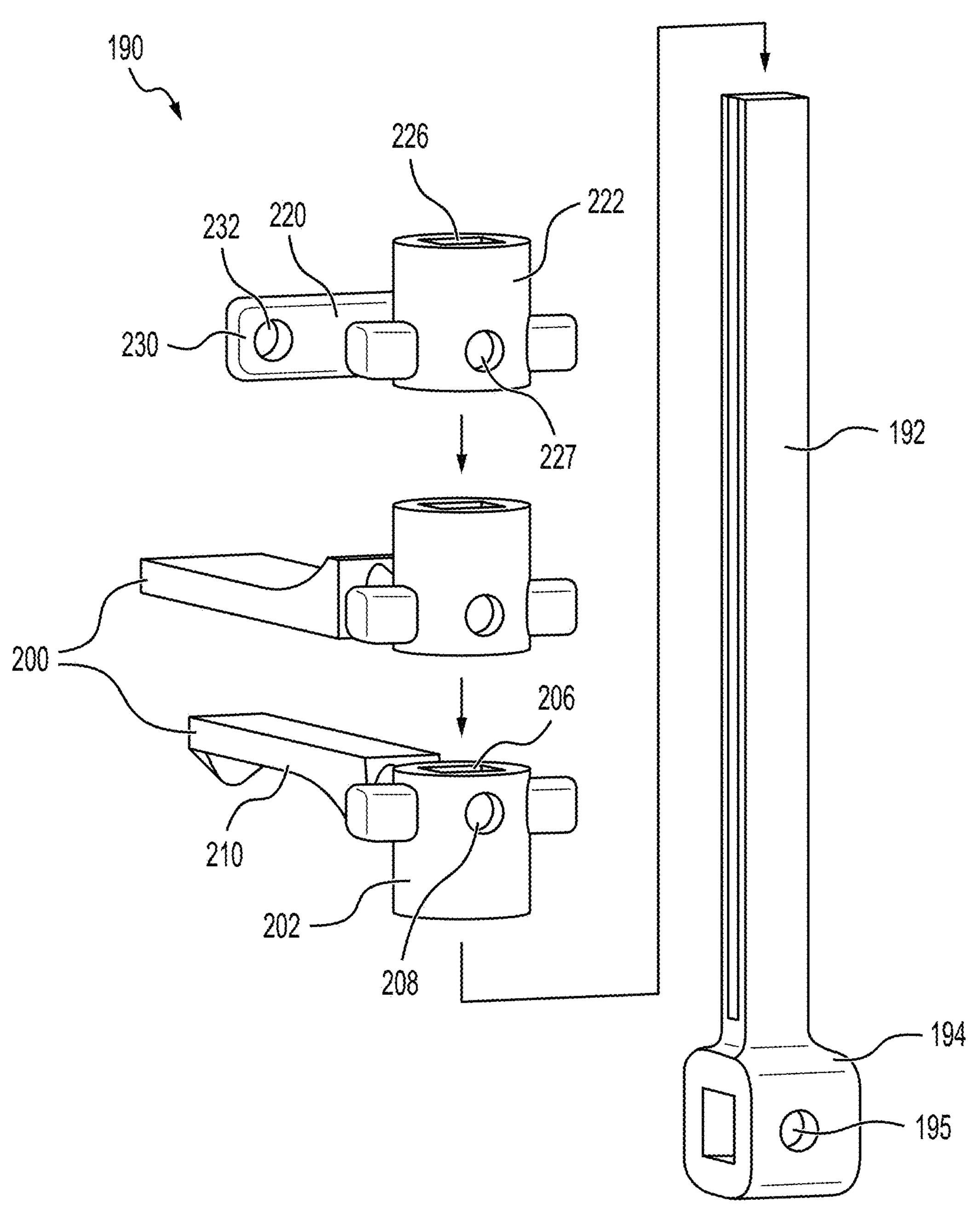
FIG. 10B is an exploded perspective view of an example balancing assembly.
Figure 10C:
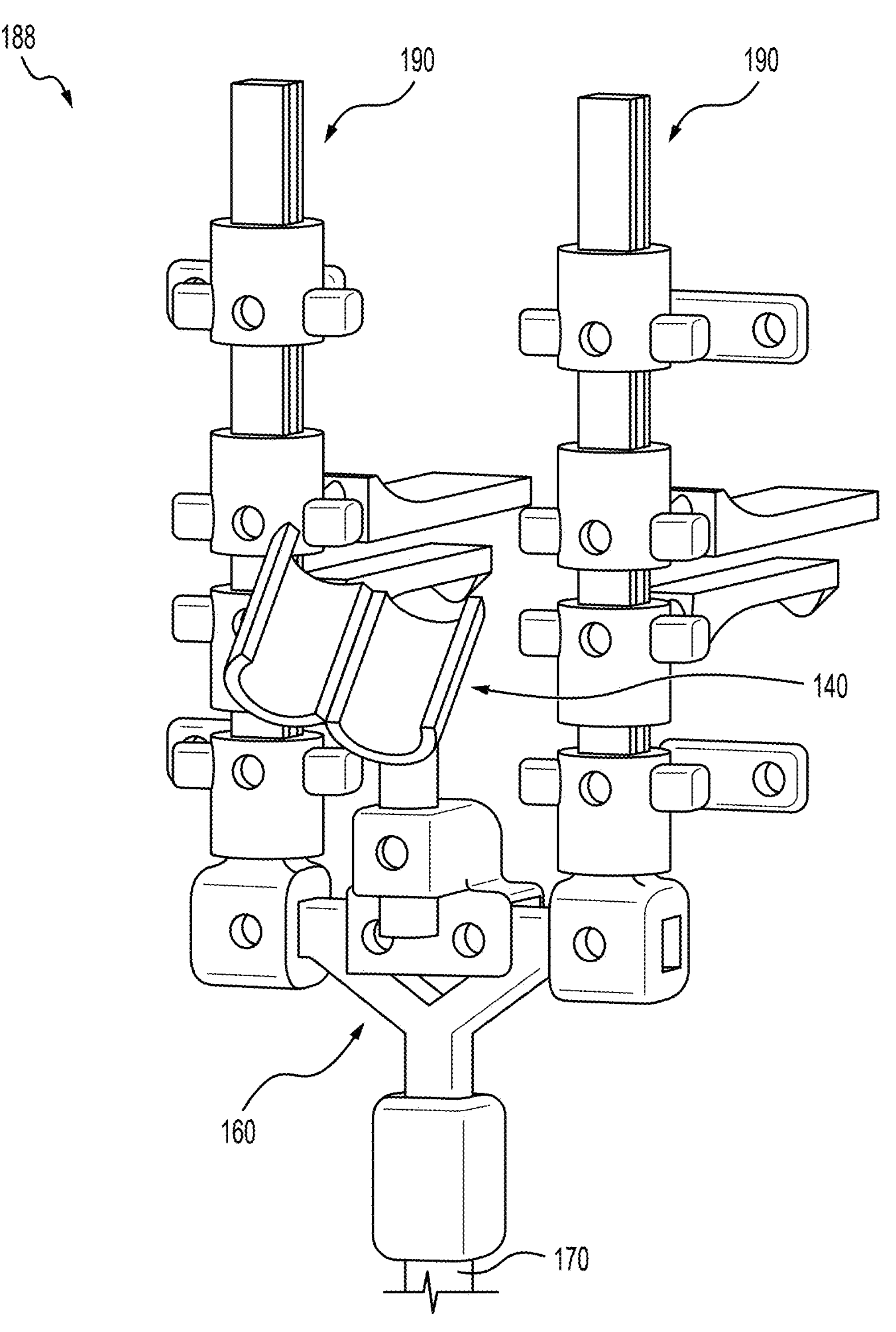
FIG. 10C is a perspective view of the example knee balancing jig with the receiving device and the balancing assemblies installed.
Figure 10D:
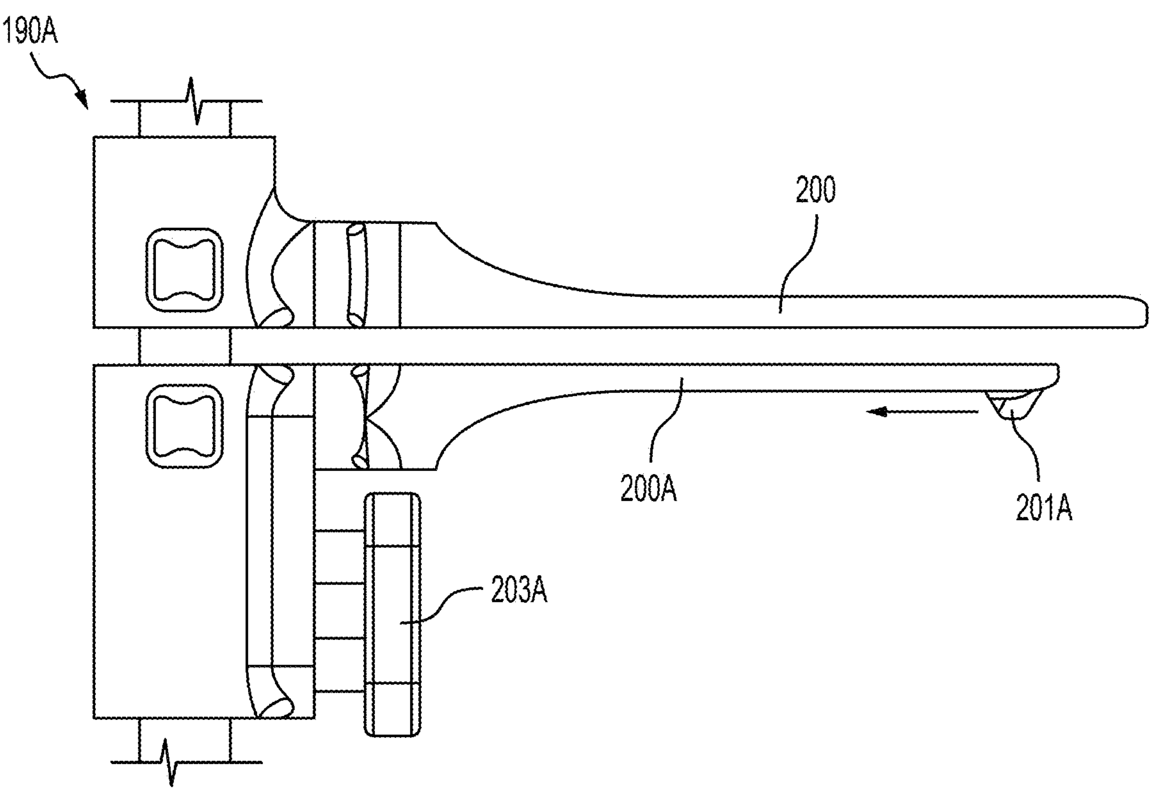
FIG. 10D is a lateral elevation view of an alternative example balancing assembly including an adjustable tibial element in a posterior position.
Figure 10E:
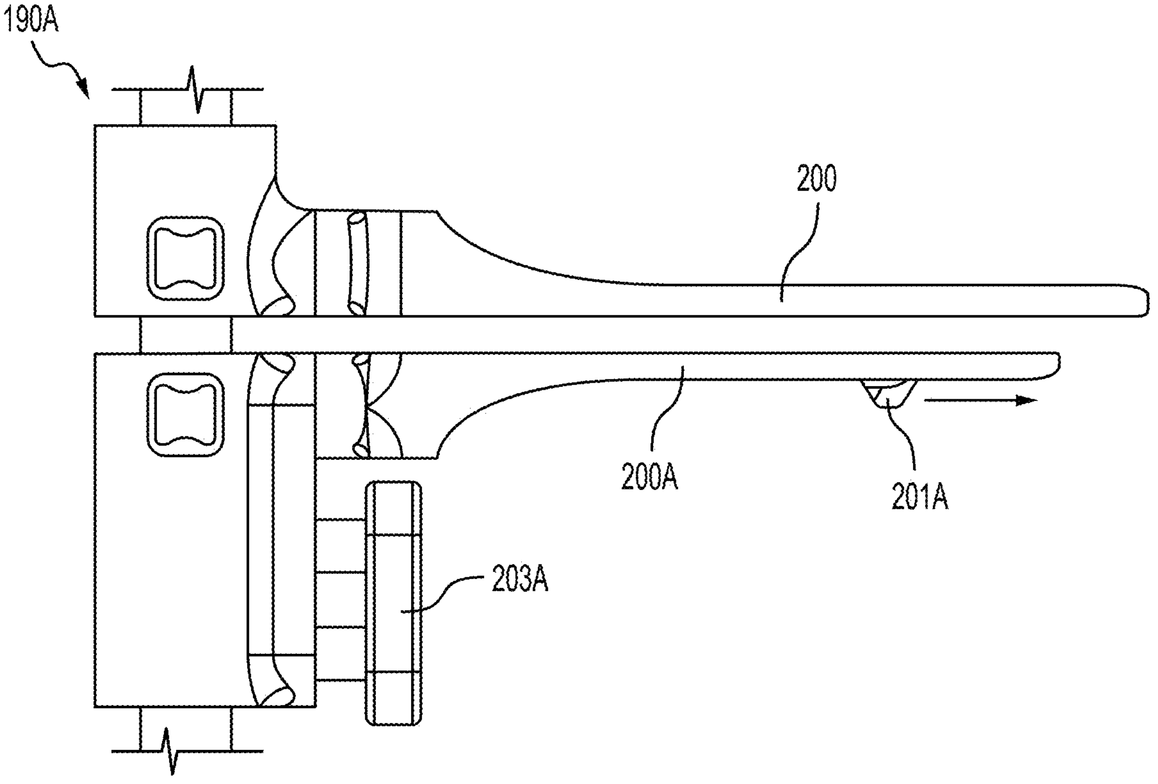
FIG. 10E is a lateral elevation view of balancing assembly of FIG. 10D with the adjustable tibial element in an anterior position.

FIG. 10A is a perspective view of an example knee balancing jig 188 with balancing assemblies 190 installed in use on a knee joint 108, and FIG. 10B is an overhead view of an exemplary positioning template 191, and FIG. 10C is an exploded perspective view of an example balancing assembly 190, and FIG. 10D is a perspective view of the example knee balancing jig with the receiving device and the balancing assemblies installed, all according to at least some aspects of the present disclosure. Although the knee balancing jig 188 may be configured for and/or used at any flexion angle, its use is described below in connection with an example mid-flexion balancing approach.

In exemplary form, the knee balancing jig 188 is initially used in connection with making the posterior chamfer cut 122 on the femur 110. With the knee 108 secured at the desired initial flexion angle, such as using the receiving device 140 and the intramedullary rod 134 and/or external fixation, the balancing jig 188 is used to balance the soft tissues surround the knee joint. In the illustrated embodiment, the knee is held in mid-flexion—at about 45 degrees of flexion—which corresponds to the proper chamfer angle for the intended implant. In other embodiments, the mid-flexion position may be between about 30 degrees and about 75 degrees of knee flexion, for example. As alternative femoral component designs may have different chamfer angles, in some embodiments the receiving device 140 may be adjustable to rotate to a proper angle corresponding with the femoral component chamfer angle.

Figure 9A:
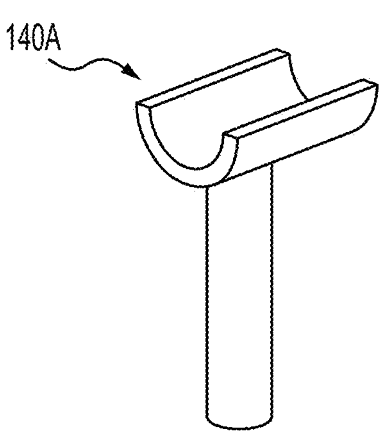
FIG. 9A is a perspective view of an alternative receiving device 140A configured for about 90 degrees of flexion.
Figure 9B:
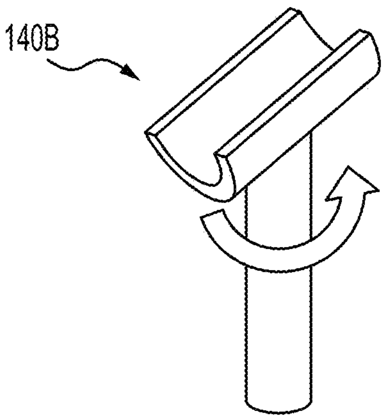
FIG. 9B is a perspective view of an alternative receiving device 140B configured for about 60 degrees of flexion.
Figure 9C:
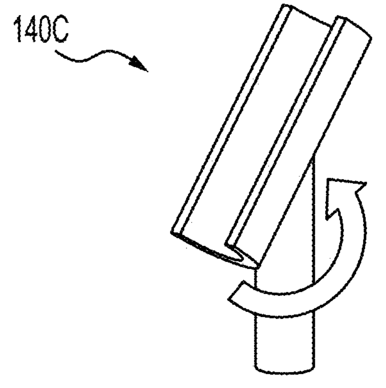
FIG. 9C is a perspective view of an alternative receiving device 140C configured for about 30 degrees of flexion.

In some embodiments, the receiving device 140 may be modular and/or removable/replaceable on the balancing jig 188, and a plurality of receiving devices 140 corresponding to different chamfer angles may be provided. FIG. 9A is a perspective view of an alternative receiving device 140A configured for about 90 degrees of flexion and for use with an alternate intramedullary rod 134A as shown in FIG. 9D, while FIG. 9B is a perspective view of an alternative receiving device 140B configured for about 60 degrees of flexion, and FIG. 9C is a perspective view of an alternative receiving device 140C configured for about 30 degrees of flexion, all according to at least some aspects of the present disclosure. Generally, if the chamfer angle is 45 degrees, then the receiving device 140 that will be used by the surgeon may be angled at a fixed angle of 45 degrees. Alternatively, for other chamfer angles, an appropriate receiving device 140A, 140B, 140C may be selected and used. Further, other positioning devices can also be used, such as an external brace or external positioner.

In some example procedures, the intramedullary rod 134 may be removed from the femur 110 and removed from the collar 144. In addition, the femoral placement guide 140 and the follower 150 may be disengaged from the tibial placement guide 160, thus leaving the tibial placement guide 160 mounted with respect to the tibia and retained in position via the tibial extramedullary rod 170. Knee position may be maintained using external fixation, for example. In other example procedures, the intramedullary rod 134 and receiving device 140 may remain in place and/or may be used to maintain the position of the knee.

Referring to FIGS. 10A-10D, an example knee balancing jig 188 may include a pair of balancing assemblies 190 mounted to the beam 166, with one balancing assembly 190 disposed generally medially (e.g., for use on the medial condyle) and the other balancing assembly being disposed generally laterally (e.g., for use on the lateral condyle). In exemplary form, a balancing assembly 190 may include a vertical guide 192 having a rectangular cross-section. It should be noted that the cross-section of the vertical guide 192 may differ from that of a rectangular cross-section and include any other shape (e.g., triangular, rounded, four or more sided, etc.) repetitively reproduced vertically to maintain a constant or near constant horizontal cross-section. In this exemplary embodiment, the vertical guide 192 is configured to releasably mount to the tibial placement guide 160 in a generally inferior-superior orientation. For example, in the illustrated embodiment, the vertical guide 192 includes an adapter 194 configured to engage the beam 166 and retain the three-dimensional position of the vertical guide with respect to the beam. In the illustrated embodiment, the adapter is releasably secured to the beam 166 using a set screw. Both sides are opened so that medial/lateral sliding can occur.

One exemplary component of the balancing assembly 190 may include a paddle 200, which may extend generally anteriorly relative to the vertical guide 192. By way of example, a balancing assembly 190 may include one or more paddles 200, such as a superior paddle and an inferior paddle. As will be discussed in more detail hereafter, one or more paddles 200 may be utilized to measure the spacing between the tibia 112 and femur 110. In exemplary form, a paddle 200 may include a connector 202 configured to engage the vertical guide 192 and allow for selective vertical repositioning of the paddle with respect to the vertical guide. By way of example, the connector 202 may include an opening or cavity 206 resembling the cross-section of the vertical guide 192, but slightly larger to accommodate throughput of the vertical guide. The connector 202 may also include a set screw 208 or spring-loaded projection that extends into the cavity 206 and it used to selectively secure the paddle 200 to the vertical guide 192. Extending from the connector 202 is a blade 210 that, in exemplary form, has a dominant longitudinal dimension extending away from the connector, and a rectangular profile from both horizontal and vertical directions. By way of example, the blade 210 may embody a cuboid shape. Other shapes can be used such as spoons or even pre-operative derived shapes that mimic the shape of each condyle. This may be accomplished with pre-operative imaging. Another shape could be a rectangular shape. In some example embodiments, the blade 210 may be quite thin, while being sufficiently rigid to perform the balancing functions described herein. The shape could also be patient specific based on the shape of the patient's condyles.

While not required, the vertical dimension (i.e., thickness) of the paddle 200 may be constant along its longitudinal length. Moreover, while not required, the horizontal widthwise dimension across the entire paddle 200 may be constant. Further, while not required, the horizontal length across the paddle 200 may be constant. Still further, while not required, the uppermost and bottommost surfaces of the blade 210 and the connector 202 may be coplanar with one another. In this manner, measurements involving the uppermost or bottommost surface of the blade 210 can be readily utilized.

Another exemplary component of the balancing assembly 190 may be one or more pin guides 220. By way of example, the pin guide 220 may include a connector 222 configured to engage the vertical guide 192 and allow for selective vertical repositioning of the pin guide with respect to the vertical guide. By way of example, the connector 222 may include an opening or cavity 226 resembling the cross-section of the vertical guide 192, but slightly larger to accommodate throughput of the vertical guide. The connector 222 may also include a set screw 227 or spring-loaded projection that extends into the cavity 226 and is used to selectively secure the pin guide 220 to the vertical guide 192. Extending from the connector 222 is a pin flange 230 that, in exemplary form, includes an opening 232 configured to receive throughput of at least one of a drill bit and a bone pin as described below.

While not required, the vertical dimension (i.e., thickness) of the pin guide 220 may be constant. In this manner, measurements at the uppermost or bottommost surface of the pin flange 230 can be readily utilized.

Turning specifically to FIGS. 10A and 10B, in use, prior to mounting the vertical guides 192 to the beam 166, each vertical guide may have mounted thereto a pair of paddles 200 and a pin guide 220. In exemplary form, the paddles 200 mounted to each vertical guide 192 are oriented to overlap one another so that the medial vertical guide 192 has its paddles orientated to interpose the femoral medial condyle articular surface and the medial tibial condyle receiver articular surface. Similarly, the lateral vertical guide 192 has its paddles orientated to interpose the femoral lateral condyle articular surface and the lateral tibial condyle receiver articular surface.

While the knee joint 108 is bent at approximately 45 degrees or another desired mid-flexion angle (e.g., the same angle of the posterior chamfer cut angle) and retained in position (such as by using an external brace, not shown), the surgeon may insert the positioning template 191 between the tibia and femur and perform a soft tissue balance for the medial and lateral sides of the knee. As part of this soft tissue balance, the surgeon may rotationally orient the femur 110 with respect to the tibia 112 so that the central contact location or contact point (i.e., dwell point) of the medial condyle and the lateral condyle directly overlaps the contact point of the medial condyle 193A and the lateral condyle 193B on the template. In accordance with the instant disclosure, one may account for not only the degree of flexion with respect to the tibia and femur, but also the rotation of the distal femur with respect to the proximal tibia (along a longitudinal axis extending through the tibia and femur). As referenced in FIG. 1, the dwell points of the medial condyle and lateral condyle with respect to the proximal tibia change across a range of motion of a healthy knee joint. Specifically, at a knee flexion angle of approximately 30 degrees, the dwell points lie along a midline between the anterior aspect and the posterior aspect of the tibia. For angles less than 30 degrees and approaching zero degrees, the dwell points become more anterior, with the lateral condyle dwell points increasingly becoming more anterior than the medial condyle dwell points for a given angle. For angles greater than 30 degrees and approaching 75 degrees, the dwell points become more posterior, with the lateral condyle dwell points increasingly becoming more posterior than the medial condyle dwell points for a given angle. For angles greater than 75 degrees and approaching 120 degrees, the dwell points no longer share movement in a common direction. Specifically, the lateral condyle dwell points increasingly becoming more posterior, while the medial condyle dwell points become more anterior for a given angle, with angles approaching 120 degrees exhibiting a dwell point of the medial condyle that passes anteriorly beyond the midline demarcating the anterior aspect from the posterior aspect.

In accordance with the instant disclosure, soft tissue balancing as part of a total or partial knee arthroplasty procedure should be undertaken at a given angle of flexion and while maintaining the general rotational position of the femur with respect to the tibia for that given angle of flexion. In contrast, the prior art teaches knee ligament balancing at differing ranges of knee flexion, while not varying the rotational position of the femur and tibia. This prior art approach, unfortunately, leads to improper balancing and orthopedic implants that function more like a hinge joint (with little to no rotational motion), rather than like an atomically correct knee joint. See FIG. 3.

By way of example, turning to FIGS. 10A-10C, the positioning template 191 may be patient specific or may be generalized to approximate the size of the patient's tibia. In cases where the positioning template 191 is patient specific, an outline 195 of the template may be sized to precisely match a cross-sectional outline of the patient's tibia. Alternatively, if the positioning template is not patient specific, the outline 195 may be generalized to approximate a cross-sectional outline of a generic tibia, where the outline 195 may be sized in one of a plurality of sizes to generically match a predetermined number of groups. By way of example, the outline 195 may envelope one or more of the medial condyle, the lateral condyle, the intercondylar eminence, the posterior intercondylar area, the anterior intercondylar area, and the lateral intercondylar tubercle.

Figure 10F:
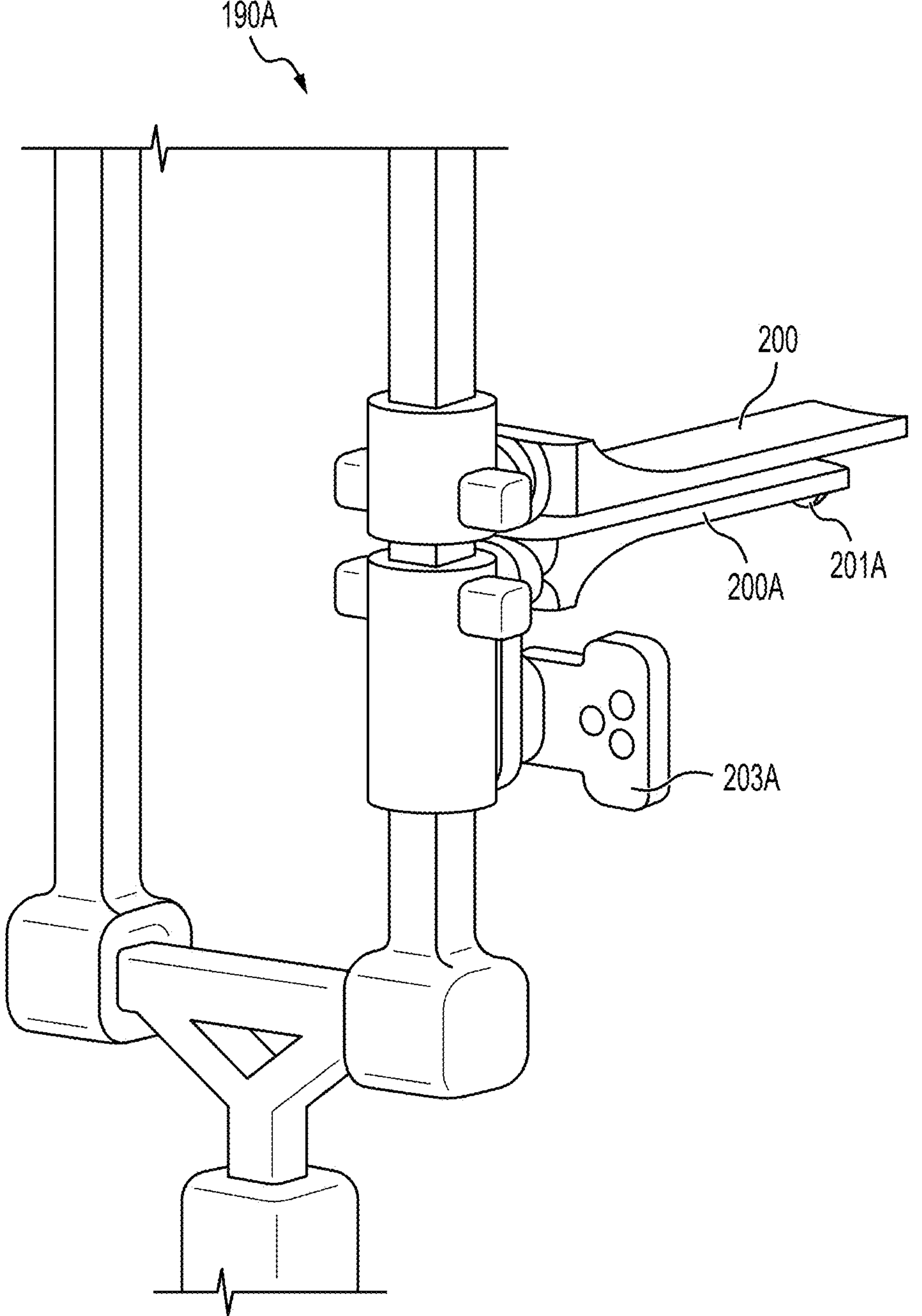
FIG. 10F is a perspective view of the example balancing assembly of FIGS. 10D and 10E.

In some embodiments, components that mate with bones may be adjustable to allow for different bone sizes. For example, the portion of a balancing assembly that mates with the tibial may be adjustable (e.g., in the anterior-posterior direction) for use with different sizes of tibias. FIG. 10F is a lateral elevation view of an alternative example balancing assembly 190A including an adjustable tibial element in a posterior position; FIG. 10G is a lateral elevation view of the balancing assembly 190A of FIG. 10F with the adjustable tibial element in an anterior position; and FIG. 10H is a perspective view of the example balancing assembly 190A of FIGS. 10F and 10G, all according to at least some aspects of the present disclosure. Various elements of the balancing assembly 190A are similar in structure and operation to corresponding components in other embodiments described herein, and repeated description is omitted for brevity. Further, features described in connection with the balancing assembly 190A may be utilized in connection with any other embodiment described herein. For example, generally similar adjustable femoral elements may be utilized in some embodiments.

In the balancing assembly 190A, one of the paddles 200A comprises an adjustable engagement feature 201A. In the illustrated embodiment, the engagement feature 201A is linearly repositionable generally in an anterior-posterior direction, such as between the posterior position illustrated in FIG. 10F and the anterior position illustrated in FIG. 10G. Accordingly, the tibial element may be adjusted to better fit a particular tibia. In the illustrated embodiment, the adjustable engagement feature 201A may be movable by operation of actuator 203A, which may be disposed on the connector 202A. For example, sliding and/or rotating the actuator 203A may cause the engagement feature 201A to traverse anteriorly and/or posteriorly along a track formed on the distal side of the paddle 200A.

In some example embodiments, the knee balancing jig 188 may include one or more read-out devices configured to indicate the gap distance between the medial condyle to the medial tibial plateau and the lateral condyle to the lateral tibial plateau and/or tension in one or more ligaments. Generally, if a surgeon is gap balancing the goal will be to have these distance measurements to be equal or nearly equal. If a surgeon is attempting to anatomically balance or use a form of kinematic balancing, the gap distances for the medial and lateral condyles (and subsequently medial and lateral collateral ligaments) may be different. Either way, these values may be stored and/or recorded, such as for use as the future goal (or in calculations for future goals) for gaps and tensions at other flexion angles. In some example procedures, the mid-flexion readings may be used as the baseline as well as the desired gaps and tensions for that individual person's knee. As discussed above, mid-flexion may be an important flexion range for balancing and/or it may be easier for a surgeon to maintain this balance at full extension and 90 degrees of knee flexion.

Figure 36A:
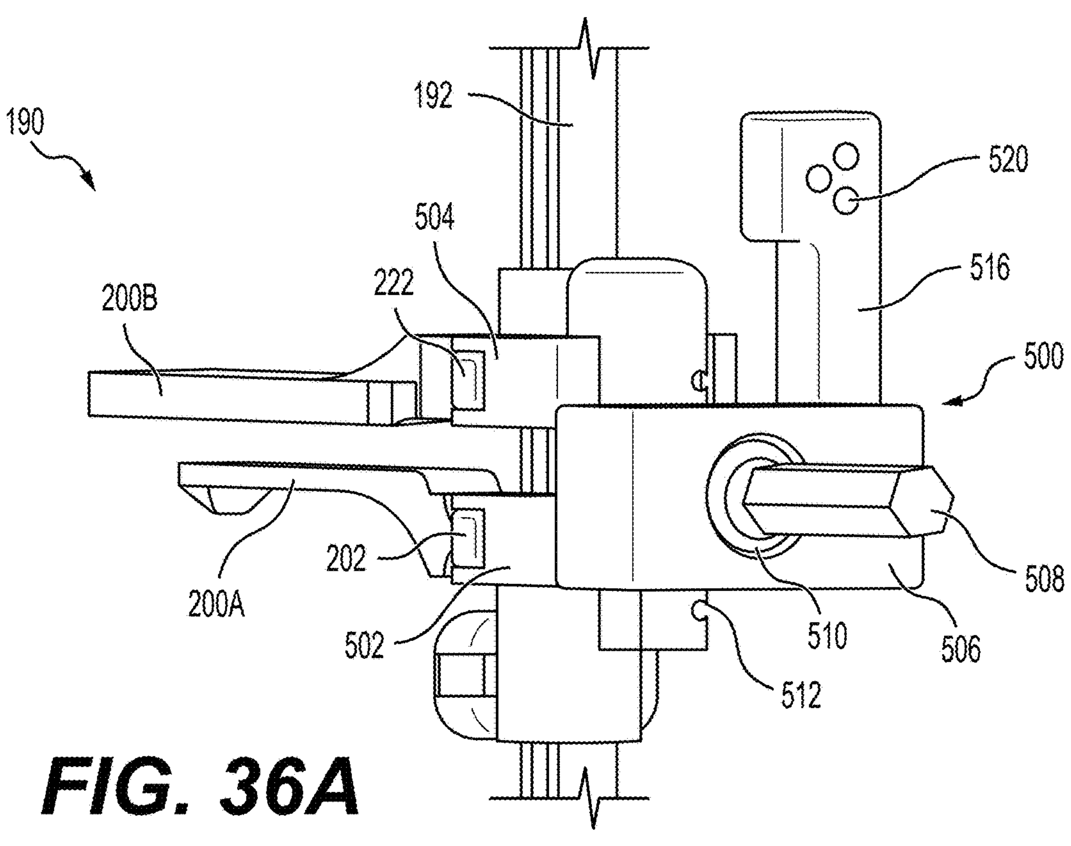
FIGS. 36A and 36B are perspective views illustrating an example gap tensioner disposed on a balancing assembly.
Figure 36B:
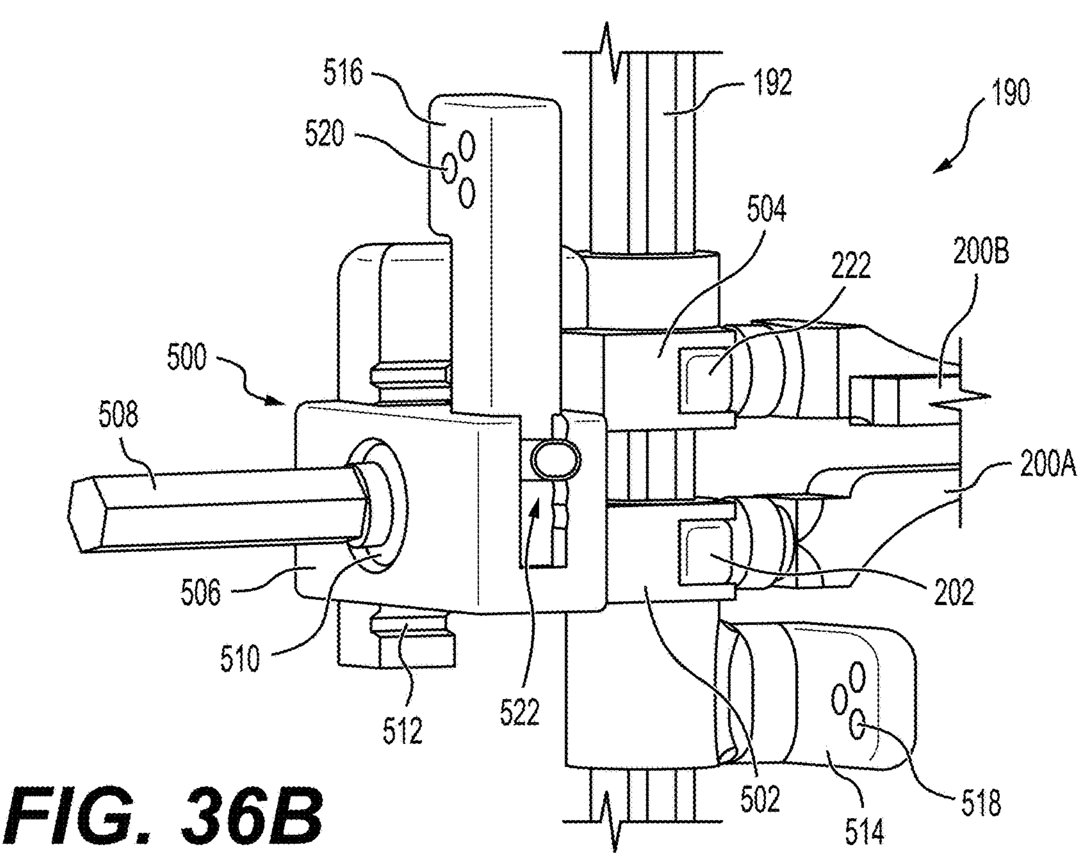

FIG. 36A is a perspective view of another exemplary gap tensioner 500 disposed on a balancing assembly 190, and FIG. 36B is a perspective view of the gap tensioner 500, all according to at least some aspects of the present disclosure. Generally, the gap tensioner 500 includes a linear actuating mechanism operatively coupled between a lower (first) paddle 200A and an upper (second) paddle 200B so that operating of the mechanism changes the vertical spacing between the paddles 200A, 200B.

In the illustrated embodiment, the gap tensioner 500 includes a lower (first) engagement element 502 configured to engage the connector 202 associated with the lower paddle 200A and an upper (second) engagement element 504 configured to engage the connector 222 associated with the upper paddle 200B. In the illustrated embodiment, the lower engagement element 502 is rigidly mounted relative to a gap tensioner housing 506, and the upper engagement element 504 is vertically slidably disposed relative to the housing 506. An actuating shaft 508 is rotatably disposed relative to the housing 506 and is configured to be selectively engaged by a rotational tool, such as a torque wrench (not shown).

A linear actuating mechanism may operatively interpose the actuating shaft 508 and the movable upper engagement element 504. In the illustrated embodiment, the linear actuating mechanism is generally in the form of a rack and pinion mechanism. A pinion 510 (e.g., a circular gear) is mounted for rotation with the actuating shaft 508. A rack 512 (e.g., a linear gear) is mounted for linear movement with the upper engagement element 504 so that the teeth of the rack 512 and the teeth of the pinion 510 are intermeshed. In the illustrated embodiment, rotation of the shaft 508 in a clockwise direction causes the rack 512 and pinion 510 mechanism to move the upper and lower paddles 200A, 200B apart. Rotation of the shaft 508 in a counterclockwise direction causes the rack 512 and pinion 510 mechanism to move the upper and lower paddles 200A, 200B closer together. In alternative embodiments, the arrangement may be reversed, so that the mechanism moves the lower engagement element 502 relative to the housing 506.

In operation, the gap tensioner 500 may be used to apply separating forces to the femur and tibia as described elsewhere herein. In the illustrated embodiment, a torsional force applied to the shaft 508 results in a linear force exerted by the paddles 200A, 200B. One of skill in the art will appreciate that, in the illustrated embodiment, a linear separating force exerted by the paddles 200A, 200B will be directly related to a torsional force applied to the shaft 508. Accordingly, application of a measured or mechanically limited torsional force to the shaft 508 may be used to apply a desired linear separating force to the femur and tibia via the paddles 200A, 200B, such as to provide a desired ligament or other soft tissue tension in connection with an arthroplasty procedure. For example, a torque wrench with a clutch mechanism may be set at a specific torque value associated with a desired soft tissue tension. The torque wrench may be used to apply torsion to the shaft 508, up to the preset torque value. Alternatively, a torque wrench with a torque read-out may be used to apply a desired torque and/or to measure an applied torque, such as may be indicative of ligament tension at a particular gap distance.

Although the gap tensioner 500 has been illustrated and described as comprising a manually operated, rack-and-pinion-type, linear actuating mechanism, it is within the scope of this disclosure to utilize any suitable actuating mechanism. For example, any other mechanical or electromechanical mechanism capable of applying a controlled separating force to the femur and tibia via the paddles 200A, 200B may be utilized in alternative embodiments.

In the illustrated embodiment, the gap tensioner 500 is provided with pin guides 514, 516, which may be generally similar to other pin guides 220 described herein. In the illustrated embodiment, a lower pin guide 514 is rigidly disposed relative to the housing 506 of the gap tensioner 500. Accordingly, the location of one or more openings 518 is fixed with respect to the housing 506. The openings 518 of the lower pin guide 514 may be used to locate pins associated with a tibial cut guide, as described elsewhere herein.

In the illustrated embodiment, an upper pin guide 516 may be movably disposed relative to the housing 506 of the gap tensioner 500. For example, the upper pin guide 516 may be vertically slidably disposed on the housing 506. Accordingly, the vertical location of one or more openings 520 may be adjusted relative to the housing 506. In some embodiments, the upper pin guide 516 may be incrementally adjustable, such as in steps of about 2 mm. In some embodiments, a locking mechanism 522 may be operable to releasably secure the upper pin guide 516 with respect to the housing 506. The openings 520 of the upper pin guide 516 may be used to locate pins associated with a femoral cut guide, as described elsewhere herein.

Figure 12:
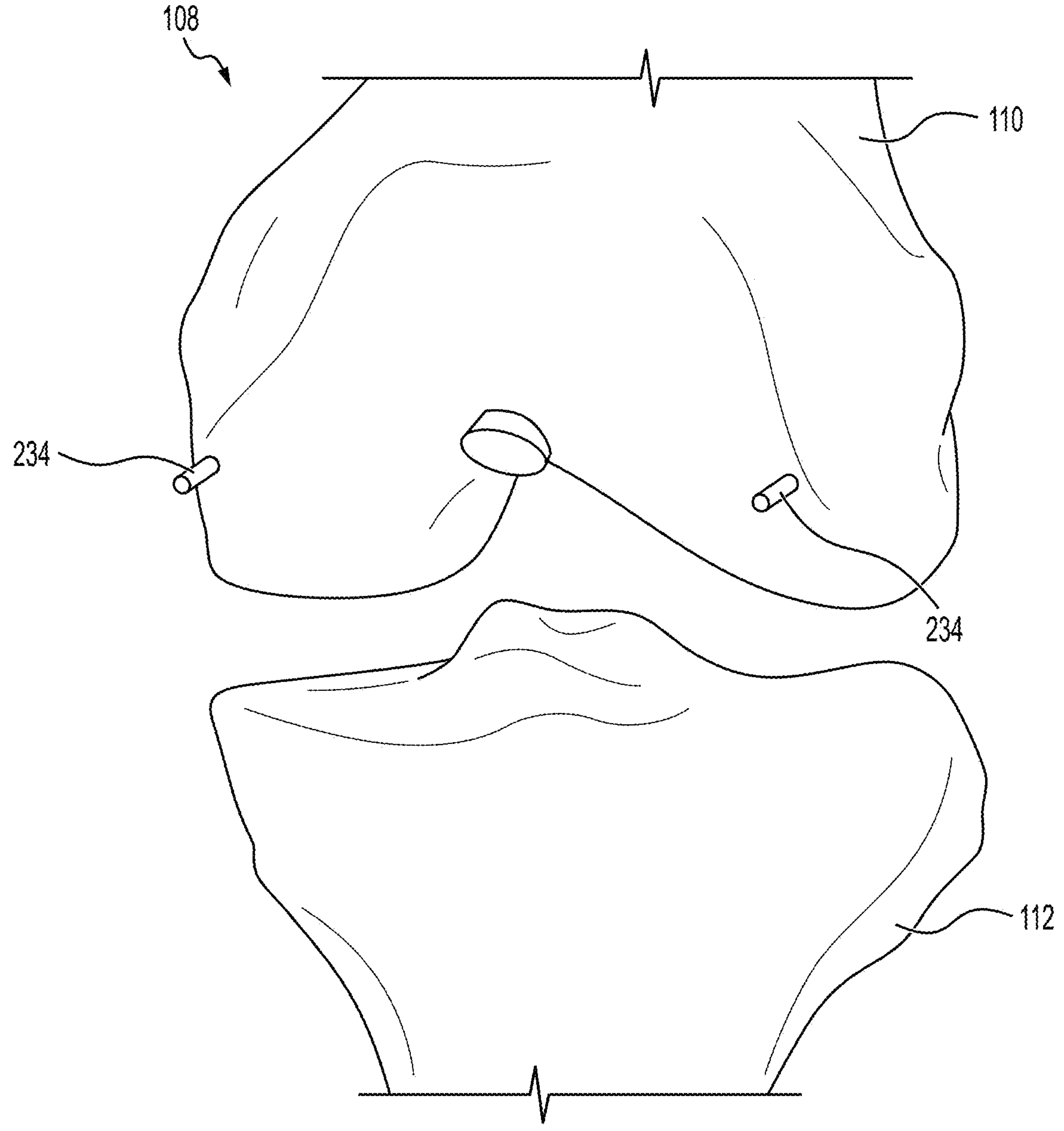
FIG. 12 is a perspective view of the knee with femoral bone pins installed.

Turning to FIG. 12A, in accordance with the instant disclosure, as part of planning a TKA procedure, the surgeon may create a geometric constraint 550 to represent how much bone will be resected from the distal femur and proximal tibia locations. In exemplary form, this geometric constraint 550 comprises a rectangle or trapezoid having an overall height 552 that is equal to the total thickness of the femoral and tibial components (subtracting the thickness of the femoral and tibial components that overlap either bone), when implanted, with respect to anatomical axes of the femur and tibia. By way of example, this height may correspond to a total implant height, such as 18 millimeters. In contrast, the width of this rectangle is defined by a series of three lines. A first of these lines is the femoral cut line 554, which represents the planar cut performed on the femur at or near mid-flexion for the posterior chamfer cut. This cut will be referred to as the most proximal bone cut for purposes of the constraint 550. A second of these lines is the tibial cut line 558, which represents the planar cut performed at the proximal end of the tibia, which is referred to as the most distal bone cut for purposes of the constraint 550. In between these cut lines 554, 558 is a third line, called the joint line 556. The joint line 556 represents where the distalmost aspect of the femoral implant contacts the tibial implant relative to the two bone cut lines. In accordance with the instant disclosure, the two cut lines 554, 588 may be parallel to one another and each parallel to the joint line 556. A vertical dotted line 560 represents the divide between the medial side M and the lateral side L. Those skilled in the art will understand that for purposes of explanation, the precise width of the constraint 550 need not be specified, nor does the precise width of the medial component or the lateral component need to be specified of the constraint.

Referring to FIG. 12B, an exemplary series of cut diagrams 552 are depicted reflecting how much bone from the tibia T and femur F is intended to be removed on a medial or lateral side to account for the 18 millimeters of height added by implantation of the tibial and femoral orthopedic implants. In the first cut diagram 558A, it is presumed that the joint is properly tensioned (i.e., relatively tight, but not too tight), so much so that the spacing between the bones measured at mid-flexion, as discussed herein, is less than 1.0 millimeter. In this case, the additional 18 millimeters attributable to the orthopedic implants needs to be offset by removing a total of 18 millimeters from the proximal tibia T and distal femur F. If one presumes the joint line 560, depicted as a dotted line, the surgeon may elect to remove 8 millimeters from the distal femur F and 10 millimeters from the proximal tibia T to maintain the same total height of the joint pre and post operatively. But in a situation where a measurable gap (generally greater than 1 millimeter) between the distal femur and proximal tibia contact points is present during mid-flexion balancing, this gap is preferably accounted for by adjusting the amount of bone resected.

The second cut diagram 558B is an example where either the medial or lateral joint at mid-flexion was loose and included a 3-millimeter gap needing to be filled in order to bring the joint to its proper tension. In such a case, the amount of distal femur F resected needs to be less than 8 millimeters because the 8-millimeter resection presumed the joint was properly tensioned at mid-flexion with no bone gap. Accordingly, in this case, the 3-millimeter gap measured during mid-flexion balancing is used to reduce the total bone ultimately resected. In this example, the joint line remains the same, but instead of resecting 8 millimeters of the distal femur F, the surgeon will only resect 5 millimeters of the distal femur F because the surgeon needs to leave 3 more millimeters of distal femur F (that would otherwise be resected if there was no gap measured during mid-flexion balancing) to effectively fill the 3 millimeter gap measured during mid-flexion balancing. And by doing so, the 10-millimeter cut to the proximal tibia T remains unchanged.

The third cut diagram 558C is another example where either the medial or lateral joint at mid-flexion was loose and included a 3-millimeter gap needing to be filled in order to bring the joint to its proper tension. In such a case, the surgeon chooses to maintain the distal femur F resection at 8 millimeters and maintains the joint line. As a result, the amount of bone resected on the tibia T will need to account for the 3-millimeter gap measured during mid-flexion balancing. Accordingly, in this case, the 3-millimeter gap measured during mid-flexion balancing is used to reduce the total bone ultimately resected, in this case on the proximal tibia by 3 millimeters. As a result, instead of resecting 10 millimeters of the proximal tibia T, the surgeon will only resect 7 millimeters of the proximal tibia T because the surgeon needs to leave 3 more millimeters of proximal tibia T (that would otherwise be resected if there was no gap measured during mid-flexion balancing) to effectively fill the 3 millimeter gap measured during mid-flexion balancing. And by doing so, the 8-millimeter cut to the distal femur F remains unchanged.

The fourth cut diagram 558D is a further example where either the medial or lateral joint at mid-flexion was loose and included a 3-millimeter gap needing to be filled in order to bring the joint to its proper tension. In such a case, the surgeon chooses to leave the joint line in place (as if the joint when mid-flexion balanced included no gap), but allocates a first portion (approximately 1 millimeter) of the 3-millimeter gap to the distal femur F and a second portion (approximately 2 millimeters) of the 3-millimeter gap to the proximal tibia T. As a result, the amount of bone resected on the tibia T and femur F will need to account for the 3-millimeter gap measured during mid-flexion balancing. As with the other cases, a 3-millimeter gap measured during mid-flexion balancing is used to reduce the total bone ultimately resected by 3 millimeters. In this example, instead of resecting 10 millimeters of the proximal tibia T, the surgeon will only resect 8 millimeters of the proximal tibia T because 2 millimeters of the proximal tibia T will be used to effectively fill the second portion the 3-millimeter gap measured during mid-flexion balancing. And by doing so, instead of resecting 8 millimeters of the distal femur F, the surgeon will only resect 7 millimeters of the distal femur because 1 millimeter of the distal femur F will be used to effectively fill the first portion the 3-millimeter gap measured during mid-flexion balancing.

The fifth cut diagram 558E is similar to the fourth cut diagram 558D, with the distinction of having more of the 3-millimeter gap being made up by a lesser cut to the distal femur F. Specifically, the surgeon chooses to leave the joint line in place (as if the joint when mid-flexion balanced included no gap), but allocates a first portion (approximately 2 millimeters) of the 3-millimeter gap to the distal femur F and a second portion (approximately 1 millimeter) of the 3-millimeter gap to the proximal tibia T. In this example, 6 millimeters of the distal femur F is resected, while 9 millimeters of the proximal tibia T is resected.

The foregoing cut diagrams 558A-558E are exemplary and show how the amount of bone resected from the proximal tibia T and the distal femur F depends upon the total added height of the orthopedic implant (which may be more or less than 18 millimeters) as well as the gap measured during mid-flexion (which may be zero or greater millimeters). It should be noted that these cut diagrams may be applicable to the medial and/or lateral side of an orthopedic knee replacement surgical procedure.

Turning to FIG. 12C, two pairs of cut diagrams 568M, 568L, 570M, 570L are depicted and will be discussed in the context in a situation where the gaps measured during mid-flexion on the medial and lateral sides are not the same.

By way of example, looking at diagrams 568M and 568L, in a circumstance where the mid-flexion balancing results in measured gap of 2 millimeters on the medial side, but the measured gap on the lateral side is 3 millimeters, the surgeon may elect to make the joint line 560 the top of the proximal tibia T. And in so doing, the surgeon will presume that a planar cut on the proximal tibia T will be made to sacrifice 10 millimeters of bone. But on the distal femur F, the planar bone cut cannot be parallel to the joint line 560 and the proximal tibia cut, otherwise an equal amount of femur will be resected and this will not correctly account for the differing measured gaps. In such as case, the distal planar cut to the femur will be angled so that the cut effectively removes 2 less millimeters from the medial side and removes 3 fewer millimeters from the lateral side.

Turning to diagrams 570M and 570L, in a circumstance where the mid-flexion balancing results in measured gap of 3 millimeters on the medial side, but the measured gap on the lateral side is 2 millimeters, the surgeon may elect to make the joint line 560 the end of the resected distal femur F. And in so doing, the surgeon will presume that a planar cut on the distal femur FT will be made to sacrifice 7 millimeters of bone, and have the joint line 1 millimeter distal from the femoral bone cut. But on the proximal tibia T, the planar bone cut cannot be parallel to the joint line and the distal femur cut, otherwise an equal amount of tibia will be resected and this will not correctly account for the differing measured gaps. In such as case, the proximal tibial cut will be angled so that the cut effectively removes 2 less millimeters from the medial side and removes 1 fewer millimeter from the lateral side.

Figure 11:
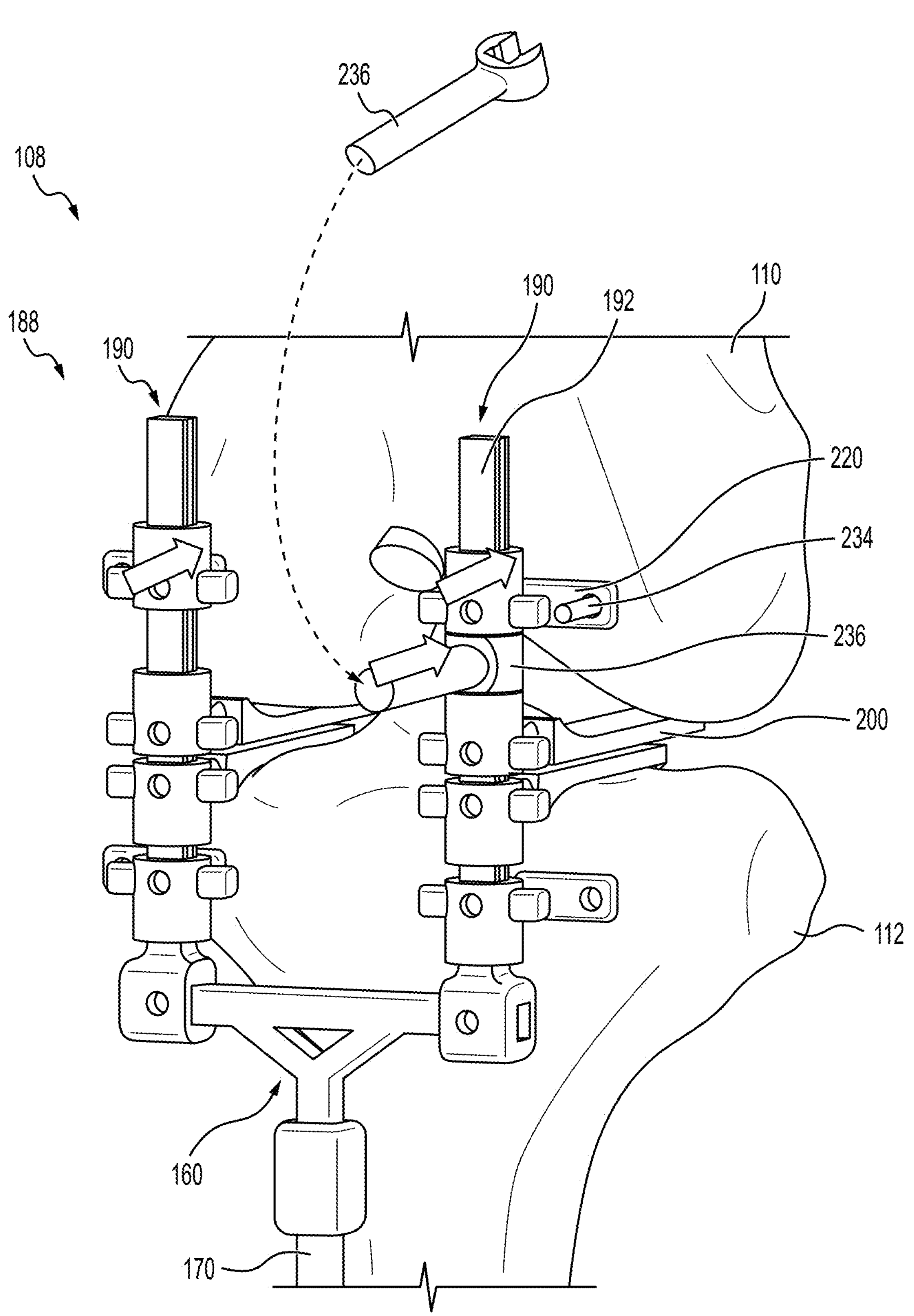
FIG. 11 is a perspective view of the balancing jig with a spacer establishing a femoral bone pin location.

Referring to FIG. 11A, the balancing jig 188 includes a spacer 236 for establishing at least one of a tibial and a femoral bone pin location. After the desired balance at mid-flexion is achieved and gaps between the bone measured, locations of one or more femoral bone pins 234 are determined. In the illustrated embodiment, a spacer 236 is positioned on the vertical guide 192 above and against the top paddle 200 while the paddles 200, 200A occupy positions measuring the full gap between the femur and tibia when balanced. Those skilled in the art will understand that the height of each spacer 236 along the vertical guide 192 is dependent upon the geometric constraint 550 established by the surgeon as a function of the implant dimensions, the location of the joint line, and the measured mid-flexion balancing gaps. For example, if the joint line is parallel to the femoral planar cut, then the heights of the spacers 236 on the medial and lateral sides may be identical. Similarly, if the joint line is parallel to the tibial planar cut and the measured mid-flexion balancing gaps are identical, then the heights of the spacers 236 on the medial and lateral sides may be identical. Conversely, if the if the joint line is parallel to the tibial planar cut and the measured mid-flexion balancing gaps are not identical, then the heights of the spacers 236 on the medial and lateral sides may not be identical. In any event, the geometric constraint 550 established by the surgeon drives the height of the spacers 236 utilized and, thus, the resulting locations of respective pin guides 220.

Post incorporating the spacers 236 above the top paddles 200, respective pin guides 220 are positioned above and against the spacers 236. In this fashion, the spacer 236, having a known vertical dimension, locates the pin guide 220 at a known position relative to both top paddles 200. And a similar process may be utilized for inserting a spacer 236 between the lower paddle 200A and corresponding pin guides 220.

These steps of paddle distraction of the joint allow pins to be placed in both the femur and the tibia that have a rectangular relationship for symmetric balancing or a trapezoid for asymmetric spacing based on ligament balance and predicated on standard TKA resection levels.

FIG. 11B is a perspective view of the knee with femoral bone pins installed, all according to at least some aspects of the present disclosure. After the position of each pin guide 220 is finalized, a bone drill bit (not shown) is inserted through the opening 232 so that the walls of the flange 230 delineating the opening act as a guide for the drill bit. Two holes are drilled into the distal femur that are aligned with the respective openings 232. Thereafter, a pair of bone pins 234 are inserted through the respective openings 232 of the pin guide 220 and secured within the drilled femoral cavities. Post bone pin 234 placement, the remining components may be removed (pin guide 220, paddles 200, vertical guides 192, tibial placement guide 160), resulting in the configuration depicted in FIG. 12. The tibial guide and/or the EM rod can be removed for cutting bones or to reposition the leg. The guide and/or rod can be replaced at a later time to recreate the previously defined fixed relationship (for example the angle of the knee during the chamfer cut) between the femur and the tibia.

Figure 13:
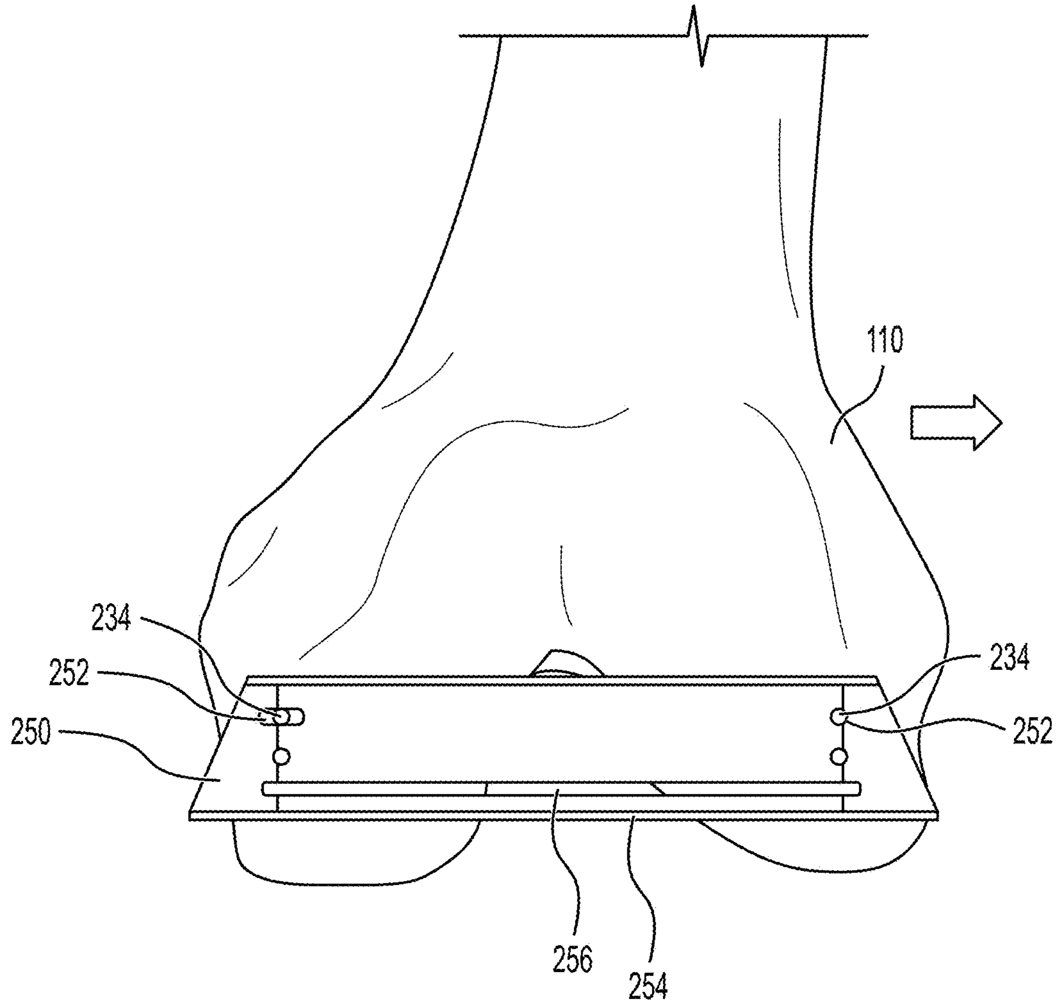
FIG. 13 is an anterior view of the femur with a posterior chamfer cut guide installed.
Figure 14A:
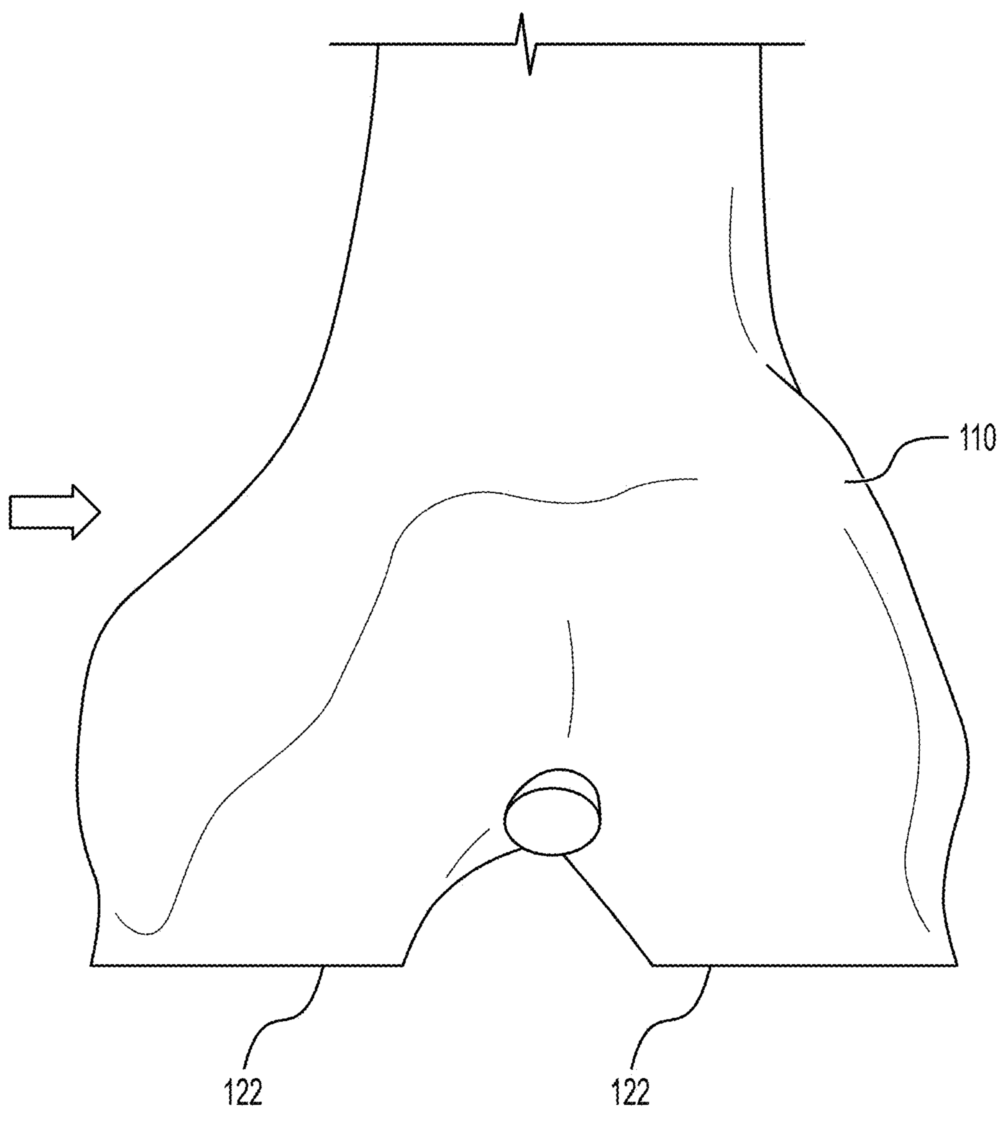
FIG. 14A is an anterior view of the femur showing the posterior chamfer cut.
Figure 14B:
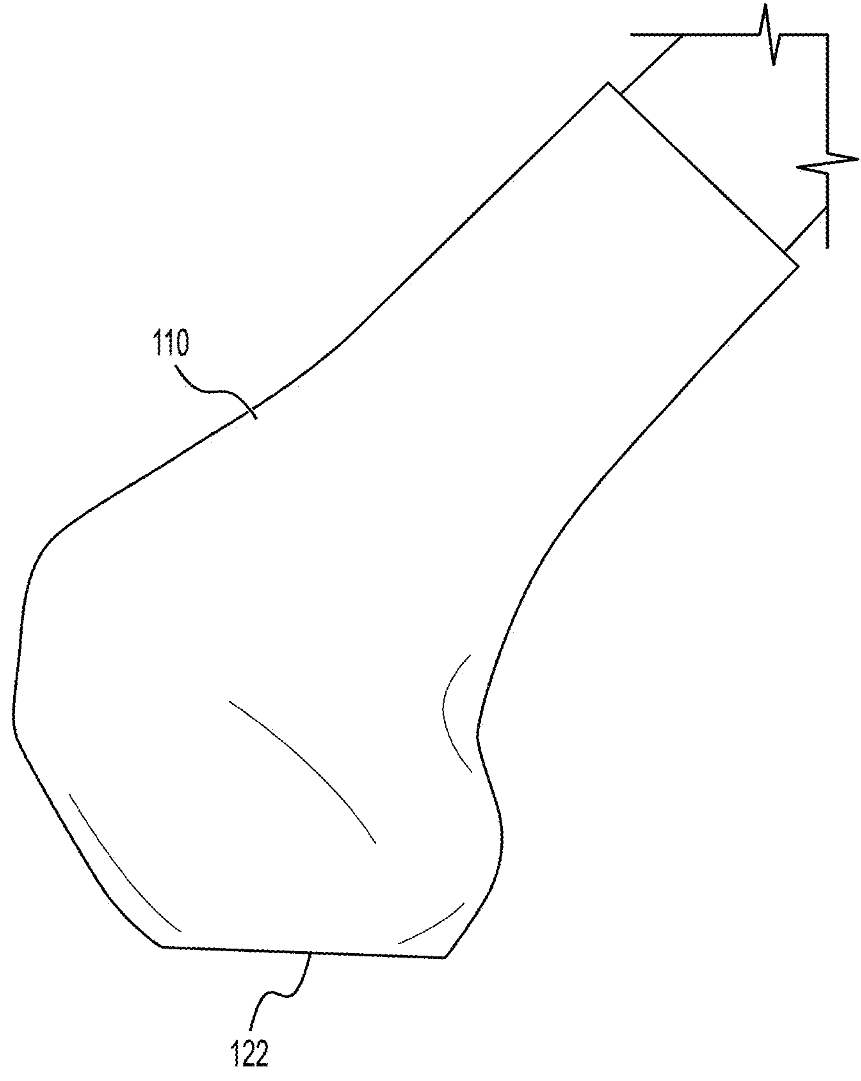
FIG. 14B is a lateral view of the femur showing the posterior chamfer cut.

FIG. 13 is an anterior view of the femur with a posterior chamfer cut guide installed, FIG. 14A is an anterior view of the femur showing the posterior chamfer cut, and FIG. 14B is a lateral view of the femur showing the posterior chamfer cut, all according to at least some aspects of the present disclosure. Referring to FIGS. 13, 14A, and 14B, a posterior chamfer cut guide 250 is mounted to the distal femur 110 using the bone pins 234 for use in performing a resection to create a posterior chamfer cut 122. Specifically, the posterior chamfer cut guide 250 may comprise a pair of through holes 252 that are sized to receive respective bone pins 234. In the illustrated embodiment, one of the through holes 252 is substantially circular to match the shape of the respective bone pin 234, and the other through hole 252 is generally horizontally elongated. As a result, small horizontal variations in locating the bone pins 234 may be accommodated while the desired vertical positioning—and thus location and orientation of the cut plane—of the posterior chamfer cut guide 250 is maintained. The specific shape of the posterior chamfer cut guide 250 is freely assignable so long as the guide includes an appropriate guide surface, such as a flat surface 254 or cutting slit 256 adapted to guide a surgical saw blade (not shown) or burring device to make the posterior chamfer cut. In this exemplary embodiment, the posterior chamfer cut guide 250 includes both a flat bottom surface 254 and a cutting slit 256 that are adapted to guide the surgical saw blade while effectuating the posterior chamfer cut 122. It should be understood, however, that the posterior chamfer cut guide 250 may omit the slit 256 or the flat surface 254. Moreover, it should be understood that the posterior chamfer cut guide 250 may include a plurality of slits 256. In any event, the posterior chamfer cut guide 250 is utilized by a surgeon to guide the surgical saw blade in order to make a planar posterior chamfer cut 122. After the posterior chamfer cut is complete, the posterior chamfer cut guide 250 and bone pins 234 may be removed from the femur 110, resulting in the femur depicted in FIGS. 14A and 14B with the posterior chamfer cut 122 being the first completed bone cut on the femur. In some alternative example procedures, the bone pins 234 may remain in the femur 110 for later use, such as in connection with locating a tibial plateau cut as described below.

The present disclosure contemplates that some conventional TKA procedures may not include referencing of tibial cuts with respect to the femoral cuts or vice versa. That is, in some conventional surgeries, femoral bone cuts and tibial bone cuts are made independently. In contrast, in some example embodiments according to at least some aspects of the present disclosure, knee balancing and bone cuts are made with devices and jigs that are referenced with respect to each other. For example, since the femoral chamfer cut is initially made, then ligament balancing has been determined at mid-flexion or the prescribed angle of flexion, leading to the tibial bone cut may be which is made with respect to the femoral chamfer cut and therefore, the tibial bone cut is made with respect to the chamfer cut and ligaments were properly balanced to ensure a desired relationship of the femur with respect to the tibia. In contrast, some conventional TKA procedures do not spatially link one bone cut to another.

Figure 15:
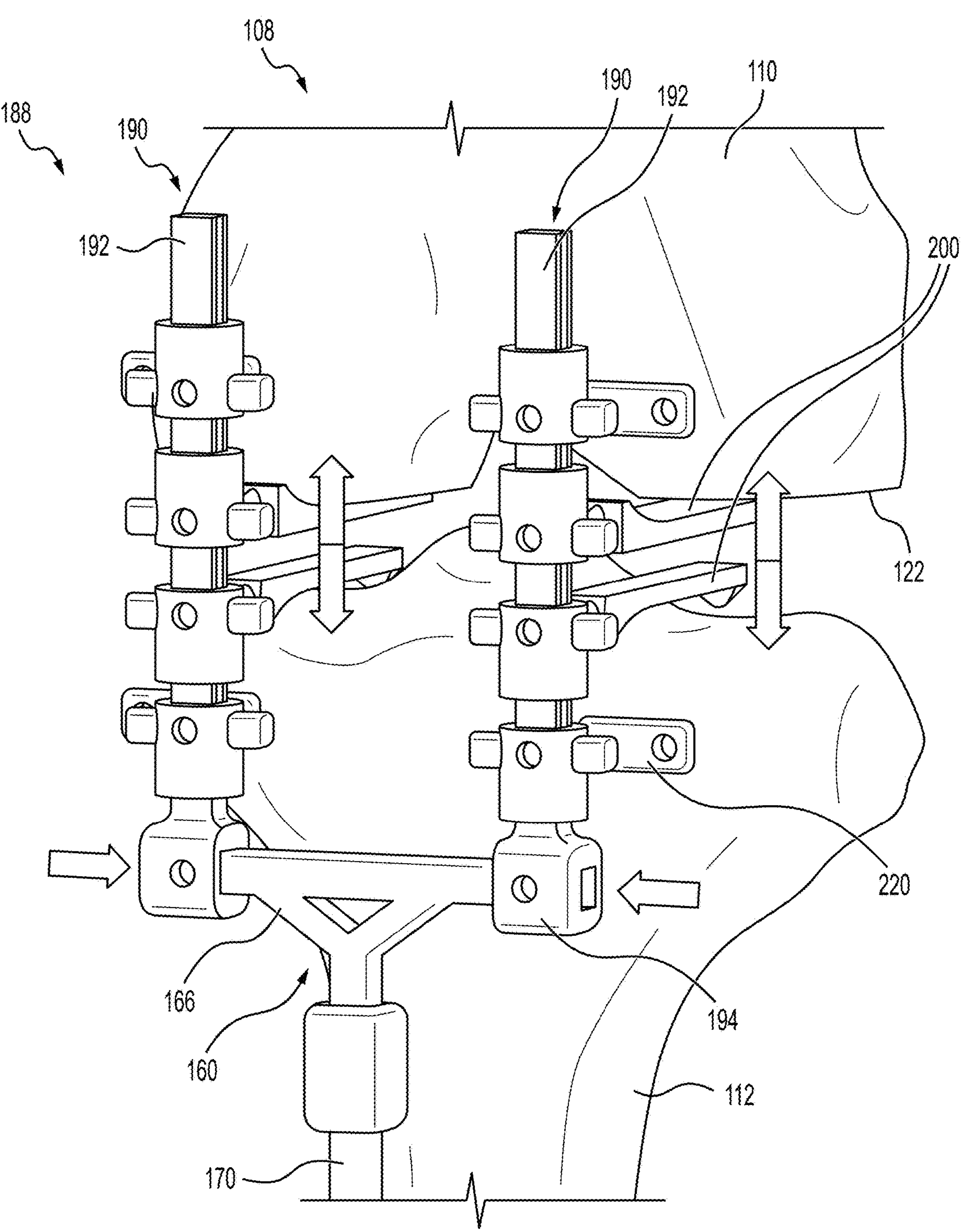
FIG. 15 is a perspective view of the balancing jig in use on the knee after the posterior chamfer cut.

FIG. 15 is a perspective view of the balancing jig in use on the knee after the posterior chamfer cut, according to at least some aspects of the present disclosure. With reference to FIG. 15, the tibial placement guide 160 may be mounted to the tibia 112 after making the posterior chamfer cut 122. The vertical guides 192 may also be mounted to the tibial placement guide 160, specifically mounted to the beam 166. When mounted to the beam 166, each vertical guide 192 may include one or more pin guides 220 and one or more paddles 200. In exemplary form, a pair of paddles 200 may be mounted to each vertical guide 192, as well as a pin guide 220, so that the pin guide is closer to the adapter 194 than are the paddles. In exemplary form, the paddles 200 mounted to each vertical guide 192 are oriented to overlap one another so that the medial vertical guide 192 has its paddles orientated to interpose the femoral medial chamfer cut surface and the medial tibial condyle receiver articular surface. Similarly, the lateral vertical guide 192 has its paddles orientated to interpose the femoral lateral chamfer cut surface and the lateral tibial condyle receiver articular surface.

While the knee joint is bent at approximately 45 degrees or mid-flexion (same angle of the posterior chamfer cut angle) and retained in position (such as by using an external brace, not shown or the intramedullary canal rod mated with respect to the receiver on the tibial jig), the surgeon performs a soft tissue balance for the medial and lateral sides of the knee. As part of this soft tissue balance, the surgeon manipulates the spacing between the overlapping paddles 200 on both the medial and lateral sides until reaching the desired balance. For example, the ligament length and/or tensions and/or condylar separation from the tibial plateau are recorded and set as the goal for balancing at other degrees of flexion, such as full extension and at 90 degrees of flexion. After reaching the balance on the medial and lateral sides, as previously stated the surgeon records the spacing of the paddles on both sides (medial and lateral) using the position of the paddles 200 with respect to the vertical guide 192. In cases where the vertical guide 192 includes markings, these markings may be utilized to record the spacing between the paddles 200 simply by using the position of the connectors 202 with respect to the vertical guides.

After the desired balance is achieved, locations of one or more tibial bone pins 264 are determined. In some example embodiments, a spacer may be used in a manner generally similar to the use of spacer 236, above, except that the spacer may be positioned below and against the respective paddle 200 and the pin guide 220 may be positioned below and against the respective spacer.

Figures 15A, 15B:
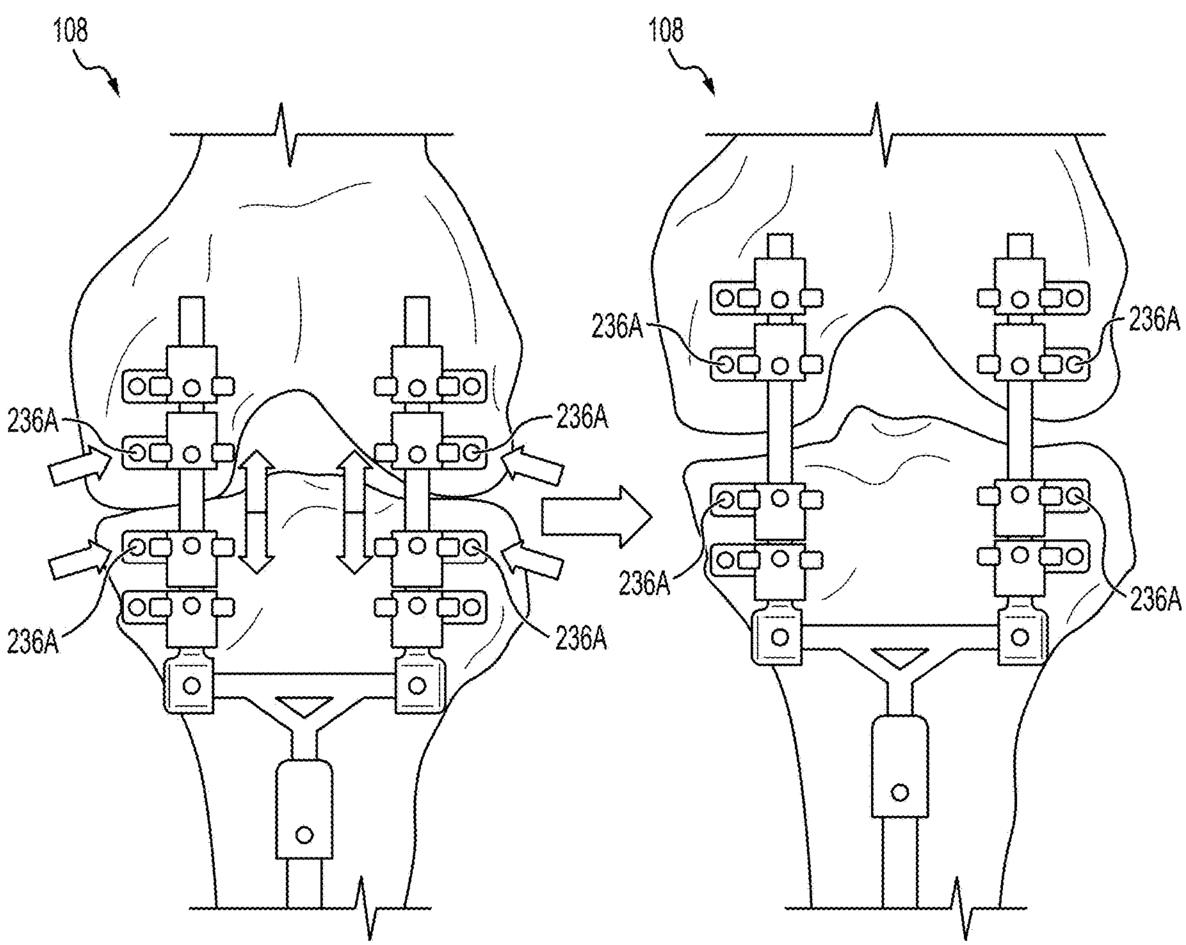
FIG. 15A is a perspective view of an alternative balancing jig in use on the knee after the posterior chamfer cut.
FIG. 15B is a perspective view of the alternative balancing jig of FIG. 15A in use on the knee after the posterior chamfer cut.

FIG. 15A is a perspective view of an alternative balancing jig 188A in use on the knee 108 before the posterior chamfer cut, and FIG. 15B is a perspective view of the alternative balancing jig 188A in use on the knee 108 before the posterior chamfer cut, all according to at least some aspects of the present disclosure. The alternative balancing jig 188A is generally similar in construction and operation to the balancing jig 188 described elsewhere herein, and repeated description is omitted for brevity. The alternative balancing jig 188A may be useful when the gap between the condyle and the tibial plateau is too tight for use of paddles 200, for example. In the illustrated embodiment, balancing pins 236A can be used instead of spacers 236. Once the jig 188A is fixated to the femur and the tibia, the gap between the condyles and the plateau can be created and measured in a manner generally similar to that for jig 188, generating a balanced gap, using the balancing pins 236A.

Figure 16A:
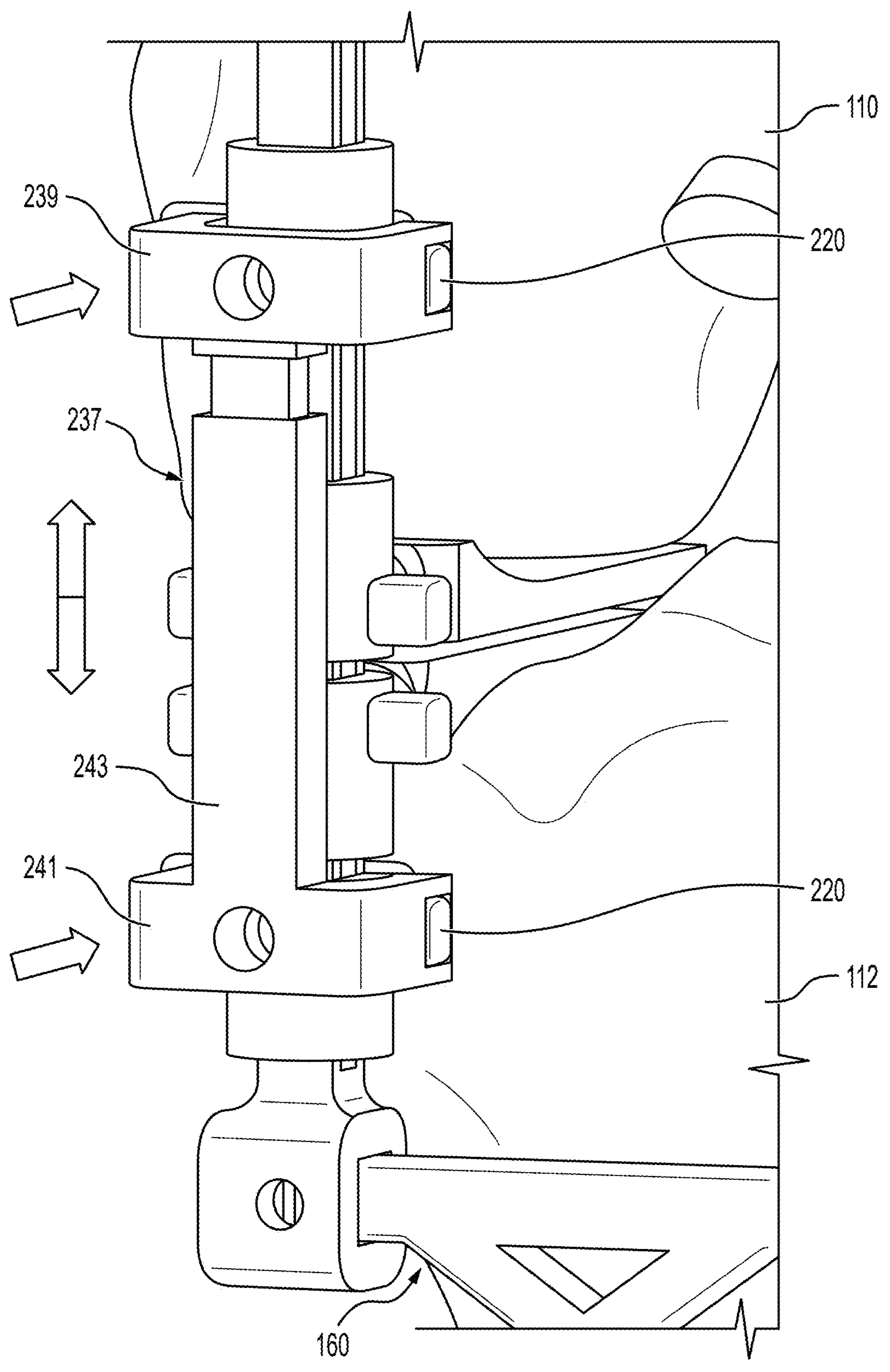
FIG. 16A is a detailed perspective view of an example balancing assembly including a pin-pin spacer for establishing a desired vertical separation between a femoral bone pin and a tibial bone pin.

FIG. 16A is a detailed perspective view of an example balancing assembly including a pin-pin spacer for establishing a desired vertical separation between a femoral bone pin and a tibial bone pin, according to at least some aspects of the present disclosure. Referring to FIG. 16A, in some alternative example embodiments, a pin-pin spacer 237 may be used to establish a desired vertical separation between a femoral bone pin 234 and a tibial bone pin 264. The soft tissue balance has been done by application of the balancing jig 188. That leads to the pin placement for the posterior chamfer cut and the proximal tibial cut. In the illustrated embodiment, the pin-pin spacer 237 includes a femoral component 239, a tibial component 241, and a spacing section 243 interposing the femoral component 239 and the tibial component 241. The femoral component 239 is configured to engage the pin guide 220 for one of the femoral bone pins 234. The tibial component 241 is configured to engage the pin guide 220 for one of the tibial bone pins 264. The spacing section 243 is configured to define the distance between the femoral component 239 and the tibial component 241. In some example embodiments, the spacing section 243 may provide a fixed distance between the femoral component 239 and the tibial component 241. In the illustrated embodiment, the spacing section 243 has an adjustable length so that the distance between the femoral component 239 and the tibial component 241 is adjustable.

Figure 16B:
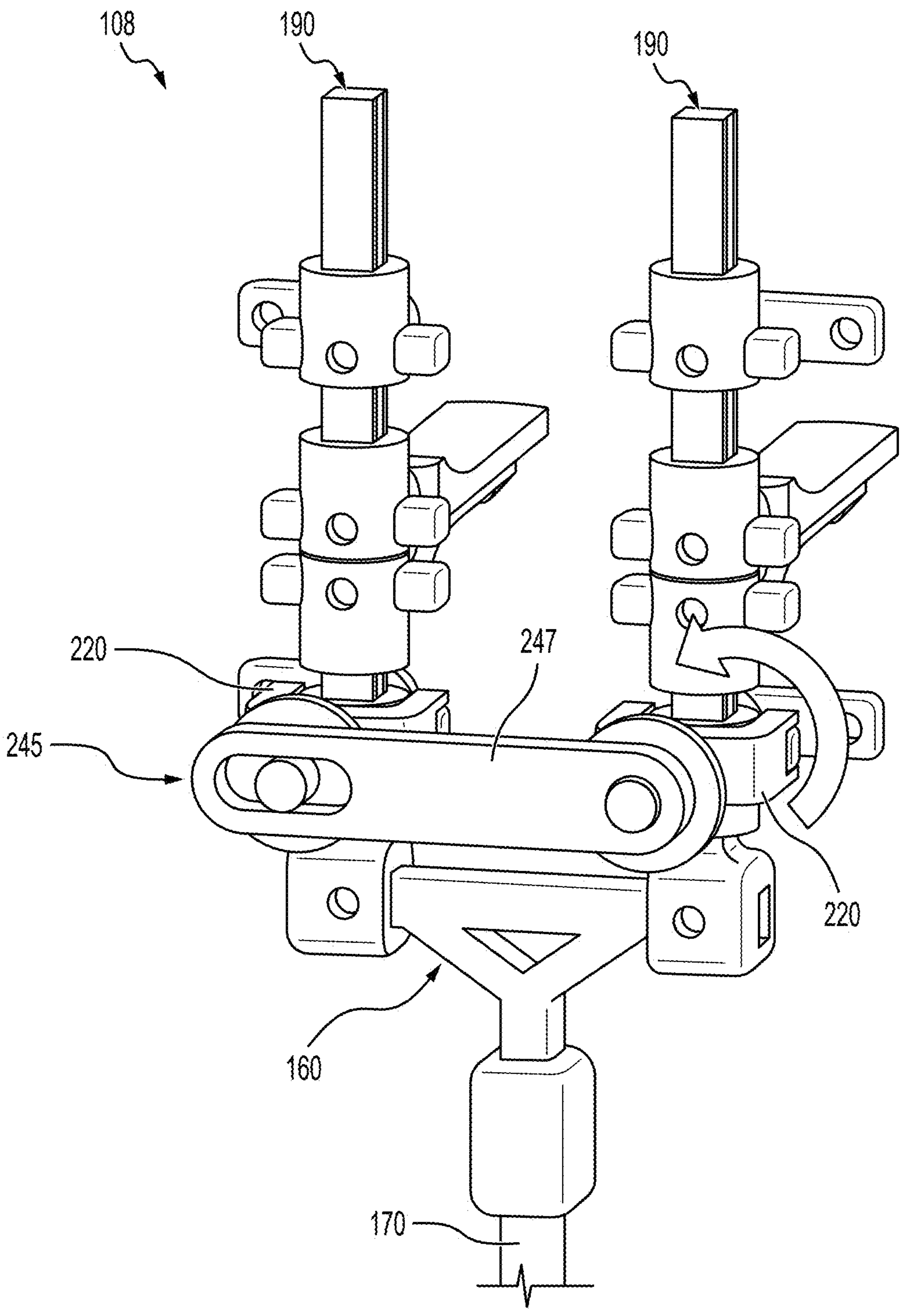
FIG. 16B is a perspective view of the knee balancing jig with a varus-valgus alignment tool installed.

FIG. 16B is a perspective view of the knee balancing jig with a varus-valgus alignment tool installed, according to at least some aspects of the present disclosure. Referring to FIG. 16B, in some alternative example embodiments, a varus-valgus alignment tool 245 may be utilized to determine and/or establish varus-valgus angles for tibial plateau cuts, for example. In the illustrated embodiment, the varus-valgus alignment tool 245 includes a connecting bar 247 pivotably coupled to one tibial pin guide 220 and pivotably and slidably coupled to the other tibial pin guide 220. By determining the angle of the connecting bar 247 relative to the other components of the balancing jig 188, the varus-valgus angle may be measured. Similarly, if it is desired to establish a particular varus-valgus angle, the connecting bar 247 may be positioned relative to the other components of the balancing jig 188 at the desired angle.

In some embodiments, the balancing jig 188 may act as one or both of a ligament balancing device, allowing a force to be imposed upon two paddles that rest respectively against the medial distal femur (superior medial paddle) and medial proximal tibia (inferior medial paddle), and a force to be imposed upon two paddles that rest respectively against the lateral distal femur (superior lateral paddle) and lateral proximal tibia (inferior lateral paddle); and/or a bony resection guide, based upon accepted principles of TKA. A TKA when viewed from a lateral perspective may be described as a composite thickness of three heights, comprising the metallic height of the femoral component, an anticipated height of the polyethylene insert, and a metallic height of the tibial component. Using the balancing jig 188, that composite height can be applied to the distal femur and proximal tibia in many locations. For adherence to accepted TKA technique, the medial distal paddle's accompanying pin may generally sit about 2-4 millimeters below the surface of the native medial tibia. The lateral medial paddle's accompanying pin may generally sit about 8-10 millimeters below the surface of the native lateral tibia. These pins may then represent a 6 degrees of freedom tibial cut plane that may be referenced off of the posterior chamfer cut plane and may be geometrically related to the posterior chamfer cut. This geometric relationship may become rectangular, such as if 45 degrees is added to the tibial cut.

Figure 17:
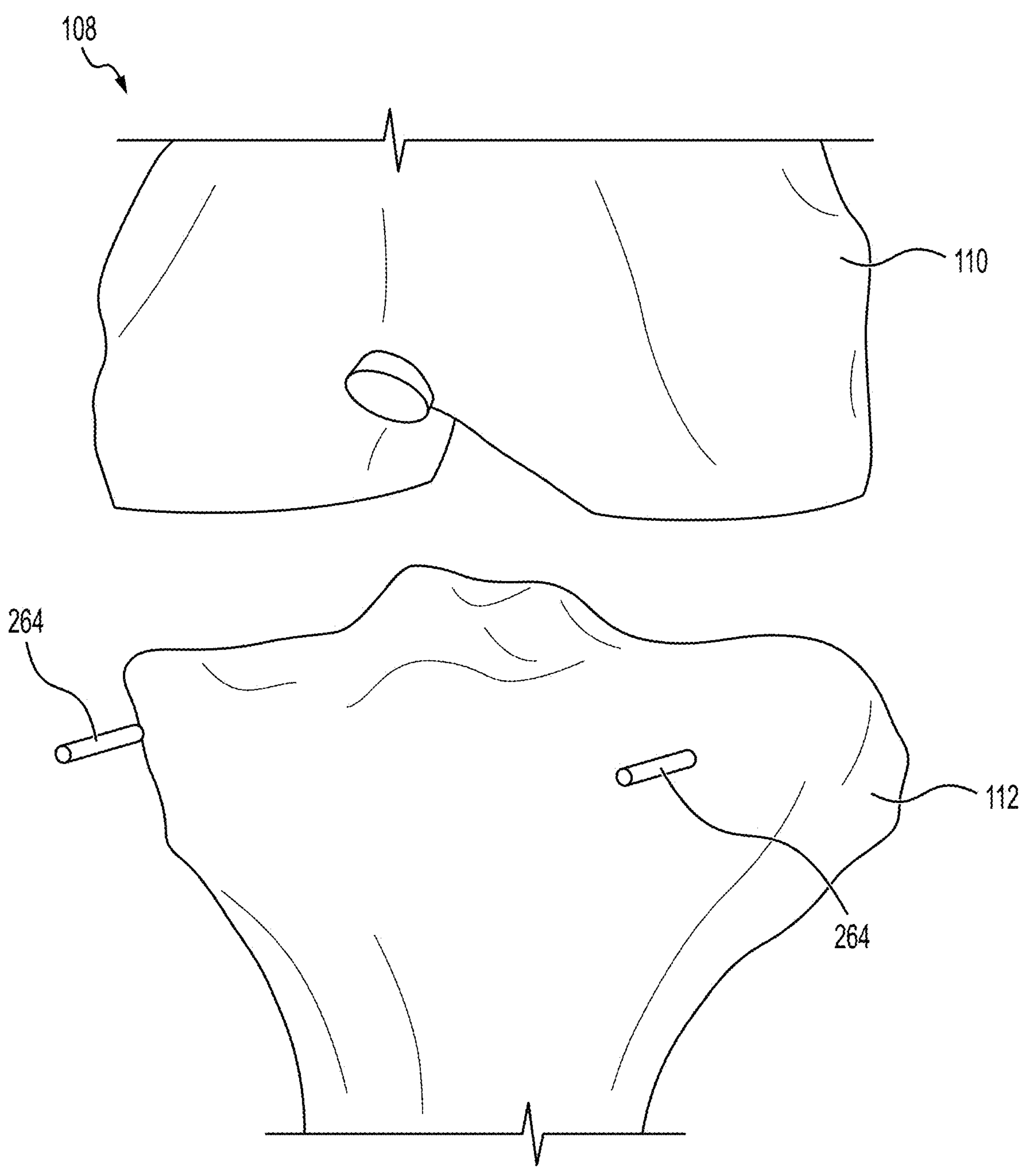
FIG. 17 is a perspective view of the knee with tibial bone pins installed.

FIG. 17 is a perspective view of the knee with tibial bone pins installed, according to at least some aspects of the present disclosure. Referring to FIGS. 15 and 17, similar to the procedure described above for the femur, after the position of each pin guide 220 for the tibial bone pins 264 is finalized, a bone drill bit (not shown) is inserted through the opening 232 so that the walls of the flange 230 delineating the opening act as a guide for the drill bit. Two holes are drilled into the proximal tibia 112 that are aligned with the respective openings 232. Thereafter, a pair of bone pins 264 are inserted through the respective openings 232 of the pin guide 220 and secured within the drilled tibial cavities. Post bone pin 264 placement, the remining components may be removed (pin guide 220, paddles 200, vertical guides 192, tibial placement guide 160), resulting in the configuration depicted in FIG. 17.

Figure 18:
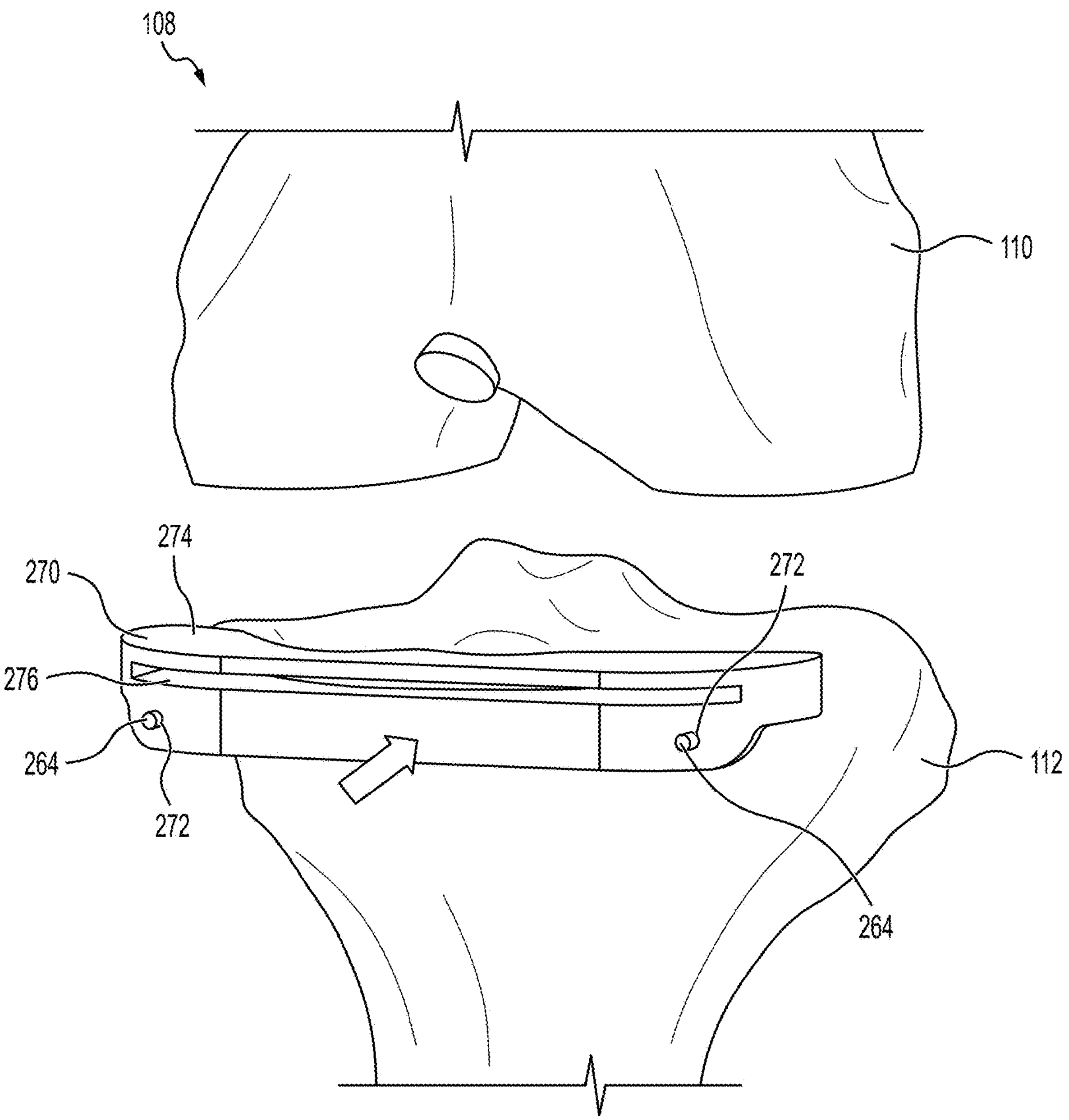
FIG. 18 is a perspective view of the knee with an example tibial cutting guide installed.
Figure 19:
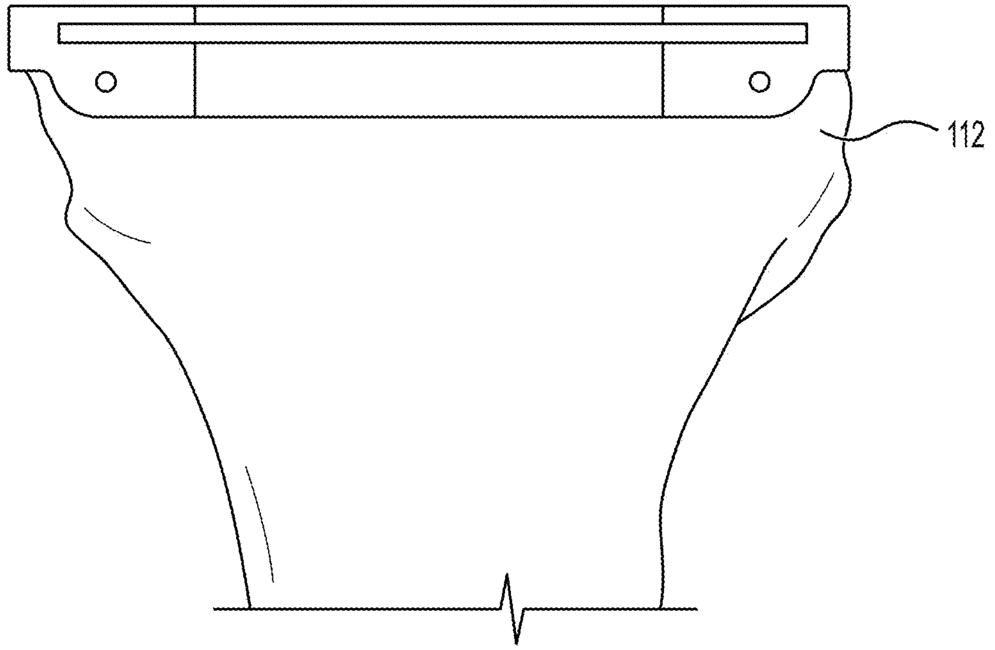
FIG. 19 is an anterior view of the tibia showing the tibial plateau cut.
Figure 20:
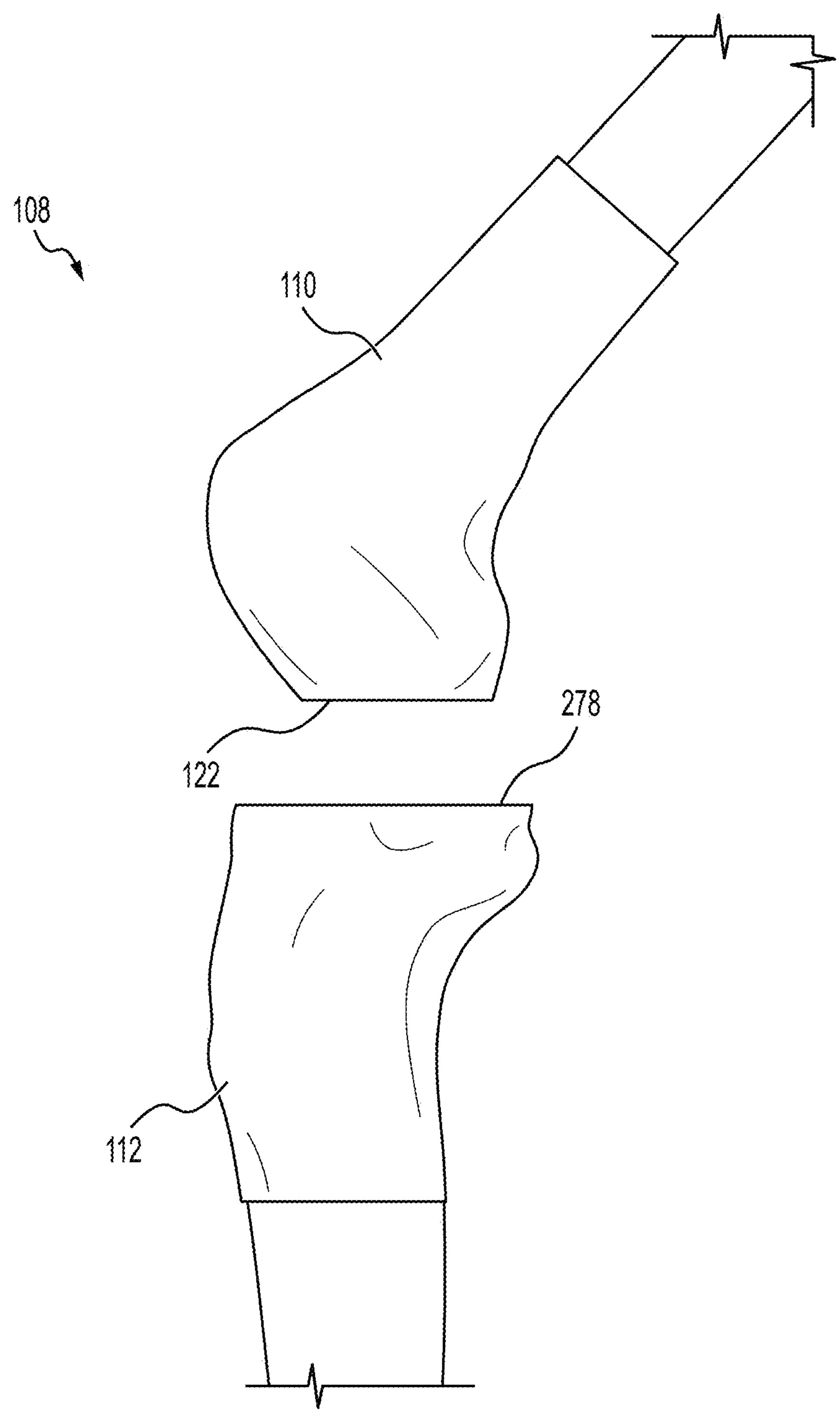
FIG. 20 is a lateral view of the knee showing the tibial plateau cut and the posterior chamfer cut.

FIG. 18 is a perspective view of the knee with an example tibial cutting guide installed, FIG. 19 is an anterior view of the tibia showing the tibial plateau cut, and FIG. 20 is a lateral view of the knee showing the tibial plateau cut and the posterior chamfer cut, all according to at least some aspects of the present disclosure. Turning to FIGS. 18-20, a tibial cutting guide 270 is mounted to the proximal tibia using the bone pins 264. Specifically, the tibial cutting guide 270 may comprise a pair of through holes 272 that are sized to receive respective bone pins 264. The specific shape of the tibial cutting guide 270 is freely assignable so long as the guide includes an appropriate guide surface, such as a flat surface 274 or cutting slit 276 adapted to guide a surgical saw blade or burring device (not shown) to make the tibial plateau cut. In this exemplary embodiment, the tibial cutting guide 270 includes both a flat top surface 274 and a cutting slit 276 that are adapted to guide the surgical saw blade while effectuating the tibial plateau cut 278. It should be understood, however, that the tibial cutting guide 270 may omit the slit 276 or the flat surface 274. Moreover, it should be understood that the tibial cutting guide 270 may include a plurality of slits 276. In any event, the tibial cutting guide 270 is utilized by a surgeon to guide the surgical saw blade in order to make a planar tibial plateau cut 278. After the tibial plateau cut 278 is complete, the tibial cutting guide 270 and the remaining bone pins 234, 264 may be removed, resulting in the tibia depicted in FIG. 20 with the tibial plateau cut being the first completed bone cut on the tibia and the second completed bone cut for the overall procedure.

In some alternative procedures, the tibial plateau cut 278 may be performed before the femoral posterior chamfer cut 122, using generally similar operations to those described above. For example, the location of the tibial plateau cut 278 may be determined first, and the tibial bone pins 264 may be placed. The tibial cutting guide 270 may be installed, and the tibial plateau cut 278 may be made. Then, the balancing jig 188 may be used to balance the knee 108 relative to the tibial plateau cut 278 and the locations of the femoral bone pins 234 may be established. The posterior chamfer cut guide 250 may be installed, and the posterior chamfer cut 122 may be made.

Figures 21, 22:
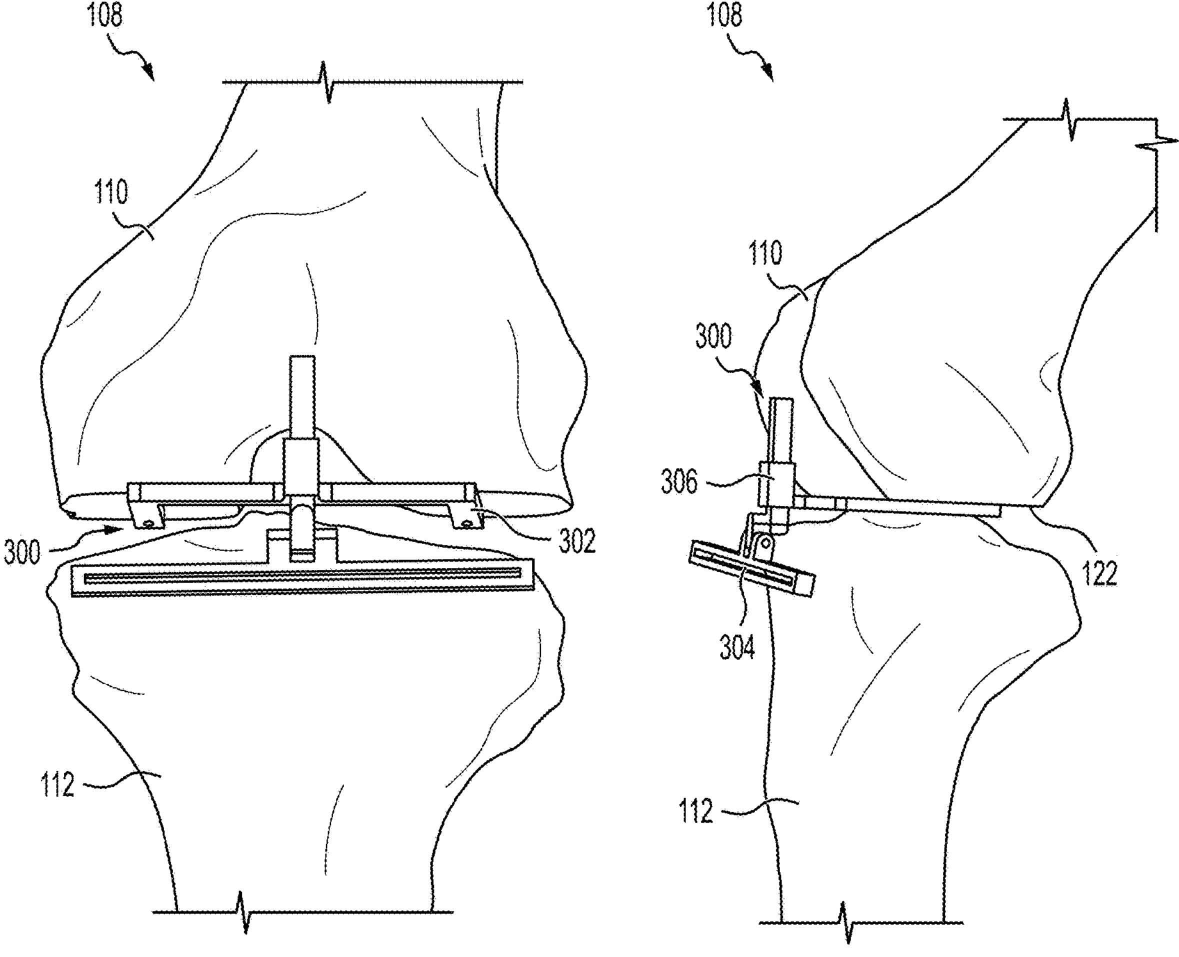
FIG. 21 is an anterior view of an alternative example tibial plateau cut guide.
FIG. 22 is a lateral view of the alternative example tibial plateau cut guide.

FIG. 21 is an anterior view of an alternative example tibial plateau cut guide, and FIG. 22 is a lateral view of the alternative example tibial plateau cut guide, all according to at least some aspects of the present disclosure. Referencing FIGS. 21 and 22, an alternate exemplary tibial plateau cut guide 300 may be utilized to effectuate the tibial plateau cut 278. The plateau cut guide 300 can be adjusted before installation or after installation and may serve to rigidly connect the femur 110 to the desired tibial cut.

By way of example, after the posterior chamfer cut 122 is complete, and the posterior chamfer cut guide 250 and bone pins 234 are removed from the femur 110. The cut guide 300 is mounted to the femoral posterior chamfer cut 122 by means of the chamfer cut reference mounting plate 302. The tibial cut guide slot 304 can be translated superiorly or inferiorly through the extension mechanism 306, which may allow the vertical distance between the posterior chamfer cut 122 and the tibial plateau cut 278 to be adjusted. Additionally, pivot coupling mechanisms integrated into the extension mechanism 306 can be used to adjust the varus/valgus or slope angle of the tibial cut, per the discretion of the surgeon. Necessary distance and angle readouts can be viewed on the extension mechanism 306, and once the desired tibial position is determined, the system is locked in place and the tibial plateau cut 278 is made through tibial cut guide slot 304.

Figure 23:
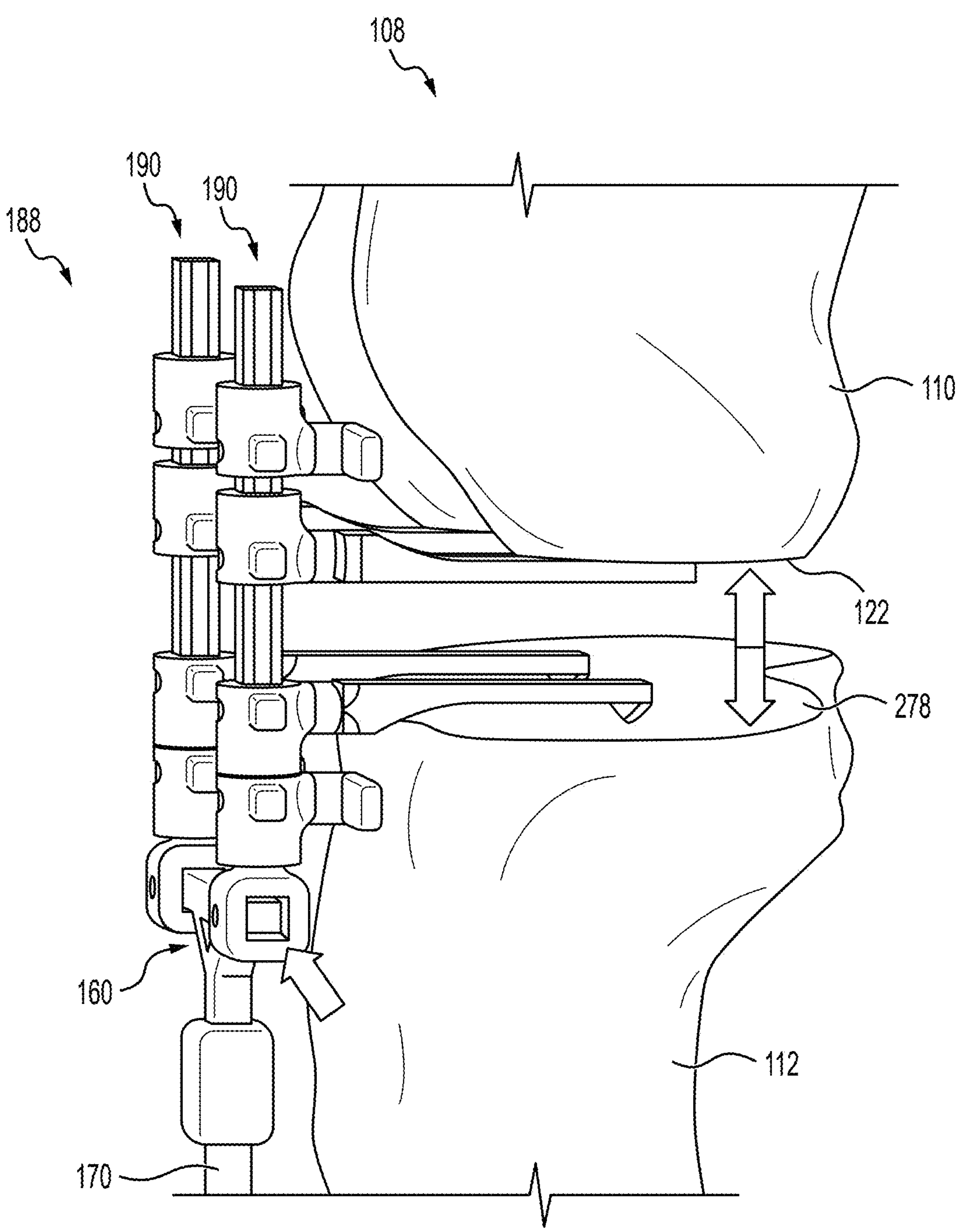
FIG. 23 is a perspective view of the knee balancing jig in use on the knee after the tibial plateau cut.

FIG. 23 is a perspective view of the knee balancing jig in use on the knee after the tibial plateau cut, according to at least some aspects of the present disclosure. Turning to FIGS. 10A-10C and 23, after the posterior chamfer cut 122 and the tibial plateau cut 278 are completed, the tibial placement guide 160 may be mounted to the tibia 112. The vertical guides 192 of the balancing assemblies 190 may also be mounted to the tibial placement guide 160, specifically mounted to the beam 166. When mounted to the beam 166, each vertical guide 192 may include one or more pin guides 220. In exemplary form, a pair of paddles 200 may be mounted to each vertical guide 192 and oriented to overlap one another so that the medial vertical guide 192 has its paddles orientated to interpose the femoral medial chamfer cut surface 122 and the tibial plateau cut surface 278. Similarly, the lateral vertical guide 192 has its paddles orientated to interpose the femoral lateral chamfer cut surface 122 and the tibial plateau cut surface 278. The jig is configured for cut distance measurement. Specifically, the distance between the posterior chamfer cut 122 and the tibial slope cut 278 (D_PCC_TSC) is measured.

Figure 24:
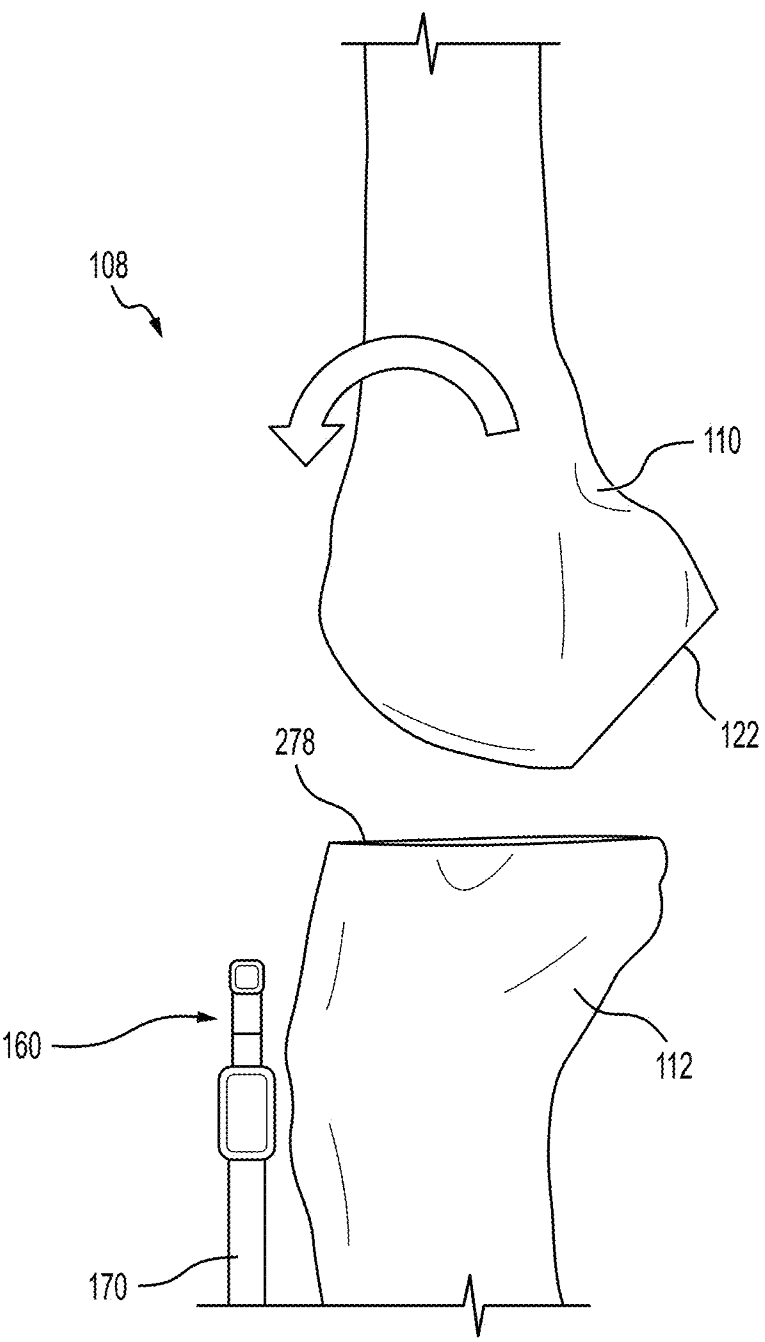
FIG. 24 is a lateral view of knee rotated to a full extension position.

FIG. 24 is a lateral view of knee rotated to a full extension position, according to at least some aspects of the present disclosure. Referring to FIG. 24, the surgeon may rotate the tibia 112 with respect to the femur 110 to reach a full extension position. While the knee joint 108 is retained in full extension (such as by using an external brace, not shown), the surgeon performs a soft tissue balance for the medial and lateral sides of the knee, balancing the knee again with the information gained for mid-flexion balancing and making of the femoral chamfer cut. The same distance and soft-tissue tensions derived for the chamfer cut with respect to the tibial cut may be maintained for the femoral extension cut.

Figure 25:
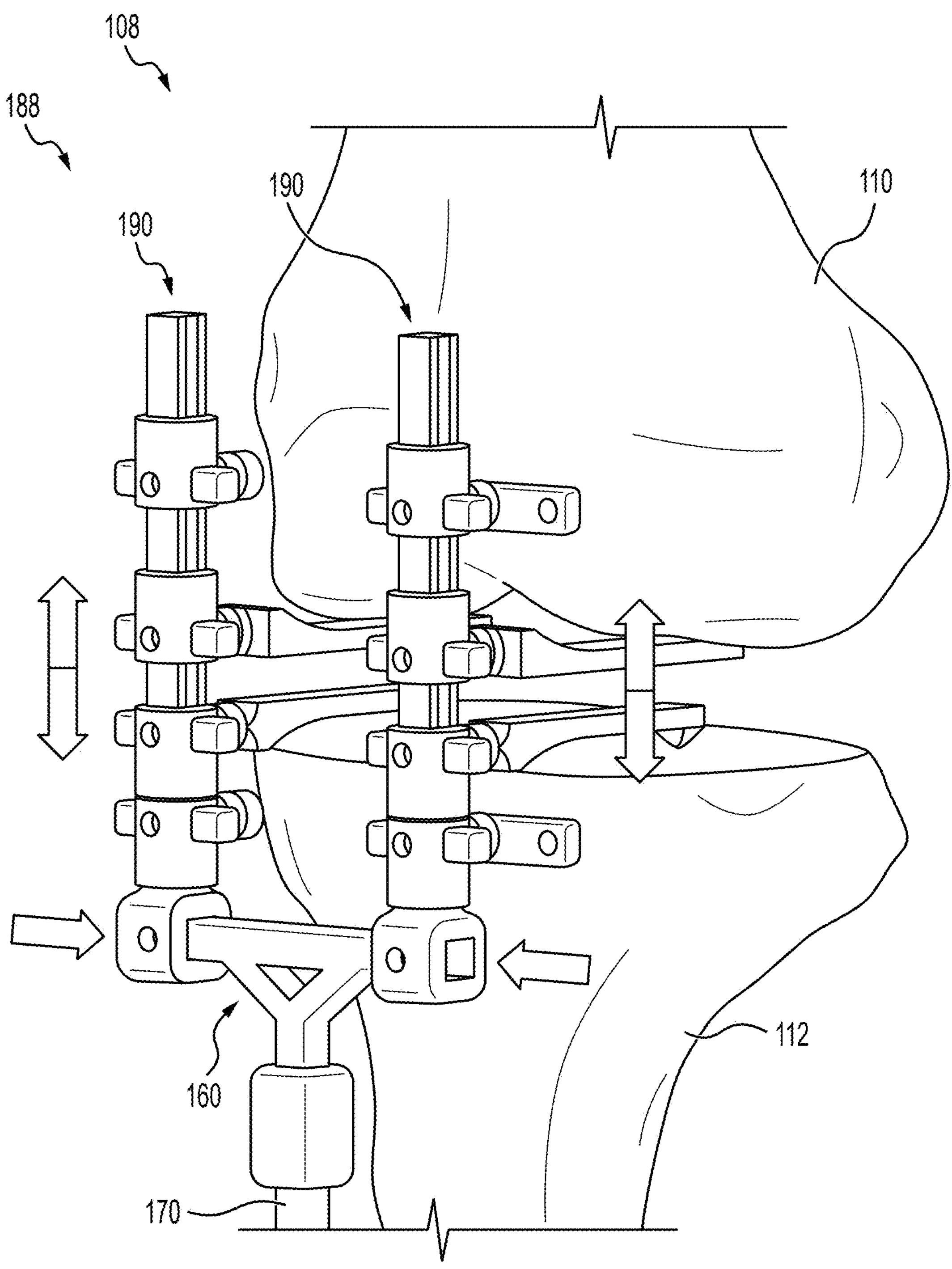
FIG. 25 is a perspective view of the knee balancing jig in use on the knee in preparation for the femoral extension cut.

FIG. 25 is a perspective view of the knee balancing jig in use on the knee in preparation for the femoral extension cut, according to at least some aspects of the present disclosure. Referring to FIGS. 10A-10C and 25, as part of this soft tissue balance, the surgeon manipulates the spacing between the overlapping paddles 200 of the balancing assemblies 190 on both the medial and lateral sides until reaching the desired balance. The determined distance (width) between the posterior chamfer cut and the proximal tibial resection is maintained by imposing the same distance, now based on the proximal tibial resection, to the distal femur and defining the distal femoral cut plane. After reaching the balance on the medial and lateral sides, the surgeon records the spacing of the paddles on both sides (medial and lateral) using the position of the paddles 200 with respect to the vertical guide 192. In cases where the vertical guide 192 includes markings, these markings may be utilized to record the spacing between the paddles 200 simply by using the position of the connectors 202 with respect to the vertical guides.

Post soft tissue balancing at full extension, positions of pin guides 220 mounted to the vertical guides 192 are determined in a manner similar to that described above, and the pin guides 220 are secured in position. After the position of each pin guide 220 is finalized, a bone drill bit (not shown) is inserted through the opening 232 of the pin guide so that the walls of the flange 230 delineating the opening act as a guide for the drill bit. Two holes are drilled into the distal femur that are aligned with the respective openings 232.

Figure 26:
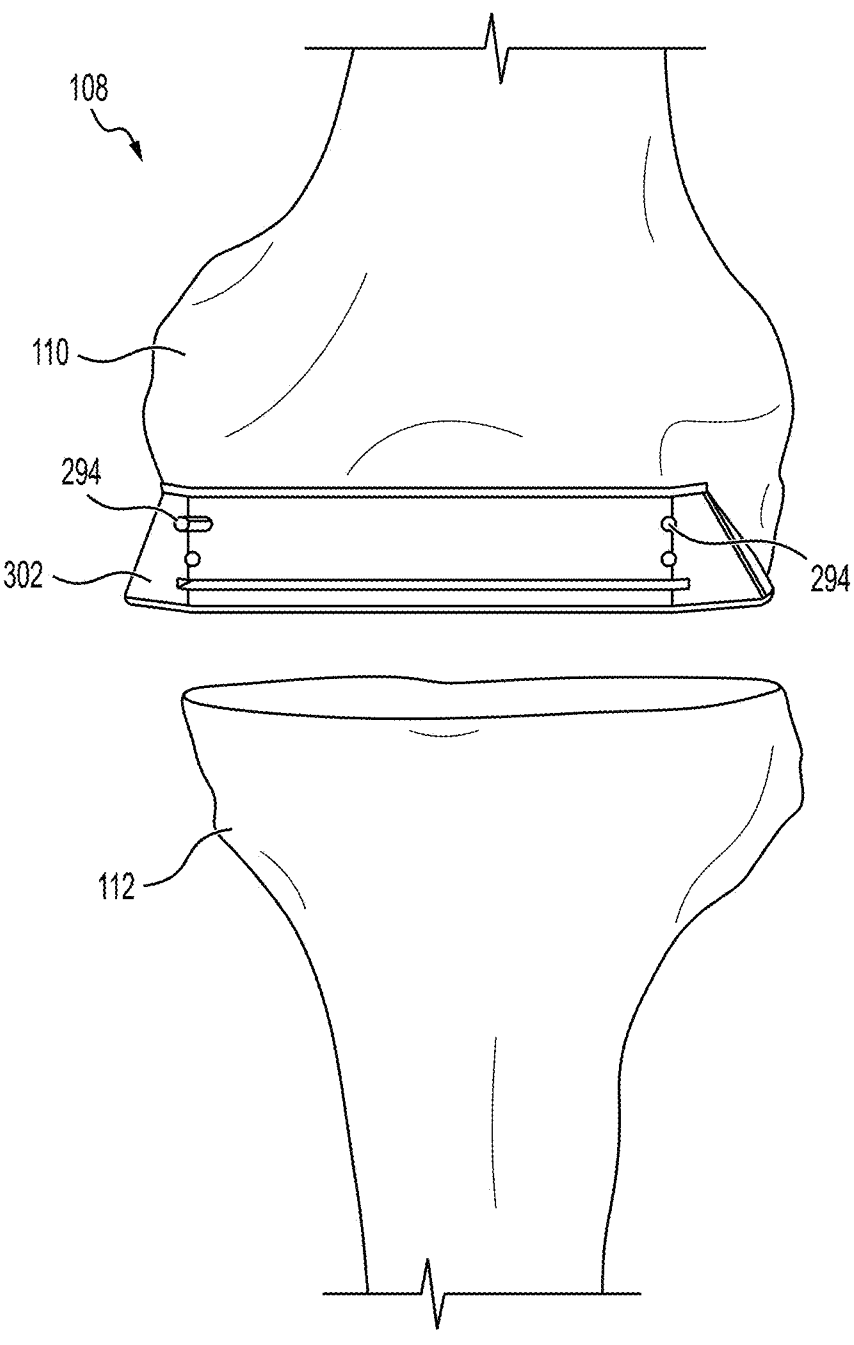
FIG. 26 is an anterior view of the knee with an example femoral extension cut guide installed.

FIG. 26 is an anterior view of the knee with an example femoral extension cut guide installed, according to at least some aspects of the present disclosure. Referring to FIGS. 25 and 26, a pair of bone pins 294 are inserted through the respective openings 232 of the pin guide 220 and secured within the drilled femoral cavities. Post bone pin 294 placement, the remining components may be removed (pin guides 220, paddles 200, vertical guides 192, tibial placement guide 160). Referring to FIG. 26, a femoral extension cut guide 302 is installed on the bone pins 294 in a manner similar to that described above.

Figure 27:
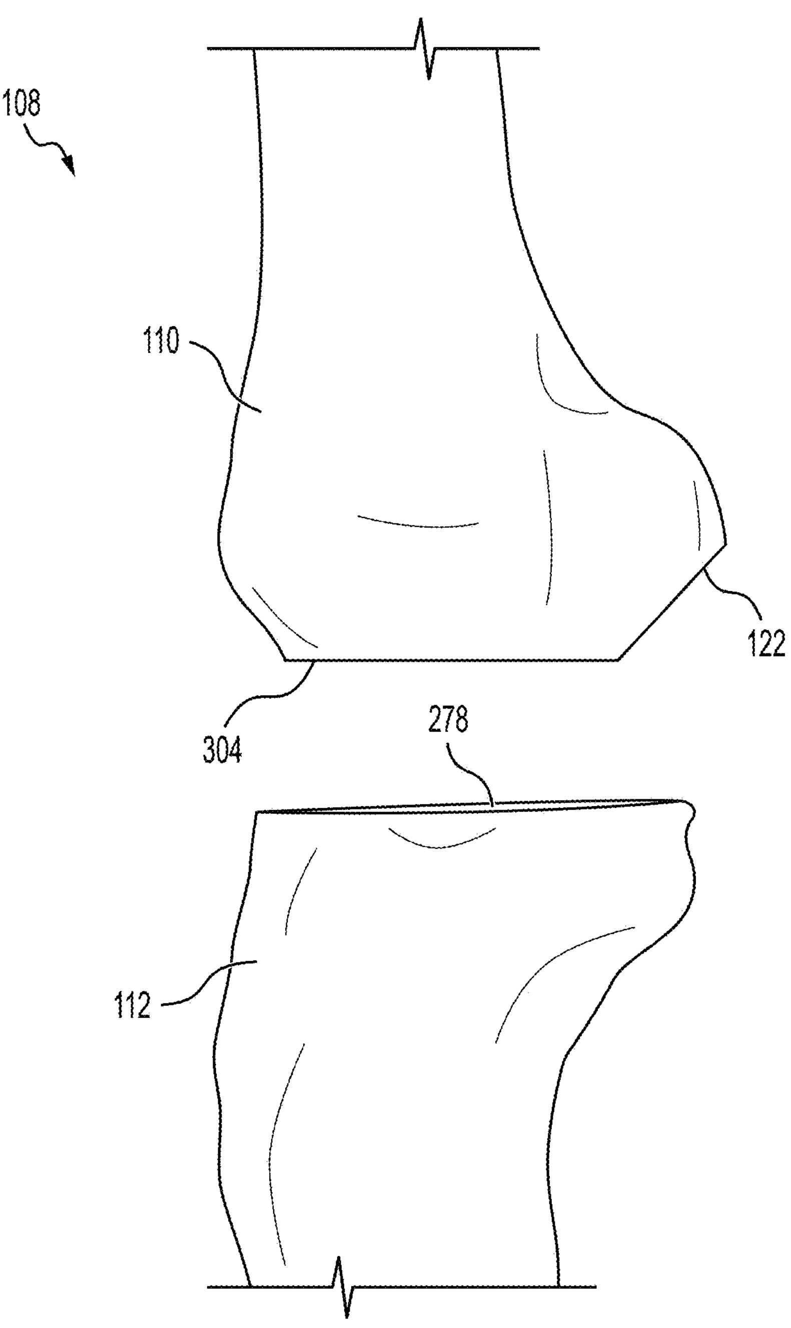
FIG. 27 is a lateral view of the knee showing the femoral extension cut, tibial plateau cut, and posterior chamfer cut.

FIG. 27 is a lateral view of the knee showing the femoral extension cut, tibial plateau cut, and posterior chamfer cut, according to at least some aspects of the present disclosure. The femoral extension cut 304 is made, resulting in the bone configuration shown in FIG. 27. As shown in the lateral view, the distal femoral cut 304 and the proximal tibial cut 278 may be substantially parallel and of known separation, which may result from use of the balancing jig 188 as described. In similar fashion, the posterior chamfer cut 122 and proximal tibial cut 278 have a substantially similar relationship. At this time, the surgeon performs femoral component sizing, which can be performed with anterior referencing or posterior referencing or a combination of both.

Figure 28:
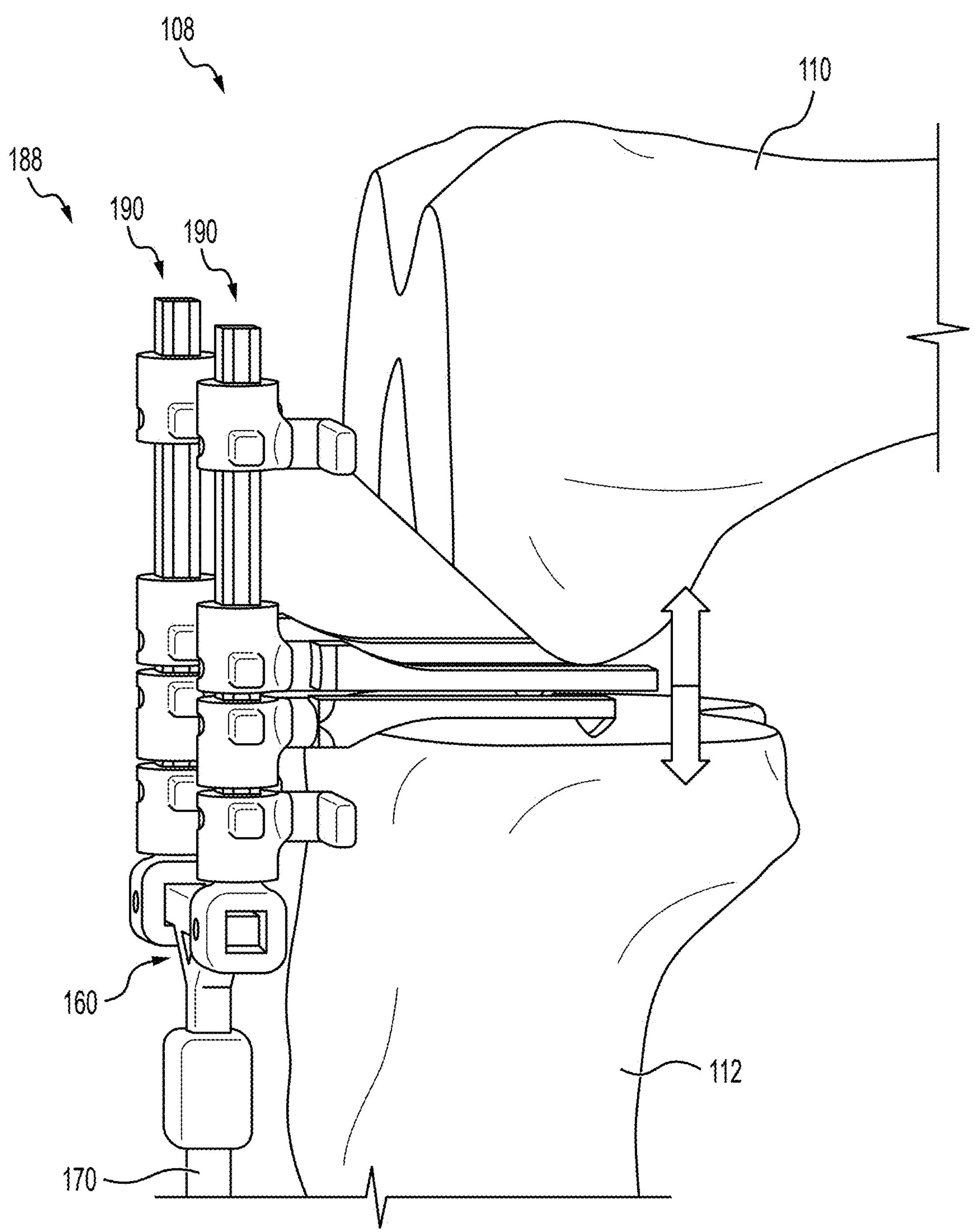
FIG. 28 is a perspective view of the knee balancing jig in use on the knee for posterior referencing.

FIG. 28 is a perspective view of the knee balancing jig in use on the knee for posterior referencing, according to at least some aspects of the present disclosure. Referring to FIG. 28, if posterior referencing is the choice, the knee is positioned at about 90 degrees of knee flexion, for example. Then, the knee is balanced as desired, such as by using the values derived between the chamfer cut and tibial cut and maintained for the femoral extension cut and tibial cut. Therefore, the same ligament lengths and tension and femoral tibial gaps may be maintained throughout the range of knee flexion. The femoral flexion cut location is determined, and the cut is made using a femoral cut guide mounted to bone pins in a manner similar to that described above.

Figure 29:
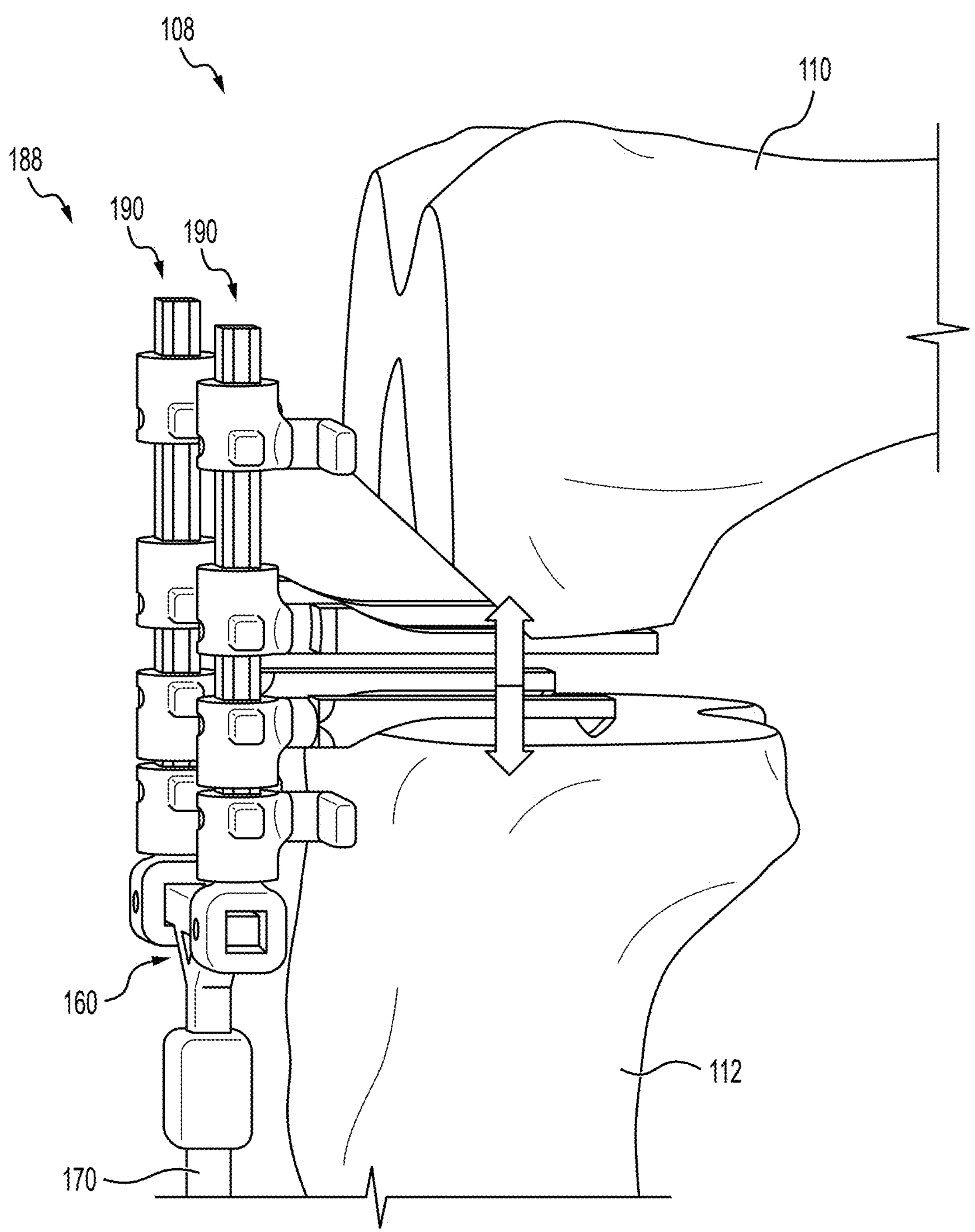
FIG. 29 is a perspective view of the knee balancing jig in use on the knee after the femoral flexion cut.

FIG. 29 is a perspective view of the knee balancing jig in use on the knee after the femoral flexion cut, according to at least some aspects of the present disclosure. Referring to FIG. 29, if desired, the balance of the knee can be confirmed using the balancing jig 188 in a manner similar to that described above. The femoral component is now sized and proper balancing is derived and maintained.

Figure 30:
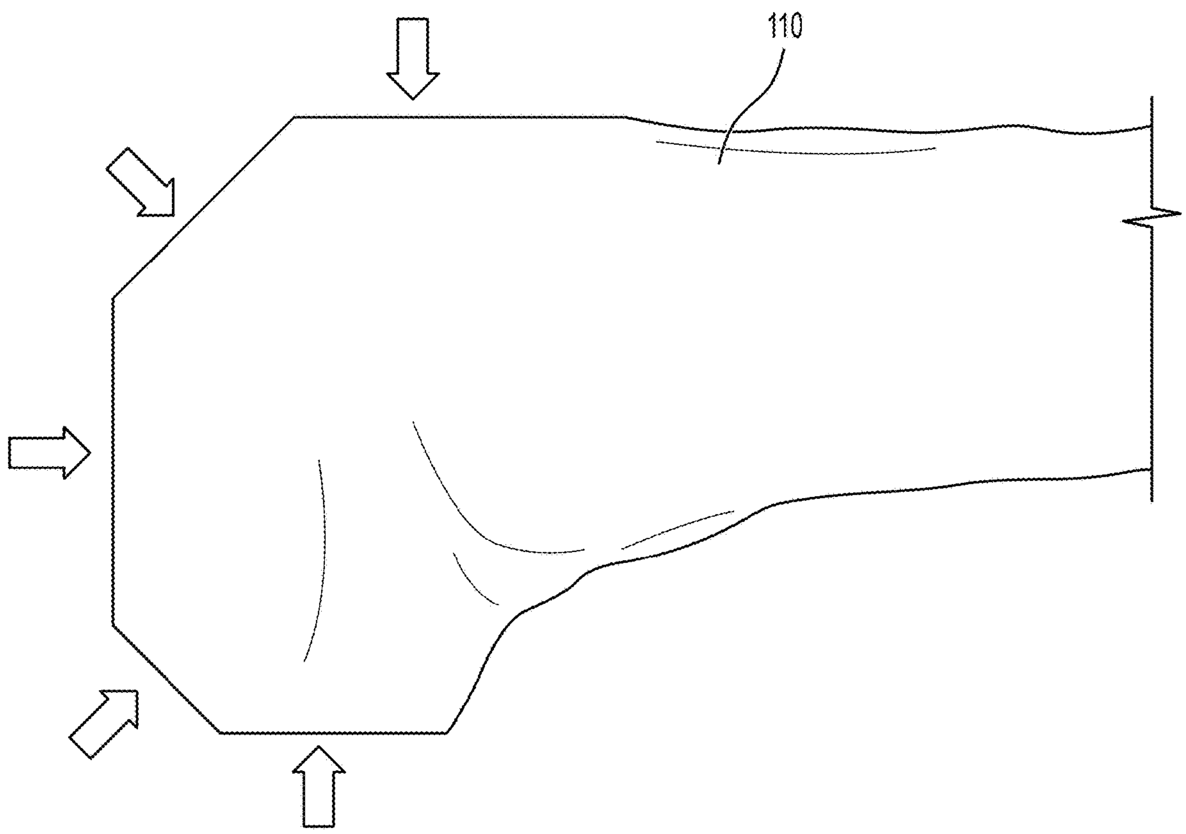
FIG. 30 is a lateral view of a distal femur showing various cuts in preparation for mounting of a femoral implant.

FIG. 30 is a lateral view of a distal femur showing various cuts in preparation for mounting of a femoral implant, according to at least some aspects of the present disclosure. Referring to FIG. 30, the remaining anterior and anterior chamfer cuts may be made, such as to fit a required implant size and/or configuration. In some example embodiments, the chosen manufacturer's femoral sizing guide may be positioned against the posterior femoral cut and posterior chamber cut and the size of the femoral component that will not result in notching of the distal femur may be selected. The manufacturer's cut guide may be positioned to be planar to the posterior femoral and distal femoral resections, and the anterior and anterior chamfer cuts may be made.

Figures 31A, 31B:
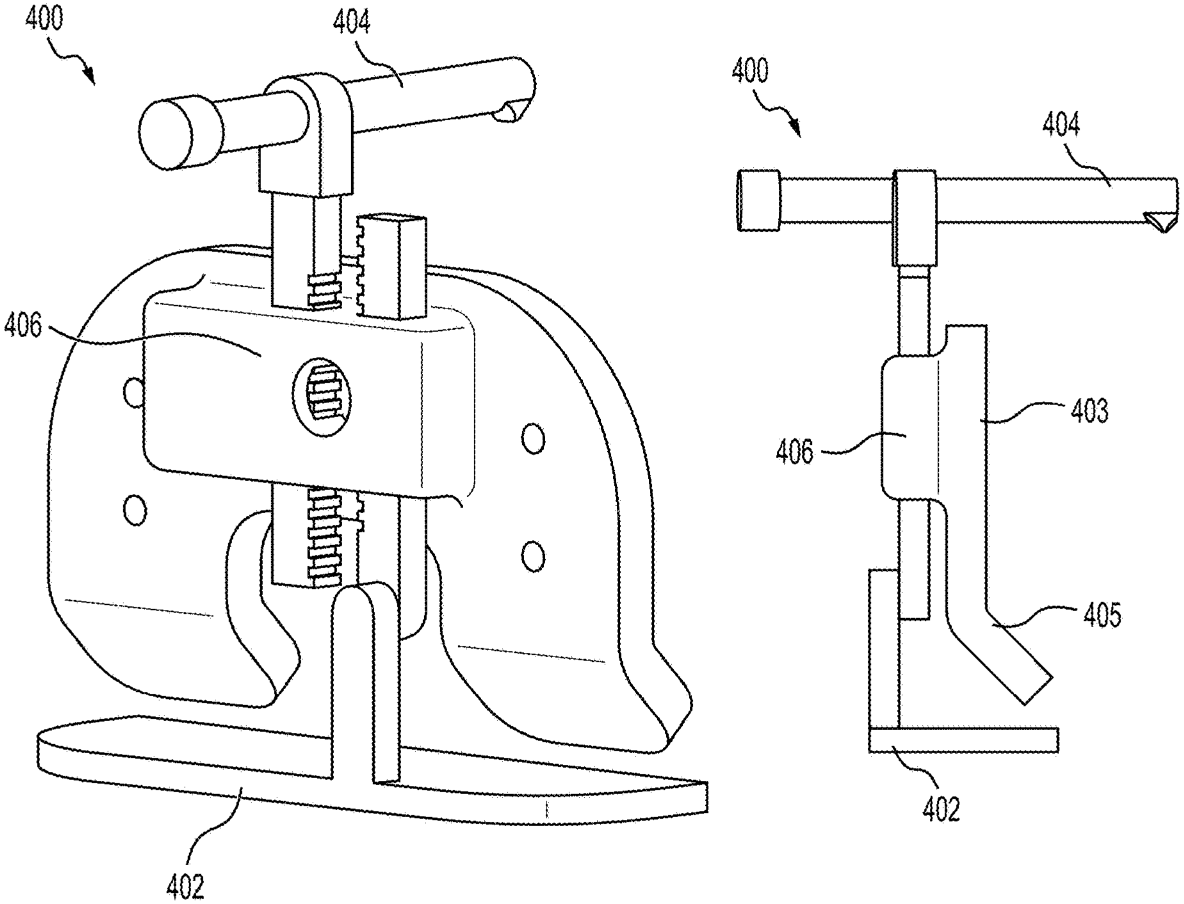
FIG. 31A is a perspective view of an example anterior reference guide.
FIG. 31B is a lateral view of the anterior reference guide.
Figure 32:
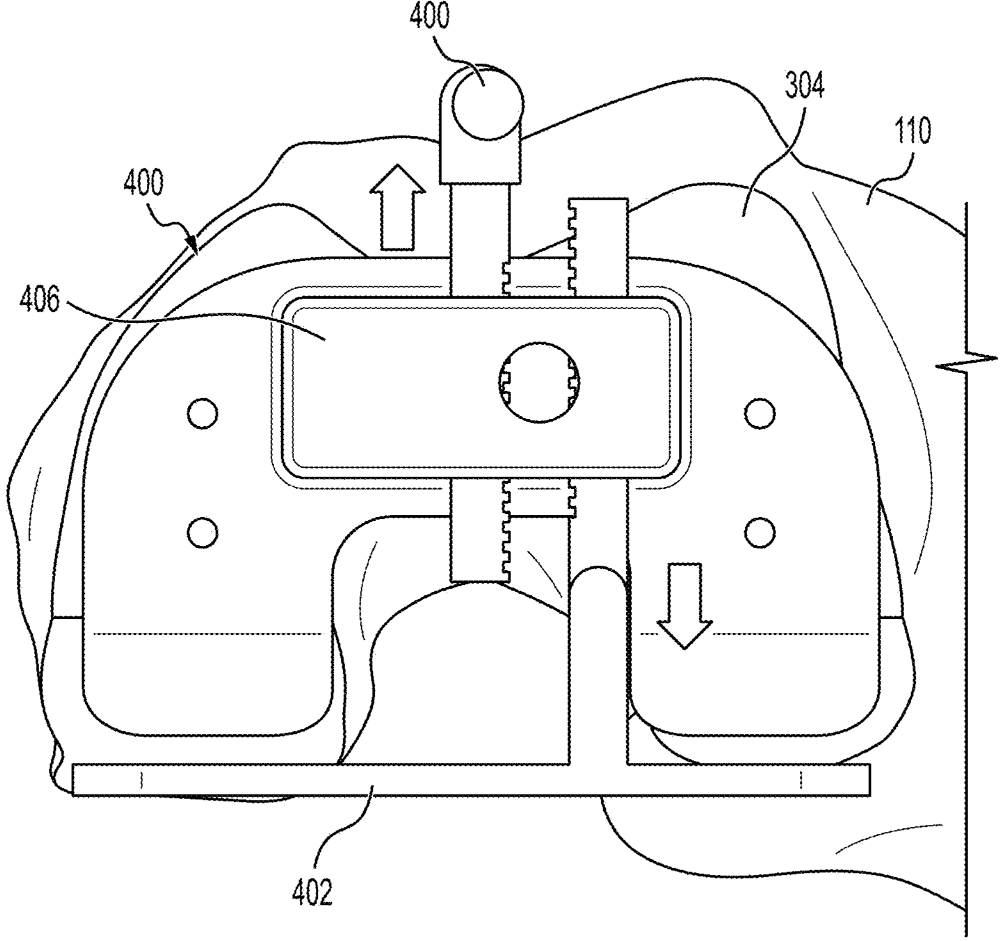
FIG. 32 is a distal view of the anterior reference guide in use on the femur.
Figure 33:
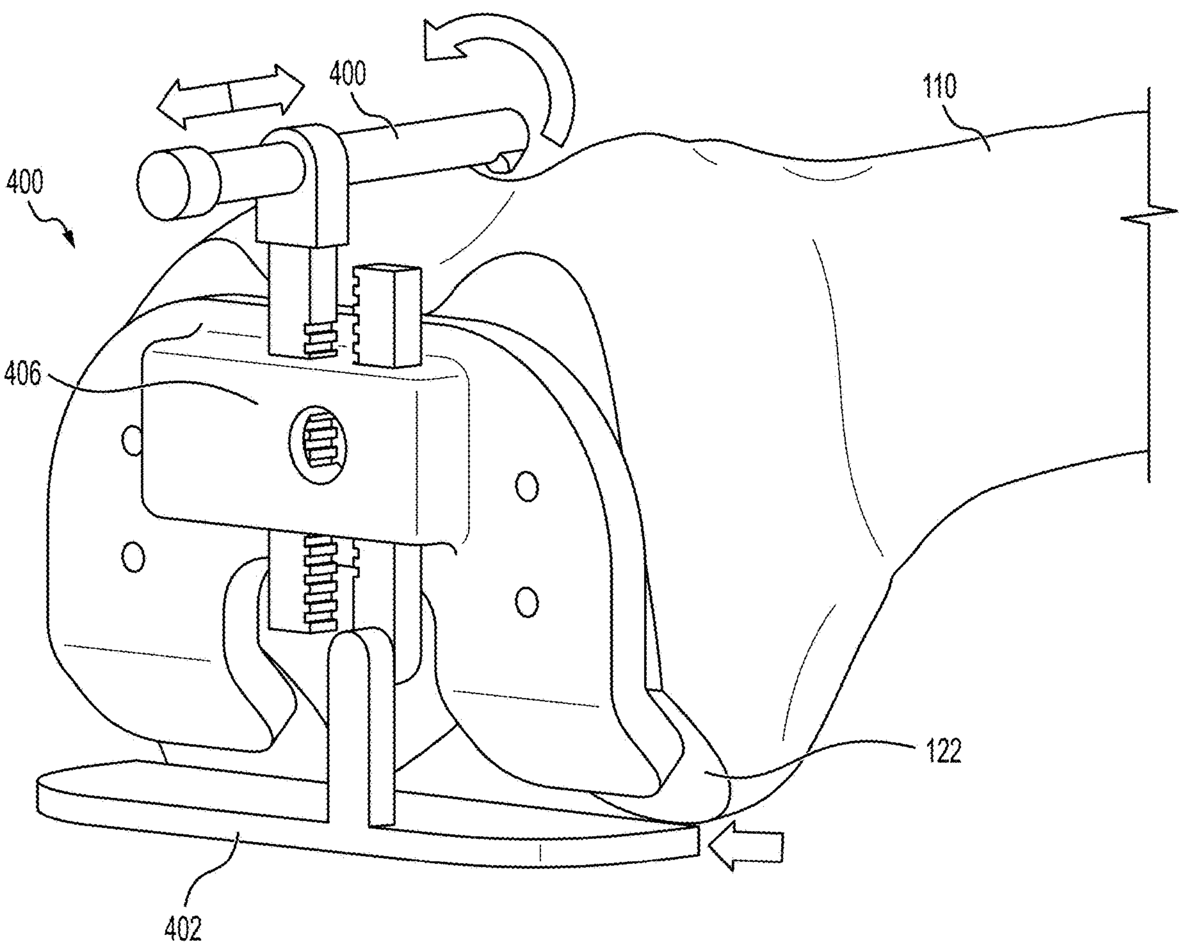
FIG. 33 is a perspective view of the anterior reference guide in use on the femur.

FIG. 31A is a perspective view of an example anterior reference guide, FIG. 31B is a lateral view of the anterior reference guide, FIG. 32 is a distal view of the anterior reference guide in use on the femur, and FIG. 33 is a perspective view of the anterior reference guide in use on the femur, all according to at least some aspects of the present disclosure. Referring to FIGS. 31A-33, if a surgeon chooses to utilize anterior referencing the following procedure may be used, such as with the knee positioned at 90 degrees of flexion. An anterior reference guide 400 with a posterior cutting plane indicator 402 is used for anterior referencing. A femoral extension cut contact surface 403 is placed against the femoral extension cut 304. Some embodiments may include a posterior chamfer cut contact surface 405, which may be placed against the posterior chamfer cut 122. An anterior stylus 404 is linked in the anterior/posterior direction with the posterior cutting plane indicator 402. As the anterior stylus 404 translates and sweeps to find the correct component size, the posterior indicator 402 will translate accordingly. For example, the guide 400 may include a mechanism 406 with opposed racks operatively connected by a rotatable pinon gear. Translation of one rack (e.g., which may be coupled to the anterior stylus 404) may cause rotation of the pinon, which may cause translation—in the opposite direction—of the other rack (e.g., which may be coupled to the posterior cutting plan indicator 402). The posterior indicator 402 shows the location of the posterior cutting plane. Once the guide 400 is properly positioned and the femoral component sized, the posterior femoral cut may be made (e.g., at 90 degrees).

Figure 34A:
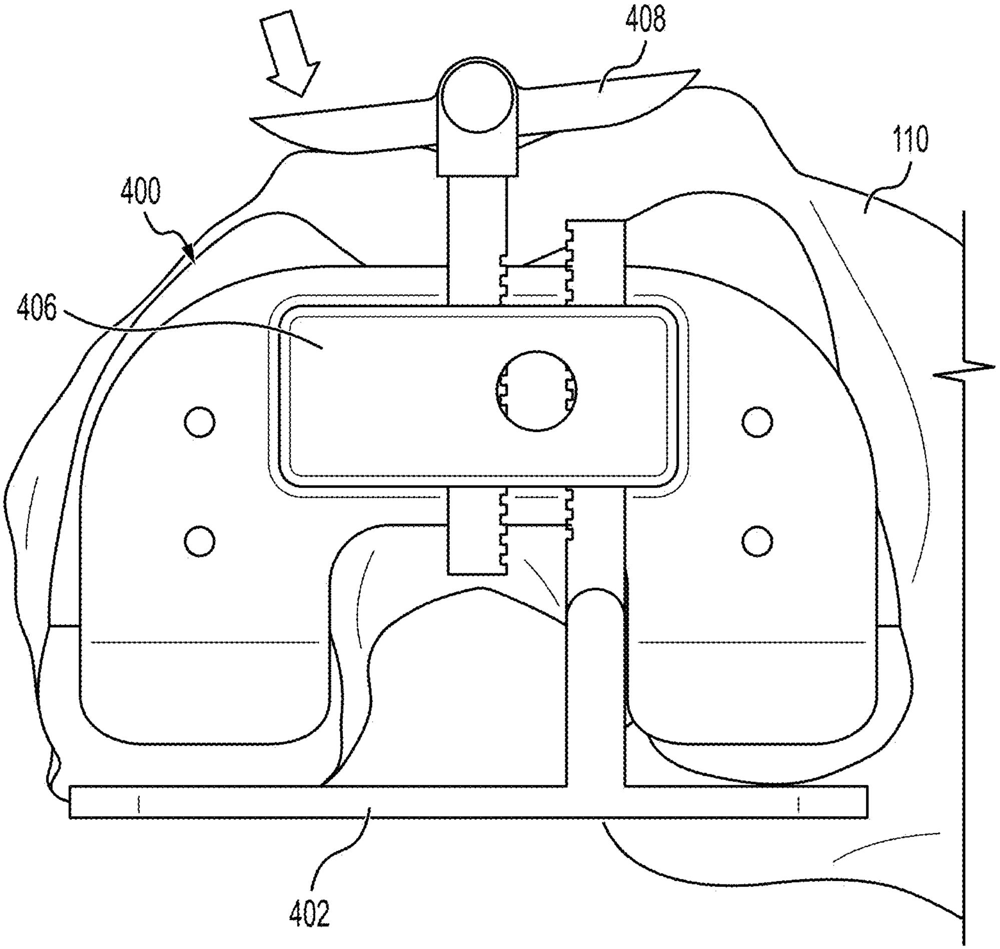
FIG. 34A is a distal view of the anterior reference guide including an alternative anterior stylus in use on the femur.
Figure 34B:
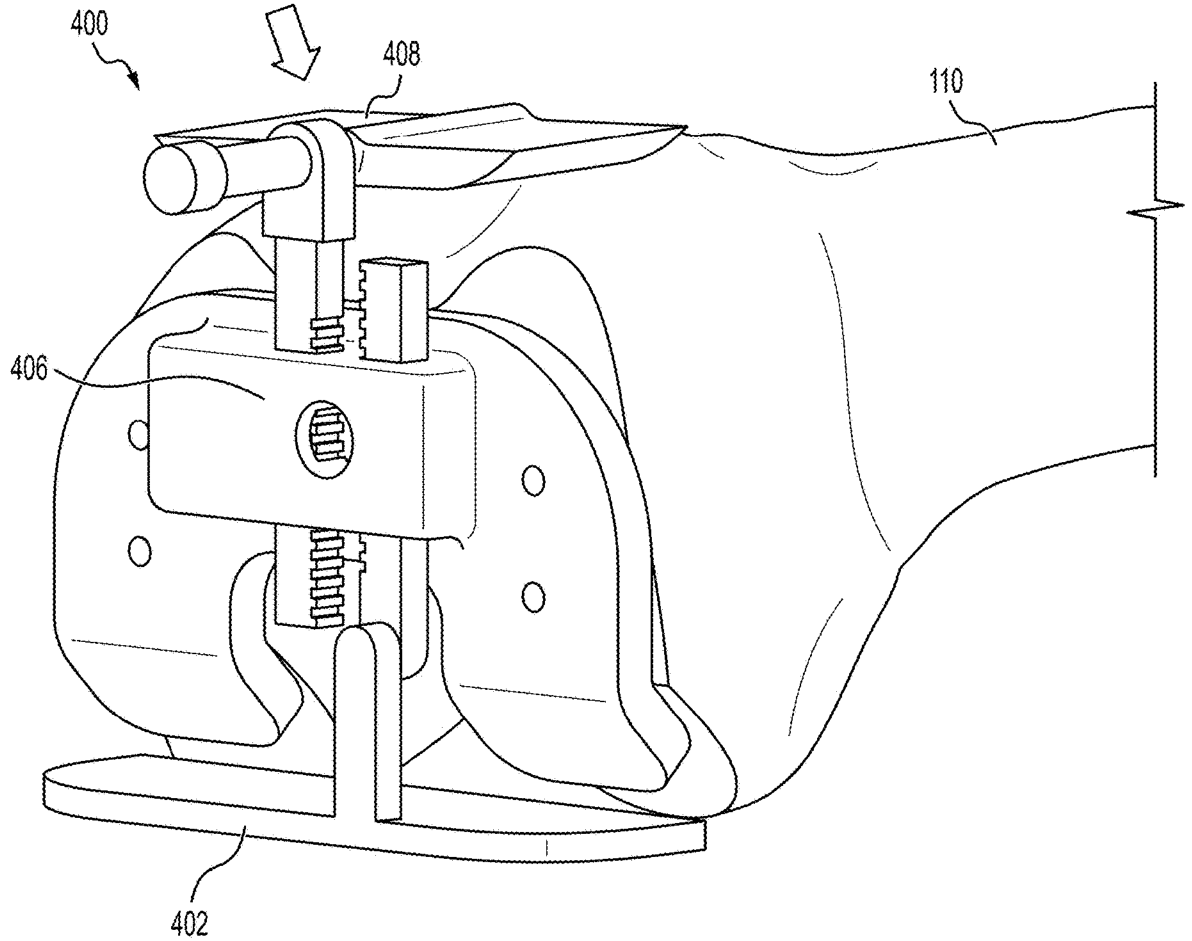
FIG. 34B is a perspective view of the anterior reference guide including the alternative anterior stylus in use on the femur.

FIG. 34A is a distal view of the anterior reference guide including an alternative anterior stylus in use on the femur, and FIG. 34B is a perspective view of the anterior reference guide including the alternative anterior stylus in use on the femur, all according to at least some aspects of the present disclosure. Referring to FIGS. 34A and 34B, alternative anterior styluses may be attached for alternative anterior referencing methods. In the illustrated embodiment, an alternative stylus 408 can be in the shape of a trough, spoon, or saucer, for example, and may be positioned in the trochlear groove. In some example methods, the shape of the trochlear groove may be derived using preoperative planning (such as using pre-operative imaging) and then this shape can be made into a patient-specific jig, which may be disposable. A patient-specific-shaped-jig may fit in the trochlear groove tightly and/or may minimize errors that may be introduced by use of a pointed stylus that could contact the trochlear groove in multiple positions. If it is not desirable to create a patient-specific, trough-like stylus using pre-operative imaging, multiple sizes and/or shapes of styluses may be provided, and such styluses could be disposable or re-used after sterilization.

Figure 35A:
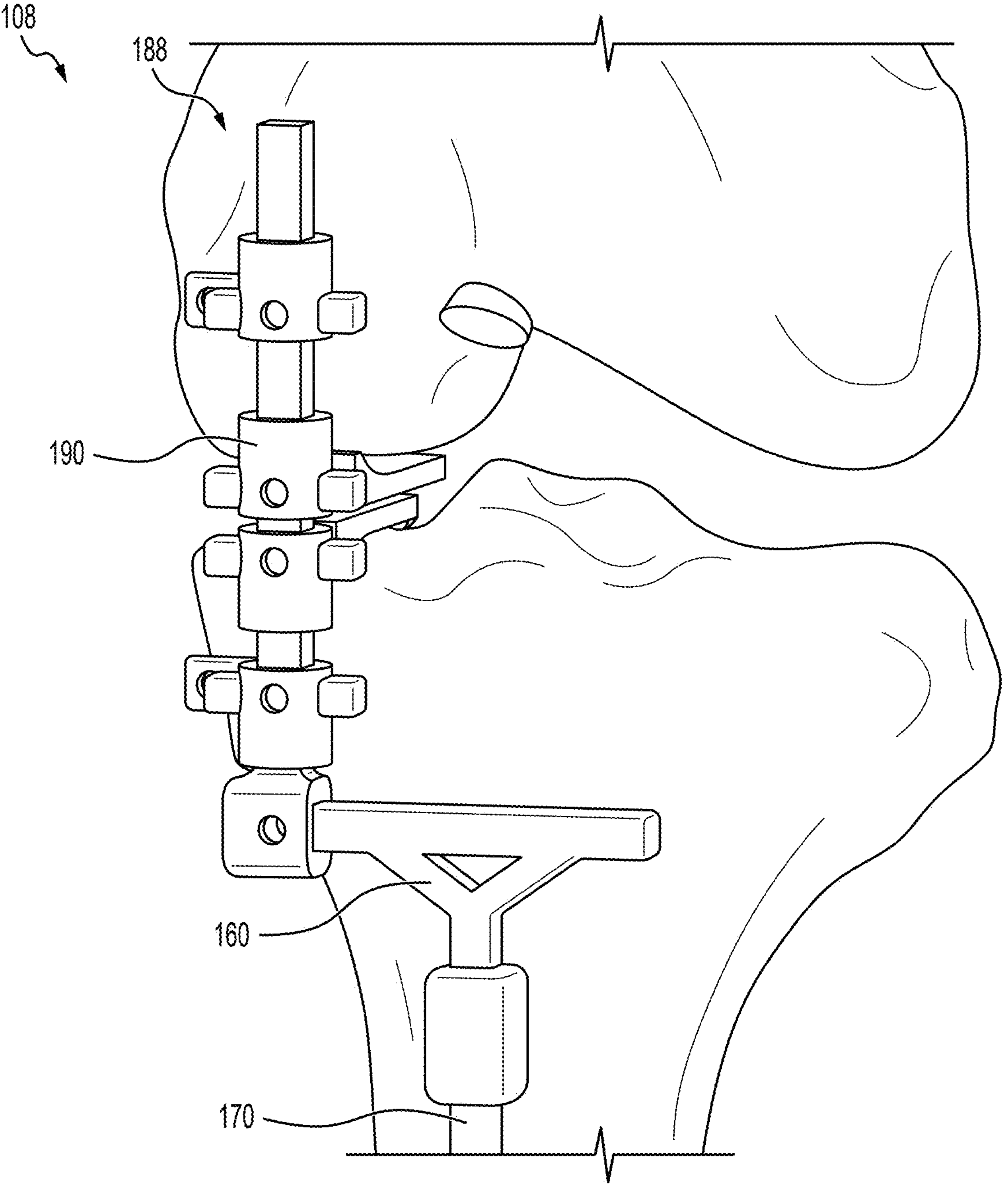
FIGS. 35A and 35B are perspective views illustrating unicompartmental use of the knee balancing jig.
Figure 35B:
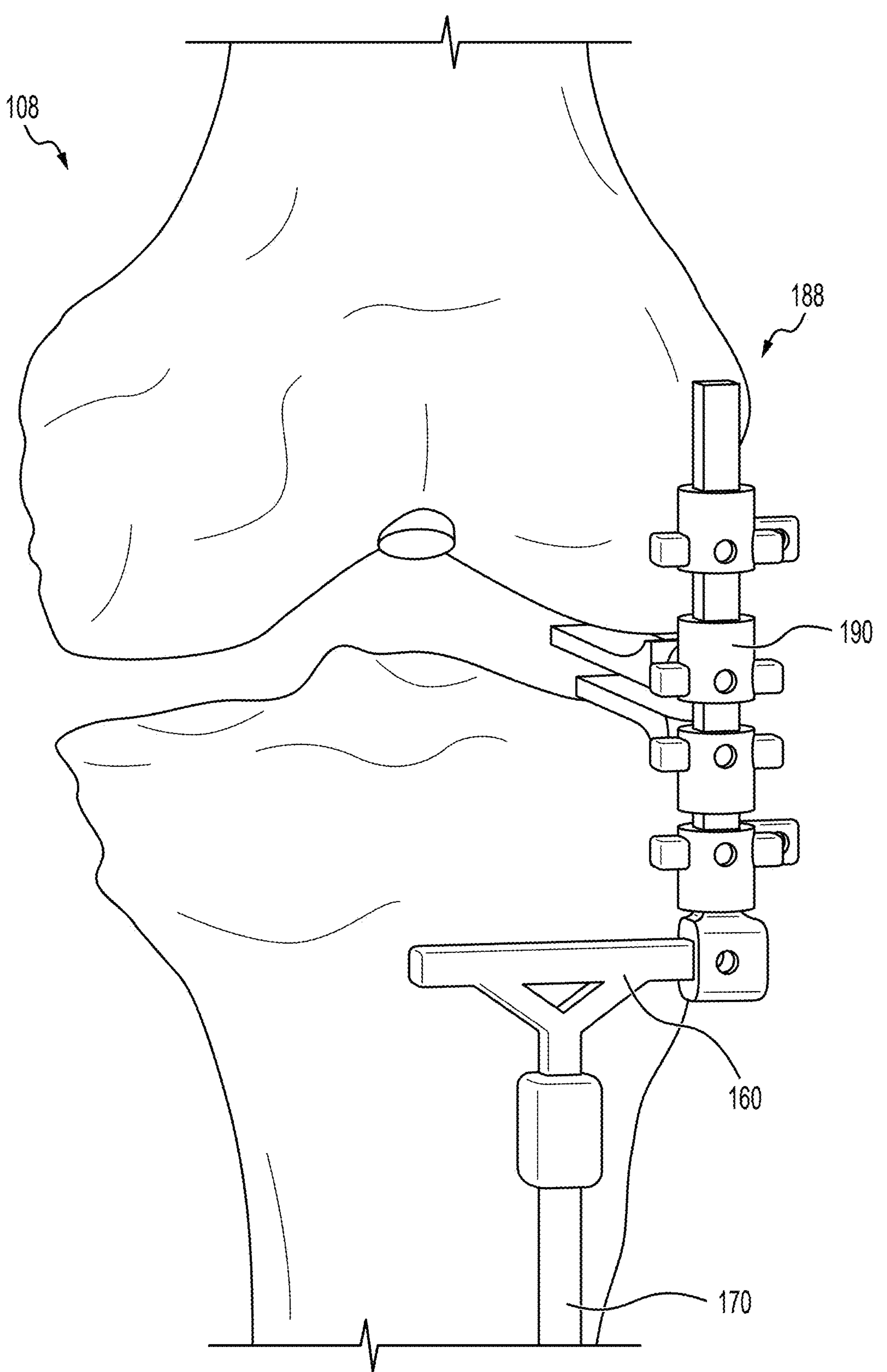

FIGS. 35A and 35B are perspective views illustrating unicompartmental use of the knee balancing jig 188. Generally, the balancing jig 188 may be used in a manner described above for TKA. However, in some circumstances, only one of the balancing assemblies 190 may be utilized in connection with the affected portion of the knee.

In some example embodiments according to at least some aspects of the present disclosure, the order in which bone cuts are made may include, without limitation, any of the following exemplary cut orders: (1) posterior chamfer cut, tibial cut, distal femoral cut, anterior chamfer and other cuts; (2) posterior chamfer cut, tibial cut, posterior femoral cut, anterior chamfer and other cuts; (3) tibial cut, posterior chamfer cut, distal femoral cut, anterior chamfer cut and other cuts; or (4) tibial cut, posterior chamfer cut, posterior femoral cut, anterior chamfer cut and other cuts.

Figure 37:
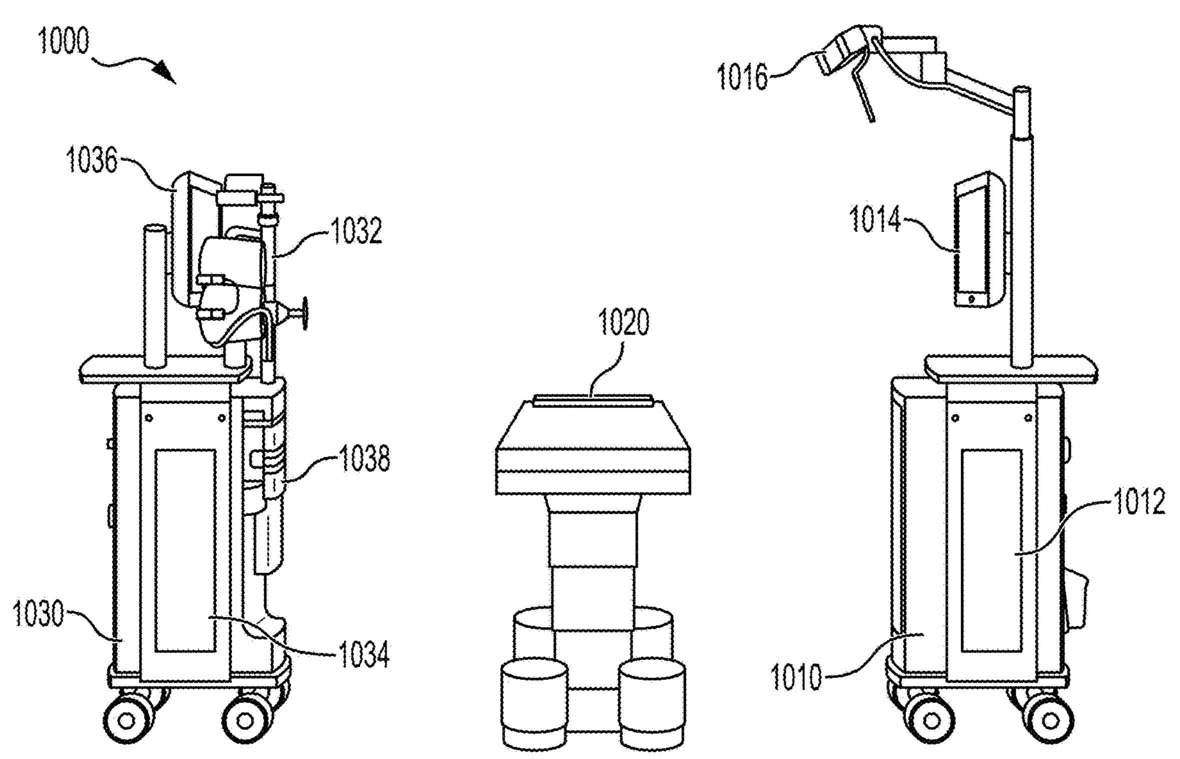
FIG. 37 is a schematic diagram showing components of an exemplary robotic system in accordance with the instant disclosure.

Referring to FIG. 37, it is within the scope of the present disclosure to make use of a robotic system 1000 to carry out a total knee arthroplasty procedure. In exemplary form, the robotic system includes a mobile primary controller 1010 having that includes an onboard computer 1012 and a user interface 1014 that may comprise a keyboard, mouse, and display, or may comprise a touchscreen display that incorporates the functionality of a keyboard, mouse, and display. In circumstances where the controller 1010 makes use of optical guidance, the controller may also include one or more cameras 1016 to capture images from an operating table 1020 upon which the patient is positioned during surgery and feed this information to the onboard computer 1012.

The robotic system 1000 may also include a mobile robot station 1030 that includes a surgical robot 1032, a robot controller 1034, a visual display 1036, and a tool carrier 1038. By way of example, the primary controller 1010 communicates wirelessly with the robot controller 1034 to provide instructions regarding the position of the robot 1032 relative to the one or more points of reference.

Figure 38:
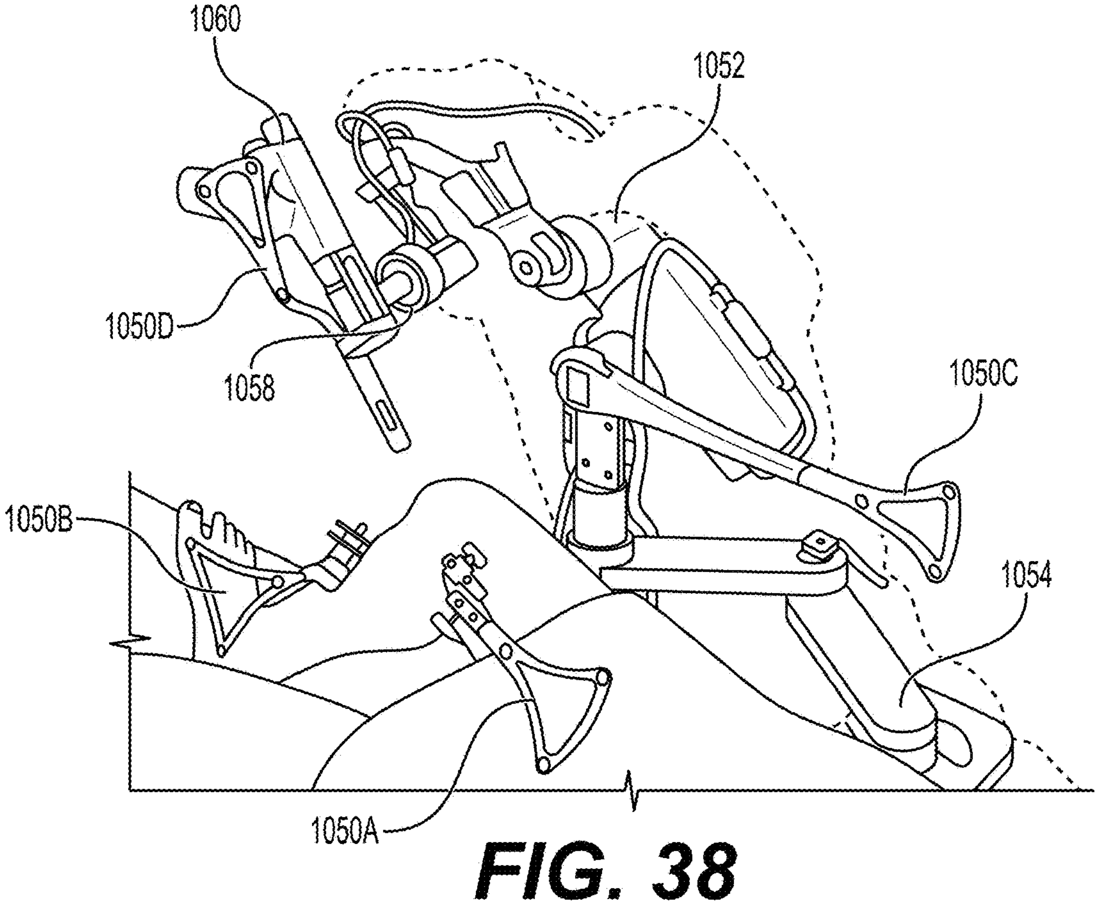
FIG. 38 is an elevated perspective view of a portion of the exemplary robotic system of FIG. 37 shown relative to a patient's knee on an operating table.

Turning to FIG. 38, the points of reference the camera(s) 1016 may utilize may include one or more optical tracking arrays 1050A-1050D having a series of optical markers positioned in a known, static arrangement. In this manner, as the camera(s) 1016 sequentially capture images having the optical tracking arrays 1050A, 1050B within the field of view, the camera images are fed to the primary controller programmed with a position tracking algorithm that analyzes each camera image and determines the relative motion of each tracking array. By way of further example, a first array 1050A may be mounted to the patient's femur, while a second array 1050B may be mounted to the patient's tibia. In this fashion, the primary controller 1010 is able to know the relative position of the femur with respect to the tibia and use this information as part of guiding the surgical robot 1032.

In exemplary form, the surgical robot 1032 may comprise a multi-axis robotic arm 1052 coupled to a manually repositionable multi-axis frame 1054 fixedly mounted to the operating table 1020 (see FIG. 37). The multi-axis frame 1054 is operative to stabilize the robotic arm 1052 and provide a fixed frame of reference as to the robotic arm and the operating table 1020. While there is no specific number of axes around which the robotic arm 1052 or the frame 1054 may be repositioned, in exemplary form, the robotic arm includes six axis freedom of motion, while the frame includes four axis freedom of motion. The surgical robot 1032 includes an end effector 1058 that couples to various pieces of surgical equipment 1060 that may be used during the surgical procedure including, without limitation, a surgical drill, a surgical saw, a surgical driver. These surgical instruments are stored for use via the tool carrier 1038 (see FIG. 37) and used as needed during the surgical procedure.

In order to know the relative positions of the surgical equipment 1060 and the frame 1054, each of these elements may include its own array 1050D, 1050C. In this fashion, as the camera(s) 1016 sequentially capture images having the optical tracking arrays 1050C, 1050D within the field of view, the camera images are fed to the primary controller programmed with a position tracking algorithm that analyzes each camera image and determines the relative motion of each tracking array. In this fashion, the primary controller 1010 is able to know the relative position of the surgical equipment 1060 with respect to the frame 1054. Likewise, the primary controller 1010 is able to know the relative position of the surgical equipment 1060 with respect to the tibia and femur using the respective arrays 1050A, 1050B mounted thereto.

Unlike current robotic systems, the instant robotic system 1000 does not rely on pre-operative or intra-operative imaging data of a patient's anatomy. Instead, as discussed in more detail hereafter, the robot controller 1034 identifies the position of the femur and tibia relative to the surgical equipment 1060 after the posterior chamber cut is initially made and performs the remaining bone cuts on the distal femur and proximal tibia exclusively off of registration from the posterior chamfer cut.

As discussed herein, exemplary methods have been described for how to properly balance a knee during a knee replacement surgery so that the knee more closely approximates kinematics of the patient's natural knee. More specifically, the exemplary methods disclosed herein concurrently address two primary problems in modern joint arthroplasty surgical procedures. The first of these problems is little to no femoral rotation as the tibia is flexed, resembling a simple hinge joint. A kinematically correct knee joint has the contact points of the femoral condyles changing anteriorly and posteriorly as a function of joint flexion angle, whereas a simple hinge joint does not. And a second of these problems is attaining and maintaining proper soft tissue tension of the joint envelope across nearly the full range of motion of a knee joint. Because present day orthopedic knees are balanced at full extension or 90 degrees of flexion, compromises are generally made that leave the joint envelope too loose or too tight at either end of this range of motion.

The advent of robotic surgical technology brings with it increased precision, but not necessarily better accuracy or natural kinematic replication. Conventional robotic surgical technology is heavily reliant on pre-operative imaging and creating pre-operative surgical plans that need to be registered from the virtual world into the real world. Many devices and options are available to perform anatomical registration to ensure pre-operative image data and accompanying 3D models are registered with the patient's actual anatomy. But in the context of total knee arthroplasty, those skilled in the art have misunderstood how to precisely use robotics, and undervalued making use of a vivo assessments by surgeons about anatomy that cannot be readily discerned or predicted from pre-operative data. Many experienced total knee arthroplasty surgeons feel that proper joint balancing is more artform than science. But by understanding what drives kinematics of a natural knee, as well as understanding how the patient's retained anatomy is predisposed to move, the inventors have greatly simplified what is necessary to surgically prepare a patient's anatomy to receive an orthopedic knee implant that maximizes the effectiveness of the knee implant. And in so doing, the inventors have greatly simplified the resulting surgical procedure and truly make appropriate use of a robot's precision.

Figure 39:
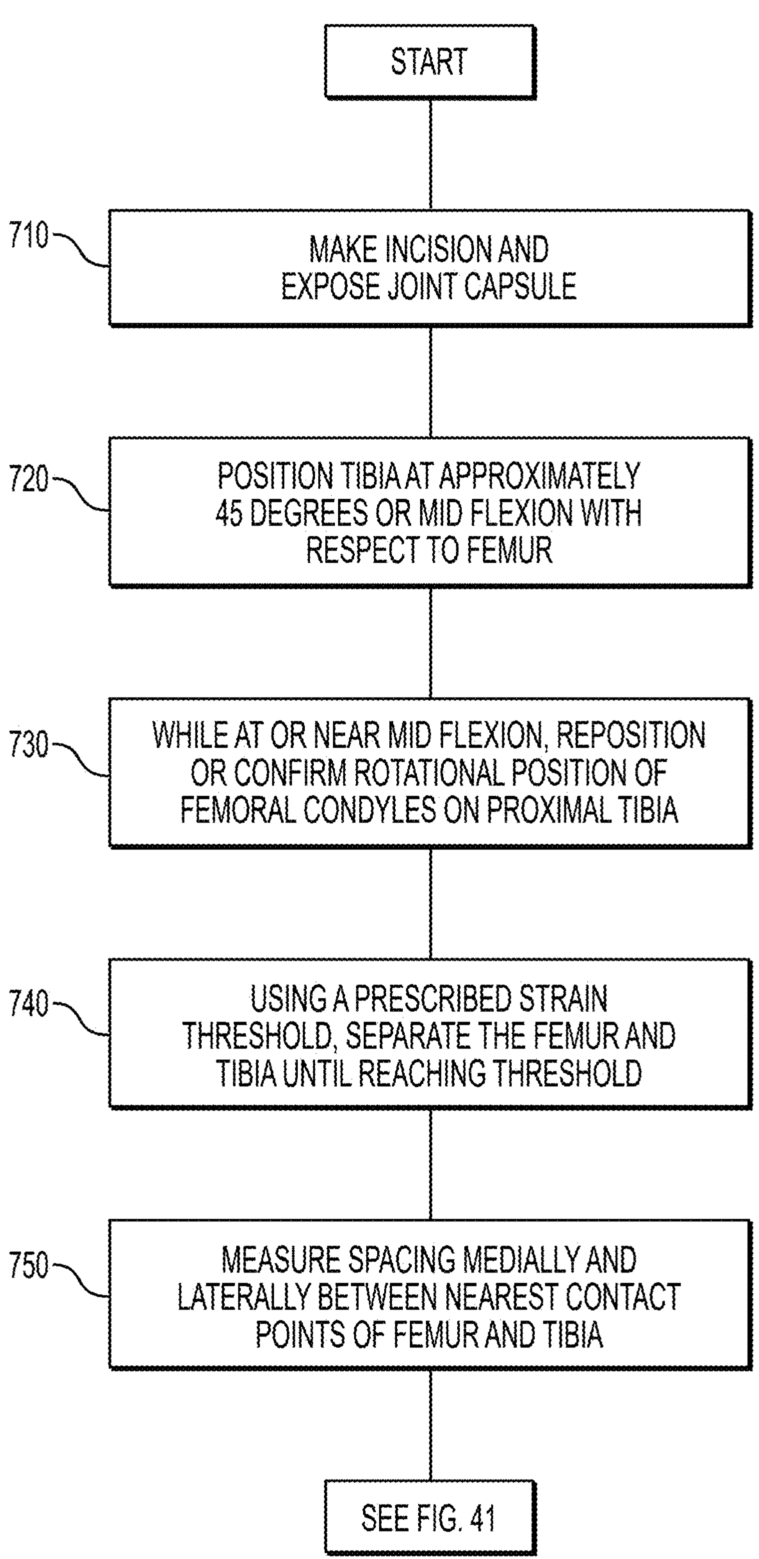
FIG. 39 is a first portion of an exemplary process flow for carrying out a total knee arthroplasty procedure in accordance with the instant disclosure.

Referring to FIG. 39, an exemplary process flow will be discussed in the context of a total knee arthroplasty. Those skilled in the art will understand that this process flow is equally adaptable to partial knee replacement and other joint replacements where soft tissue envelop balancing is relevant. As an initial step 710, the surgeon will make an incision at the front of a joint (in this case, the knee joint) and remove any soft tissues necessary to expose the joint capsule (in this case, removal of the patella in order to expose the knee capsule). Thereafter, the surgeon may excise one or more other soft tissues including, but not limited to, the cruciate ligaments, depending upon the orthopedic implant chosen (cruciate retaining versus cruciate sacrificing). After exposing the joint capsule, the surgeon may optionally address any osteophytes that would not otherwise be resected via the cuts to the bones (in this case, the distal femur and proximal tibia) in preparation for receiving the implant components.

Thereafter, in the context of a knee joint, the surgeon positions or flexes the tibia with respect to the femur at step 720 so that the tibia is at a mid-flexion angle or one that kinematically approximates mid-flexion. By way of example, this mid-flexion angle may be generally between 30 degrees of flexion and about 60 degrees of flexion, with angles more closely approximating or equaling 45 degrees also considered mid-flexion.

While at mid-flexion, the surgeon also performs a step 730 confirming the rotational position of the femoral condyles with respect to the proximal tibia. By way of example, the surgeon may utilize the positioning template 191 to align dwell points on the femoral condyles (medial and lateral) to overlap with the proximal tibia approximate the anterior-posterior midline or slightly posterior thereof. In this step, dwell point refers to the most distal point on the medial femoral condyle and lateral femoral condyle, respectively, and the most proximal point on the medial tibial condyle receiver and the lateral tibial condyle receiver, respectively, at mid-flexion when the joint is balanced in proper tension. Said another way, the dwell points of the medial and lateral femoral condyles and the medial and lateral tibial condyle receivers are the respective points that minimize the straight-line distance between the distal femur and proximal tibia at mid-flexion when the knee joint is soft tissue balanced to exhibit the correct strain (not too tight, not too loose). While not required, one may utilize the exemplary embodiments disclosed herein including, without limitation, the femoral placement guide 140 and the intramedullary rod 134 to stabilize the position of the distal femur 110 with respect to the proximal tibia 112 (see FIG. 8).

While at mid-flexion and ensuring the proper rotational position of the femur with respect to the tibia, the surgeon carries out step 740 and uses an expansion device, optionally such as those disclosed herein (including, without limitation, 600, 600A, 600B), inserted between the femur and tibia (one on the medial side and a second on the lateral side) to measure a straight-line distance (referred to herein also as the "gap") between the dwell points of the femur and tibia on both the medial and lateral sides. It should be noted that the expansion devices may also be used with the paddles 200, 200A and other exemplary structures disclosed herein to facilitate measuring of the straight-line distances between the femur and tibia on the medial and lateral sides at mid-flexion when the joint is soft tissue balanced. In order to determine the straight-line distance between the dwell points, each expansion device may include an appropriate measurement indicium to discern the overall height of the expansion device at any given time, where the height changes to fill this straight-line distance between the dwell points (presuming some gap exists on at least one of the medial side and the lateral side). By way of further example, one or two expansion devices are, respectively for each condyle if a gap exists, increased in height by inputting stresses until the ratio of stress to strain markedly increases. Said another way, one or both expansion devices are respectively increased in height until the anticipated change in height (increasing the spacing between the distal femur and proximal tibia) of a respective expansion device falls short of an expected incremental height change that would be expected but for the joint being at or above the appropriate soft tissue tension.

Explained differently, each expansion device allows for incremental changes in height resulting from an input stress (the maximum of which may be limited). Given a particular expansion device, a relationship is known between input forces and anticipated changes in height. When the joint is in a loose arrangement, the joint provides relatively little resistance to increasing height of the expansion device, which is evidenced by ratios of stress to stain that stay the same, decrease, or increase slightly. During early expansion of the expansion device and little soft tissue resistance to expansion, continuing to apply stress to the expansion device causes generally constant increases in height and continued changes in strain where the ratio is not significantly changed. But as the joint goes from loose to being progressively tighter, and as the gap between the femur and tibia is occupied by the expansion device, the amount of strain will decrease as the connective tissue provides more resistance to continued expansion of the expansion device so that a given stress results in less height achieved (or to achieve this height, a greater stress is necessary). Said differently, if applied stress was fixed and continuously applied, the expansion device would eventually see decreased changes in distance as a function of time, resulting in the rate of change of the strain decreasing. Eventually, if the stress was insufficient to overcome the resistance from the soft tissue envelope of the joint, no height change would occur with the expansion device, evidenced by a rate of change in strain of zero. Conversely, if the stress applied to the expansion device was increased, but the change in height of the expansion device did not proportionally increase with this increased stress, then the ratio of stress to strain would markedly increase and be indicative of a properly tensioned knee joint.

Unlike prior art joint balancing devices and methods that purport to monitor the force applied between the tibia and femur at full extension or at 90 degrees of flexion, and considered the joint balanced when a particular force threshold pushing the femur and tibia apart had been achieved, the instant method is not driven by measurements of forces. Instead, the methods disclosed herein as part of joint balancing at mid-flexion and balancing of the joint at other angles of flexion (including full extension) may be concerned with strain and, specifically, with the rate of change of strain as a function of stress. When the rate of change in strain for each medial and lateral side, having a distance measured as the straight-line distance between the dwell points of the femur and tibia, markedly decreases and the stress has not markedly decreased, the maximum straight-line distance between the femur and tibia has been achieved for that side and the joint is appropriately balanced as to that side. In other words, the forces acting on the expansion device may be constant or changing/changed, but what may be the focal point is the rate of change in strain as a function of input stress to the expansion device. When the rate of change in strain markedly decreases on the medial side and the stress input on the medial side has not proportionally decreased, then this condition is indicative of a properly balanced joint on the medial side. The same can be said for the lateral side when the rate of change in strain markedly decreases and the stress input on the lateral side has not proportionally decreased, thus being indicative of a properly balanced joint on the lateral side. But this opens the question about whether active measurement of forces is required to balance a joint in accordance with the instant disclosure. The answer is that active measurement of forces is not required to balance a joint in accordance with the instant disclosure.

FIGS. 40A-40F depict curves reflecting how actual changes in incremental length of expansion devices on the medial side and lateral side, respectively, of a knee joint changes as a function of overall anticipated gap length on that respective side during a soft tissue balance in accordance with the instant disclosure. In accordance with the instant disclosure, each expansion device may provide for predetermined incremental changes in height/length. And these predetermined incremental changes in height may vary across expansion devices. For example, a first expansion device may be configured to have height adjustments in 1.0-millimeter increments given a known applied force, while a second expansion device may have height adjustments in 0.5-millimeter increments given a known applied force, and a third expansion device may have height adjustments in 0.1-millimeter increments given a known applied force, and so on. In this manner, it is anticipated that multiple expansion devices may be used during a single knee joint balancing for one or both of the medial and lateral sides (including where only one side may be an issue such as during a unicompartmental or partial knee replacement) to achieve whatever level of soft tissue balance fine tuning a surgeon desires.

For example, it is anticipated that a surgeon could use one or a pair of first expansion devices having height adjustability in 1.0-millimeter increments given a known applied force. In this fashion, the first expansion device is anticipated to output successive 1.0 millimeter increases in height upon input of a predetermined force to mechanically reposition the expansion device. It should be noted that this predetermined force need not be static across the entire range of motion of the first expansion device. Instead, as the first expansion device increases in height, it is within the scope of the disclosure that the required force needed to continue increasing the height of the expansion device may change, such as requiring increasing forces to achieve the same incremental height change or requiring decreasing forces to achieve the same incremental height change. Any changes in force needed to continue increasing the height of the first expansion device to achieve the same incremental height change are predetermined and accounted for as part of increasing the height of the explanation device. In this fashion, the first expansion device does not have predetermined height steps per se (meaning the expansion device can take on heights between the millimeter increments, not just fixed positions at 1.0 millimeter, 2.0 millimeters, etc.), but instead provides for a predetermined continuum of height changes so that when the input force is counteracted by tension forces of a properly balanced knee joint, the change in height will be less than 1.0 millimeter. Accordingly, when successive 1.0 millimeter changes in height are described with respect to the first exemplary expansion device, it should be understood that these changes in height are not rigid step changes jumping in successive 1.0 millimeter increments, but are instead continuum changes that are evaluated at 1.0 millimeter increments to see whether the anticipated height change given a known input force matches the actual height change of the expansion device. And a similar explanation applies to the other expansion devices when described as having height adjustability in certain predetermined increments.

In exemplary form, the surgeon may insert the first expansion device in between the dwell points of the distal femoral medial condyle and the proximal tibial medial condyle receiver, presuming at least a 1.0-millimeter gap exists between the dwell points. If a 1.0-millimeter gap is not present, but at least a 0.5-millimeter gap is present, the surgeon may begin by inserting a second expansion device having height adjustability in 0.5-millimeter increments. Similarly, if a gap between the dwell points is at least 0.1 millimeters, but not at least 0.5 millimeters, the surgeon may begin by inserting a third expansion device having height adjustability in 0.1-millimeter increments. For purposes of explanation only, it will be presumed that at least a 1.0-millimeter gap exists and the surgeon inserts the first expansion device having 1.0-millimeter height increments. And a similar approach applies to the dwell points of the distal femoral lateral condyle and the proximal tibial lateral condyle receiver to determine which expansion device is appropriate.

Figure 40A:
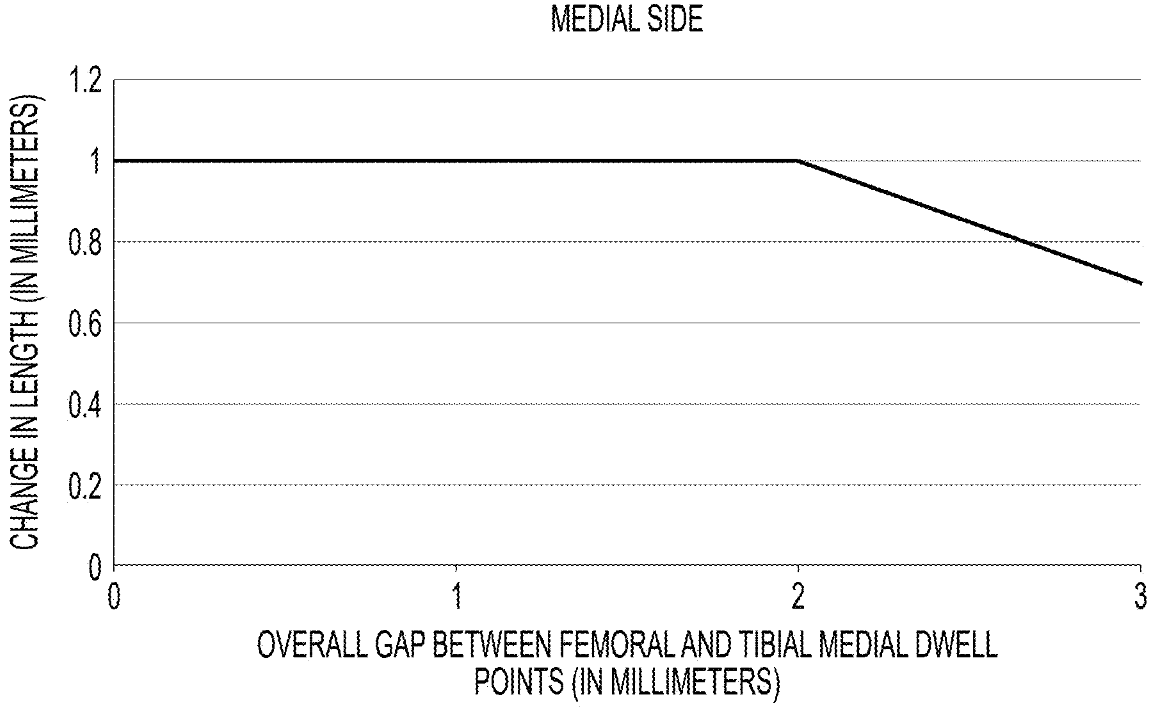
FIG. 40A represents an exemplary curve reflecting how actual changes in gap length on the medial side of a knee joint changes as a function of overall anticipated gap length on the medial side during a soft tissue balance using an exemplary expansion device in accordance with the instant disclosure when using a first expansion device.
Figure 40B:
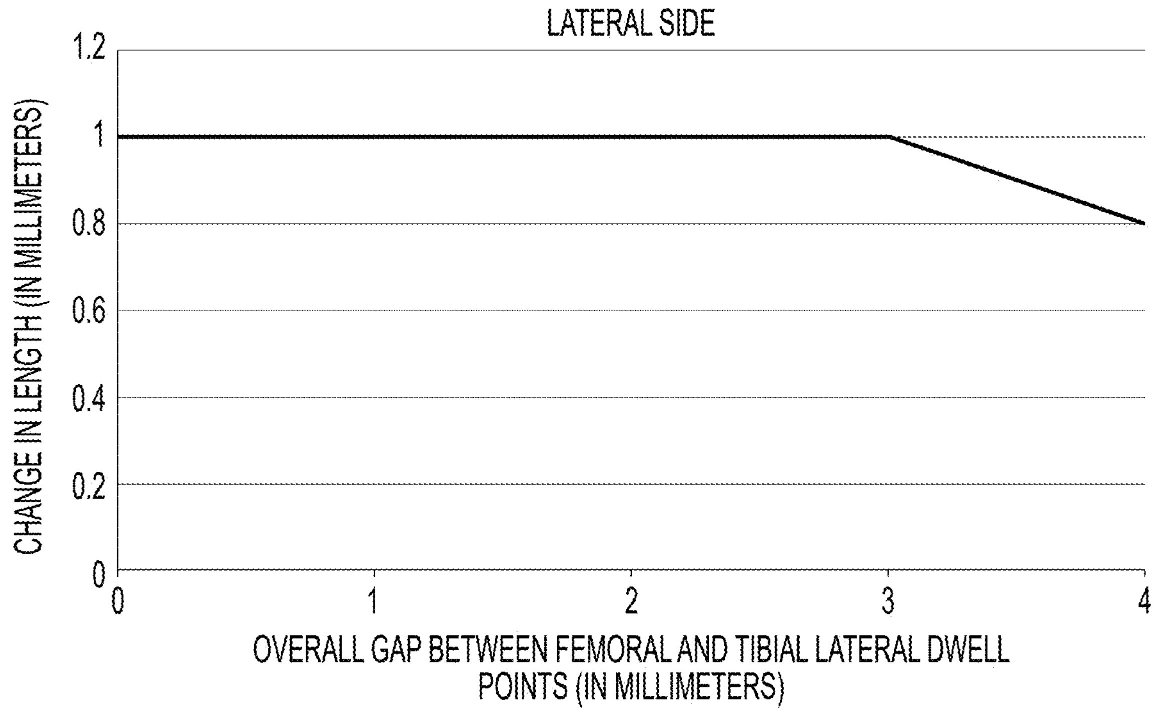
FIG. 40B represents an exemplary curve reflecting how actual gap length on the lateral side of a knee joint changes as a function of overall anticipated gap length on the lateral side during a soft tissue balance using an exemplary expansion device in accordance with the instant disclosure when using a first expansion device.

Referring to FIGS. 40A and 40B, respective first expansion devices are inserted on the medial and lateral sides between the dwell points, at or near mid-flexion and with the rotational position of the femur tracking the appropriate mid-flexion position for kinematic purposes as disclosed herein. Forces are applied to the first expansion devices to cause height increases in order to fill the gaps between the tibia and femur on the medial and lateral sides.

Referring specifically to FIG. 40A, on the medial side, the applied force causes the first expansion device to be repositioned from 1.0 millimeter to 2.0 millimeters. This match between the anticipated height change of 1.0 millimeter for the expansion device and the actual height change of the expansion device means the medial side of the joint is not over-tensioned. Accordingly, the surgeon applies additional force to the first expansion device to cause a further height increase in order to fill the gap between the tibia and femur. Again, on the medial side, the applied force causes the first expansion device to be repositioned from 2.0 millimeter to 2.7 millimeters. Because the actual height change of the expansion device (0.7 millimeters) did not match the 1.0-millimeter height increase anticipated, the surgeon realizes that the joint is properly tensioned on the medial side at a gap between 2.0 millimeters to 3.0 millimeters. In some circumstances, the surgeon may feel the tension of the joint at a gap of 2.0 millimeters is appropriate and discontinue use of further expansion devices. But other surgeons may feel that greater precision is helpful to find a more precise gap between 2.0 millimeters and 3.0 millimeters for proper medial side soft tissue balancing. In such a case, the surgeon may remove the first expansion device and replace it with the second expansion device.

Referring specifically to FIG. 40B, on the lateral side, the applied force causes the first expansion device to be repositioned from 1.0 millimeter to 2.0 millimeters. This match between the anticipated height change of 1.0 millimeter for the expansion device and the actual height change of the expansion device means the lateral side of the joint is not over-tensioned. Accordingly, the surgeon applies additional force to the first expansion device to cause a further height increase in order to fill the gap between the tibia and femur on the lateral side. Again, the applied force causes the first expansion device to be repositioned from 2.0 millimeters to 3.0 millimeters. Again, this match between the anticipated height change of 1.0 millimeter for the expansion device and the actual height change of the expansion device (now at 3.0 millimeters) means the lateral side of the joint is not over-tensioned. Therefore, the surgeon applies additional force to the first expansion device to cause a still further height increase in order to fill the gap between the tibia and femur on the lateral side. This applied force causes the first expansion device to be repositioned from 3.0 millimeter to 3.8 millimeters. But when this additional force is applied to the expansion device, the actual height change of the expansion device (0.8 millimeters) did not match the 1.0-millimeter height increase anticipated, the surgeon realizes that the joint is properly tensioned on the lateral side at a gap between 3.0 millimeters to 4.0 millimeters. In some circumstances, the surgeon may feel the tension of the joint at a gap of 3.0 millimeters is appropriate and discontinue use of further expansion devices on the lateral side. But other surgeons may feel that greater precision is helpful to find a more precise gap between 3.0 millimeters and 4.0 millimeters for proper lateral side soft tissue balancing. In such a case, the surgeon may remove the first expansion device and replace it with the second expansion device on the lateral side.

Figure 40C:
FIG. 40C represents an exemplary curve reflecting how actual changes in gap length on the medial side of a knee joint changes as a function of overall anticipated gap length on the medial side during a soft tissue balance using an exemplary expansion device in accordance with the instant disclosure when using a second expansion device.
Figure 40C:
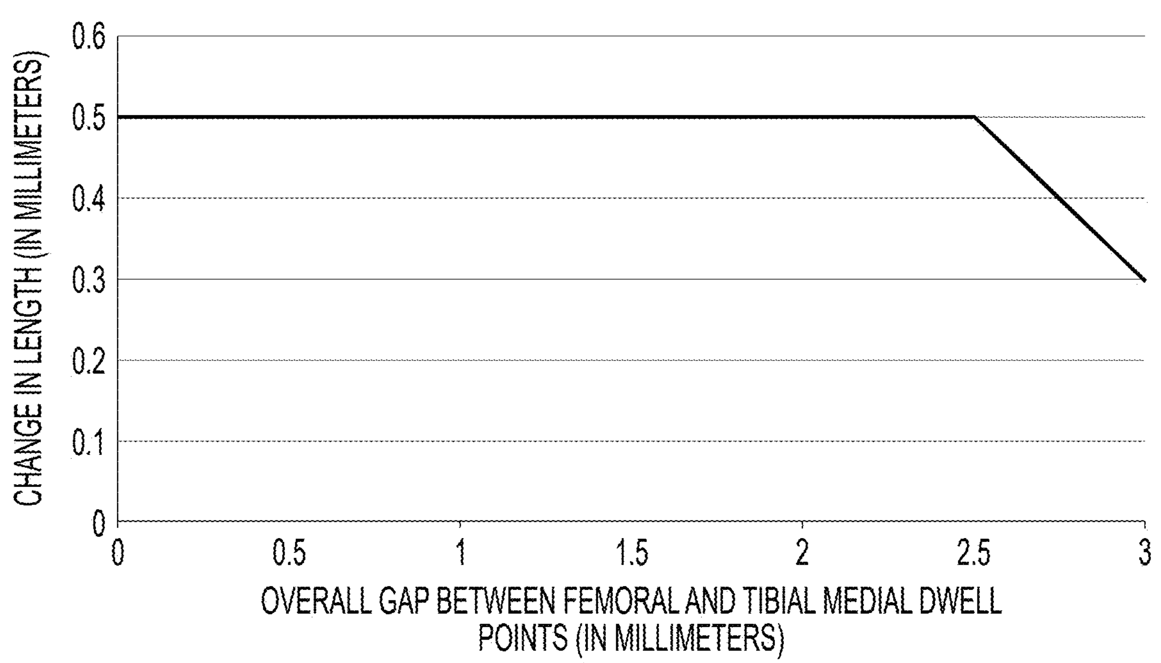

Turning to FIG. 40C, on the medial side, after the second expansion device is inserted, the surgeon may incrementally change the height of the expansion device from 0.5 millimeters in order to verify the results using the first expansion device, or the surgeon may set the second expansion device at 2.0 millimeters of height and start there. If the surgeon starts at 0.5 millimeters, for purposes of explanation, it is presumed that the applied forces result in a match between the anticipated height change and the actual height change through a height of 2.0 millimeters. At 2.0 millimeters, the surgeon applies a force to the second expansion device that results in the second expansion device being repositioned from 2.0 millimeters to 2.5 millimeters. This match between the anticipated height change of 0.5 millimeters for the expansion device and the actual height change of the expansion device means the medial side of the joint is not over-tensioned. Accordingly, the surgeon applies additional force to the second expansion device to cause a still further height increase in order to fill the gap between the tibia and femur. Again, on the medial side, the applied force causes the second expansion device to be repositioned from 2.5 millimeters to 2.8 millimeters. Because the actual height change of the expansion device (0.3 millimeters) did not match the 0.5 millimeters height increase anticipated, the surgeon realizes that the joint is properly tensioned on the medial side at a gap between 2.5 millimeters to 3.0 millimeters. In some circumstances, the surgeon may feel the tension of the joint at a gap of 2.5 millimeters is appropriate and discontinue use of further expansion devices. But other surgeons may feel that greater precision is helpful to find a more precise gap between 2.5 millimeters and 3.0 millimeters for proper medial side soft tissue balancing. In such a case, the surgeon may remove the second expansion device and replace it with the third expansion device.

Figure 40D:
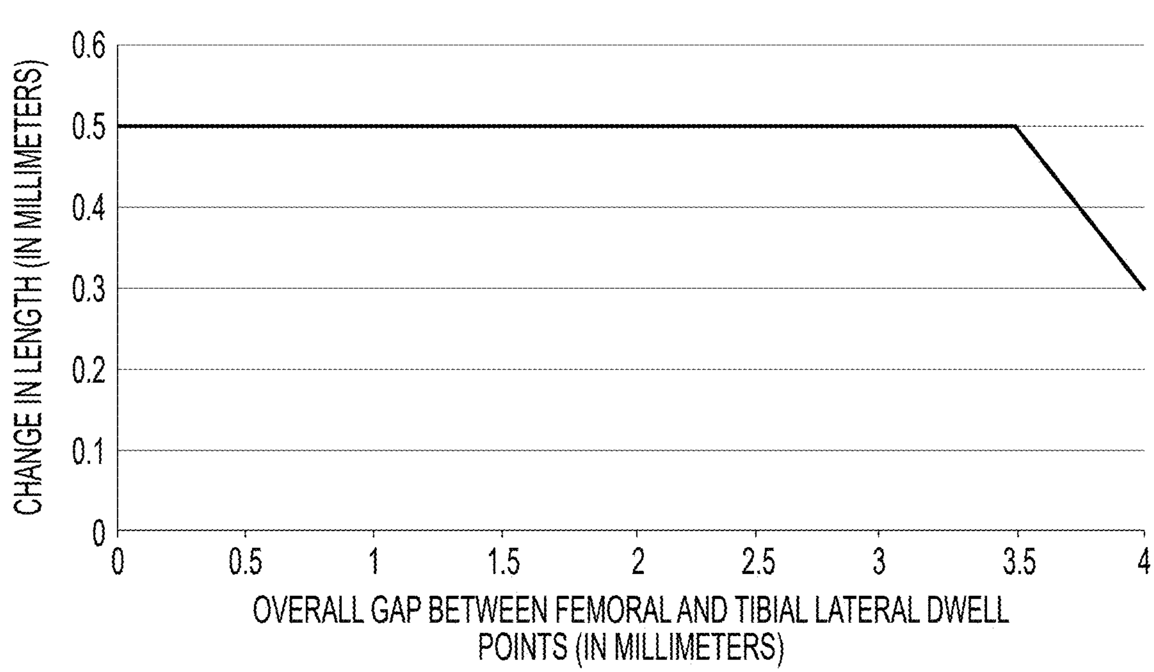
FIG. 40D represents an exemplary curve reflecting how actual gap length on the lateral side of a knee joint changes as a function of overall anticipated gap length on the lateral side during a soft tissue balance using an exemplary expansion device in accordance with the instant disclosure when using a second expansion device.

Referring specifically to FIG. 40D, on the lateral side, after the second expansion device is inserted, the surgeon may incrementally change the height of the expansion device from 0.5 millimeters in order to verify the results using the first expansion device, or the surgeon may set the second expansion device at 3.0 millimeters of height and start there. If the surgeon starts at 0.5 millimeters, for purposes of explanation, it is presumed that the applied forces result in a match between the anticipated height change and the actual height change through a height of 3.0 millimeters. At 3.0 millimeters, the surgeon applies a force to the second expansion device that results in the second expansion device being repositioned on the lateral side from 3.0 millimeters to 3.5 millimeters. This match between the anticipated height change of 0.5 millimeters for the expansion device and the actual height change of the expansion device means the lateral side of the joint is not over-tensioned. Accordingly, the surgeon applies additional force to the second expansion device to cause further height increases in order to fill the gap between the tibia and femur. Again, on the lateral side, the applied force causes the second expansion device to be repositioned from 3.5 millimeters to 3.8 millimeters. Because the actual height change of the expansion device (0.3 millimeters) did not match the 0.5 millimeters height increase anticipated, the surgeon realizes that the joint is properly tensioned on the lateral side at a gap between 3.5 millimeters to 4.0 millimeters. In some circumstances, the surgeon may feel the tension of the joint at a gap of 3.5 millimeters is appropriate and discontinue use of further expansion devices. But other surgeons may feel that greater precision is helpful to find a more precise gap between 3.5 millimeters and 4.0 millimeters for proper lateral side soft tissue balancing. In such a case, the surgeon may remove the second expansion device and replace it with the third expansion device.

Figure 40E:
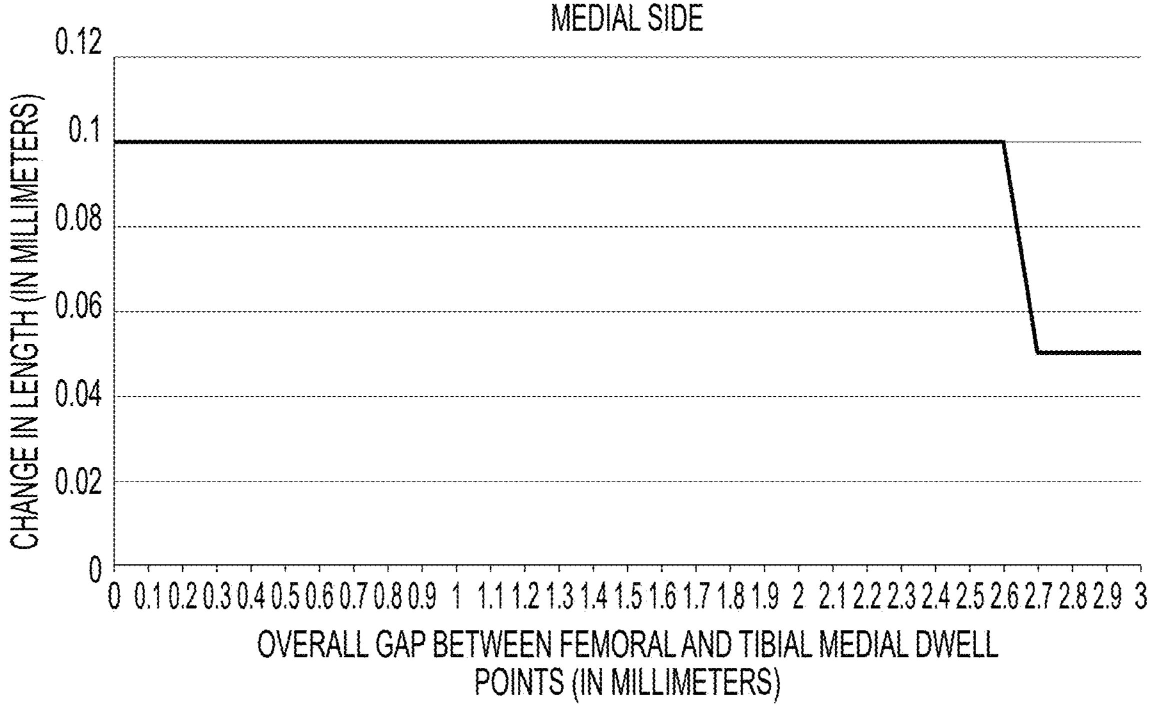
FIG. 40E represents an exemplary curve reflecting how actual changes in gap length on the medial side of a knee joint changes as a function of overall anticipated gap length on the medial side during a soft tissue balance using an exemplary expansion device in accordance with the instant disclosure when using a third expansion device.

Turning to FIG. 40E, on the medial side, after the third expansion device is inserted, the surgeon may incrementally change the height of the expansion device from 0.1 millimeters in order to verify the results using the first expansion device (and/or the second expansion device), or the surgeon may set the third expansion device at 2.0 or 2.5 millimeters of height and start there. If the surgeon starts at 0.1 millimeters, for purposes of explanation, it is presumed that the applied forces result in a match between the anticipated height change and the actual height change through a height of 2.5 millimeters. At 2.5 millimeters, the surgeon applies a force to the third expansion device that results in the third expansion device being repositioned from 2.5 millimeters to 2.6 millimeters. This match between the anticipated height change of 0.1 millimeters for the expansion device and the actual height change of the expansion device means the medial side of the joint is not over-tensioned. Accordingly, the surgeon applies additional force to the third expansion device to cause a further height increase in order to fill the gap between the tibia and femur. Again, on the medial side, the applied force causes the second expansion device to be repositioned from 2.6 millimeter to 2.65 millimeters. Because the actual height change of the expansion device (0.05 millimeters) did not match the 0.1 millimeters height increase anticipated, the surgeon realizes that the joint is properly tensioned on the medial side at a gap of 2.6 millimeters.

Figure 40F:
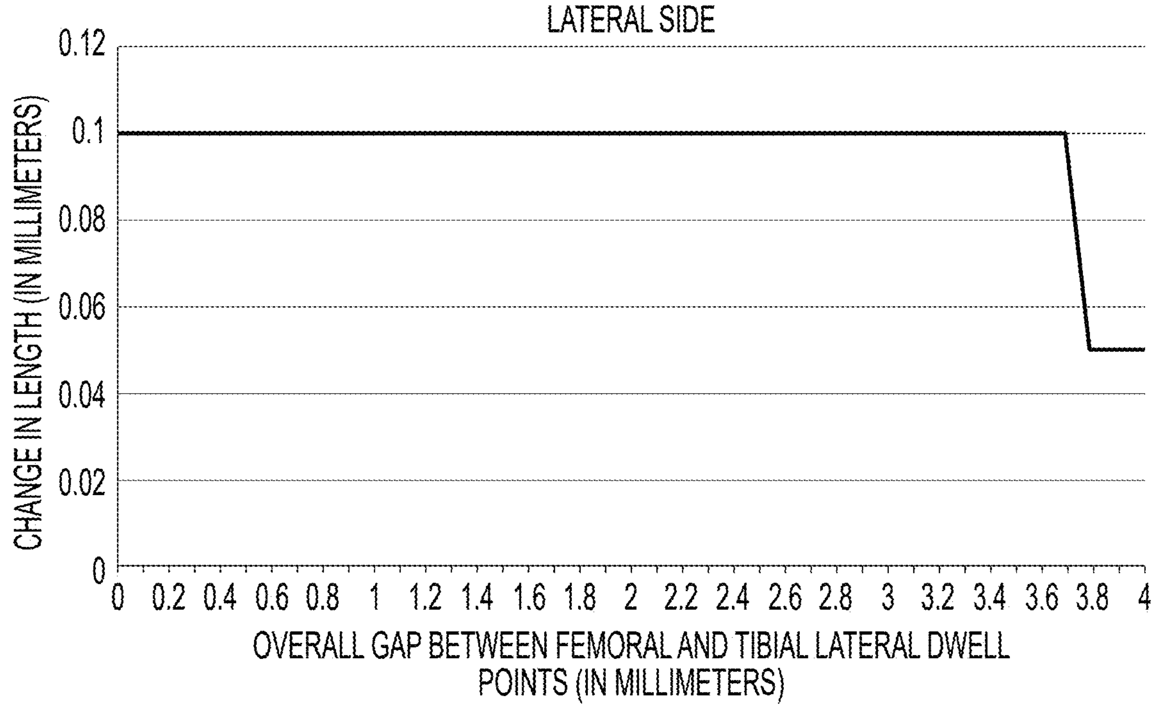
FIG. 40F represents an exemplary curve reflecting how actual gap length on the lateral side of a knee joint changes as a function of overall anticipated gap length on the lateral side during a soft tissue balance using an exemplary expansion device in accordance with the instant disclosure when using a third expansion device.

Referring specifically to FIG. 40F, on the lateral side, after the third expansion device is inserted, the surgeon may incrementally change the height of the expansion device from 0.1 millimeters in order to verify the results using the first expansion device (and/or the second expansion device), or the surgeon may set the third expansion device at 3.0 or 3.5 millimeters of height and start there. If the surgeon starts at 0.1 millimeters, for purposes of explanation, it is presumed that the applied forces result in a match between the anticipated height change and the actual height change through a height of 3.5 millimeters. At 3.5 millimeters, the surgeon applies a force to the third expansion device that results in the third expansion device being repositioned on the lateral side from 3.5 millimeters to 3.6 millimeters. This match between the anticipated height change of 0.1 millimeters for the expansion device and the actual height change of the expansion device means the lateral side of the joint is not over-tensioned. Accordingly, the surgeon applies additional force to the third expansion device to cause further height increases in order to fill the gap between the tibia and femur. Again, on the lateral side, the applied force causes the third expansion device to be repositioned from 3.6 millimeters to 3.7 millimeters. This match between the anticipated height change of 0.1 millimeters for the expansion device and the actual height change of the expansion device means the lateral side of the joint is not over-tensioned. Therefore, the surgeon applies further force to the third expansion device to cause a still further height increase in order to fill the gap between the tibia and femur. In such a case, on the lateral side, the applied force causes the third expansion device to be repositioned from 3.7 millimeters to 3.75 millimeters. Because the actual height change of the expansion device (0.05 millimeters) did not match the 0.1 millimeters height increase anticipated, the surgeon realizes that the joint is properly tensioned on the lateral side at a gap of 3.7 millimeters.

After the soft tissue balancing discussed for the medial and lateral sides, the straight-line distances (i.e., gaps) are recorded for both the medial and lateral sides in step 750. Specifically, by way of example, the straight-line distance for the medial side is recorded as 2.0, 2.5, or 2.6 millimeters depending upon the process the surgeon follows and the expansion devices utilized. Similarly, by way of example, the straight-line distance for the lateral side is recorded as 3.0, 3.5, and/or 3.7 millimeters depending upon the process the surgeon follows and the expansion devices utilized.

Figure 41:
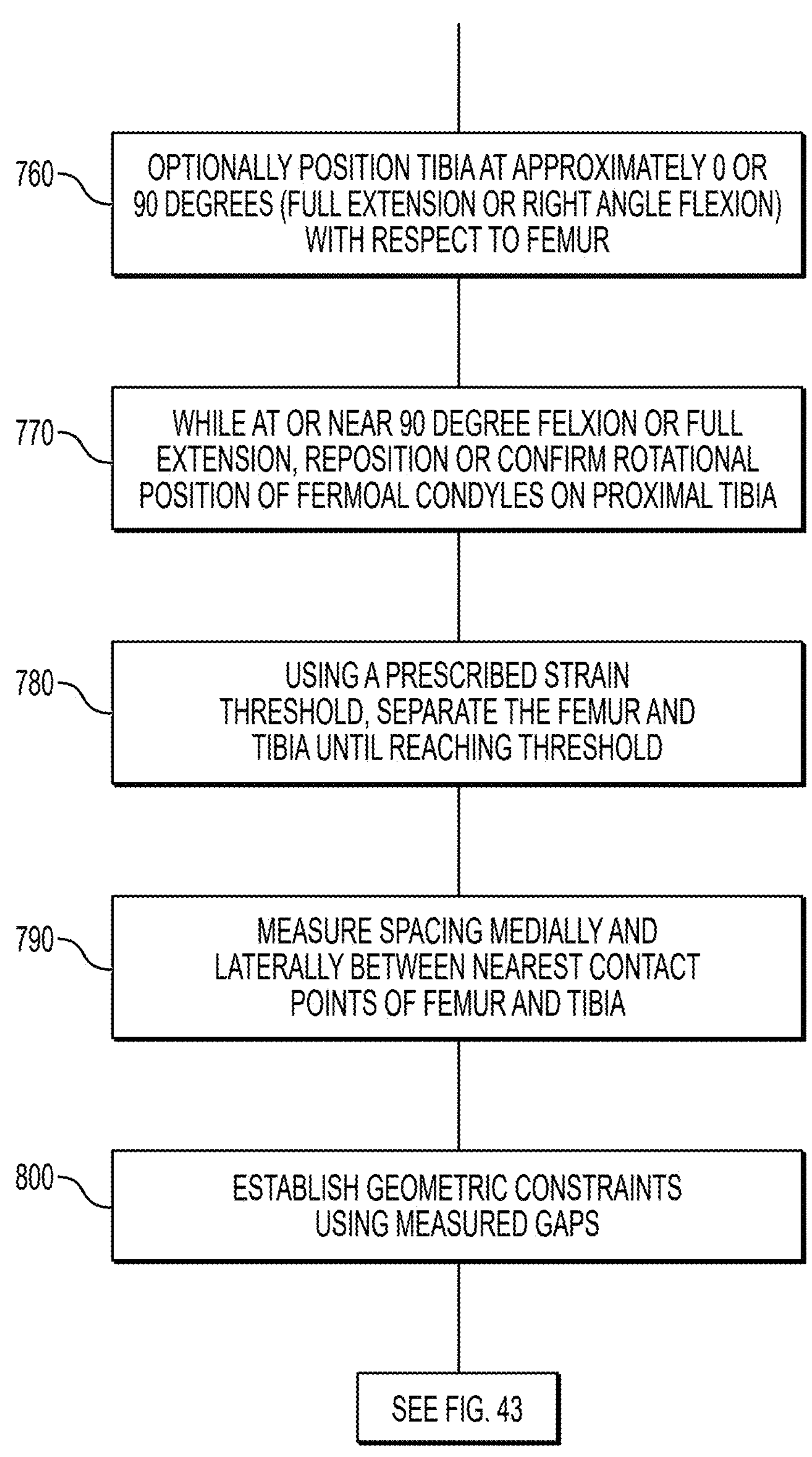
FIG. 41 is a second portion of an exemplary process flow for carrying out a total knee arthroplasty procedure in accordance with the instant disclosure.

Referring to FIG. 41, though not required, the surgeon may optionally perform steps 760-790 as part of balancing the knee joint at either full extension or at 90 degrees of flexion in accordance with the foregoing discussion on using expansion devices. Moreover, while certainly not required, the surgeon may optionally repeat steps 760-790 and perform balancing of the knee joint at the other of full extension or 90 degrees of flexion so that gap measurements are available for both full extension and 90 degrees of flexion.

While at either full extension or 90 degrees of flexion, the surgeon may perform step 770 confirming the rotational position of the femoral condyles with respect to the proximal tibia. By way of example, the surgeon may utilize the positioning template 191 to align dwell points on the femoral condyle and the medial condyle to overlap corresponding points on the proximal tibia. In the case of the knee at full extension, the medial condyle should overlie the medial condyle receiver of the tibia slightly anterior to the anterior-posterior midline of the tibia, and the lateral condyle should overlie the lateral condyle receiver very near the anterior edge, well anterior to the anterior-posterior midline of the tibia. In the case of the knee at 90 degrees of flexion, the medial condyle should overlie the medial condyle receiver of the tibia slightly posterior to the anterior-posterior midline of the tibia, and the lateral condyle should overlie the lateral condyle receiver very near the posterior edge, well posterior to the anterior-posterior midline of the tibia. While not required, one may utilize the exemplary embodiments disclosed herein including, without limitation, the femoral placement guide 140 and a modified intramedullary rod 134A (See FIG. 9D) to stabilize the position of the distal femur 110 with respect to the proximal tibia 112.

While at full extension or 90 degrees of flexion, and ensuring the proper rotational position of the femur with respect to the tibia, the surgeon may perform step 780 and uses an expansion device, optionally such as those disclosed herein (including, without limitation, 600, 600A, 600B), inserted between the femur and tibia (one on the medial side and a second on the lateral side) to measure a straight-line distance (referred to herein also as the "gap") between the dwell points of the femur and tibia on both the medial and lateral sides. It should be noted that the expansion devices may also be used with the paddles 200, 200A and other exemplary structures disclosed herein to facilitate measuring of the straight-line distances between the femur and tibia on the medial and lateral sides. The performance of step 780 is essentially the same as that described for step 740, with the angle of flexion being different, and accordingly will not be repeated in furtherance of brevity.

When properly balanced, at either full extension or 90 degrees of flexion, the straight-line distances (i.e., gaps) are recorded for both the medial and lateral sides in step 790.

In accordance with the instant description, it is anticipated that the gaps measured at either full extension or 90 degrees of flexion will be generally the same as those measured during mid-flexion. If a surgeon chooses to not balance the knee at or near 45 degrees, it is highly likely that the surgeon will not be able to properly balance the knee, with the same gaps, from full extension to 90 degrees of flexion because there is a 90-degree difference and ligaments often loosen or tighten throughout mid flexion, leading to laxity and instability.

After having the measured gaps for both the medial side and the lateral side, the total arthroplasty procedure may progress to step 800, where the geometric constraints 550 (see FIG. 12A) for the surgery are established.

Referring back to FIG. 37, as part of the geometric constraints 550, the surgeon may use the interface 1014 of the robotic system 1000 to identify the particular implant to be used during the surgery. In exemplary form, the primary controller 1010 may be pre-programmed with a plurality of orthopedic knee implants, as well as a plurality of different sizes for each of the plurality of orthopedic knee implants. More specifically, for each orthopedic implant that the primary controller 1010 is programmed with, the controller knows the relative dimensions of the implant and how much thickness/length/height the implant will contribute to the patient's anatomy along a vertical axis extending through the knee joint. In exemplary form, most orthopedic knee implants (including femoral component, tibial tray, and tibial tray insert) will contribute approximately 10 to 30 millimeters of increased length. As a result, and in accordance with the teachings of the instant disclosure, this increase in length must be accounted for as part of the bone cuts made to the tibia and femur.

In addition to using the interface 1014 to identify/select the implant that will be the subject of the total knee arthroplasty procedure, the surgeon may also use the interface to input the gap measurements previously taken on the medial and lateral side. It should be understood, however, that the primary controller 1010 may be directly or communicatively coupled to the expansion devices so that measurements accomplished using the expansion devices may be directly fed to the primary controller or the primary controller may calculate these measurements directly from signals from the expansion devices. In any event, the primary controller 1010 is aware of the gap measurements on the medial and lateral sides, as well as the implant chosen by surgeon, which allows the primary controller 1010 to configure the geometric constraints 550 based upon surgeon input.

In exemplary form, the primary controller 1010 communicates to the surgeon via the user interface 1014 that based upon the implant chosen, and the gaps measured, a total resection on the medial and lateral side is necessary. For instance, in a case where the implant adds 18 millimeters in length, and the measured gaps are less than 18 millimeters, the primary controller will indicate to the surgeon that bone resection is necessary. In exemplary form, the primary controller 1010 may prompt/request the surgeon to use the interface 1014 to establish a joint line, where the femoral component's dwell points (from the femoral medial condyle and the femoral lateral condyle) will contact corresponding points on the proximal tibial tray (generally polyethylene replicating the medial and lateral condyle receivers). After establishing a joint line, the primary controller may provide the surgeon via the interface 1014 with a number of cut options to concurrently account for the measured gaps (if any) and the added length attributable to the knee implant. These cut options may include those similar to the examples depicted and discussed herein from FIG. 12B. Essentially, the primary controller 1010 requests input from the surgeon about how much bone will be resected from the distal femur and proximal tibia. After receiving these inputs from the surgeon via the user interface 1014, the primary controller 1010 is operative to plan all bone cuts associated with the surgical procedure without preoperative or intraoperative imaging.

Figure 42A:
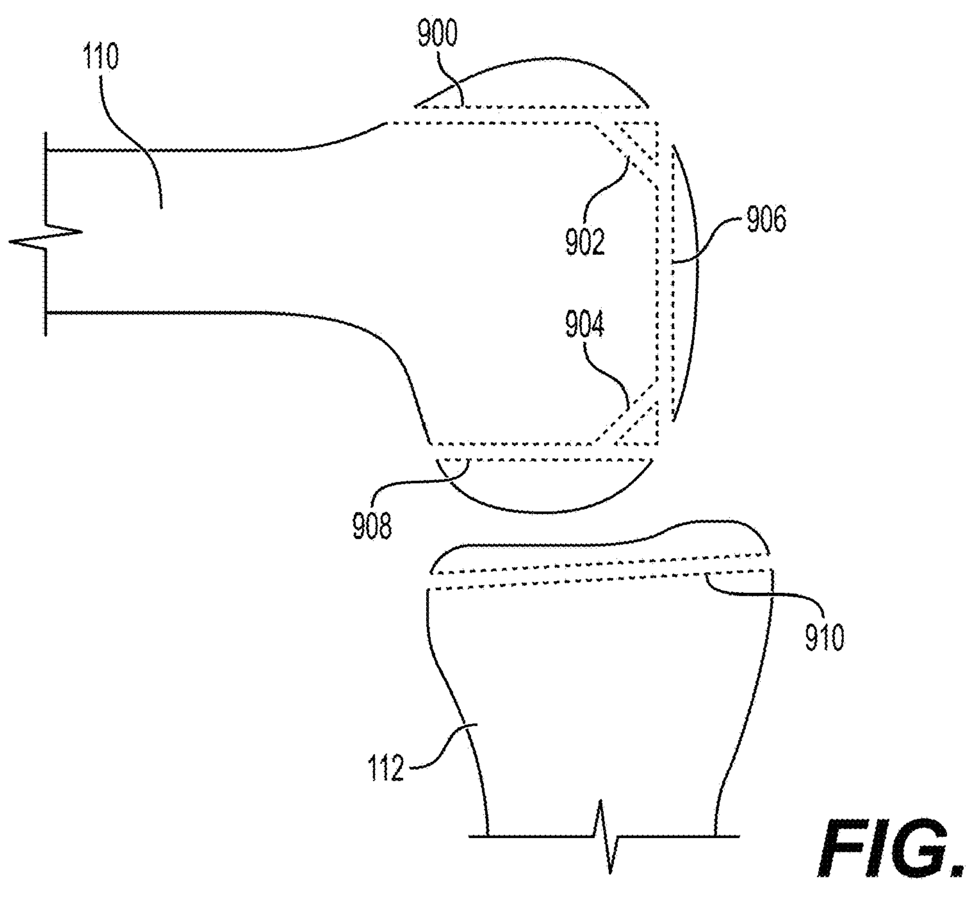
FIG. 42A is a lateral representation of a distal femur and proximal tibia, shown at 90 degrees of flexion, with spaces corresponding to a series of bone cuts made to accept corresponding orthopedic implants.
Figure 42B:
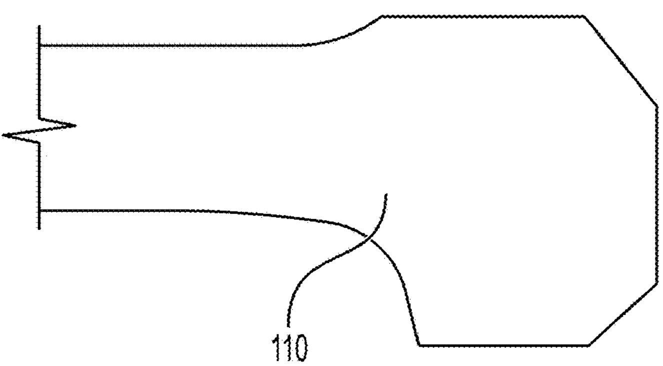
FIG. 42B is a lateral representation of the distal femur and proximal tibia after the bone cuts of FIG. 42A are completed.
Figure 42B:
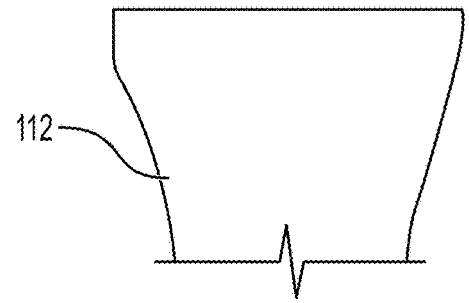
Figure 43:
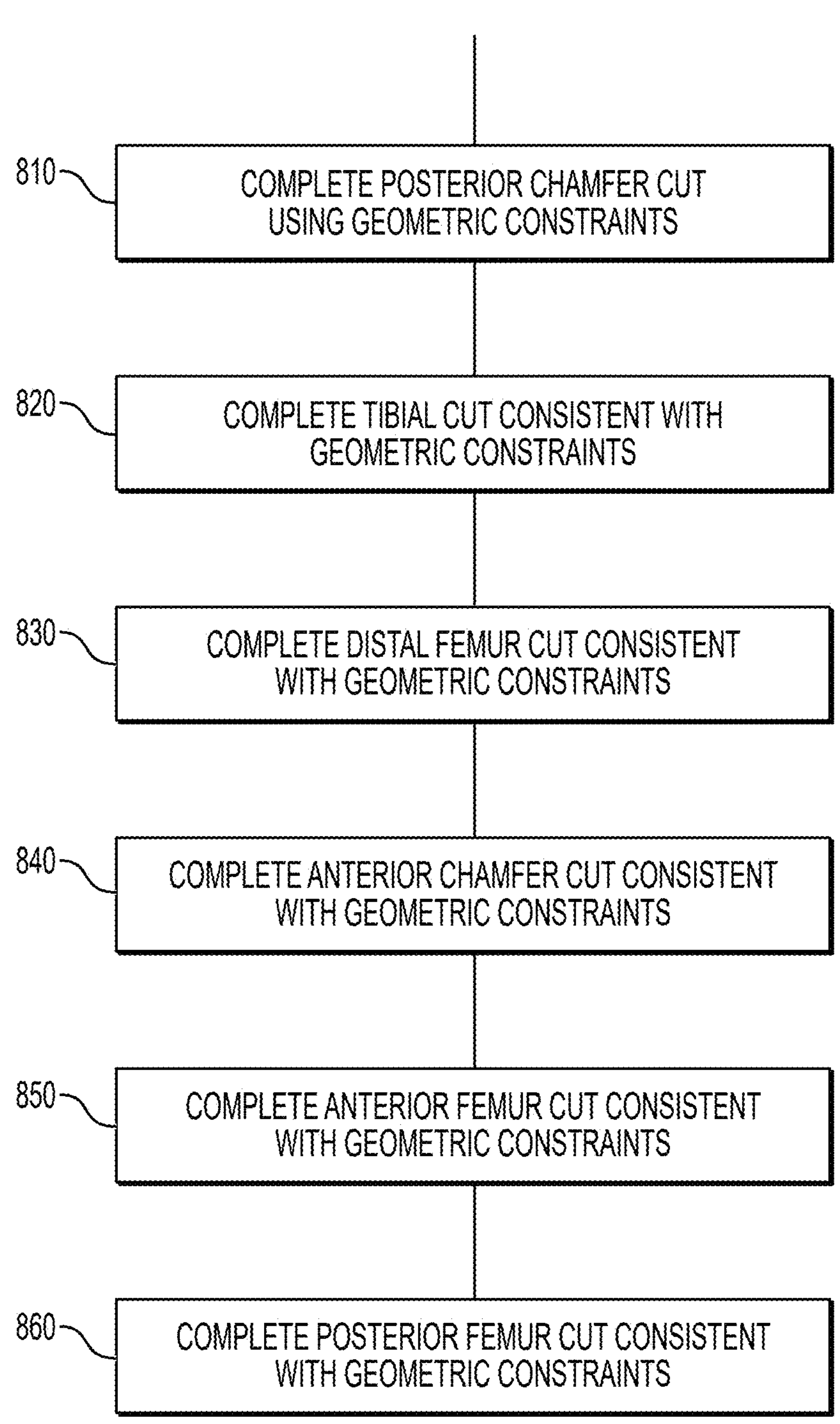
FIG. 43 is a third portion of an exemplary process flow for carrying out a total knee arthroplasty procedure in accordance with the instant disclosure.
Figure 44:
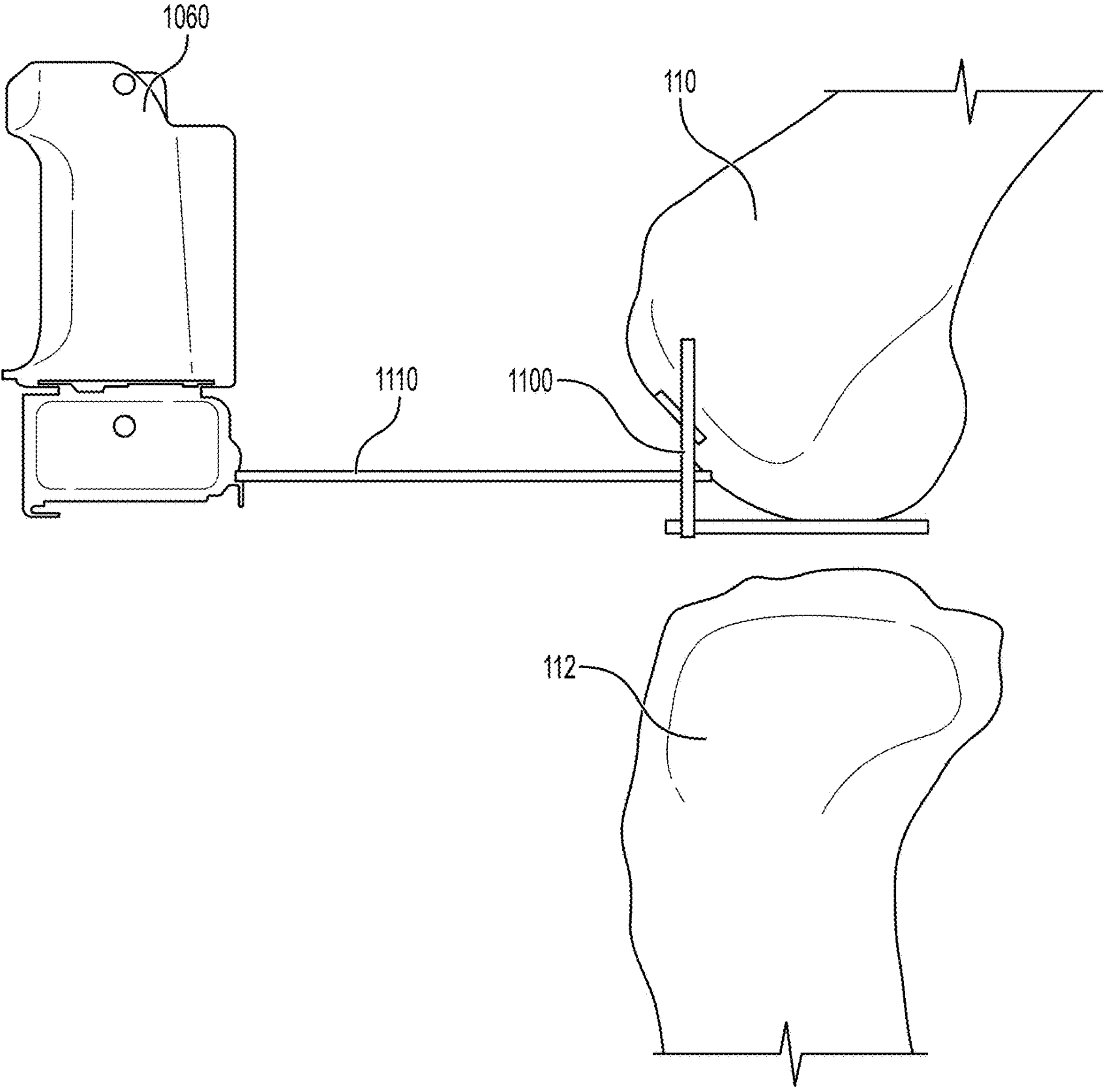
FIG. 44 is a perspective view of the robotic surgical saw and a cutting guide that may be used in accordance with the instant disclosure to complete a posterior chamfer cut on a distal femur.
Figure 45:
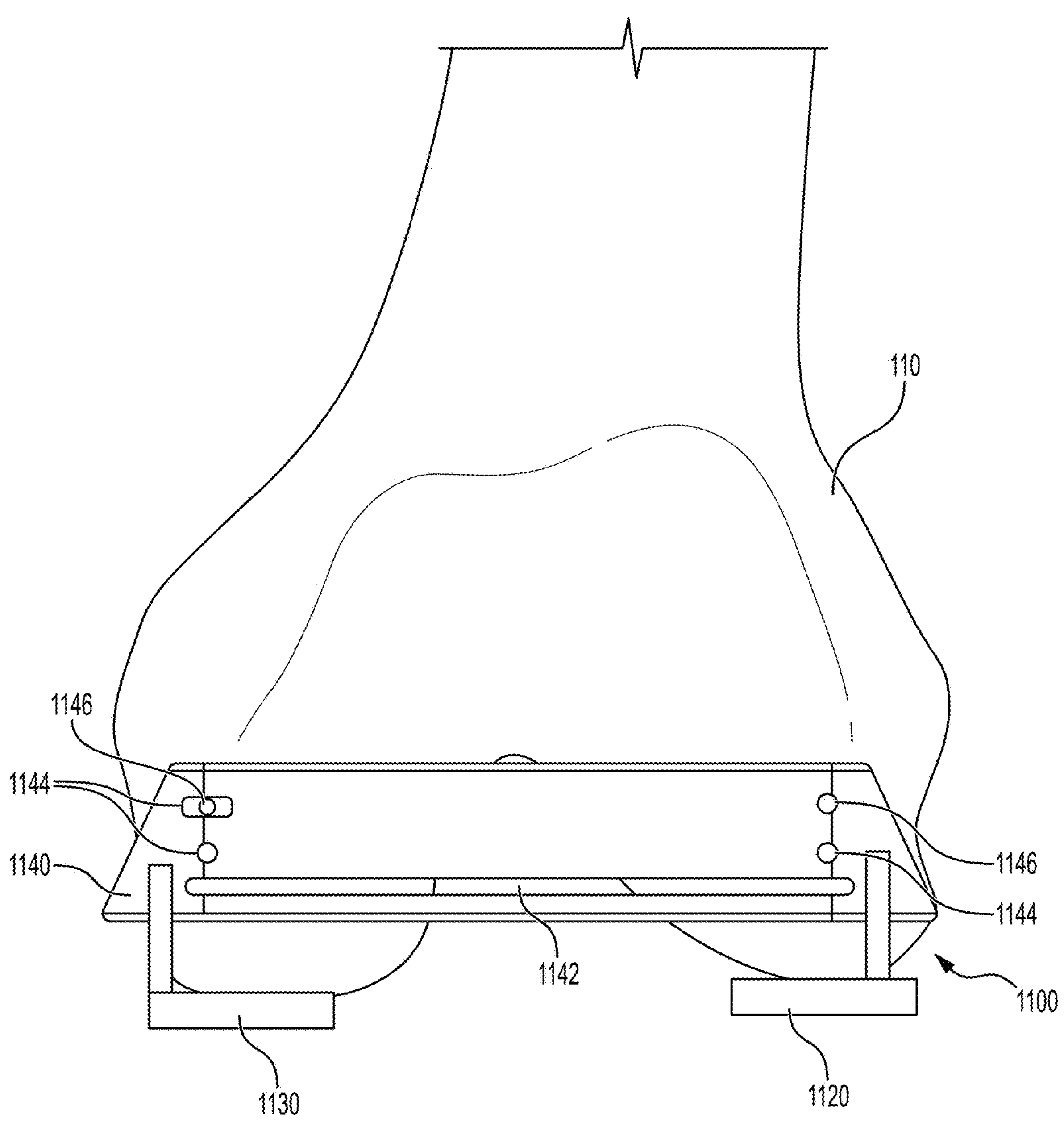
FIG. 45 is a rear view of the cutting guide of FIG. 44.

Referring to FIGS. 42 and 43, exemplary diagrams show the common bone cuts undertaken for a total knee arthroplasty using a conventional orthopedic implant for the femur and tibia. For the femur 110, there are typically five planar bone cuts consisting of the anterior cut 900, the anterior chamfer cut 902, the posterior chamfer cut 904, the distal cut 906, and the posterior cut 908. For the tibia 112, there is typically just one planar cut 910. For the femur, the planar cuts are sequentially angled 45 degrees apart, meaning that the anterior chamfer cut 902 is angled 45 degrees from the anterior cut 900, the distal femur cut 906 is angled 45 degrees from the anterior chamfer cut 902, and so on, ultimately ending with the posterior cut 908 being parallel to the anterior cut 900. Accordingly, consistent with the instant disclosure, by making the posterior chamfer cut 904 first, the remaining cuts on the femur may be undertaken without pre-operative or intra-operative imaging because the angles between the posterior chamfer cut 904 and the other femoral cuts are known. In other words, after the posterior chamfer cut 904 is completed, the remaining cuts may be automated by using the robotic system 1000 using the posterior chamfer cut as a starting reference. And because the geometric constraints 550 set the distance between the femoral chamfer cut 904 and the tibial cut 910, the femoral chamfer cut can also be used as a starting reference for the tibial cut.

Turning to FIGS. 37, 38, and 44-46, the exemplary surgical process may make use of the robotic system 1000 to make the posterior chamfer cut 904 on the distal femur 110. It should be noted, however, that the posterior chamfer cut 904 may be made other than using the robotic system 1000 and, thereafter, make use of the robotic system to make the remaining cuts to the femur and tibia using the posterior chamfer cut as the sole registration. In exemplary form, the robotic system 1000 may utilize arrays 1050A, 1050B mounted to the femur and tibia, as well as an array 1050D mounted to the surgical instrument 1060 (in this case, a surgical saw), to know the relative position of the tibia relative to the femur and surgical instrument to ensure the angle between the femur and tibia is at or near mid-flexion. In this exemplary procedure, the surgical instrument 1060 may be outfitted with cutting guide 1100 removably coupled to a saw blade 1110 of the surgical instrument.

By way of example, the cutting guide 1100 may include a medial foot 1120 and a lateral foot 1130 that are repositionably mounted to a face plate 1140. The face plate 1140 includes a through elongated opening 1142 configured to receive a saw blade 1110 such that the opening allows the saw blade to traverse side to side, yet maintain a planar cut as the saw blade is repositioned while traversing the opening. Also included with the face place 1140 are a series of openings 1144 that allow drilling therethrough so as to eventually receive bone pins 1146 that may be used to secure the face plate 1140 to the femur 110. In exemplary form, the geometric constraints may be utilized to establish the position and orientation of the opening 1142 with respect to the distal femur 110. Namely, the geometric constraints will establish how much bone on the medial side and the lateral side will be resected as a function of the dwell points on each side (medial and lateral). Accordingly, the surgeon will use these geometric constraints to adjust and fix the positions of the medial foot 1120 and lateral foot 1130 with respect to the face plate 1140 to provide sufficient offset from the dwell points to the opening 1142 to achieve the desired cutting line. After the medial foot 1120 and lateral foot 1130 are fixed in position with respect to the face plate 1140, the face plate may be guided onto the surgical saw 1060 so that the saw blade 1110 extends through the opening 1142 and thereafter use the surgical saw to position the cutting guide 1100 with respect to the distal femur. Namely, while the femur 110 is at mid-flexion, the medial foot 1120 is positioned against the medial dwell point on the medial condyle, and the lateral foot 1130 is positioned against the lateral dwell point on the lateral condyle, both while the saw blade is held at 45 degrees with respect to the distal face of the femur. Given these constraints, the guide 1100 is positioned distally along the saw blade until contacting the femur and optionally secured in position to the femur. Thereafter, the surgical saw may be activated to remove bone from the distal femur to effectuate the posterior chamfer cut 904 and complete step 810 (see FIG. 44).

Figure 46:
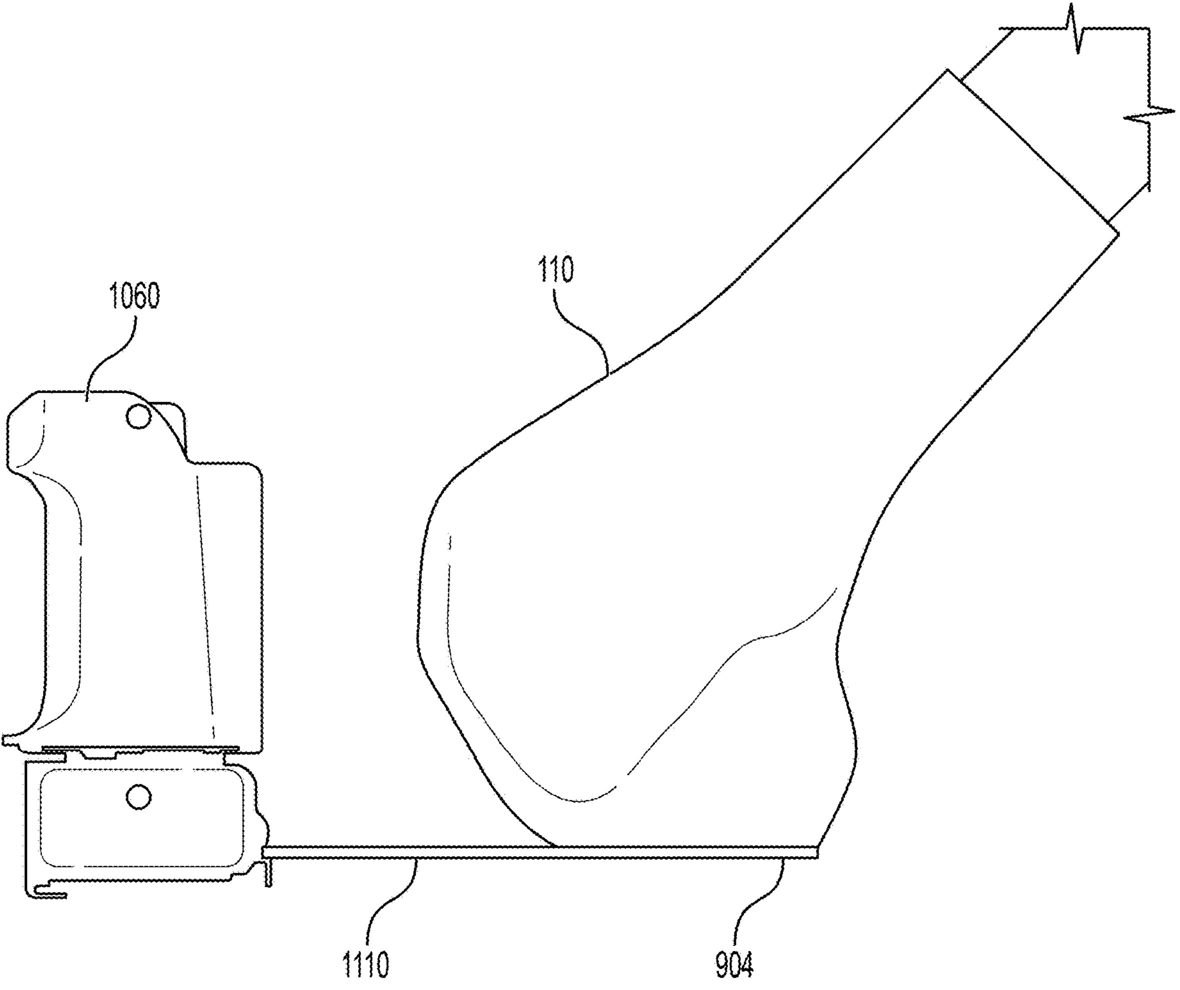
FIG. 46 is a lateral representation showing completion of a posterior chamfer cut using a robotic surgical saw in accordance with the instant disclosure.

Referring to FIG. 46, it is also within the scope of the disclosure that the robotic system 1000 need not use a physical guide at all when carrying out the posterior chamfer cut 904. Instead, the surgeon may make use of a manual registration option to manually orient the surgical saw with respect to the femur 110. Because the robotic system is tracking the position of the femur 110 and the surgical saw 1060, this manual registration established for the primary controller 1010 the starting position of the surgical saw with respect to the distal femur. Given that the primary controller is programmed to know the cut dimensions necessary to accept the prosthetic implants, as well as the sequence of the cuts as determined by the physician (starting with the posterior chamfer cut), the controller can instruct the surgical robot 1032 to precisely reposition the surgical saw 1060 in the manner necessary to resect the distal femur, starting with a completed posterior chamfer cut.

Figure 47:
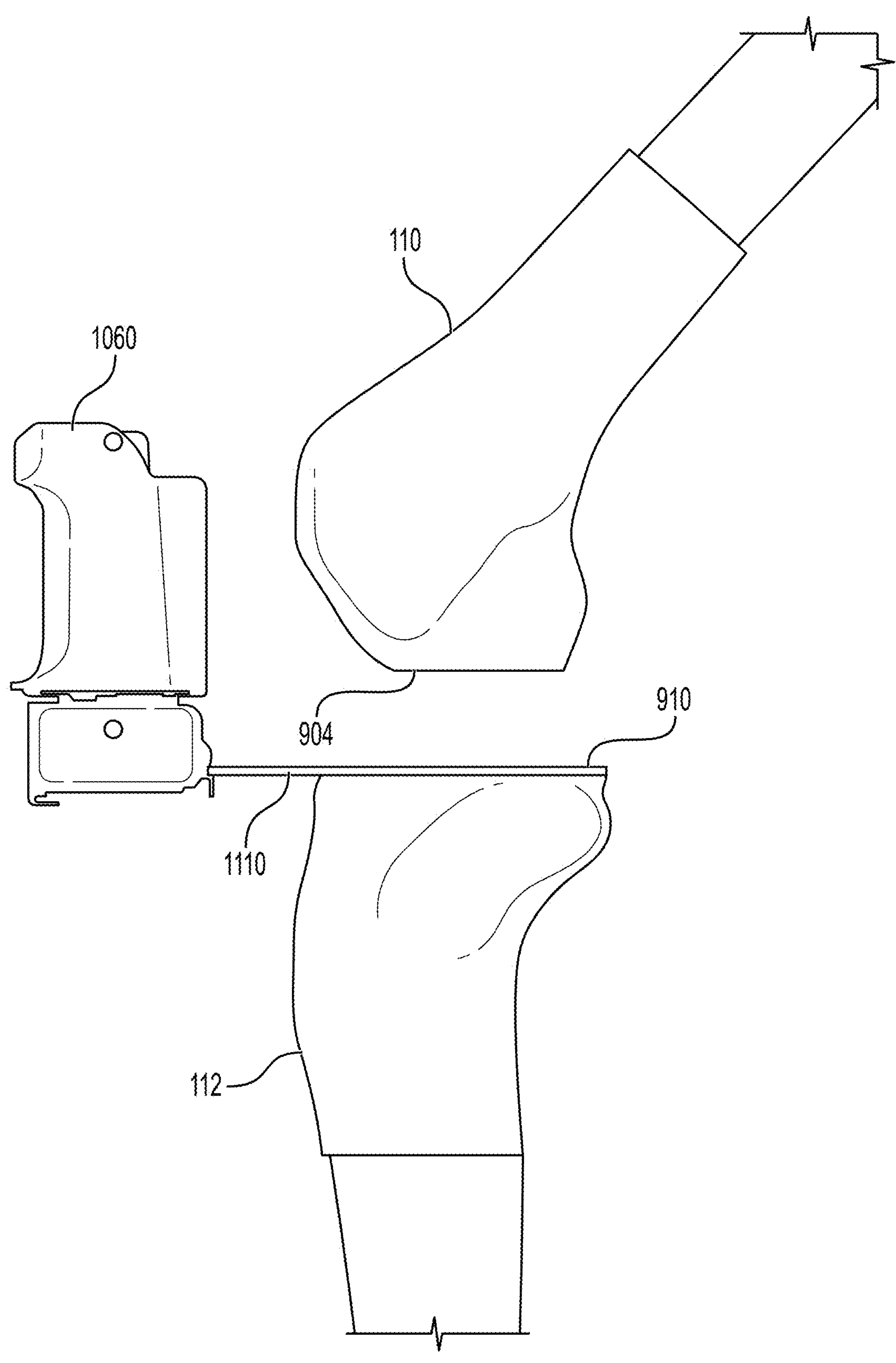
FIG. 47 is a lateral representation showing completion of a proximal tibial cut using a robotic surgical saw in accordance with the instant disclosure.

With reference to FIG. 47, after the posterior chamfer cut 904 is completed, the robotic system 1000 may utilize this completed cut to register a subsequent bone cut without requiring further registration. As referenced, the robotic system 1000 is tracking the relative positions of the femur 110 and tibia 112. And knowing the geometric constraints, the robotic system 1000 knows the intended orientations between the posterior chamfer cut 904 and the tibial cut 910. Because the robotic system 1000 knows the positions of the femur and tibia, as well as the geometric relationship between the two that will result if the tibia cut is completed, the robotic system 1000 can automatically instruct the surgical robot 1032 to reposition the surgical saw 1060 and complete the tibial cut without any tangible guide. Accordingly, the surgical saw 1060 may be activated to remove bone from the proximal tibia to effectuate the tibial cut 910 and complete step 820 (see FIG. 44).

Figure 48:
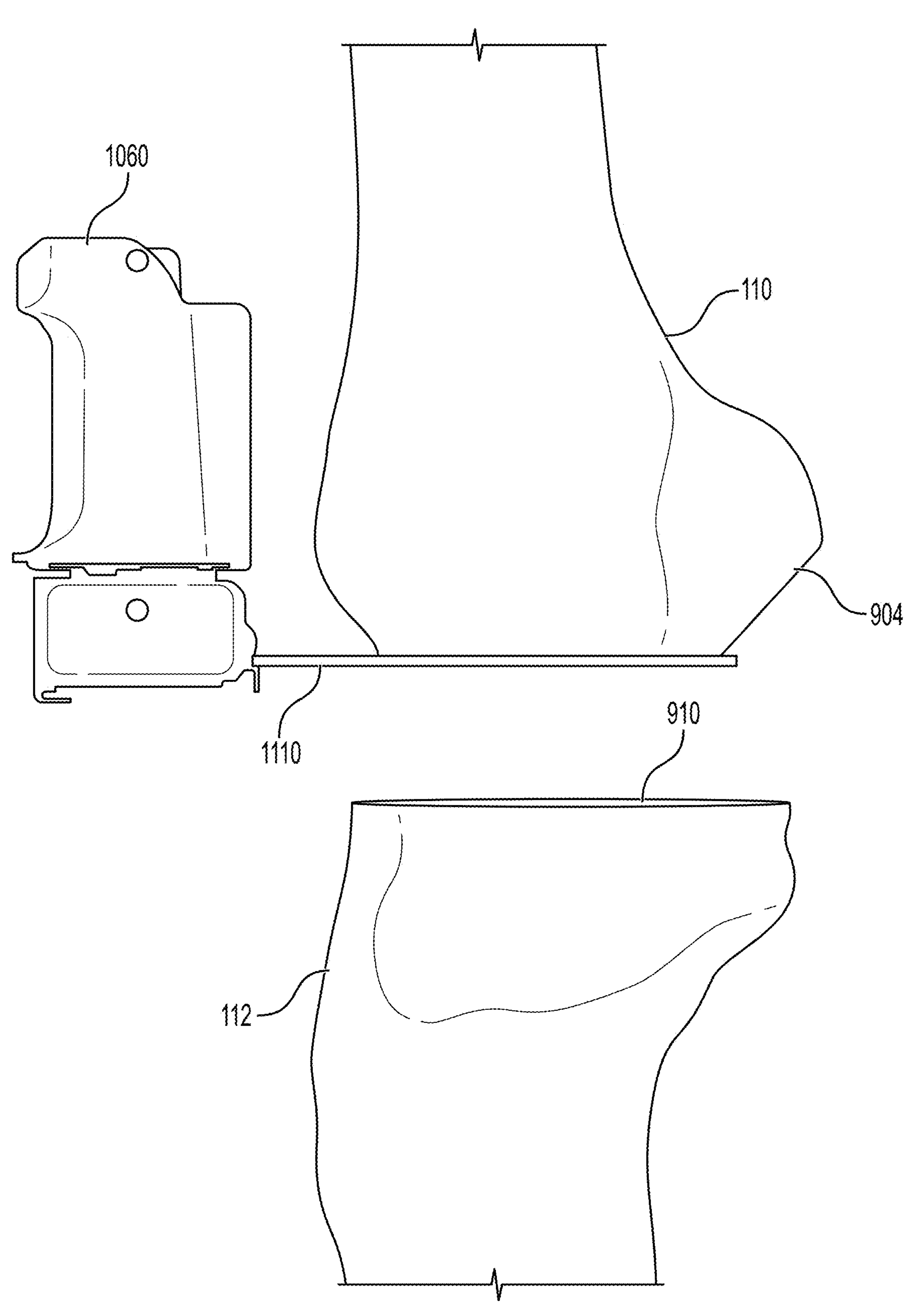
FIG. 48 is a lateral representation showing completion of a distal femur cut using a robotic surgical saw in accordance with the instant disclosure.

Turning to FIG. 48, after the posterior chamfer cut 904 is completed, the robotic system 1000 may utilize this completed cut to register a subsequent bone cut without requiring further registration. As referenced, the robotic system 1000 is tracking the relative positions of the femur 110 and tibia 112. And knowing the geometric constraints, the robotic system 1000 knows the intended orientations between the posterior chamfer cut 904 and the distal femur cut. Because the robotic system 1000 knows the position of the femur, as well as the geometric relationship (namely, the angles between the cuts), the robotic system 1000 can automatically instruct the surgical robot 1032 to reposition the surgical saw 1060 and complete the distal femur cut 906 without any tangible guide. Given that the position of the femur is being tracked, the surgeon may manually reposition the femur to take on a full extension position with respect to the tibia. In any event, the surgical saw 1060 may be activated to remove bone from the distal femur to effectuate the distal femur cut 906 and complete step 830 (see FIG. 44).

A similar sequence can occur in order to complete the anterior chamfer cut 902 at step 840, the anterior femur cut 900 at step 850, and the posterior femur cut 908 at step 860. It should be understood, however, that any sequence of cuts may be undertaken in accordance with the instant disclosure and that the bone cut steps summarized in FIG. 44 need not be performed in any particular order as a requisite to fall within the scope of the instant disclosure.

Figure 49:
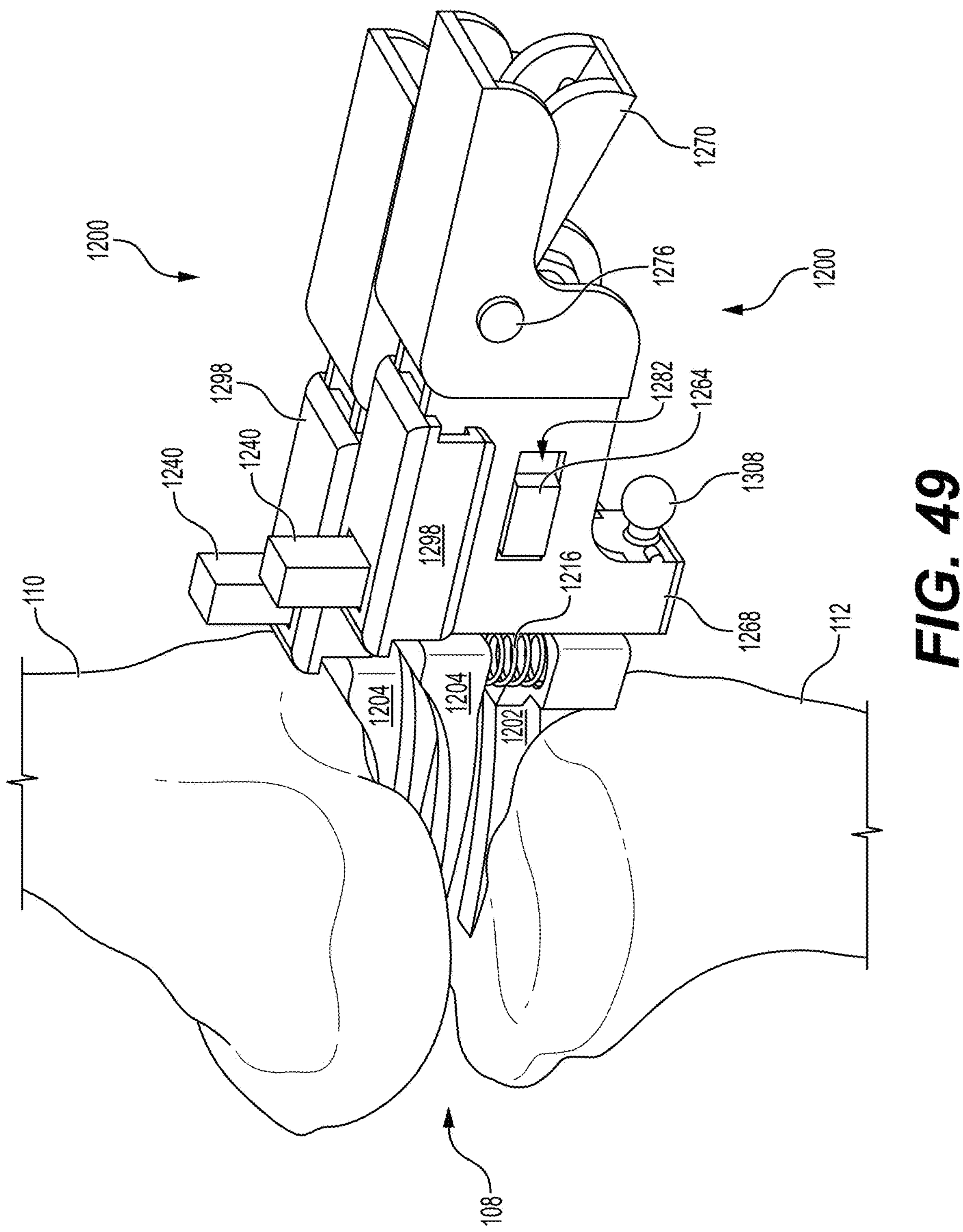
FIG. 49 is an elevated perspective view of a knee joint and a pair of balancing assemblies in accordance with the instant disclosure.
Figure 50:
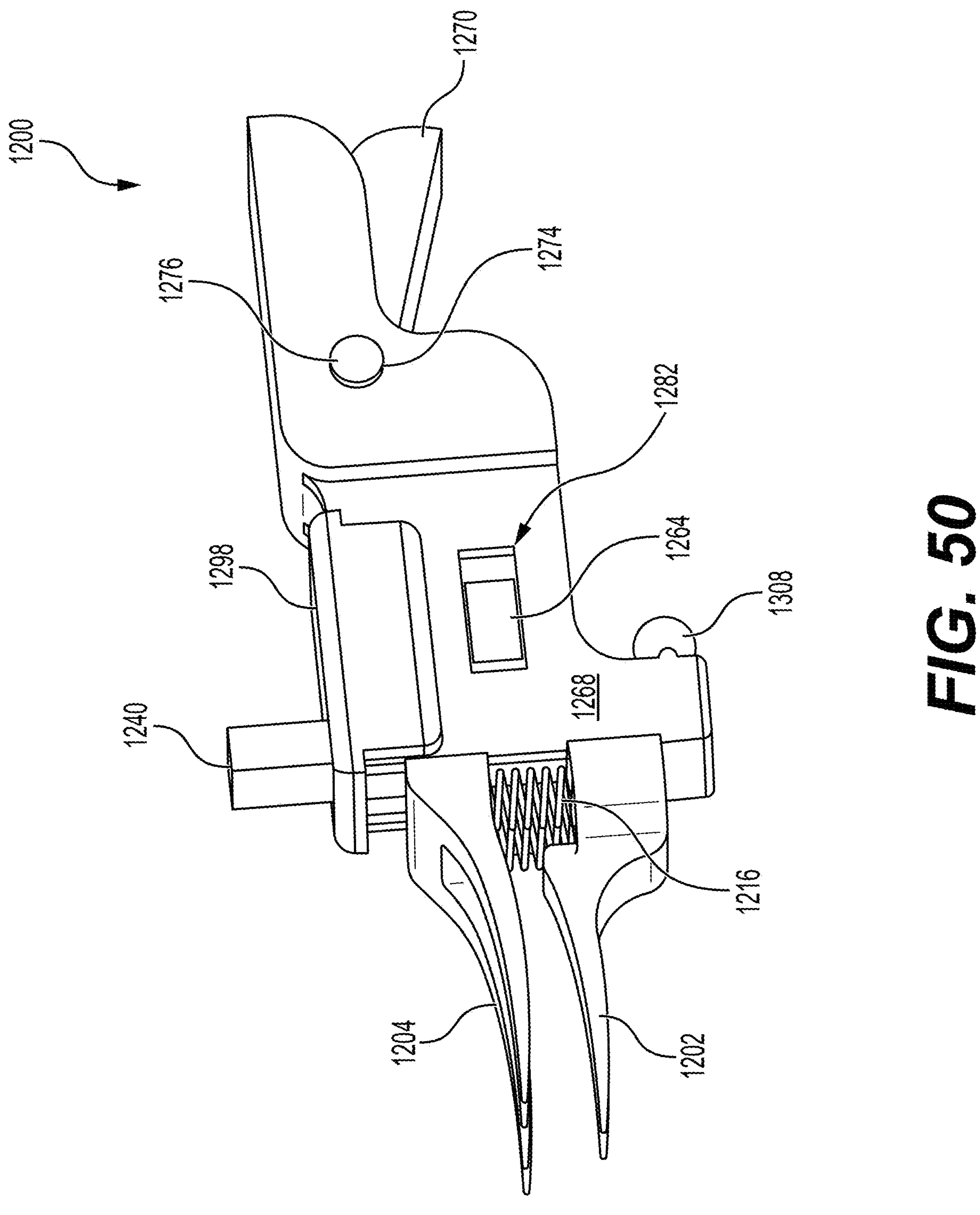
FIG. 50 is front perspective view of a balancing assembly in accordance with the instant disclosure.
Figure 51:
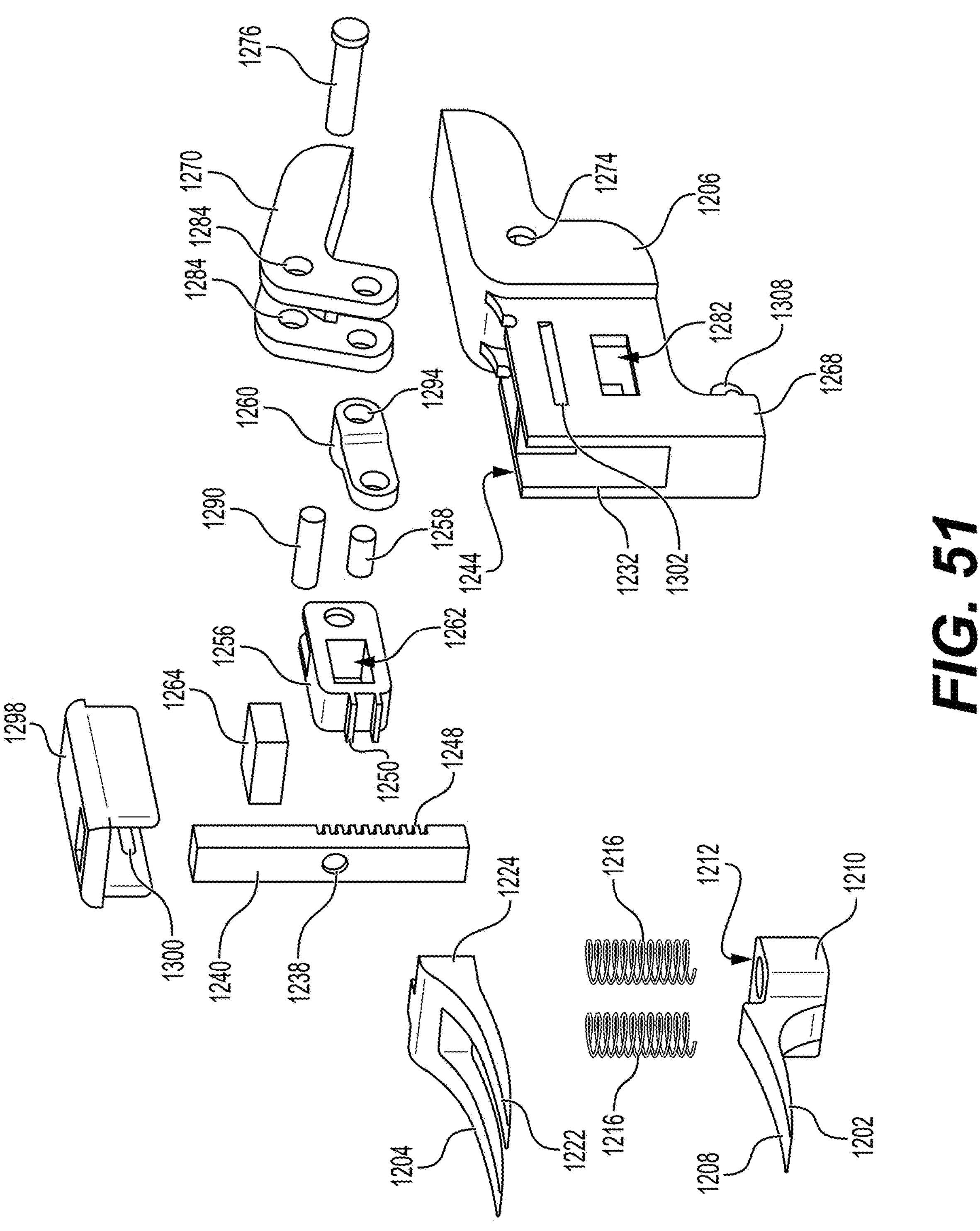
FIG. 51 is an exploded view of the balancing assembly of FIG. 50.
Figure 52:
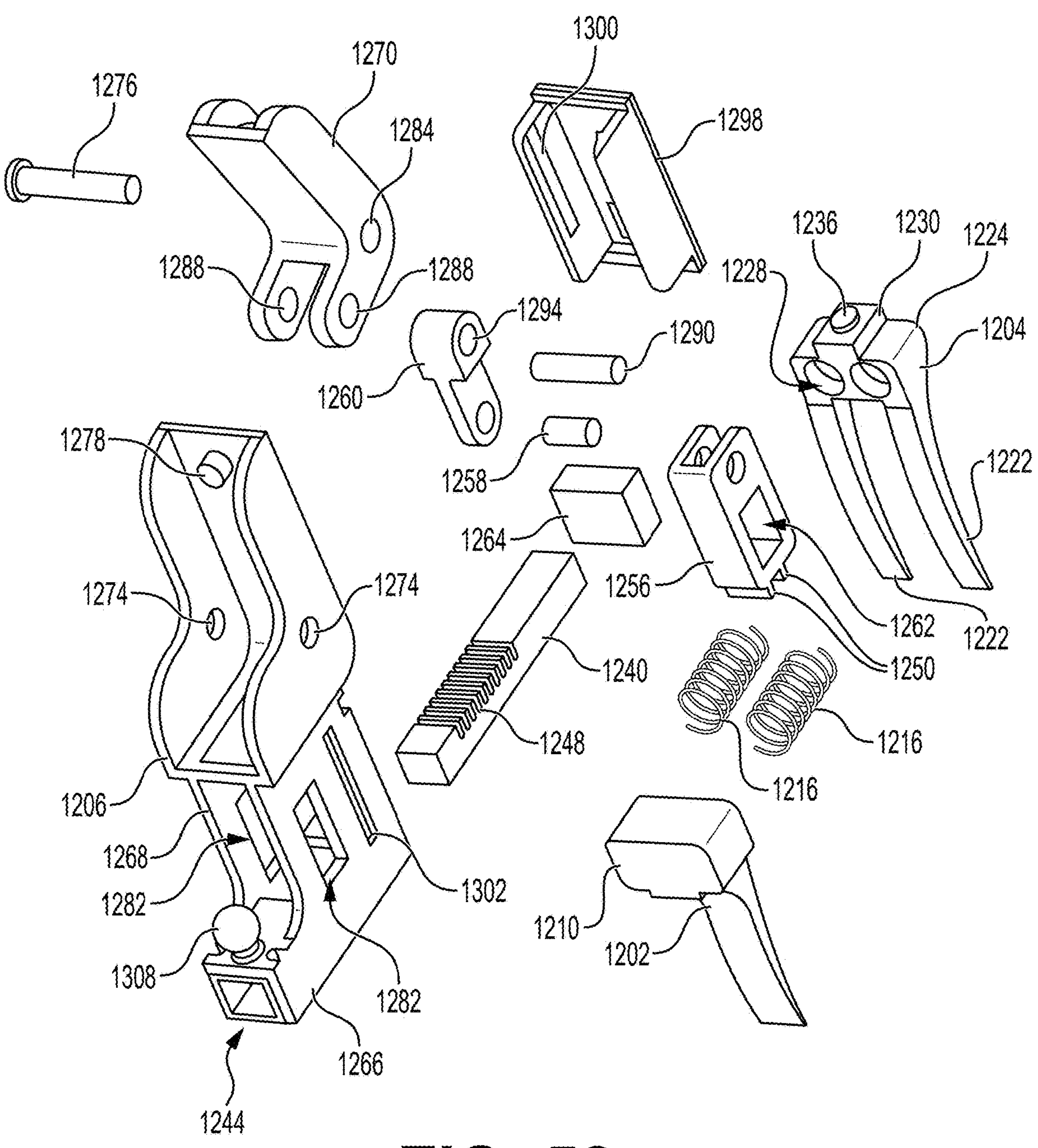
FIG. 52 is another exploded view of the balancing assembly of FIG. 50.

Turning to FIG. 49, an alternate exemplary balancing assembly 1200 may be utilized individually or in multiples (such as the two shown) individually or concurrently as part of soft tissue balancing a joint during a joint revision or replacement surgery. In exemplary form, a knee joint 108 is depicted that includes a distal femur 110 and a proximal tibia 112 having spaces or gaps between these bones, namely a first space between the medial condyle and condyle receiver, and a second space between the lateral condyle and condyle receiver. As will be discussed in more detail hereafter, the exemplary balancing assembly 1200 may be positioned to partially occupy either space between a condyle and its corresponding condyle receiver as part of soft tissue balancing.

Referring to FIGS. 50-56, the exemplary balancing assembly 1200 may include a pair of paddles 1202, 1204 that may be individually repositionable or have only one of the paddles being repositionable. In exemplary form, the paddles are depicted as having a lower paddle 1202 that is stationary and fixedly mounted to a primary housing 1206, while the upper paddle 1204 is repositionable vertically with respect to the lower paddle and primary housing. Nevertheless, it is within the scope of the disclosure that the lower paddle 1202 is repositionably mounted to the primary housing and/or detachably mounted to the primary housing. In such a circumstance, the upper paddle 1204 may be fixedly mounted to the primary housing 1206 or repositionably mounted to the primary housing. In this manner, both paddles 1202, 1204 may be repositionably mounted to the primary housing 1206.

The lower paddle 1202 may include a dish-shaped finger 1208 extending away from a lower base 1210 that includes a pair of cylindrical cavities 1212 (that may or may not be through cavities) sized to each receive a portion of a coil spring 1216. It should be noted, however, that the finger 1208 may have any number of shapes and need not be dish-shaped. For example, the finger 1208 may have a planar undersurface configured to sit on top of a resected tibia 112. The coil springs may include various spring rates and, as will be discussed in more detail hereafter, it is envisioned that the balancing assembly 1200 includes several different coil springs to allow surgeons to interchange springs having different spring rates as part of soft tissue balancing. It is also within the scope of the disclosure that the coil springs 1216 may be replaced or supplemented with magnets having the same poles facing one another, or with piezoelectric actuators, linear actuators, geared motors, threaded rods, or any other structures operative to reposition one or more of the paddles 1202, 1204 to expand or to span the gap between the tibia 112 and femur 110.

In exemplary form, the finger 1208 may be generally centered with respect to the base 1210 and inset medially and laterally from the sides of the base. The finger 1208 may include a constant medial-to-lateral width and a thickness that tapers until reaching a distal tip. It is also within the scope of the disclosure that the lower paddle 1202 includes more than one finger 1208. A proximal portion of the finger 1208 may be elevated vertically above the base 1210 in order to allow overlapping and alignment with the upper paddle 1204.

In exemplary form, the upper paddle 1204 may include one or more fingers 1222 that are dish-shaped and extend away from a corresponding upper base 1224. It should be noted, however, that the fingers 1222 may have any number of shapes and need not be dish-shaped. For example, the fingers 1222 may have a planar top surface configured to sit against a resected femur 110. By way of example, the pair of depicted fingers 1222 are generally aligned with respect to the base 1210 and outset from one another medially and laterally to form a corresponding gap therebetween. Each finger 1222 may include a constant medial-to-lateral width and a thickness that tapers until reaching a distal tip. The gap between the fingers 1222 may be sized to allow the lower paddle finger 1208 to occupy this gap and, when the first and second paddles are compressed to a maximum extent, the fingers 1208, 1222 are perfectly aligned to exhibit a uniform profile. As with the lower paddle 1202, the upper base 1224 includes a pair of cylindrical cavities 1228 (that may or may not be through cavities) sized to each receive a portion of the coil spring 1216. A rear of the upper base 1224, opposite the distal tips of the fingers 1222, may include a rectangular key 1230 that may be configured to ride within a corresponding keyway 1232 of the primary housing 1206. In this fashion, the shape of the keyway 1232 may restrict and guide the motion of the upper paddle 1204 to, in exemplary form, provide for only vertical motion of the upper paddle with respect to the primary housing 1206. Extending from the key 1230 is a projection 1236 that is configured to be received within a corresponding opening 1238 of a rack 1240. It should be understood, however, that the rack 1240 may include the projection 1236, while the key 1230 may include the corresponding opening 1238. In any event, an engagement between the upper paddle 1204 and the rack 1240 is operative to control motion of the upper paddle.

A well 1244 of the primary housing 1206 includes vertical guides 1246 delineating a cavity sized to receive the rack 1240. By way of example, the rack 1240 may comprise a straight rod having a constant rectangular longitudinal cross-section with four exterior surfaces arranged in ninety-degree increments. A first of the four exterior surfaces may include the opening 1238 to receive the projection 1236 from the key 1230, while a third of the exterior surfaces, oriented 180 degrees from the first surface, includes a series of depressions correspondingly forming teeth 1248 that are longitudinally distributed. It should be noted that the rack 1240 may have longitudinal cross-sections that are constant or irregular, as well as cross-sections that are square, oblong, circular, or embody various shapes. In exemplary form, the teeth 1248 may be evenly distributed along all or a portion of an exterior surface. Nevertheless, the teeth 1248 may be formed to have a tapered leading edge to ensure that one or more catches 1250 associated with a detent assembly are fixedly received within openings in between the teeth in order to fix the vertical position of the rack 1240 relative to the primary housing 1206.

A distal end of a stopper 1256 may include the catches 1250 and may be repositionably coupled to a link 1260 via a first link pin 1258 concurrently extending into openings in the link and the stopper. By way of example, the openings occupied by the first link pin 1258 may be circular in cross-section and through as to the link 1260 and through or partially closed as to the stopper 1256. The stopper 1256 may include a main body having a rectangular distal-toproximal cross-section that demarcates at least one through opening 1262 extending from medial to lateral sides and configured for accepting a guide block 1264. In this example, the guide block 1264 may embody a cuboid shape and have a rectangular cross-section slightly smaller than the boundaries demarcating the through opening 1262. It should be noted, however, that the guide block 1264 and through opening 1262 may embody different shapes so long as the guide block 1264 can extend medially and/or laterally away from the medial and/or lateral sidewall of the stopper 1256. By way of further example, the guide block 1264 may have a medial-to-lateral length greater than the medial-to-lateral length of the through opening 1262 so that guide block extends beyond one or both ends of the opening. A proximal end of the stopper 1256 is hollowed to accommodate insertion of the distal end of the link 1260 and the first link pin 1258 in order to allow pivotal motion between the stopper 1256 and the link 1260 when the link and stopper concurrently receive the first link pin 1258. In exemplary form, the guide block 1264 may be frictionally received within the through opening 1262 so that once inserted, the guide block does not move medially-to-laterally unless specifically forced to do so using a tool such as, without limitation, a mechanical punch. The guide block 1264 may be utilized to operatively couple the stopper 1256 to the primary housing 1206.

To operatively couple the stopper 1256 to the primary housing 1206, the primary housing includes a pair of through openings 1282 that extend respectively through medial and lateral side walls 1266, 1268. Each of the through openings 1282 is elongated and sized to allow at least partial throughput of the guide block 1264 so that the guide block can travel along a proximal-to-distal predefined path. As will be discussed in more detail hereafter, this predefined path allows traversal of the guide block 1264 in only two degrees of freedom (one being the guide block can travel medial to lateral and vice versa, and a second being the guide block can travel proximal to distal and vice versa). In exemplary form, the through openings 1282 may be sized to inhibit travel of the guide block 1264 vertically with respect to the primary housing 1206. By way of example, once the guide block 1264 is seated within the stopper 1256 and, preferably the guide block extends into both openings 1282, the stopper may be repositioned with respect to the primary housing 1206 in only one degree of freedom corresponding to the guide block and stopper traveling proximal to distal and vice versa. Such a configuration effectively precludes the stopper 1256 from traveling appreciably vertically with respect to the primary housing 1206 and the side walls 1266, 1268 constrain motion of the stopper medially-to-laterally with respect to the primary housing.

To effectuate the proximal-to-distal motion (and vice versa) of the stopper 1256 with respect to the primary housing 1206, the detent assembly may also include a handle 1270 pivotally mounted to the primary housing and to the link 1260. In exemplary form, the handle 1270 includes an L-shape within upstanding medial and lateral side walls that are connected via an underwall. Specifically, the primary housing 1206 may include a pair of pin openings 1274 sized to receive a pivot pin 1276 that is configured to be concurrently received within corresponding holes 1284 of the handle 1270 that extend through the medial and lateral side walls and are positioned proximate the turn in the L-shape. In this manner, the handle 1270 may pivot about an axis of the pivot pin 1276 with respect to the primary housing. In this exemplary configuration, the handle 1270 may be biased away from the housing 1206 (see FIG. 53) using a coil spring extending between corresponding cups 1278, 1280 on the housing and handle. In addition, the handle 1270 also includes another set of through holes 1288 extending through the medial and lateral side walls that are sized to receive a second link pin 1290. The second link pin 1290 is sized to be received within a corresponding cylindrical cavity 1294 formed within the proximal end of the link 1260. Consequently, when assembled, the handle 1270 pivots around the second link pin 1290, as does the link 1260. In this fashion, when the handle 1270 is pivoted to overcome the spring bias so that the cups 1278, 1280 are nearer one another, the handle operates to reposition the link proximally and correspondingly repositions the stopper 1256 proximally so that eventually the catches 1250 are no longer received within depressions between adjacent teeth 1248. When this occurs, external forces acting on the paddles 1202, 1204 can operate to overcome the spring bias of the coils springs 1216 and reposition at least one of the paddles so that the gap therebetween is lessened. Conversely, if the external forces acting on the paddles 1202, 1204 is less than the spring bias of the coil springs 1216, at least one of the paddles will be repositioned so that the gap therebetween is increased. If the external forces acting on the paddles 1202, 1204 is equal and opposite to the spring bias of the coil springs 1216, the gap between the paddles will not change. In this fashion, by allowing the handle 1270 to pivot away from the housing 1206 so that the distance between the cups 1278, 1280 is at a maximum, repositioning of the paddles 1202, 1204 with respect to one another is precluded because the stopper 1256 engages the rack 1240 and inhibits vertical repositioning of at least one of the paddles 1204.

To further constrain the motion of the rack 1240 with respect to the housing 1206, a cap 1298 may be mounted to the top of the housing. By way of example, the cap 1298 may include a through opening in a top wall having a cross-section slightly larger than that of the rack 1240 to allow throughput of the rack when the cap is mounted to the housing 1206. By way of example, this opening cross-section may be rectangular, circular, oblong, or any other cross-section that allows throughput and traversal of the rack 1240 with respect to the cap 1298. The cap 1298 may include vertical medial and lateral side walls that are joined by the top wall. In exemplary form, the medial and lateral side walls may include corresponding ledges 1300 that project inward and toward one another and are configured to be received within corresponding depressions or openings 1302 formed into the medial and lateral side walls of the housing 1206. In this fashion, the cap 1298 cooperates with the housing 1206 to provide a guide along which the rack 1240 is able to vertically traverse.

Projecting from underneath the housing 1206, facing proximally and opposite the cap 1298, is a spherical projection 1308. In exemplary form, the spherical projection 1308 may be fixedly mounted to the primary housing 1206. In an alternative embodiment, the spherical projection 1308 may be repositionably mounted to the primary housing 1206. For example, the spherical projection 1308 may be vertically and/or laterally repositionable relative to the primary housing 1206. When repositioning the spherical projection 1308 vertically relative to the primary housing 1206, one may accommodate for different depths of bone resection.

As will be discussed in more detail hereafter, this spherical projection 1308 is configured to interface with a surgical guide 1320 and allow for one or more fixation holes and/or devices to be located on the distal femur 110 and proximal tibia 112 as alignment guides for further surgical procedures as part of providing uni or multi condylar knee replacement.

Each of the foregoing elements of the balancing assembly 1200 may be fabricated separately and thereafter assembled. Exemplary fabricating techniques for the foregoing elements of the balancing assembly 1200 may include one or more of machining, casting, and additive manufacturing (e.g., 3D printing). The foregoing elements may be fabricated from surgically acceptable materials that include metals, metal alloys, ceramics, plastics, and composites that are suitable to function in surgical applications.

Turning to FIGS. 57-61, an exemplary surgical guide 1320 may be used with one or more balancing assemblies 1200 and may include a pair of block C-shape frame members 1322, 1324 that may be adjustable in order to provide vertical height adjustments between the members. The frame members 1322, 1324 cooperate to delineate a central opening that is wide and vertically long enough to accommodate throughput of one or two balancing assemblies 1200. As will be discussed in more detail hereafter, the surgical guide 1320 is configured to fit over at least a portion of one or both balancing assemblies 1200 while the balancing assemblies are positioned so that the paddles 1202, 1204 interpose the tibia 12 and femur 110 (see FIG. 59).

By way of example, the first frame member 1322 may include a hollow tube 1328 sized to accommodate insertion of a corresponding projection 1330 of the second member 1324. By way of further example, the hollow tube 1328 may be rectangular and may delineate a cavity having a rectangular cross-section that is substantially constant, while the projection 1330 may comprise a linear projection having a substantially constant rectangular cross-section sized to fit within the hollow tube 1328. A set screw (not shown) may be inserted into a hole 1332 extending through a wall of the hollow tube 1328 in order to mount the projection 1330 to the tube and correspondingly fix the linear position of the projection with respect to the tube and fix the vertical position of the first frame member 1322 with respect to the second frame member 1324.

In exemplary form, the first frame member 1322 may also include a first rectangular block 1334, above the hollow tube 1328, that extends both forward and rearward with respect to the downwardly extending hollow tube. The first rectangular block may include one or more through holes 1336 that are in parallel with corresponding through holes 1338, 1340, 1342 extending through corresponding rectangular blocks 1346, 1348, 1350. It is envisioned that the through holes 1336-1342 are sized to accommodate and guide a surgical drill bit (not shown) for creation of corresponding holes 1394 within the tibia 112 and femur 110, and post bone hole creation the holes may guide and accommodate surgical pins 1354 (see FIGS. 66-68). In exemplary form, the rectangular blocks 1334, 1346 of the first frame member 1322 may be integrally formed with a cross bar 1356 to maintain the spacing and orientation of the blocks. By way of example, the cross bar 1356 may include a linear segment with a substantially constant rectangular cross-section that rounds over on opposing ends and joins the blocks 1334, 1346. While the cross bar 1356 is depicted as a having a fixed width (to maintain the spacing between the blocks 1334, 1346), it is also within the scope of the disclosure that the cross bar 1356 comprises multiple segments joined to one another that allow the medial-to-lateral spacing between the blocks 1334, 1346 to be changed. For example, the cross bar 1356 may include telescopic components that include visual markings showing the overall width or spacing between the blocks 1334, 1346 as the telescopic components are repositioned to increase or decrease the spacing between the blocks. Moreover, the telescopic components may include various shapes and cross-sections such as, without limitation, rectangular, multi-faced (triangular, pentagonal, etc.), circular, and oblong.

Opposite the first frame member 1322 is the second frame member 1324, which also includes corresponding blocks 1348, 1350 spaced apart in the widthwise dimension by a second cross bar 1360. In exemplary form, one side of the second frame member 1324 includes the corresponding projection 1330 extending from and inset with respect to a rectangular column 1362. An end of the column 1362, opposite the projection 1330, may be integrally formed with the third rectangular block 1350, which extends both forward and rearward with respect to the downwardly extending column. The third rectangular block 1350 may include one or more through holes 1342 that are in parallel with corresponding through holes 1338, 1340, 1342 extending through corresponding rectangular blocks 1334, 1348, 1350. Attached to the third rectangular block 1350, opposite the column 1362, is the second cross bar 1360. In exemplary form, the second cross bar 1360 includes a pair of longitudinal cavities 1364 having a trapezoidal cross-section and formed into opposing sides that extend generally along an entire widthwise dimension underneath the third and fourth blocks 1348, 1350. As will be discussed in more detail hereafter, these cavities 1364 may be traversed by a drop rod mount 1370.

Integrally mounted to the second cross bar 1360, in between the third and fourth blocks 1348, 1350, is a balancing assembly mount 1372 that defines a spherical depression 1374 configured to receive the spherical projection 1308 of a balancing assembly 1200 and capture the spherical projection in a snap-fit manner that retards disconnection of the spherical projection, but allows the surgical guide 1320 to rotate and pivot with respect to the balancing assembly to which it is mounted. An opening 1376 may be provided through the mount 1372 and into the spherical depression 1374 that may accommodate a set screw (not shown) in order to fix the orientation of the surgical guide 1320 with respect to the balancing assembly 1200 to which it is mounted. By way of example, the balancing assembly mount 1372 is offset to one side (lateral or medial, depending upon perspective) in order to allow the surgical guide 1320 to be mounted to either balancing assembly 1200, presuming two balancing assemblies are concurrently used, once the spherical projection 1308 is seated within the spherical depression 1374. It should be noted that the features of the surgical guide 1320, other than the balancing assembly mount 1372, are identical from opposing sides, which allows the surgical guide to be flipped to mount the surgical guide to either the medial balancing assembly 1200 or the lateral balancing assembly 1200.

In exemplary form, the rectangular blocks 1348, 1350 of the second frame member 1324 may be integrally formed with the second cross bar 1360 to maintain the spacing and orientation of the blocks. By way of example, the cross bar 1360 may include a linear segment with a substantially constant I-shaped cross-section that mounts to the blocks 1348, 1350 on opposing ends. While the cross bar 1360 is depicted as a having a fixed width (to maintain the spacing between the blocks 1348, 1350), it is also within the scope of the disclosure that the cross bar 1360 comprises multiple segments joined to one another that allow the spacing between the blocks 1348, 1350 to be changed. For example, the cross bar 1360 may include telescopic components that include visual markings showing the overall width or spacing between the blocks 1348, 1350 as the telescopic components are repositioned to increase or decrease the spacing between the blocks, while maintaining the cavities 1364 to allow traversal of the drop rod mount 1370.

By way of example, the drop rod mount 1370 defines a spherical depression 1378 configured to receive a spherical projection 1380 of a drop rod block 1382. And the drop rod block 1382 includes a through opening 1384 sized to receive and allow traversal of a drop rod 1386. In exemplary form, the drop rod 1386 includes an extended cylinder with an oversized top 1388 to preclude the entire drop rod from passing through the opening 1384. The spherical projection 1380 of the drop rod block 1382 is configured to be received in a snap-fit manner within the spherical depression 1378 of the drop rod mount 1370 to retard disconnection of the spherical projection, but allow the drop rod block 1382 (and drop rod 1386 if inserted in the opening 1384) to rotate and pivot with respect to the drop rod mount 1370 to which it is mounted. An opening 1390 may be provided through the drop rod mount 1370 and into the spherical depression 1378 to accommodate a set screw (not shown) in order to fix the orientation of the drop rod block 1382 (and drop rod 1386 if inserted in the opening 1384) with respect to the drop rod mount. By way of example, the drop rod mount 1370 may include a projection 1392 having a trapezoidal cross-section and sized to be received within the cavities 1364. In this manner, the drop rod mount 1370 may be mounted to the second cross bar 1360 by repositioning the projection 1392 within one of the corresponding cavities 1364 and, thus, allow repositioning of the drop rod mount with respect to the second cross bar in a linear path.

Each of the foregoing elements of the surgical guide 1320 may be fabricated separately and thereafter assembled. Exemplary fabricating techniques for the foregoing elements of the surgical guide 1320 may include one or more of machining, casting, and additive manufacturing (e.g., 3D printing). The foregoing elements may be fabricated from surgically acceptable materials that include metals, metal alloys, ceramics, plastics, and composites that are suitable to function in surgical applications.

Turning to FIGS. 62-68, an exemplary sequence for using one or two balancing assembles 1200, along with a surgical guide 1320, will be described in the context of a total knee replacement procedure. It should be noted, however, that the exemplary sequence is applicable to uni knee replacement and knee revision joint surgeries, as well as other surgical procedures.

Figure 62:
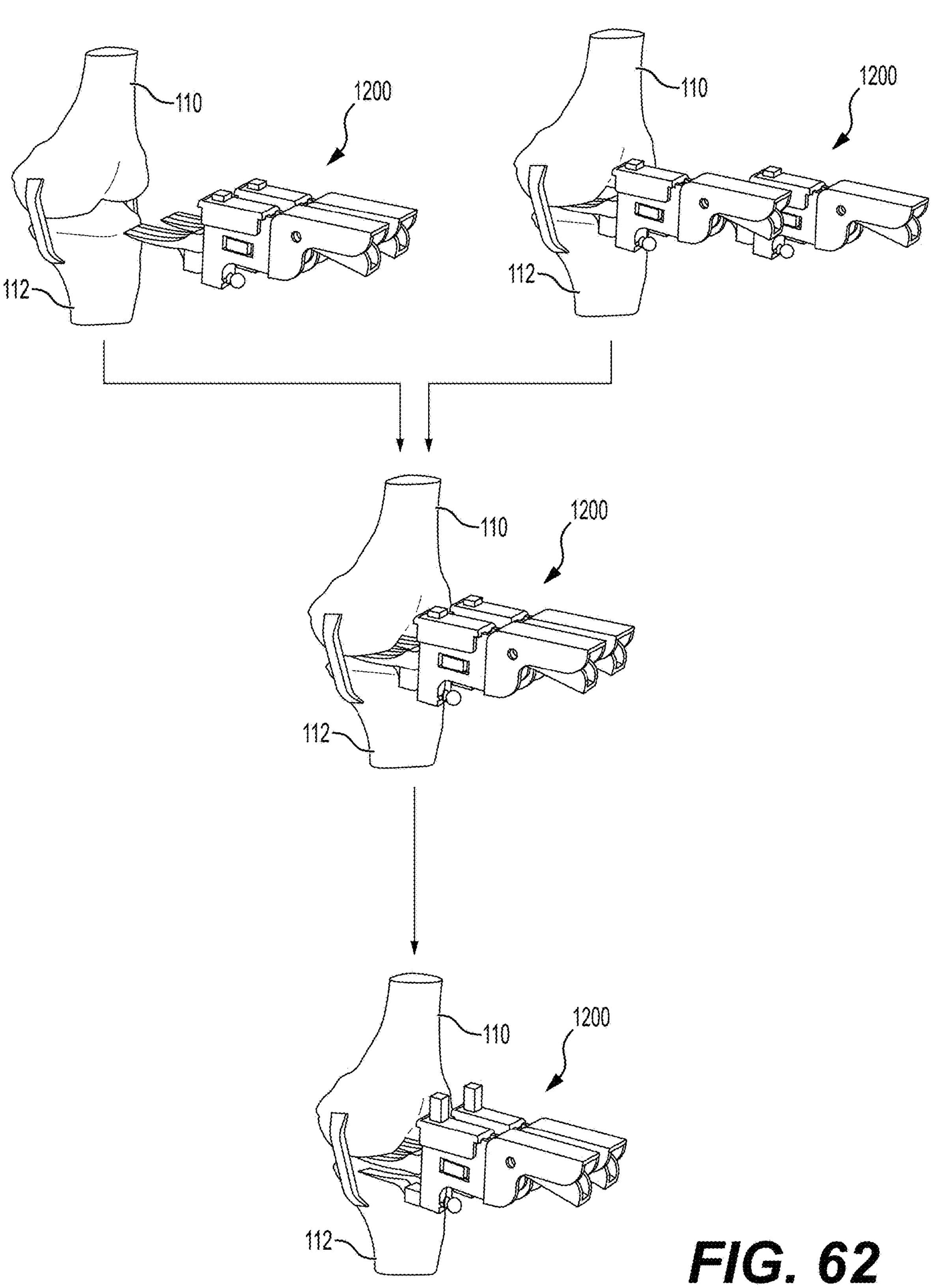
FIG. 62 is a sequential depiction including a series of elevated perspective views of a knee joint relative to balancing assemblies in accordance with the instant disclosure.

Referring to FIG. 62, as an initial step for carrying out a total knee replacement surgery, post exposing the knee joint, a pair of balancing assemblies 1200 are set so that the paddles 1202, 1204 are generally level with one another. In this configuration, the handle 1270 is extended, which corresponds to the springs 1216 being fully or substantially compressed and maintained in this position by the stopper 1256 prohibiting vertical motion of the rack 1240 (see FIG. 54) and corresponding vertical motion of the paddles 1202, 1204 with respect to one another. The balancing assemblies may be repositioned individually or as a pair with respect to a patient's joint (in this case, a knee joint comprising a distal femur 110 and a proximal tibia 112) so that the paddles 1202, 1204 interpose two bones.

By way of example, a first balancing assembly 1200 is positioned so that the paddles 1202, 1204 are positioned between the lateral condyle of the femur 110 and the lateral condyle receiver of the tibia 112. More specifically, the first balancing assembly 1200 may be repositioned so that the paddles 1202, 1204 are positioned between a lateral condyle dwell location on the femur 110 and a lateral condyle receiver dwell location on the tibia 112. And the second balancing assembly 1200 is positioned so that the paddles 1202, 1204 are positioned between the medial condyle of the femur 110 and the medial condyle receiver of the tibia 112. More specifically, the second balancing assembly 1200 may be repositioned so that the paddles 1202, 1204 are positioned between a medial condyle dwell location on the femur 110 and a medial condyle receiver dwell location on the tibia 112. It should be noted that while FIG. 62 depicts the knee joint at full extension when the balancing assemblies are initially positioned, the balancing assemblies 1200 may be positioned between the tibia and femur in various angles of flexion including, without limitation, at mid-flexion (approximately 45 degrees), at 90 degrees of flexion, at full flexion, or at any angle chosen between full flexion and full extension.

Figure 53:
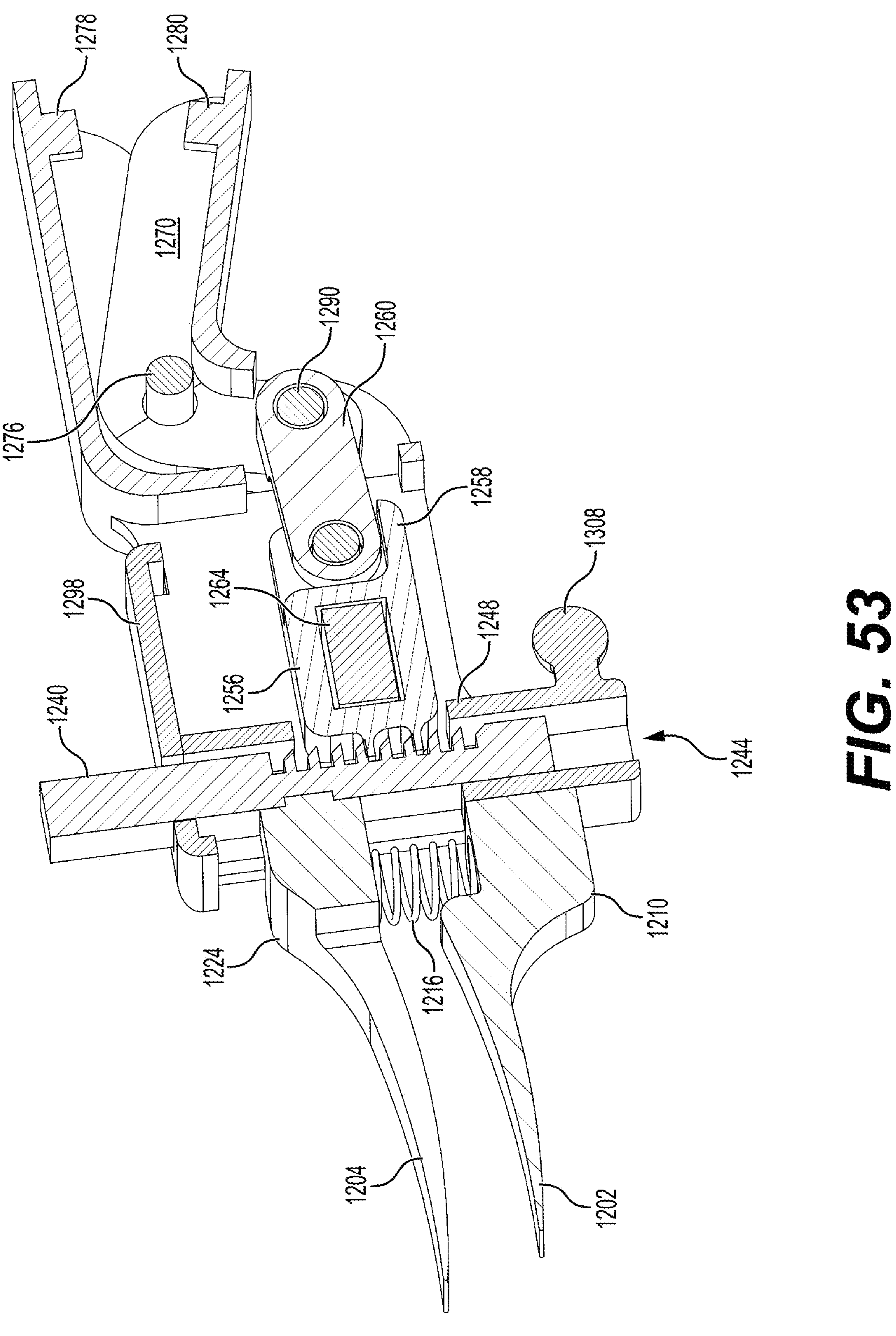
FIG. 53 is a cross-sectional view of the balancing assembly of FIG. 50.
Figure 54:
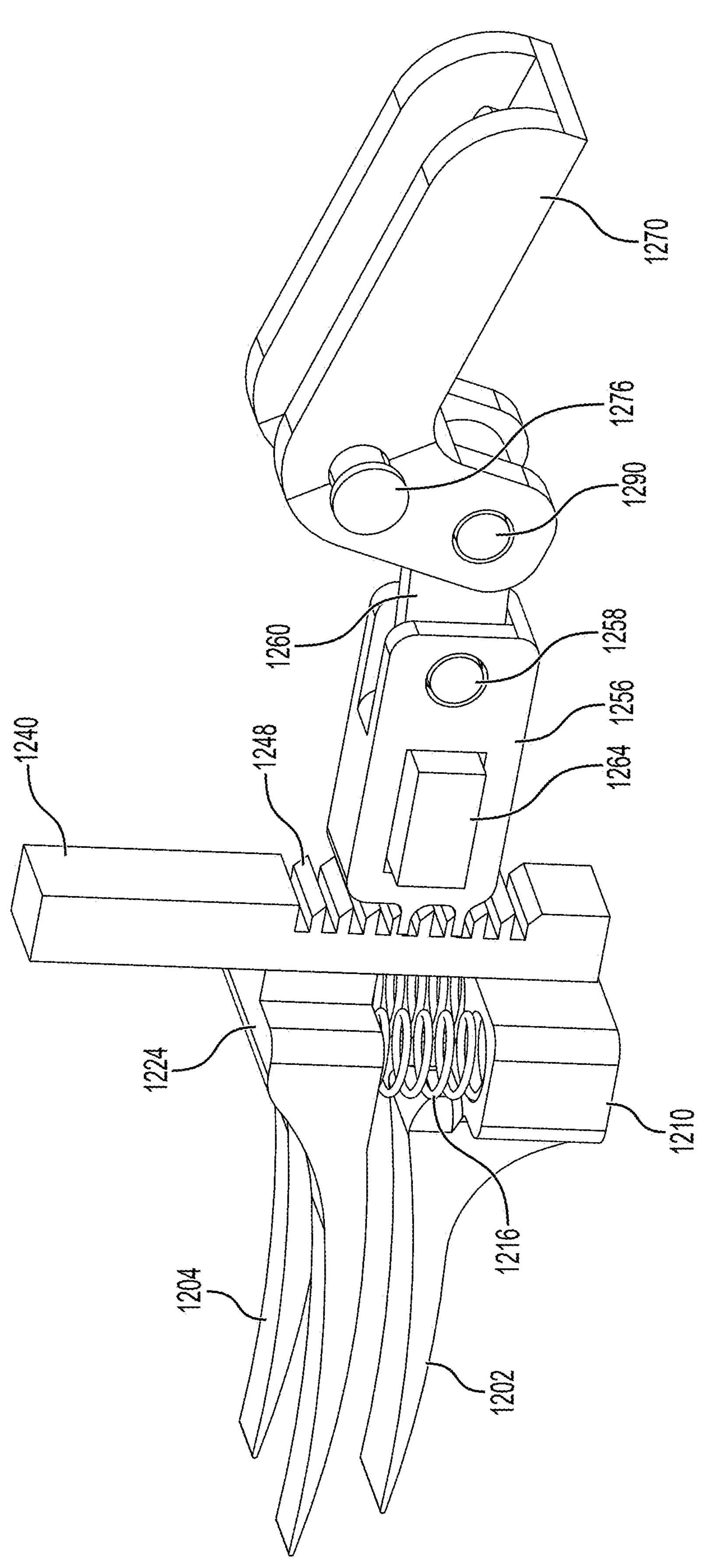
FIG. 54 is a rear perspective view of the balancing assembly of FIG. 50 without the housing and top cap.
Figure 55:
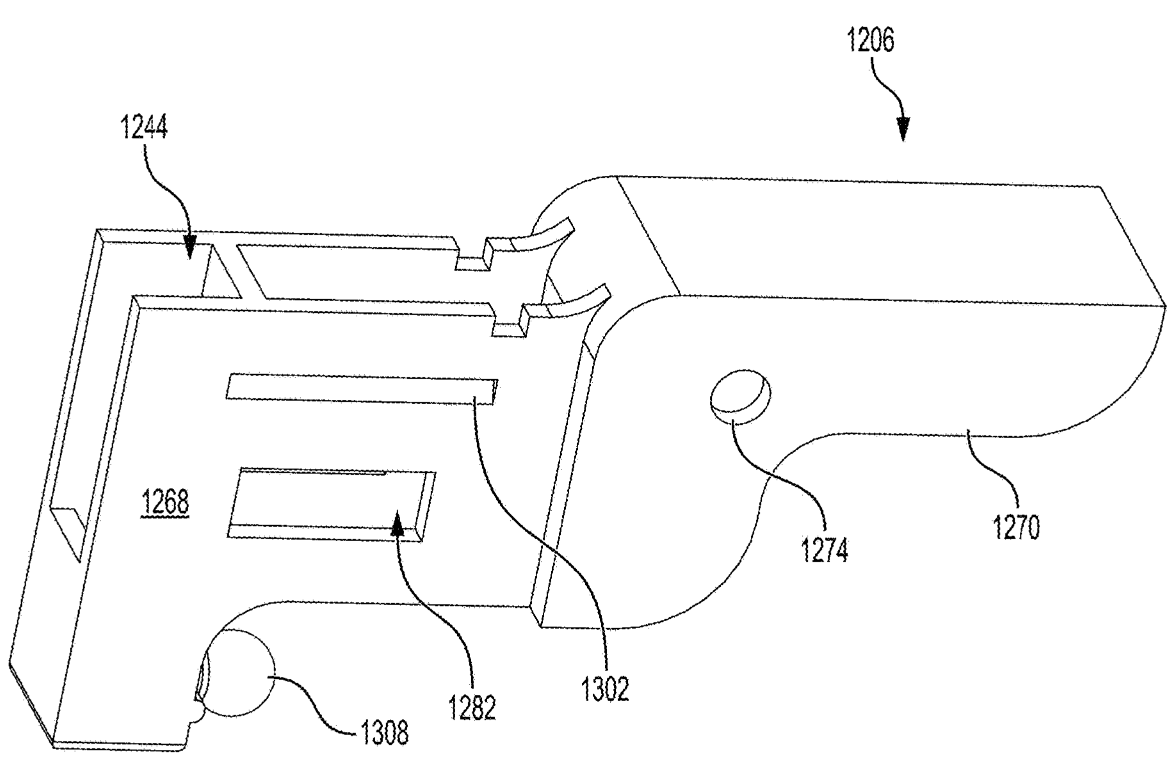
FIG. 55 is a front perspective view of an exemplary housing in accordance with the instant disclosure.
Figure 56:
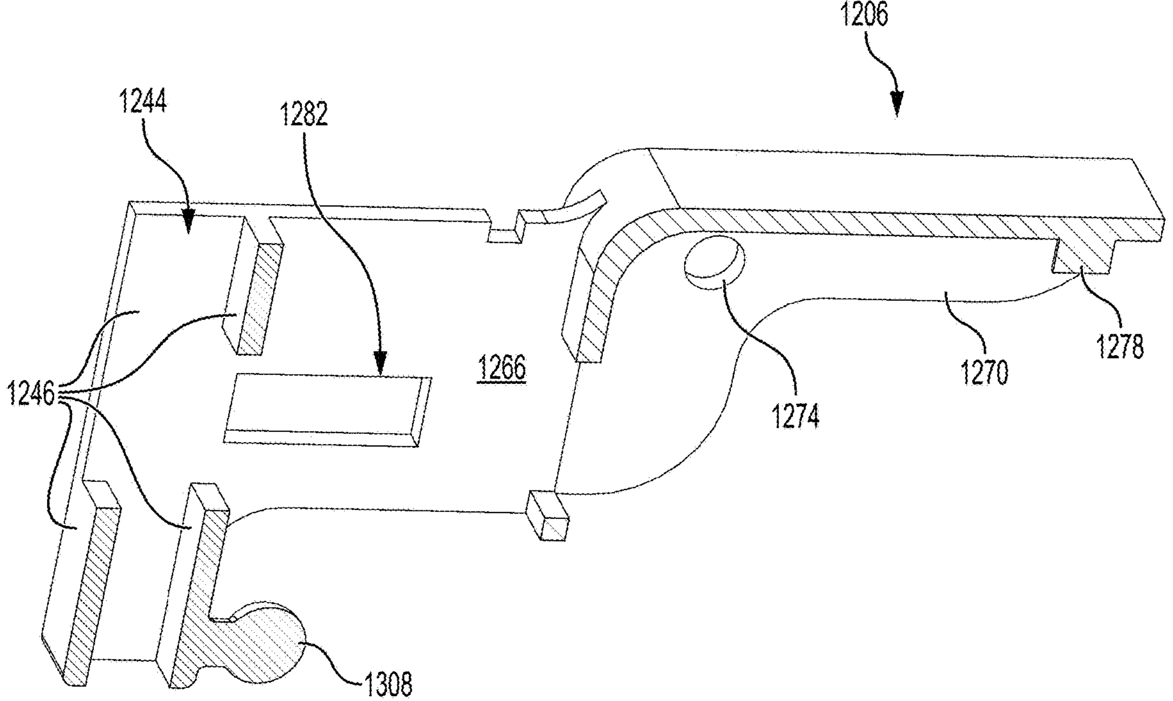
FIG. 56 is a cross-sectional view of the housing of FIG. 55.
Figure 57:
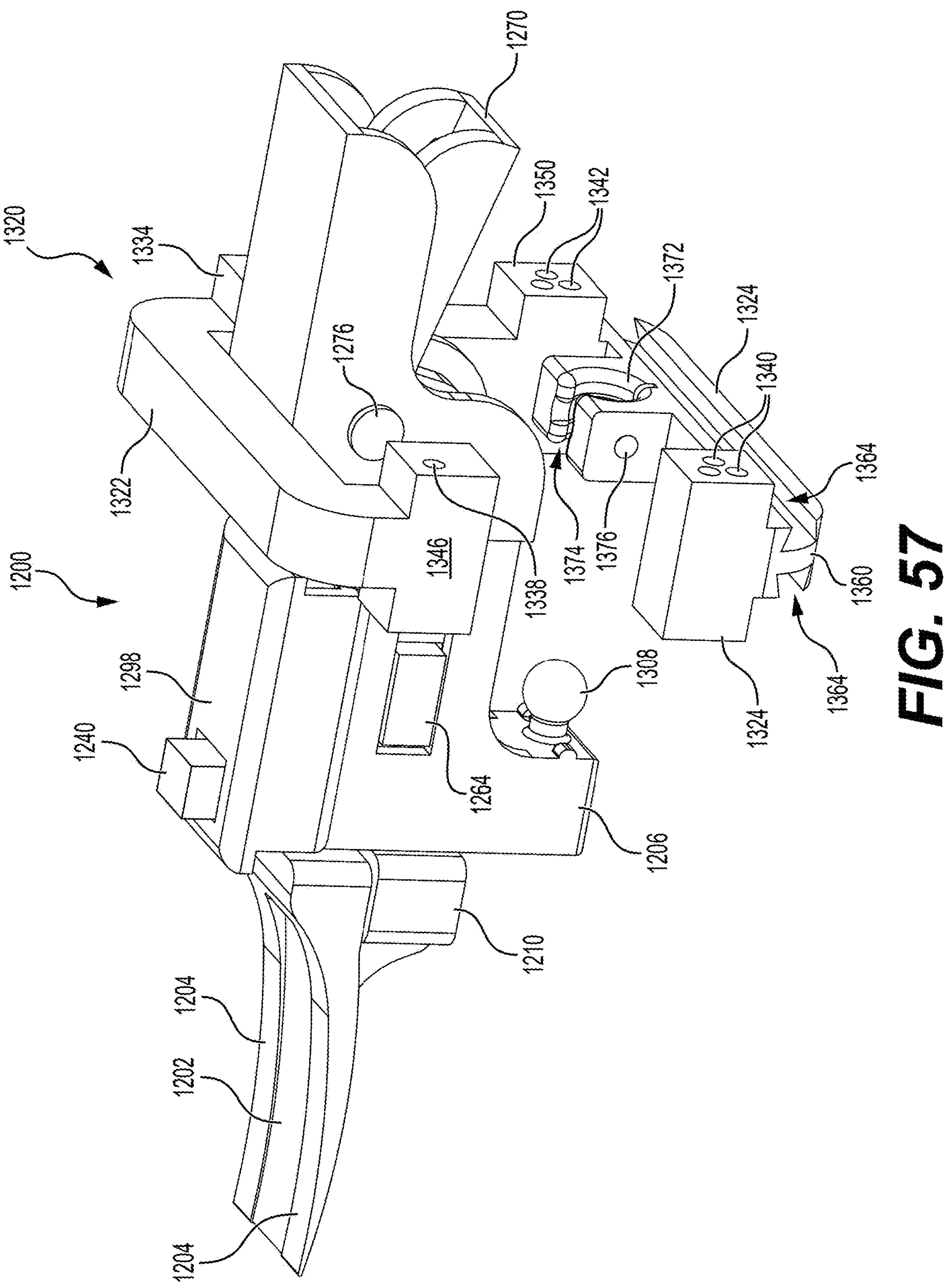
FIG. 57 is a rear perspective view of a balancing assembly decoupled from a surgical guide in accordance with the instant disclosure.
Figure 58:
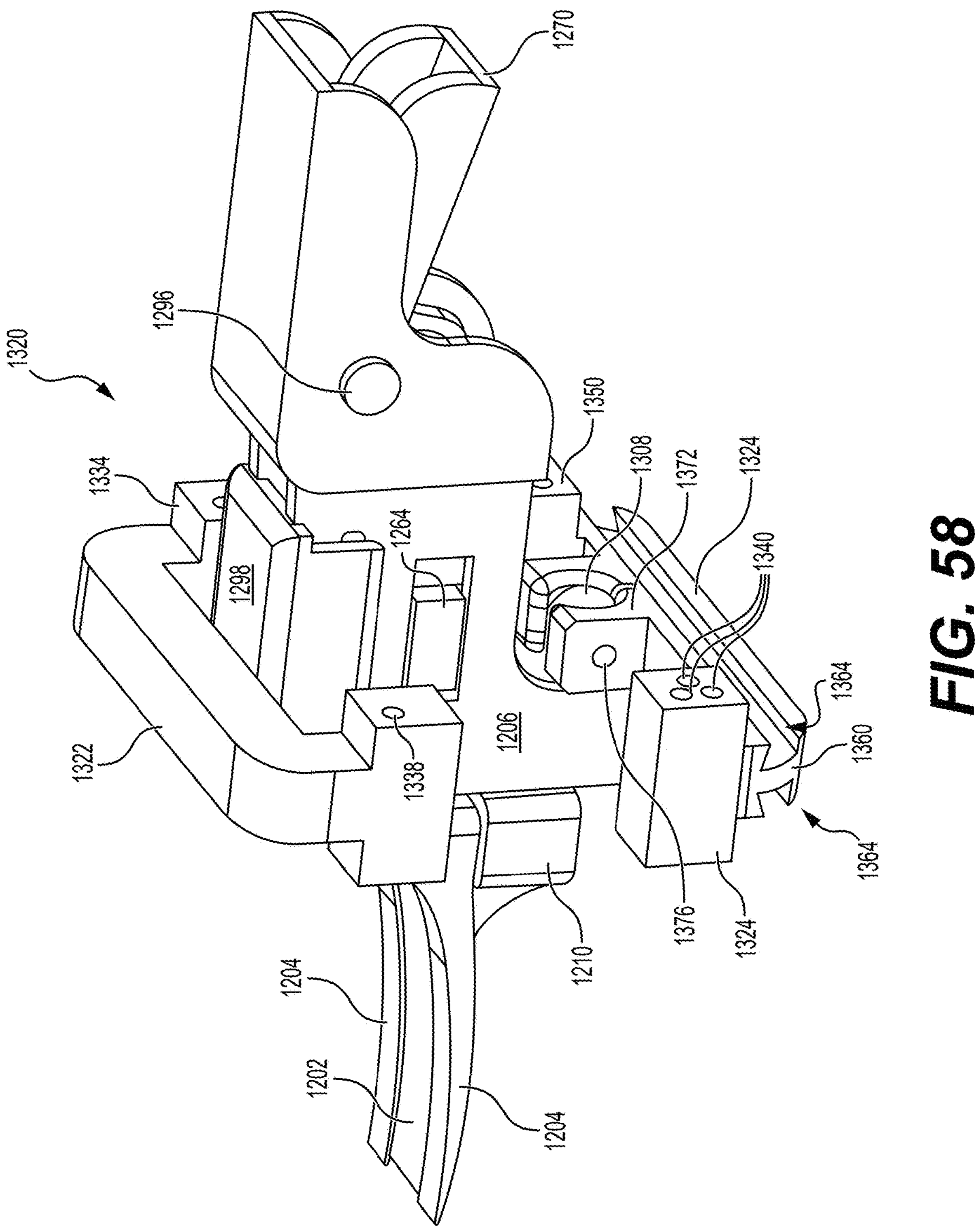
FIG. 58 is a rear perspective view of a balancing assembly coupled to a surgical guide in accordance with the instant disclosure.
Figure 59:
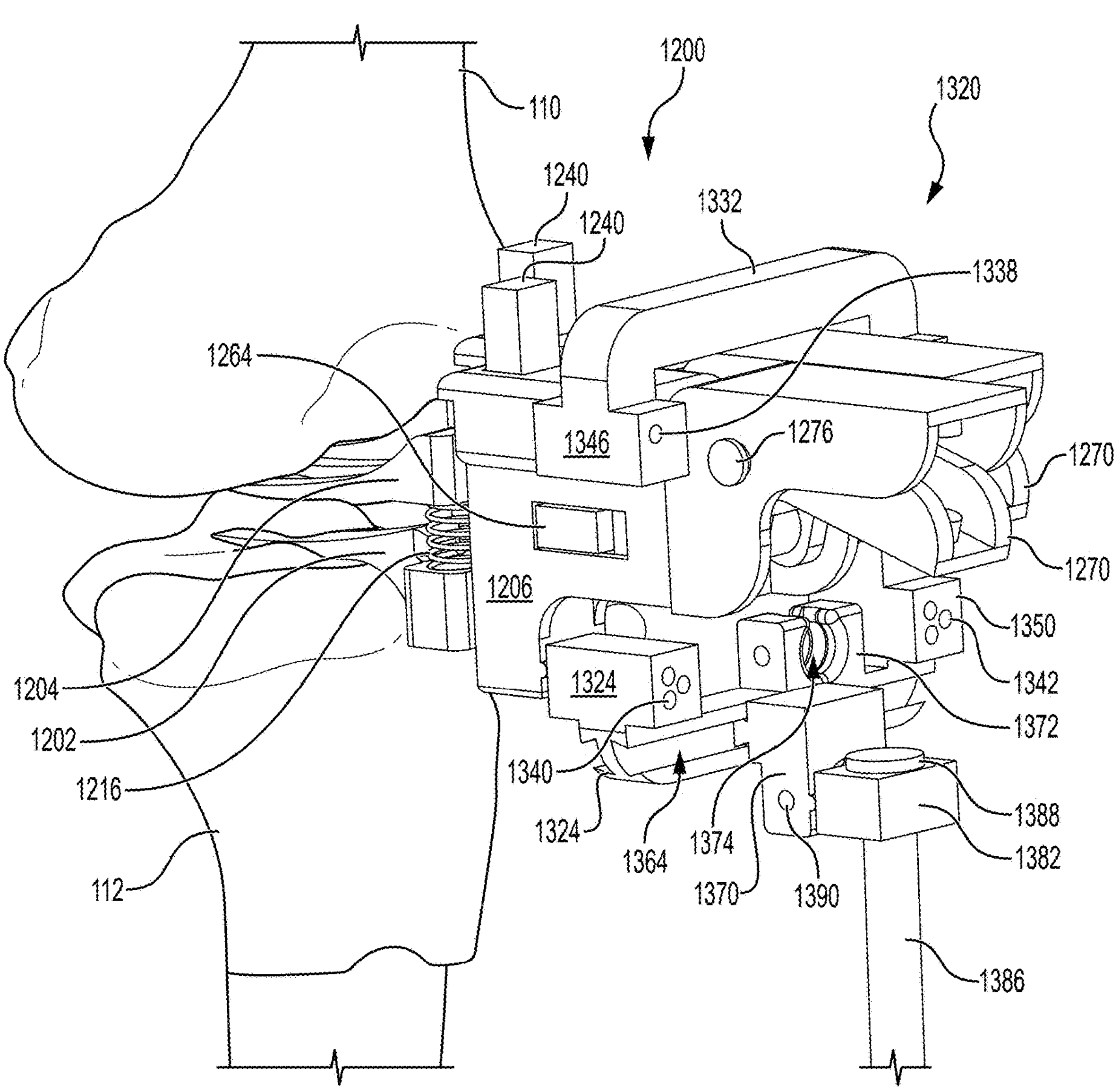
FIG. 59 is an elevated perspective view of a knee joint and a pair of balancing assemblies, with a surgical guide mounted to one balancing assembly, in accordance with the instant disclosure.
Figure 60:
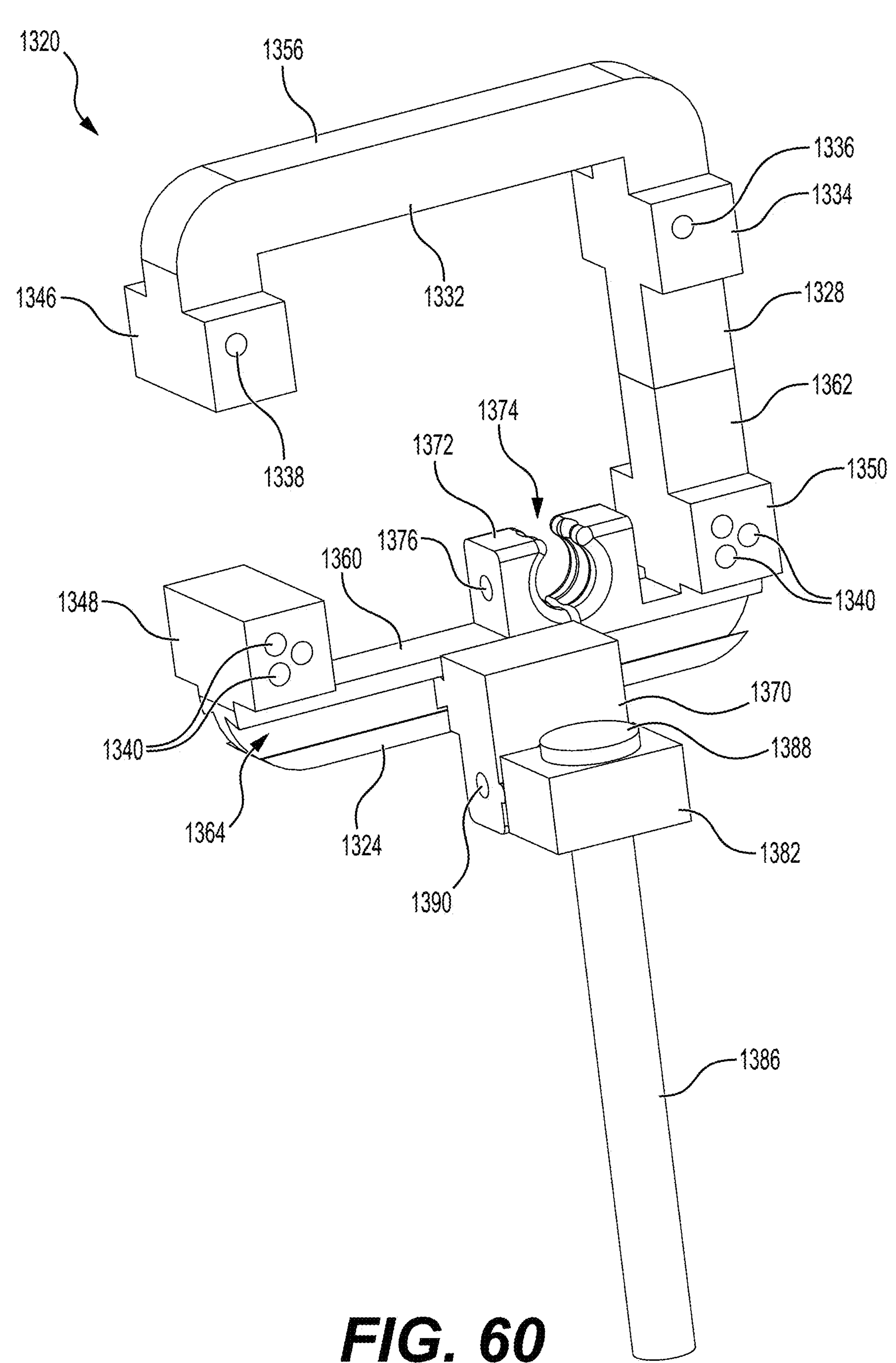
FIG. 60 is an elevated perspective view of an exemplary surgical guide in accordance with the instant disclosure.
Figure 61:
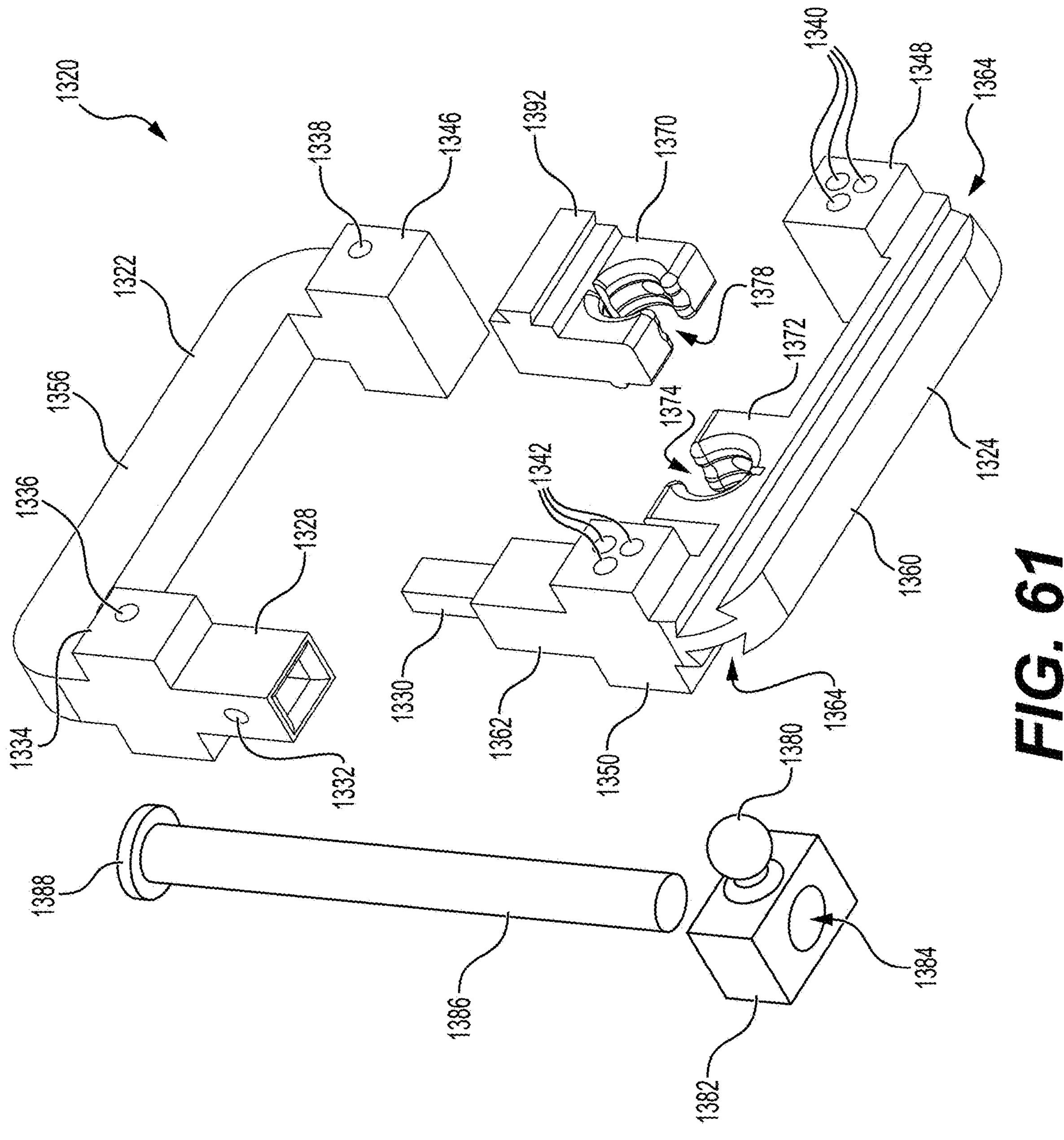
FIG. 61 is an exploded view of the exemplary surgical guide of FIG. 60.
Figure 63:
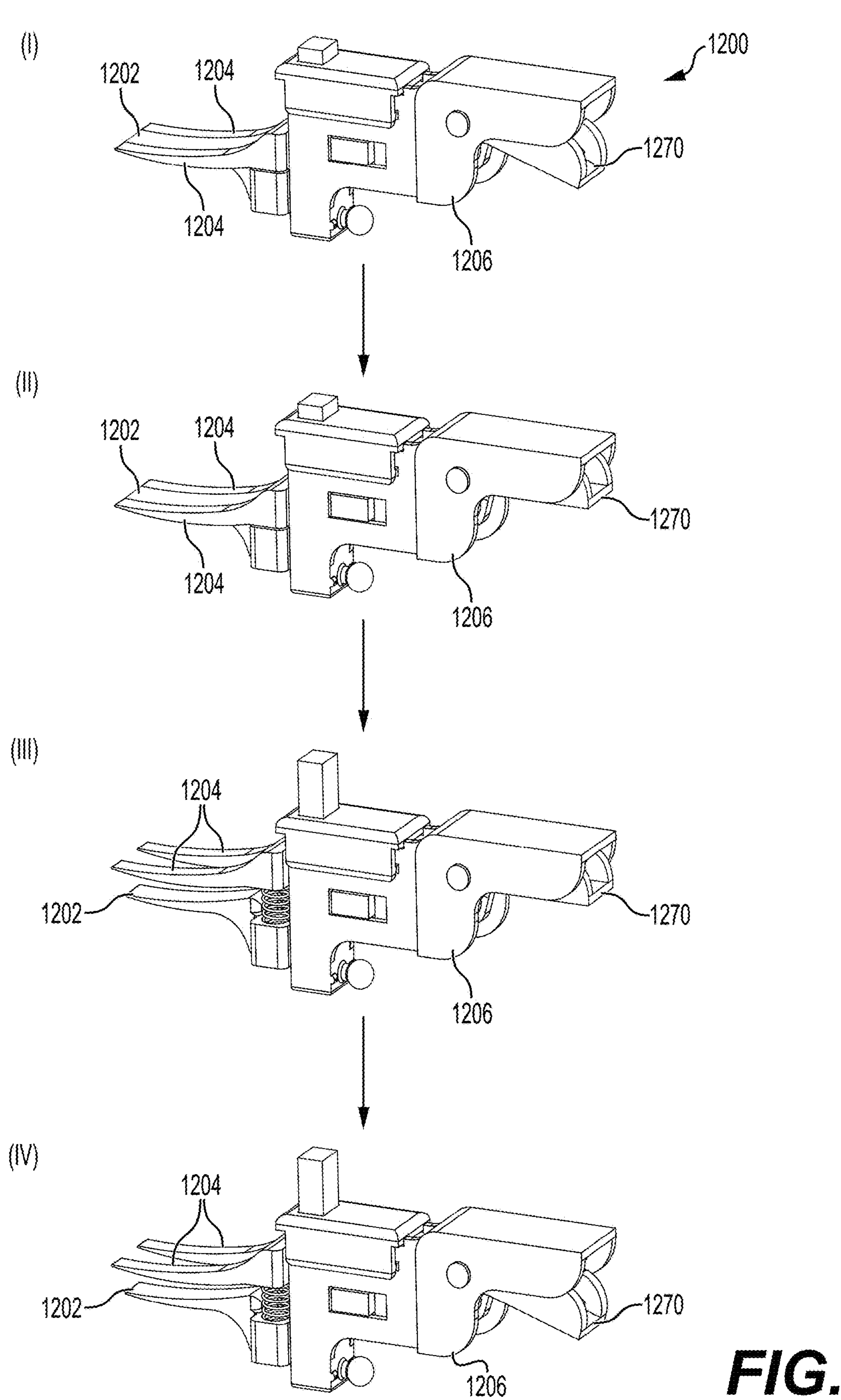
FIG. 63 is a sequential depiction including a series of elevated perspective views of a balancing assembly being repositioned in accordance with the instant disclosure.

Referencing FIGS. 53 and 63, after reaching the proper position of the paddles 1202, 1204 for each balancing assembly 1200 with respect to dwell locations on the tibia 112 and femur 110 (step I), the handle 1270 is compressed with respect to the housing 1206 (step II). Doing so is operative to pivot the handle 1270 about the pivot pin 1276, which in turn is operative to reposition the link 1260 rearward (away from the paddles 1202, 1204). As the link 1260 is positioned rearward, its coupling to the stopper 1256 results in the stopper moving rearward too. This rearward motion of the stopper 1256 coincides with rearward motion of the catches 1250 with respect to the teeth 1248 of the rack 1240, eventually causing the catches to no longer engage the teeth (step III). When the catches 1250 no longer engage the teeth 1248, the bias of the springs 1216 allows the upper base 1224 and rack to be repositioned vertically upward, coinciding with the upper paddle 1204 being able to be vertically repositioned. In this manner, the upper paddle 1204 is repositioned so that a gap between the bones (on the medial or lateral side) is spanned by the paddles 1202, 1204. It should be noted that the bias of the springs 1216 can vary depending upon physician preference (i.e., whether the physician prefers a laxer joint or a tauter joint). Accordingly, the instant balancing assembly 1200 provides for the physician to tune the balancing assembly 1200 by using different springs with different spring rates depending upon physician preference and patient considerations. In summary, after the paddles 1202, 1204 are initially positioned with respect to the tibia 112 and femur 110, the handle 1270 is compressed with respect to the housing 1206, which almost instantaneously causes the upper paddle 1204 to be repositioned vertically so the vertical spacing between the paddles is such that the paddles are wedged between the femur 110 and tibia 112. Afterwards, the handle 1270 may be repositioned (i.e., released) and no longer compressed (step IV). This process may be similarly followed for each other balancing assembly 1200.

After the handle 1270 is released (step IV), and pivots around the pivot pin 1276 in the opposite direction, the pivoting motion of the handle is operative to push the link 1260 forward (toward the paddles 1202, 1204). And the forward motion of the link 1260 pushes the stopper 1256 forward so that the catches 1250 engage the teeth 1248 and effectively lock the paddles 1202, 1204 in position. It should be noted that the teeth 1248 all include a beveled edge that works to inhibit the catches 1250 from stopping at the leading edge and not effectively being seated between corresponding teeth, which would otherwise allow free vertical motion of the rack 1240, the upper base 1224, and the upper paddle 1204. When the paddles 1202, 1204 are spaced apart from one another and locked in relative position, the surgeon may measure the vertical distance between the paddles. In this fashion, the upper base 1224 may include outside indicia that correspond to outside indicia on the housing base 1206 to allow quick reference for the physician and provide quantitative information as to the spacing between the paddles using both indicia. This process may be similarly followed for each other balancing assembly 1200.

Turning to FIGS. 64A-69B, once the spacing on the medial and lateral sides is determined from the paddles 1202, 1204, the surgical guide 1320 may be utilized to guide a drill bit (not shown) and insertion of corresponding surgical pins 1354 to occupy the drilled holes. As discussed herein, the surgical guide 1320 includes corresponding frame members 1322, 1324 that may be repositionable with respect to one another to vary the dimensions of the guide and change the location of the guide through holes 1336-1342. FIGS. 64A and 64B show, by way of example, how the frame members 1322, 1324 may be repositioned relative to one another to increase the vertical dimension of the guide 1322 and correspondingly increase the height of a rectangle eventually formed by the placement of the surgical pins 1354. By way of further example, a set screw (not shown) may be loosened to allow the projection 1330 to vertically move with respect to the hollow tube 1328 to establish the proper position (in the case of FIG. 64B, to increase the vertical dimension of the guide 1320) and thereafter tightened to fix the position of the projection with respect to the hollow tube. This adjustment may be undertaken before or after the guide 1320 is secured to a balancing assembly 1200. In any event, FIG. 65 shows a front view depicting the relative position of the surgical guide 1320 with respect to the tibia and femur.

Figure 66:
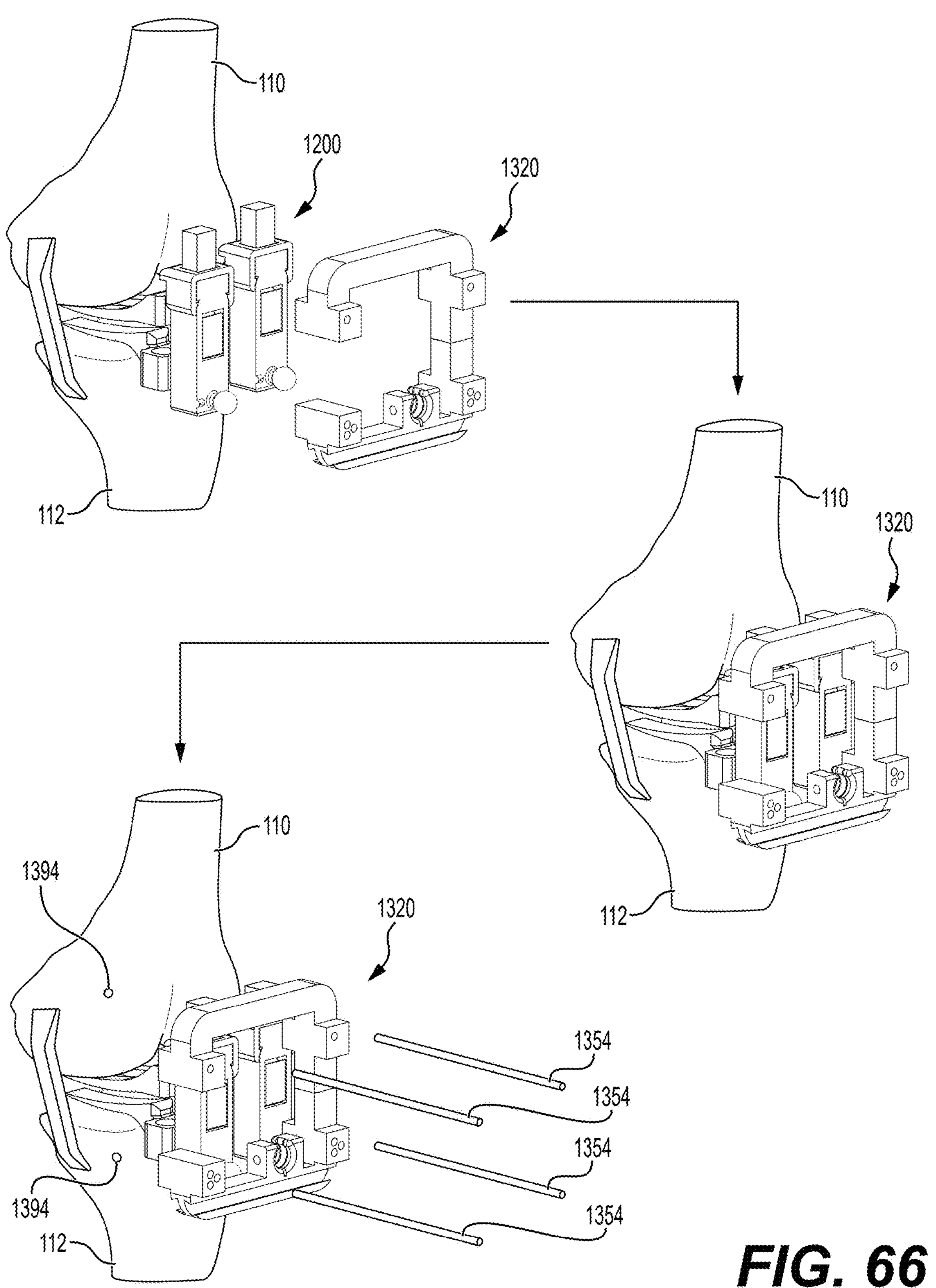
FIG. 66 is a sequential depiction including a series of elevated perspective views of a knee joint relative to partial balancing assemblies and a surgical guide in accordance with the instant disclosure.

With reference to FIG. 66, the surgical guide 1320 may be mounted to a balancing assembly 1200 using the coupling between the spherical projection 1308 and the balancing assembly mount 1372. Depending upon which balancing assembly 1200 the surgical guide 1320 is intended to be mounted to (medial or lateral), the surgical guide may be rotated 180 degrees to facilitate engagement between the spherical projection 1308 and the balancing assembly mount 1372. In any event, the surgical guide 1320 may be positioned to approach the balancing assemblies 1200 so that the first frame member 1322 extends over a top of the balancing assemblies 1200, while the second frame member 1324 extends beneath the balancing assemblies to allow throughput of the handles 1270 beyond the central opening defined by the surgical guide. Continued movement of the surgical guide 1320 toward the knee joint may occur until the spherical projection 1308 is received and secured to the balancing assembly mount 1372. When this engagement occurs, the surgical guide 1320 is able to rotate with respect the balancing assemblies 1200 in the varus/valgus (anterior/posterior) direction and rotate about the flexion/extension axis of the joint. In this manner, the surgeon can adjust the rotational position of the surgical guide 1320 relative to the knee joint for adjustments of the varus/valgus joint line and posterior slope.

By using two balancing assemblies 1200, the surgeon may mount a surgical guide 1320 to one or both assemblies (successively or concurrently) to set the rotation of the guide relative to the tibia 112 or femur 110 or any other external reference, as well as accounting for axial rotation positions of the femur that change as a function of knee flexion. Because the knee is not a simple hinge joint, the femur rotates axially with respect to the tibia during knee flexion, and the spherical connection between the spherical projection 1308 and the balancing assembly mount 1372 provides for the guide 1320 to rotate with the femur 110 depending upon the degree of knee flexion to track proper kinematic alignment of the femur and tibia across a range of motion (across knee flexion angles and full extension).

As shown in FIG. 66, it should be noted that a balancing assembly 1200 may be configured so that a portion assembly is separable after the paddles 1202, 1204 are deployed between the tibia 112 and femur 110 and allowed to span a gap between these bones (whether resected or not). By way of example, the primary housing 1206 may be formed in two or more pieces that selectively joined to one another, approximately where the through openings 1282 originate. Likewise, the cap 1298 may be formed in two or more pieces so that at least a distal portion of the cap is retained and mounted to a distal portion of the primary housing 1206 when this aspect of the primary housing is disengaged from a proximal portion of the primary housing. Likewise, the stopper 1256 may be formed in pieces so that a portion thereof is retained to lock the relative positions of the paddles 1202, 1204 with respect to one another, where another portion is removed when the proximal portions of the cap 1298 and primary housing 1206 are removed. In this manner, the link 1260 and the handle 1270 may also be removed to retain a subset of the assembly 1200 as depicted in FIG. 66. By removing the proximal portions of one or both assemblies 1200, the working freedom of repositioning the surgical guide 1320 may be increased.

Figure 69A:
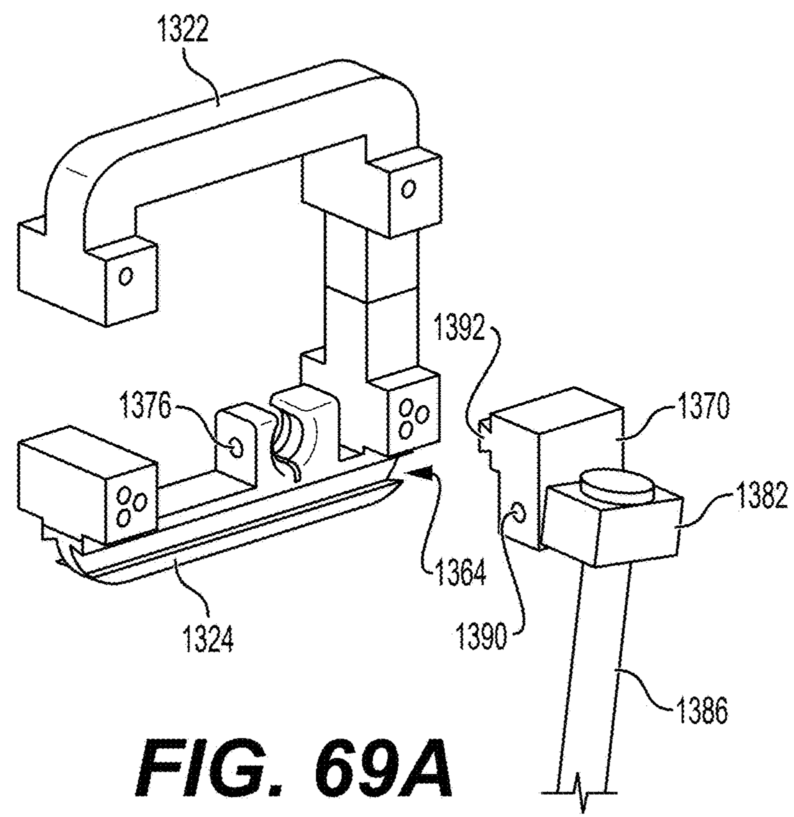
FIG. 69A is an elevated perspective view of a surgical guide with certain components dismounted from one another.
Figure 69B:
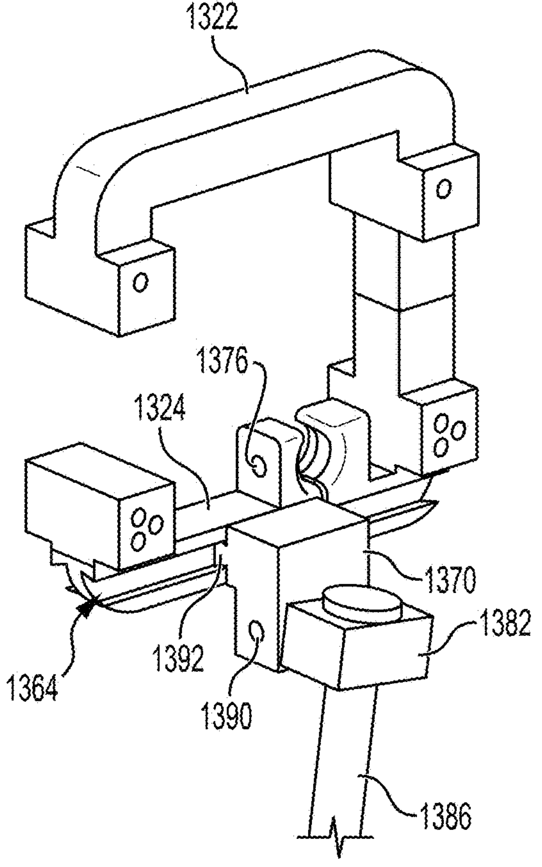
FIG. 69B is an elevated perspective view of a surgical guide with components mounted to one another.

Referring to FIGS. 69A and 69B, in order to make rotational adjustments of the surgical guide 1320 relative to the anatomy, the surgeon may make use of the drop rod 1386. In order to do so, the surgeon may align the projection 1392 of the drop rod mount 1370 with the trapezoidal cavity 1364 of the second frame member 1324 and slide the drop rod mount laterally or medially to secure the projection within the cavity. Beforehand or thereafter, the surgeon may secure the drop rod block 1386 to the drop rod mount 1370 using the interaction of the spherical projection 1380 and the spherical depression 1378, as well as inserting the drop rod 1386 through the drop rod block opening 1384. In this manner, the drop rod 1386 may be free to orient itself vertically in line with the longitudinal axis of the tibia 112.

By way of example, a surgeon may set/lock the desired flexion/extension and varus/valgus orientation of a proximal end of the drop rod 1386 with respect to the second frame member 1324. For example, the surgeon may set the drop rod 1386 at 3 degrees of posterior tibial slope and no varus/valgus (i.e., perpendicular).

The surgeon may point/orient the distal end of the drop rod 1386 parallel to the tibial 112 shaft (neutral flexion/extension) and pointed to the center of the talus (neutral varus/valgus), as an extramedullary alignment guide to set the guide 1320 into position with respect to a tibial axis. It should be noted that rather than using the tibia 112 as a point of reference, it is also within the scope of the disclosure to use the femur 110 and have the drop rod 1386 parallel to the femoral 110 shaft and pointed toward the center of the distal femur (with or without reference to the femoral head). Accordingly, the foregoing description serves only as an example of an axial reference as do the settings for flexion/extension and varus/valgus orientation. Moreover, this process can be carried out virtually as part of a surgical planning in stances where the center of the ankle or hip are known.

After establishing the proper rotational position of the surgical guide 1320, the surgical guide's orientation relative to the balancing assembly 1200 may be fixed by tightening a set screw (not shown) extending through the opening 1376 of the balancing assembly mount 1372. Thereafter, a surgical drill (not shown) and bit (not shown) may be used to establish a series of holes 1394 in the bones (both tibia 112 and femur 110). In order to properly align the holes, the surgical drill bit may be inserted through the holes 1336-1342 of the surgical guide 1320. Alternatively, the holes 1336-1342 may be used to guide a surgical marker for marking the bones 110, 112 with the intended location of the bone holes 1394. Thereafter, the holes 1394 may be drilled to a sufficient depth in the bones 110, 112. Post drilling the holes 1394, the balancing assemblies 1200 and surgical guide 1320 may be removed or retained and a series of surgical pins 1354 are inserted into the drilled holes. And these surgical pins 1354 may be utilized to align further surgical tools for subsequent surgical steps including, without limitation, guiding bone cutting guides as part of bone resection.

Figure 67:
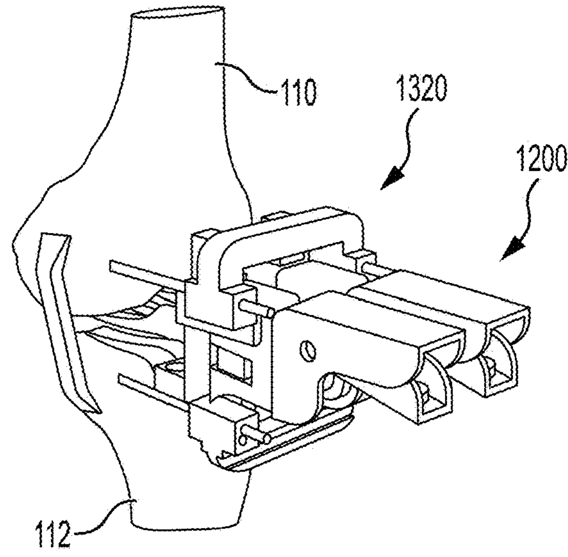
FIG. 67 is an alternative depiction including a series of elevated perspective views of a knee joint at different flexion positions relative to balancing assemblies and a surgical guide in accordance with the instant disclosure.
Figure 67:
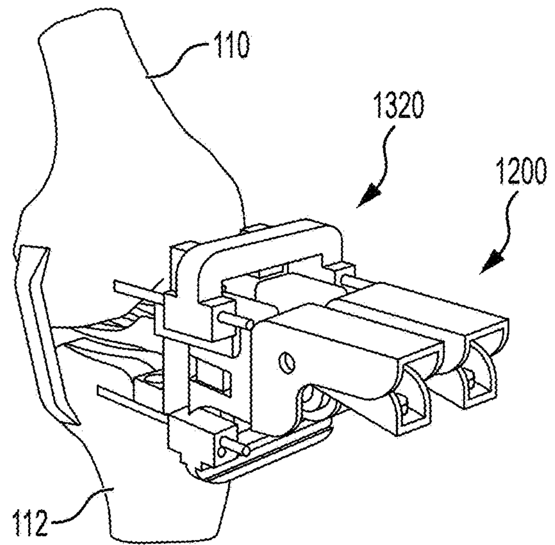
Figure 67:
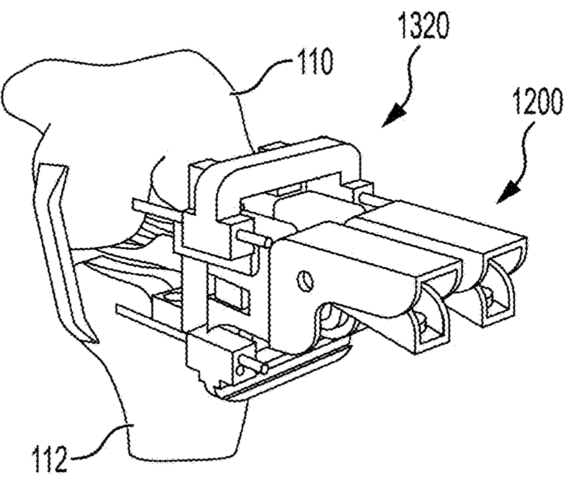

FIG. 67 shows how the surgical pins 1354 may be inserted into the bone holes 1394 using the surgical guide 1320 for different degrees of knee flexion including full extension, mid-flexion, and 90 degrees of flexion.

Figure 68:
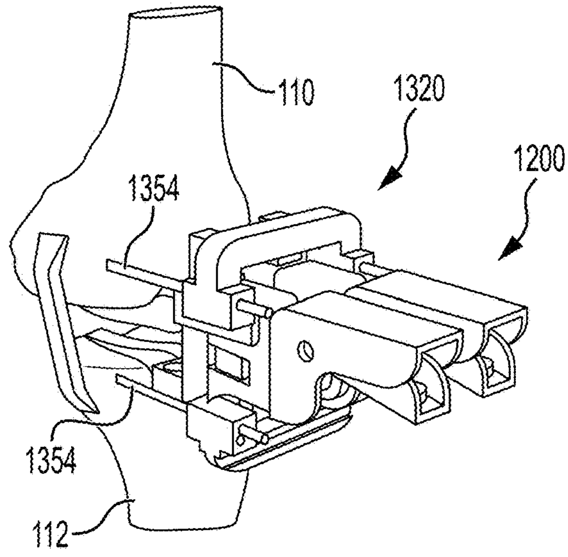
FIG. 68 is an alternative depiction including a series of elevated perspective views of a knee joint at different flexion positions and post bone cuts relative to balancing assemblies and a surgical guide in accordance with the instant disclosure.
Figure 68:
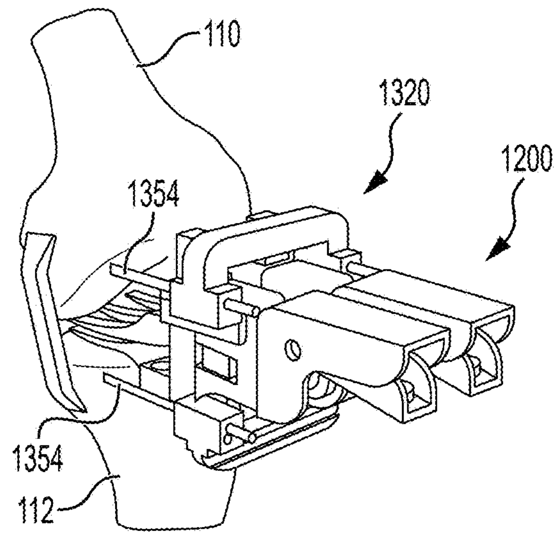
Figure 68:
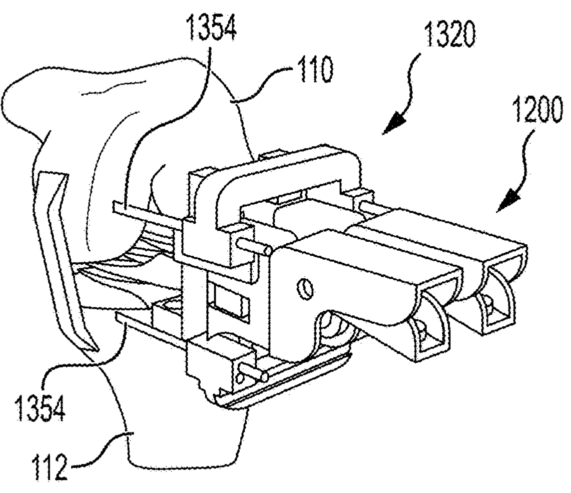

And the foregoing process may be repeated or used by itself even after one or more bone cuts on the femur 110 and tibia 112 are made. FIG. 68 shows a series of knee positions including full extension, mid-flexion, and 90 degrees of flexion using the exemplary surgical guide 1320 and balancing assemblies 1200 after completion of the tibial cut and after completion of the femoral distal cut.

While the foregoing process has been described using the tibia 112 as the reference, it is also within the scope of the disclosure to use the femur 110 or an external reference instead. In this manner, instead of what is described previously by way of placing femoral surgical pins 1354 at different degrees of knee flexion based upon at least one of the position, the orientation, and the resection condition (resected or not resected) of the tibia 112, the foregoing steps may be modified or changed to use the femur 110 as the reference for drilling holes in the tibia and positioning surgical pins 1354 into the drilled holes based upon the femur.

Figure 70:
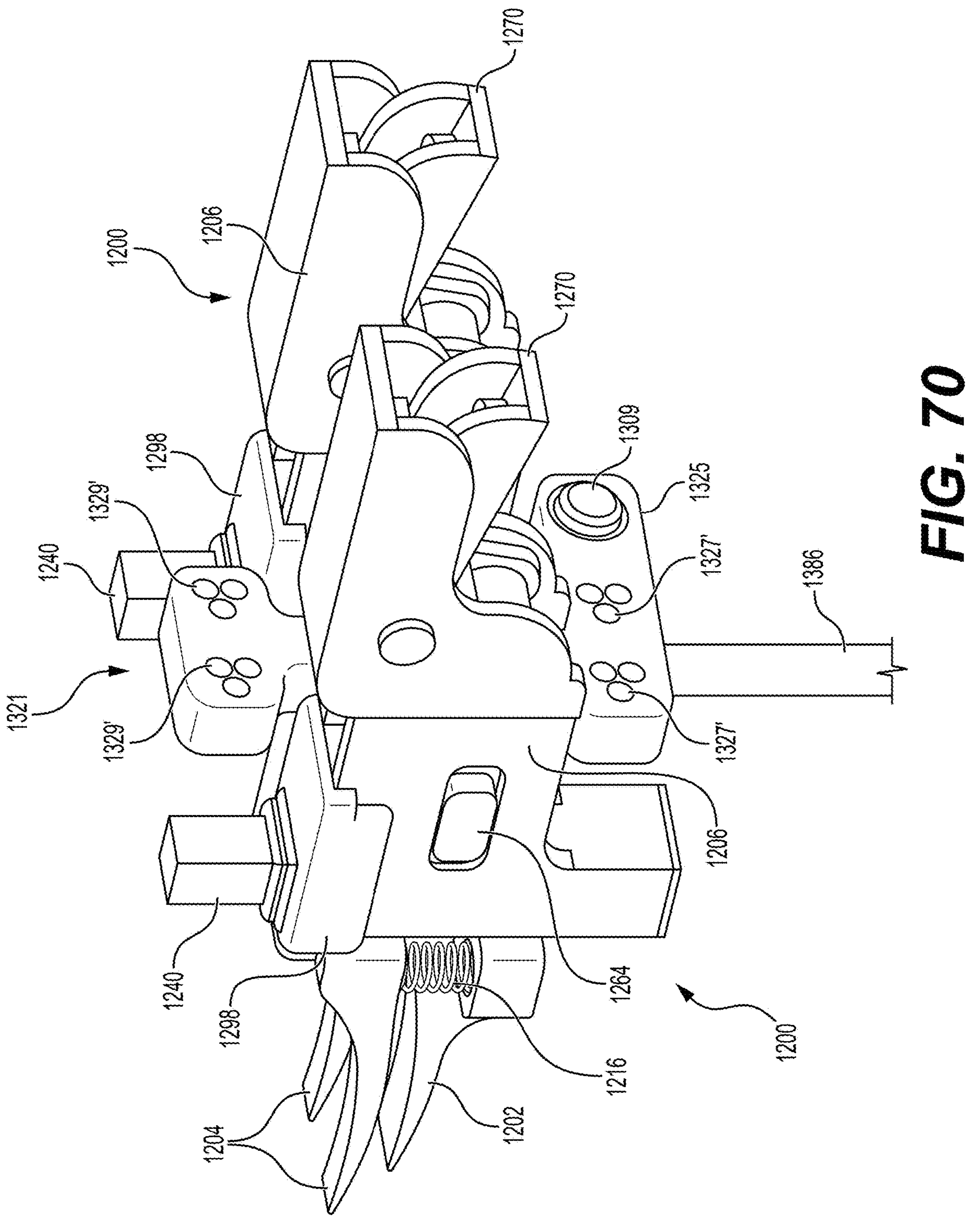
FIG. 70 is an elevated perspective view of a pair of balancing assemblies and an exemplary surgical guide in accordance with the instant disclosure.
Figure 71:
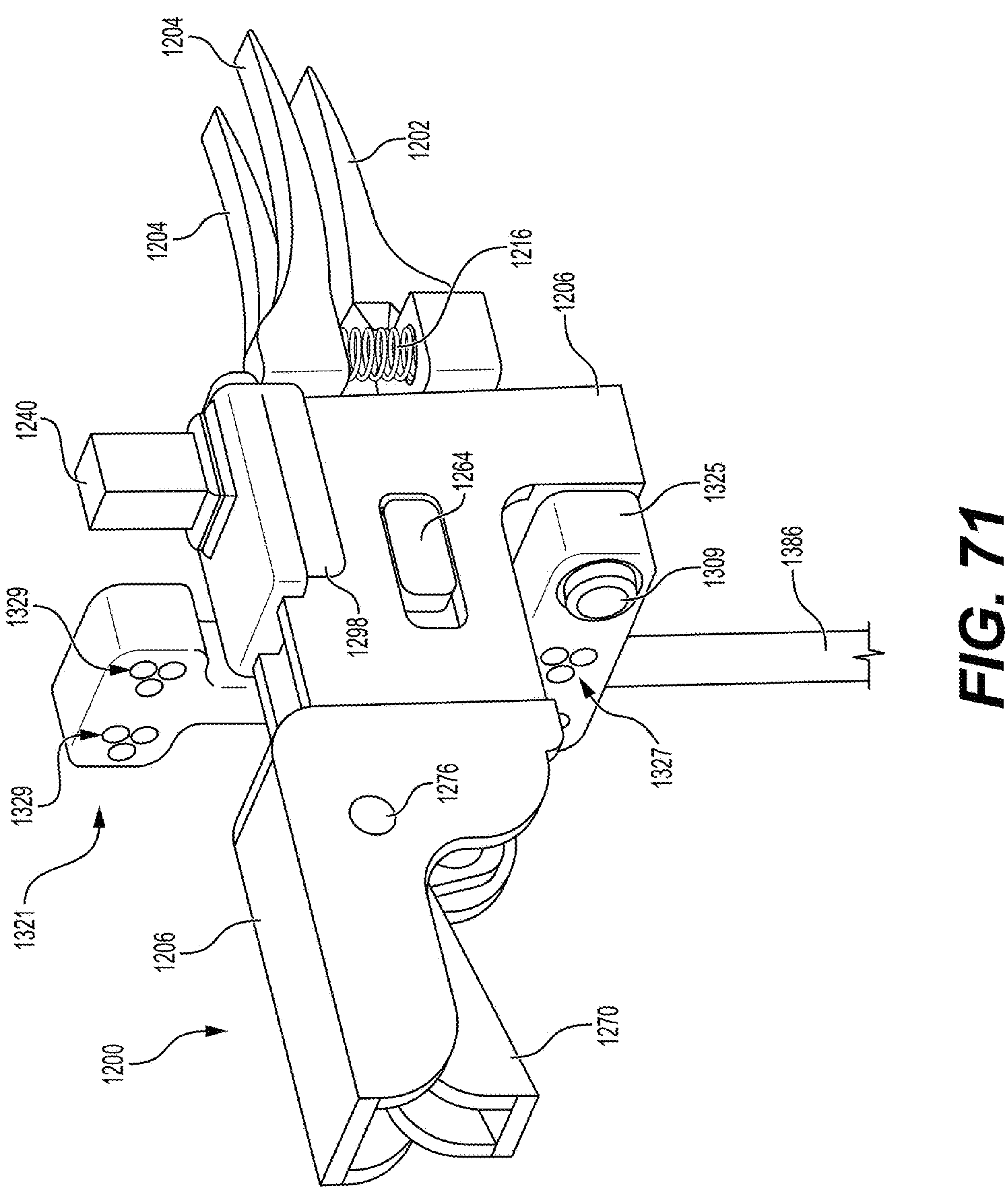
FIG. 71 is an elevated perspective view of a balancing assembly and the exemplary surgical guide of FIG. 70 in accordance with the instant disclosure.
Figure 72:
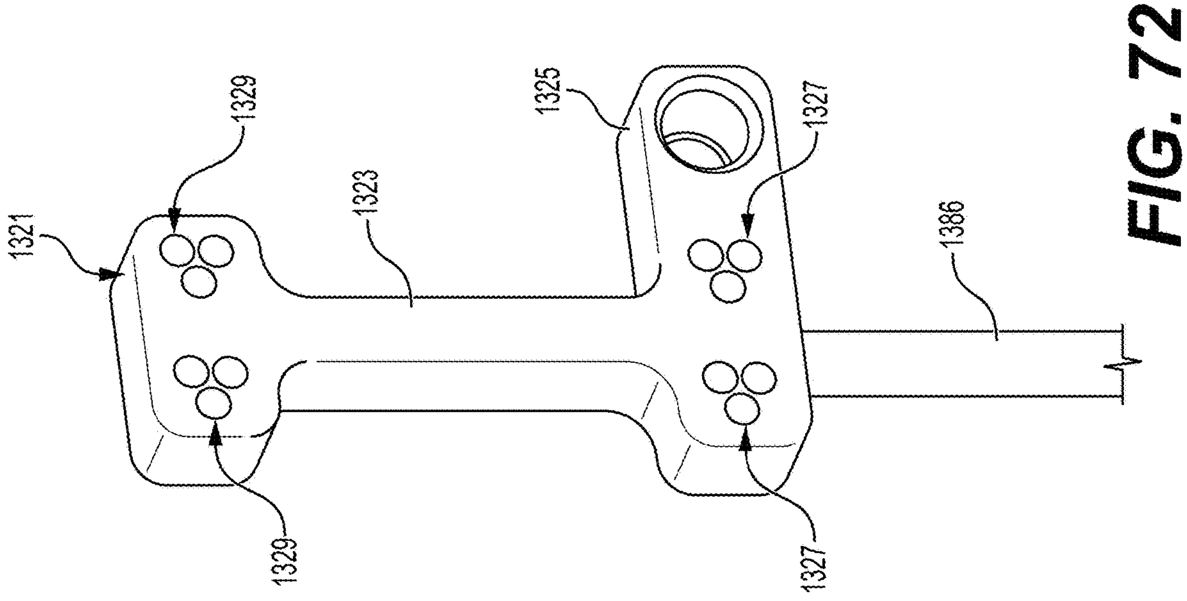
FIG. 72 is an elevated perspective view of the exemplary surgical guide of FIG. 70 in accordance with the instant disclosure.

Referencing FIGS. 70-72, the balancing assemblies 1200 discussed herein may be slightly modified to work with an alternate exemplary surgical guide 1321. In exemplary form, a balancing assembly 1200 may be modified to replace the spherical projection 1308 with a cylindrical projection 1309. Otherwise, the balancing assembly 1200 is unmodified and a duplicative explanation of the components thereof is omitted in furtherance of brevity.

As will be discussed in more detail hereafter, this cylindrical projection 1309 is configured to interface with the alternate exemplary surgical guide 1321 and allow for one or more fixation holes and/or devices to be located on the distal femur 110 and proximal tibia 112 as alignment guides for further surgical procedures as part of providing uni or multi condylar knee replacement.

The exemplary surgical guide 1321 may be used with one or more balancing assemblies 1200 and may include an L-shaped profile formed from an I-shaped segment 1323 and an arm 1325 that extends from a lower enlarged portion 1331 of the I-shaped segment. In exemplary form, the arm 1325 includes a cylindrical cavity sized to receive the cylindrical projection 1309 of a respective balancing assembly 1200. By way of example, the cylindrical cavity of the arm 1325 includes a diameter that is slightly larger than the diameter of the cylindrical projection 1309 so as to allow travel of the surgical guide 1321 in a proximal-to-distal direction with respect to a balancing assembly, and allow rotational motion of the surgical guide around the balancing assembly, but inhibit significant medial-to-lateral travel and rotation in the proximal-to-distal direction.

Opposite the arm 1325 and extending from proximal-to-distal through the lower enlarged portion 1331 of the I-shaped segment are a plurality of openings 1327 that are laterally aligned with one another. In exemplary form, the openings 1327 comprise a triangular pattern that is replicated. And this replication of patterns is not by accident. While other patterns of openings 1327 can be utilized, the primary objective is that each opening within a pattern corresponds to a like opening in the other pattern so that the orientation of each like opening is intended to be on a plane that is perpendicular to the longitudinal axis of the drop rod 1386. In this fashion, as will be discussed in more detail hereafter, it is envisioned that a surgeon will position the drop rod 1386 in parallel with the longitudinal axis of the tibia and thereafter use the openings 1327 to establish the location of surgical pins 1354 that will align with a surgical cutting guide. Similar opening patterns 1329 are present in the top of the I-shaped segment 1323 and likewise extend through the top of the I-shaped segment in the proximal-to-distal directions. In this manner, all of the openings 1327, 1329 have longitudinal central axes that extend in the proximal-to-distal direction and are parallel to one another.

In exemplary form, the vertical portion 1333 of the I-shaped segment 1323 is narrower in the lateral-to-medial direction than are the enlarged portions 1331, 1335 of the I-shaped segment at opposing ends thereof. In this manner, the narrowing allows for the surgical guide 1321 to be mounted to a first balancing assembly 1200 while a second balancing assembly is adjacent thereto, which consequently allows two balancing assemblies 1200 to be retained and utilized to measure the spacing between respective joint components (such as between medial and lateral condyles and condyle receivers of the knee joint) without the need to remove the surgical guide 1321. In this exemplary embodiment, the enlarged portions 1331, 1335 of the I-shaped segment 1323 are depicted as being fixedly mounted to one another via the vertical portion 1333. But it should be noted that the enlarged portions 1331, 1335 may be vertically repositionably with respect to one another by using a telescopic vertical portion 1333. Similarly, the enlarged portions 1331, 1335 are depicted in the figures as integral units with a fixed spacing in the medial-to-lateral direction between the pattern openings 1327, 1329. But it should also be noted that the enlarged portions 1331, 1335 may be fabricated to be telescopic so that the medial-to-lateral spacing of the openings 1327, 1329 can be varied. Also, the surgical guide 1321 is depicted in the figures as having a generally uniform thickness in the proximal-to-distal direction. However, the thickness of the surgical guide 1321 in the proximal-to-distal direction need not be constant or uniform.

In exemplary form, an underside of the lower enlarged portion 1331 may include an opening configured to fixedly receive the drop rod 1386. More specifically, the drop rod 1386 may have an end that is threaded and engages corresponding threads on the interior of the lower enlarged portion 1331 so that when properly engaged, the drop rod 1386 is perpendicular with respect to the longitudinal axes of the openings 1327, 1329.

Each of the foregoing elements of the surgical guide 1321 may be fabricated separately and thereafter assembled or may be created from a unitary material. Exemplary fabricating techniques for the foregoing elements of the surgical guide 1321 may include one or more of machining, casting, and additive manufacturing (e.g., 3D printing). The foregoing elements may be fabricated from surgically acceptable materials that include metals, metal alloys, ceramics, plastics, and composites that are suitable to function in surgical applications.

Figure 73:
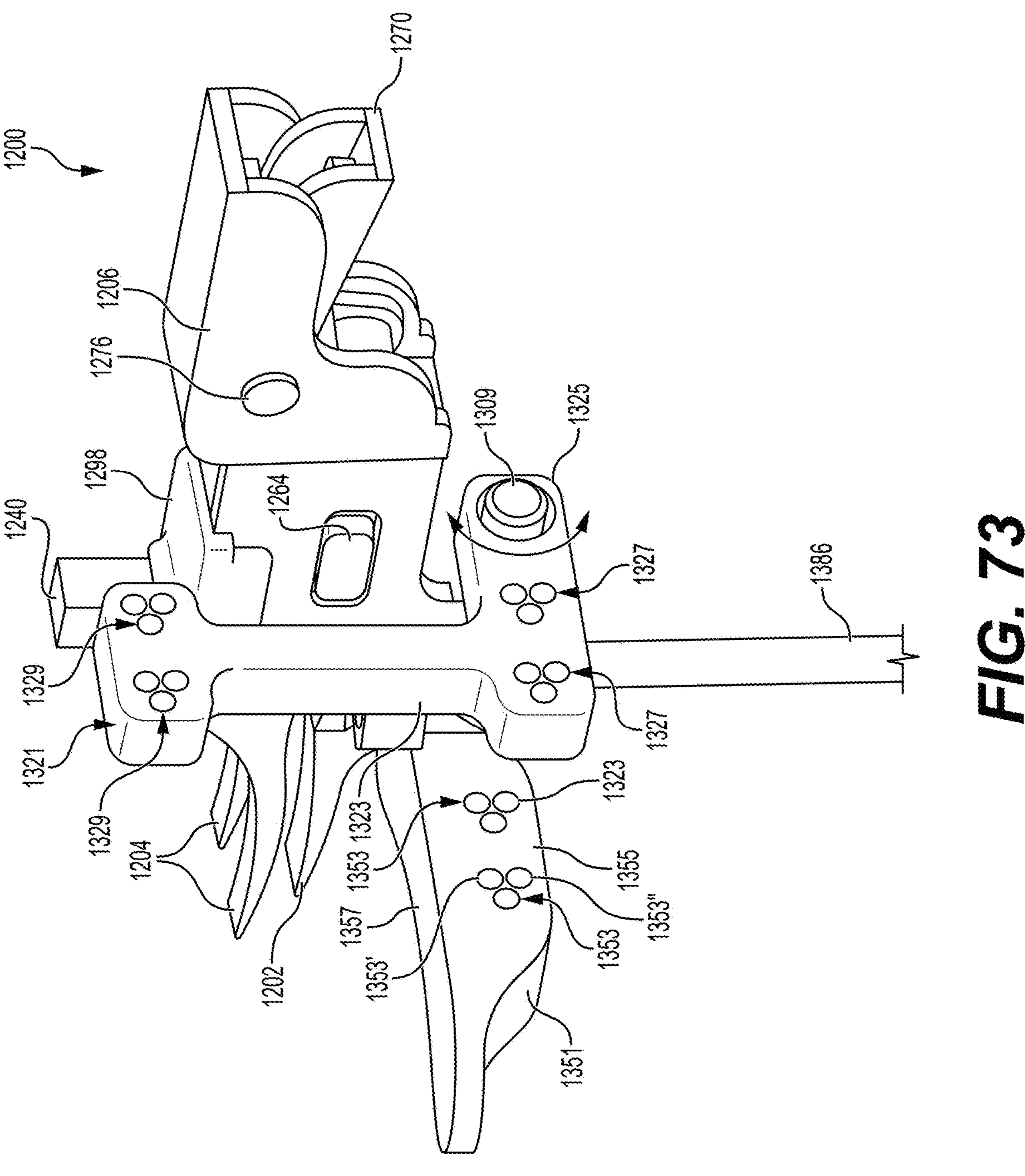
FIG. 73 is an elevated perspective view of the balancing assembly and the exemplary surgical guide of FIG. 71, along with an exemplary surgical cutting guide, all in accordance with the instant disclosure.
Figure 74:
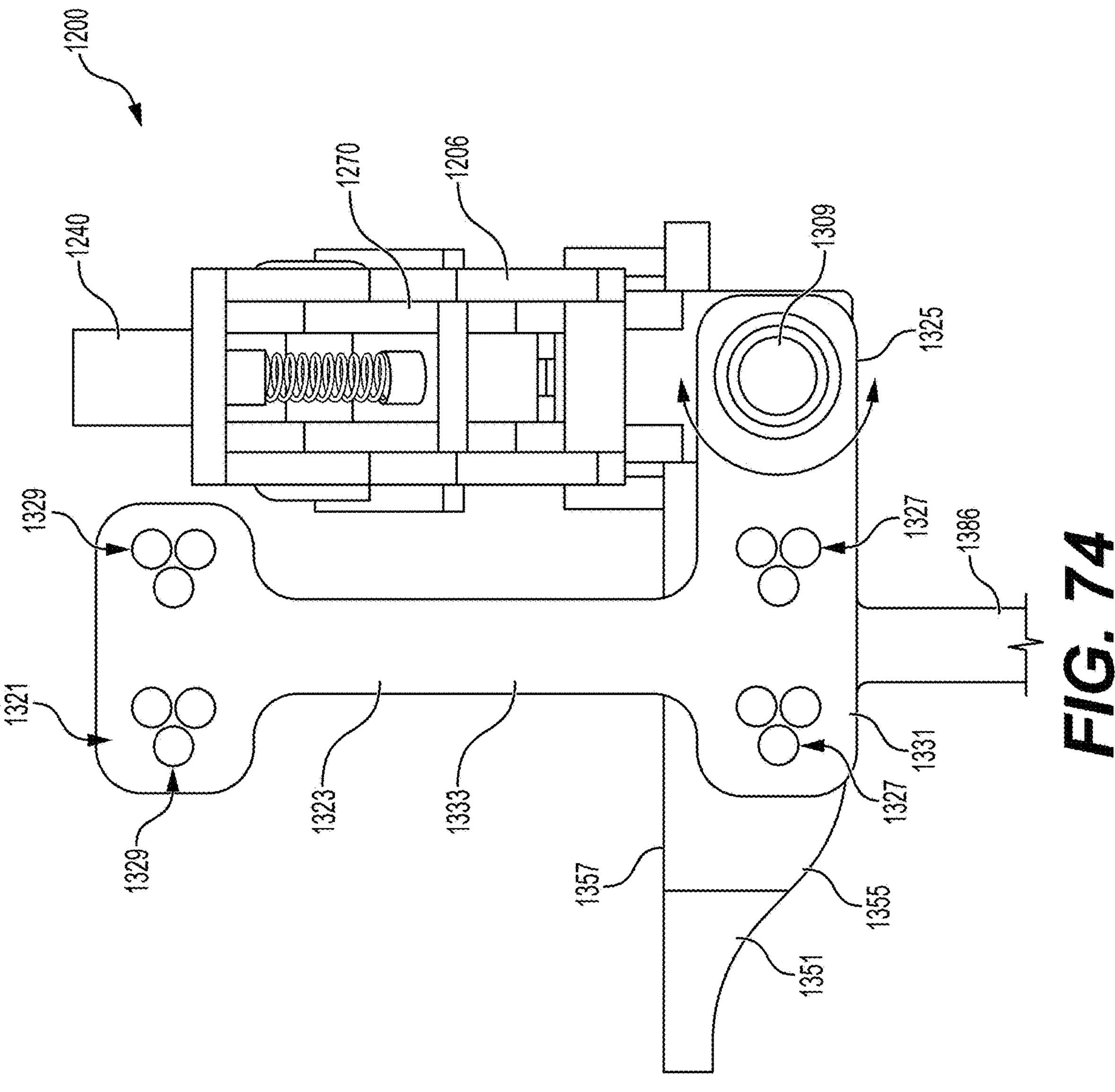
FIG. 74 is a rear view of the balancing assembly, the exemplary surgical guide, and the exemplary surgical cutting guide of FIG. 73.

Turning to FIGS. 73 and 74, after the spacing on the medial and lateral sides is determined from the paddles 1202, 1204, the surgical guide 1321 when mounted to one of the balancing assemblies 1200, via the cylindrical projection 1309, may be utilized to guide a drill bit (not shown) and insertion of corresponding surgical pins 1354 to occupy the drilled holes. When this engagement occurs, the surgical guide 1321 is able to rotate with respect the balancing assemblies 1200. In this manner, when the drop rod 1386 is mounted to the surgical guide 1321, the surgeon may rotate the surgical guide until the drop rod is parallel to the longitudinal axis of the tibia. When in the proper position, the surgeon may secure the drop rod, which correspondingly secures the surgical guide 1321 and precludes further rotation. Thereafter, depending upon the position of the surgical guide 1321 with respect to the tibia and femur, the surgeon decides which holes from the openings 1327, 1329 will be utilized to guide a surgical drill bit and drill four corresponding holes; two in the distal femur and two in the proximal tibia. Specifically, if the middle hole 1327' of the bottom openings is selected, then the middle hole for each pattern will be utilized to drill the two holes into the tibia. Similarly, if the top hole 1329' of the top openings is selected, then the top hole for each pattern will be utilized to drill the two holes into the femur. Thereafter, a surgical drill (not shown) and bit (not shown) may be used to establish a series of holes in the bones (both tibia 112 and femur 110). In order to properly align the holes, the surgical drill bit may be inserted through openings 1327, 1329 of the surgical guide 1321. Alternatively, the openings 1327, 1329 may be used to guide a surgical marker for marking the bones 110, 112 with the intended location of the bone holes to be drilled. Thereafter, the holes in the bones 110, 112 may be drilled to a sufficient depth. Post drilling the holes, the balancing assemblies 1200 and surgical guide 1321 may be removed and a series of surgical pins are inserted into the drilled holes. And these surgical pins may be utilized to align further surgical tools for subsequent surgical steps including, without limitation, guiding bone cutting guides as part of bone resection.

FIGS. 73 and 74 also show an exemplary surgical cutting guide 1351 that may be inserted over the surgical pins as part of carrying out a bone resection. In exemplary form, the surgical cutting guide may comprise a frame outlining a series of patterned openings 1353. In exemplary form, these patterned openings may be the same size, shape, and position of those of the previously described openings 1327, 1329 for the surgical guide 1321. As will be discussed hereafter, the surgeon may choose specific ones of the openings 1353 in order to vary the amount of bone resected. In any event, the frame may include a planar proximal face 1355 that is parallel to a planar distal face, with the distance between the faces attributable to a depthwise dimension that is generally uniform. Both faces 1355 include a dominant lateral dimension that is perpendicular to a lesser heightwise dimension. The frame may also outline top and bottom walls, where the top and bottom walls are perpendicular with respect to the faces 1355. On top of the cutting guide 1351 is a planar plateau 1357, optionally extending one or more of medially, laterally, anteriorly, and posteriorly beyond a footprint of the remainder of the cutting guide elements. Specifically, planar plateau 1357 may be perpendicular to the bottom wall or may be sloped in at least one of the anterior-posterior direction and the medial lateral direction. The slope of the planar plateau 1357 may be dependent upon the implant chosen by the surgeon. In any event, the planar plateau 1357 provides a planar surface upon which a surgeon may position a cutting blade and reposition the cutting place across the plateau to create a planar resection cut of the proximal tibia.

As referenced herein, the surgeon may increase or decrease the amount of bone resected based upon the placement of the cutting guide 1351 with respect to the surgical pins. For example, if the surgeon desired to remove more bone, the surgeon may position the cutting guide 1351 so that the top openings 1353' received the surgical pins. Conversely, if the surgeon desired to remove less bone, the surgeon may position the cutting guide 1351 so that the bottom openings 1353" received the surgical pins. In this fashion, the surgeon can vary the amount of bone resected using the pattern openings without sacrificing alignment of the intended bone resection. In any event, after the surgeon has chosen how much bone to resect, and aligned the cutting guide 1351 to be positioned over the surgical pins, the surgeon may utilize a surgical saw (now shown) and reposition a surgical blade across the planar plateau 1357 as a guide in order to effectuate a planar surgical resection of the bone. And the foregoing process may be repeated or used by itself to make a distal femoral resection, before or after one or more bone cuts on the femur 110 and tibia 112 are made.

While the foregoing has been discussed in the context of using the foregoing components when a joint is at or near mid-flexion, it is to be understood that the foregoing components may be utilized when a joint is other than at mid-flexion including, but not limited to, at or near full extension or at or near 90 degrees of flexion.

While the foregoing process has been described using the tibia 112 as the reference, it is also within the scope of the disclosure to use the femur 110 or an external reference instead. In this manner, instead of what is described previously by way of placing femoral surgical pins at different degrees of knee flexion based upon at least one of the position, the orientation, and the resection condition (resected or not resected) of the tibia 112, the foregoing steps may be modified or changed to use the femur 110 as the reference for drilling holes in the tibia and positioning surgical pins into the drilled holes based upon the femur.

Referring to FIGS. 75-81, a further alternate exemplary balancing assembly 1400 and surgical guide system 1550 are depicted that may be utilized as part of a total knee arthroplasty procedure. In exemplary form, the balancing assembly 1400 may be utilized individually or in multiples (such as in pairs, one for a medial side and one for a lateral side of a joint) concurrently as part of soft tissue balancing a joint during a joint revision or replacement surgery in furtherance of establishing one or more bone cuts. In exemplary form, a knee joint 108 is depicted that includes a distal femur 110 and a proximal tibia 112 having spaces or gaps between these bones, namely a first space between the medial condyle and condyle receiver, and a second space between the lateral condyle and condyle receiver. As will be discussed in more detail hereafter, the alternate exemplary balancing assembly 1400 may be positioned to partially occupy either space between a femoral condyle and its corresponding tibial condyle receiver as part of soft tissue balancing.

Referring to FIGS. 75-81, the alternate exemplary balancing assembly 1400 may include a pair of paddles 1402, 1404 that may be individually repositionable or have only one of the paddles being repositionable. In exemplary form, the paddles 1402, 1404 are depicted as having a lower paddle 1402 that is repositionable vertically with respect to the upper paddle 1404 and a primary housing 1406, while the upper paddle 1404 is stationary and fixedly mounted to the primary housing 1406. Nevertheless, it is within the scope of the disclosure that the upper paddle 1404 is repositionably mounted to the primary housing 1406 and/or detachably mounted to the primary housing. In such a circumstance, the lower paddle 1402 may be fixedly mounted to the primary housing 1406 or be repositionably mounted to the primary housing. In this manner, both paddles 1402, 1404 may be repositionably mounted to the primary housing 1406.

The lower paddle 1402 may include a dish-shaped finger 1408 extending away from a lower base 1410 that includes a pair of cylindrical cavities 1412 (that may or may not be through cavities) sized to each receive a portion of a coil spring 1416. It should be noted, however, that the finger 1408 may have any number of shapes and need not be dish-shaped. For example, the finger 1408 may have a planar undersurface configured to sit on top of a resected tibia 112. The coil springs 1416 may include various spring rates and, as will be discussed in more detail hereafter, it is envisioned that the balancing assembly 1400 includes several different coil springs to allow surgeons to interchange springs having different spring rates as part of soft tissue balancing. It is also within the scope of the disclosure that the coil springs 1416 may be replaced or supplemented with magnets having the same poles facing one another, or with piezoelectric actuators, linear actuators, geared motors, threaded rods, or any other structures operative to reposition one or more of the paddles 1402, 1404 to expand or to span the gap between the tibia 112 and femur 110.

In exemplary form, the finger 1408 may be generally centered with respect to the base 1410 and inset medially and laterally from the sides of the base. The finger 1408 may include a constant medial-to-lateral width and a thickness that tapers until reaching a distal tip. It is also within the scope of the disclosure that the lower paddle 1402 includes more than one finger 1408. A proximal portion of the finger 1408 may be elevated vertically above the base 1410 in order to allow overlapping and alignment with the upper paddle 1404.

In exemplary form, the upper paddle 1404 may include one or more fingers 1422 that are dish-shaped and extend away from a corresponding upper base 1424. It should be noted, however, that the fingers 1422 may have any number of shapes and need not be dish-shaped. For example, the fingers 1422 may have a planar top surface configured to sit against a resected femur 110. By way of example, the pair of depicted fingers 1422 are generally aligned with respect to the base 1410 and outset from one another medially and laterally to form a corresponding gap therebetween. Each finger 1422 may include a constant medial-to-lateral width and a thickness that tapers until reaching a distal tip. The gap between the fingers 1422 may be sized to allow the lower paddle finger 1408 to occupy this gap and, when the first and second paddles 1402, 1404 are compressed to a maximum extent, the fingers 1408, 1422 may be perfectly aligned to exhibit a uniform profile. As with the lower paddle 1402, the upper base 1224 includes a pair of cylindrical cavities 1428 (that may or may not be through cavities) sized to each receive a portion of the coil springs 1216.

Turning back to the lower paddle 1402, a rear of the lower base 1410, opposite the distal tip of the finger 1408, may include a rectangular key 1430 that may be configured to ride within a corresponding keyway 1432 of the primary housing 1406. In this fashion, the shape of the keyway 1432 may restrict and guide the motion of the lower paddle 1402 to, in exemplary form, provide for only vertical motion of the lower paddle with respect to the primary housing 1406. Extending from the key 1430 is a projection 1436 that is configured to be received within a corresponding opening 1438 of a rack 1440. It should be understood, however, that the rack 1440 may include the projection 1436, while the key 1430 may include the corresponding opening 1438. In any event, an engagement between the lower paddle 1402 and the rack 1440 is operative to control motion of the lower paddle.

A well 1444 of the primary housing 1406 includes vertical guides 1446 delineating a cavity sized to receive the rack 1440. By way of example, the rack 1440 may comprise a straight rod having a constant rectangular longitudinal cross-section with four exterior surfaces arranged in ninety-degree increments. A first of the four exterior surfaces may include a first opening 1438 to receive the projection 1436 from the key 1430, and a second through opening 1439 configured to accommodate a drill bit. A third of the exterior surfaces, oriented 180 degrees from the first surface, includes a series of depressions correspondingly forming teeth 1448 that are longitudinally distributed. Second and fourth exterior surfaces of the rack 1440 may include indicia 1441, such those akin to a ruler, providing information regarding the vertical spacing between the paddles 1402, 1404. In exemplary form, when the paddles 1402, 1404 are not vertically spaced apart, the indicia 1441 may have showing a "0" and a corresponding line that may be aligned with the bottoms of the vertical guides 1446 of the primary housing 1406. In exemplary form, the indicia 1441 may include a series of horizontal lines or other markings to reflect incremental distances so that each line corresponds to a particular millimeter spacing increment between the paddles 1402, 1404. For example, each line may correspond to a 2-millimeter spacing distance increment and the indicia 1441 may include a total of ten lines. For example, the tenth line may correspond to a vertical spacing distance between the paddles 1402, 1404 of twenty millimeters, whereas the third line may correspond to a vertical spacing distance between the paddles of six millimeters, and so on, for the other lines of the indicia. It should be noted that the rack 1440 may have longitudinal cross-sections that are constant or irregular, as well as cross-sections that are square, oblong, circular, or embody various shapes. In exemplary form, the teeth 1448 may be evenly distributed along all or a portion of an exterior surface of the rack 1440. Nevertheless, the teeth 1448 may be formed to have a tapered leading edge to ensure that one or more catches 1450 associated with a detent assembly are fixedly received within openings in between the teeth in order to fix the vertical position of the rack 1440 relative to the primary housing 1406.

A distal end of a stopper 1456 may include the catches 1450 and may be repositionably coupled to a link 1460 via a first link pin 1458 concurrently extending into openings in the link and the stopper. By way of example, the openings occupied by the first link pin 1458 may be circular in cross-section and through as to the link 1460 and through or partially closed as to the stopper 1456. The stopper 1456 may include a main body having a rectangular distal-to-proximal cross-section that demarcates at least one through opening 1462 extending from medial to lateral sides and configured for accepting a guide block 1464. In this example, the guide block 1464 may embody a cuboid shape and have a rectangular cross-section slightly smaller than the boundaries demarcating the through opening 1462. It should be noted, however, that the guide block 1464 and through opening 1462 may embody different shapes so long as the guide block 1464 can extend medially and/or laterally away from the medial and/or lateral sidewall of the stopper 1456. By way of further example, the guide block 1464 may have a medial-to-lateral length greater than the medial-to-lateral length of the through opening 1462 so that guide block extends beyond one or both ends of the opening. A proximal end of the stopper 1456 is hollowed to accommodate insertion of a distal end 1461 of the link 1460. Corresponding openings 1463, that are axially aligned, are provided through a proximal end of the stopper 1456, where these openings are configured to be aligned with a through opening 1465 extending through the distal end 1461 of the link 1460 and concurrently receive the first link pin 1458 in order to allow pivotal motion between the stopper 1456 and the link 1460 when the link and stopper concurrently receive the first link pin 1458. In exemplary form, the guide block 1464 may be frictionally received within the through opening 1462 so that once inserted, the guide block does not move medially-to-laterally unless specifically forced to do so using a tool such as, without limitation, a mechanical punch. The guide block 1464 may be utilized to operatively couple the stopper 1456 to the primary housing 1406.

To operatively couple the stopper 1456 to the primary housing 1406, the primary housing includes a pair of through openings 1482 that extend respectively through medial and lateral side walls 1466, 1468. Each of the through openings 1482 is elongated and sized to allow at least partial throughput of the guide block 1464 so that the guide block can travel along a proximal-to-distal predefined path. As will be discussed in more detail hereafter, this predefined path allows traversal of the guide block 1464 in only two degrees of freedom (one being the guide block can travel medial to lateral and vice versa, and a second being the guide block can travel proximal to distal and vice versa). In exemplary form, the through openings 1482 may be sized to inhibit travel of the guide block 1464 vertically with respect to the primary housing 1406. By way of example, once the guide block 1464 is seated within the stopper 1456 and, preferably the guide block extends into both openings 1482, the stopper may be repositioned with respect to the primary housing 1406 in only one degree of freedom corresponding to the guide block and stopper traveling proximal to distal and vice versa. Such a configuration effectively precludes the stopper 1456 from traveling appreciably vertically with respect to the primary housing 1406 and the side walls 1466, 1468 constrain motion of the stopper medially-to-laterally with respect to the primary housing.

To effectuate the proximal-to-distal motion (and vice versa) of the stopper 1456 with respect to the primary housing 1406, the detent assembly may also include a handle 1470 pivotally mounted to the primary housing and to the link 1460. In exemplary form, the handle 1470 includes an L-shape within upstanding medial and lateral side walls that are connected via an underwall. Specifically, the primary housing 1406 may include a pair of pin openings 1474 sized to receive a pivot pin 1476 that is configured to be concurrently received within corresponding holes 1484 of the handle 1470 that extend through the medial and lateral side walls and are positioned proximate the turn in the L-shape. In this manner, the handle 1470 may pivot about an axis of the pivot pin 1476 with respect to the primary housing. In this exemplary configuration, the handle 1470 may be biased away from the housing 1406 (see FIG. 81) using a coil spring 1486 extending between corresponding cups 1478, 1480 on the housing and handle. In addition, the handle 1470 also includes another set of through holes 1488 extending through the medial and lateral side walls that are sized to receive a second link pin 1490. The second link pin 1490 is sized to be received within a corresponding cylindrical cavity 1494 formed within the proximal end of the link 1460. Consequently, when assembled, the handle 1470 pivots around the second link pin 1490, as does the link 1460. In this fashion, when the handle 1470 is pivoted to overcome the spring bias so that the cups 1478, 1480 are nearer one another and the coil spring 1486 is compressed, the handle operates to reposition the link 1460 proximally and correspondingly repositions the stopper 1456 proximally so that eventually the catches 1450 are no longer received within depressions between adjacent teeth 1448. When this occurs, external forces acting on the paddles 1402, 1404 can operate to overcome the spring bias of the coils springs 1416 and reposition at least one of the paddles (such as the lower paddle 1402) so that the gap between the paddles is lessened. Conversely, if the external forces acting on the paddles 1402, 1404 is less than the spring bias of the coil springs 1416, at least one of the paddles (such as the lower paddle 1402) will be repositioned so that the gap between the paddles is increased. If the external forces acting on the paddles 1402, 1404 is equal and opposite to the spring bias of the coil springs 1416, the gap between the paddles will not change. In this fashion, by allowing the handle 1470 to pivot away from the housing 1406 so that the distance between the cups 1478, 1480 is at a maximum or near maximum, repositioning of the paddles 1402, 1404 with respect to one another is precluded because the stopper 1456 engages the rack 1440 (specifically via the catches binding on the teeth 1448) and inhibits vertical repositioning of at least one of the paddles 1402.

To ensure the motion of the rack 1440 is, at most, only vertical with respect to the housing 1406, a cap 1498 may be mounted to the housing proximate the lower end of the well 1444. By way of example, the cap 1498 may include a rectangular through opening sized to receive at least a portion of the rack 1440. Alternatively, this opening cross-section may be rectangular, circular, oblong, or any other cross-section that allows throughput and traversal of the rack 1440 with respect to the cap 1498. In exemplary form, medial and lateral side walls of the cap 1498 may include inwardly projecting detents 1500 in the form of pyramidal ledges that are sized and configured to be received into corresponding openings 1502 through the side walls 1466, 1468 of the housing 1406 in order to mount the cap to the housing. In this fashion, the cap 1498 cooperates with the housing 1406 to provide a guide along which the rack 1440 is able to vertically traverse.

An upper portion of the housing 1406 may include an upward facing cavity 1508 configured to receive a positioning block 1510 associated with a positioning handle. In exemplary form, the walls of the housing 1406 may generally delineate a cuboid cavity 1508 that is configured to receive at least a cuboid portion of the positioning block 1510. It should be understood, however, that any number of alternately shaped cavities may be used in place of the exemplary cuboid cavity depicted. Likewise, depending upon the shape of the cavity 1508, any number of alternatively shaped positioning blocks 1510 may be used so long as at least a portion of the positioning block is seated within the cavity. In exemplary form, the positioning block 1510 may be received within the cavity 1508 in a manner where the positioning block releasably engages the housing 1406. By way of example, the positioning block 1510 may engage the housing 1406 via a friction fit. Other forms of releasably connection between the positioning block 1510 and the housing 1406 are also within the scope of the invention, such as releasable detents, use of repositionable fasteners, and other means.

In exemplary form, an upper portion of the positioning block 1510 includes a cylindrical projection 1512 that is necked down proximate its joining to the cuboid portion. This necked down portion is of sufficient size to allow sliding engagement with one of two positioning guides 1514, each of which is pivotally connected to a handgrip 1516. In exemplary form, each positioning guide 1514 comprises an elongated beam having a rounded, rectangular longitudinal cross-section periphery delineating an internal elongated cavity 1518. By way of example, the elongated cavity 1518 is generally linear and includes a generally uniform cross-section having dimensions slightly greater than those of the cross-section of the cylindrical projection 1512. As a result, the cylindrical projection 1512 is sized to be received within the elongated cavity 1518 and allow repositioning with respect thereto. In this manner, when the cylindrical projection 1512 is received within an elongated cavity 1518, the positioning block 1510 is mounted to the positioning guide, but repositioning of the positioning block with respect to the positioning guide is available in a proximal-to-distal direction (along the length of the positioning guide 1514) as well as rotationally (given that the cylindrical projection 1512 can rotate within the elongated cavity 1518). But when the cylindrical projection 1512 is received within the elongated cavity 1518, vertical (upward or downward) motion is generally constrained between the positioning block and positioning guide 1514, as is side-to-side (medial to lateral) motion.

Each positioning guide 1514 includes an enclosed eye 1524 at its proximal end that is sized to receive a cylindrical tibial drop rod 1526. The handgrip 1516 includes a counterpart clevis 1530 at its distal end with corresponding through openings sized to receive the drop rod 1526, while the enclosed eyes 1524 are received between the clevis. In this fashion, insertion of the drop rod 1526 through the enclosed eyes 1524 and the clevis 1530 operates to pivotally mount the positioning guides 1514 to the handgrip 1516. As a result, when one or both the positioning guides 1514 is mounted to the handgrip 1516, and the corresponding positioning block 1510 engages the housing 1406, the handgrip 1516 may be used to reposition the balancing assembly 1400.

Each of the foregoing elements of the balancing assembly 1400 may be fabricated separately and thereafter assembled. Exemplary fabricating techniques for the foregoing elements of the balancing assembly 1400 may include one or more of machining, casting, and additive manufacturing (e.g., 3D printing). The foregoing elements may be fabricated from surgically acceptable materials that include metals, metal alloys, ceramics, plastics, and composites that are suitable to function in surgical applications.

As will be discussed in more detail hereafter, the balancing assembly 1400 may be used with or apart from a surgical guide system 1550, where the surgical guide system components may be used to establish one or more fixation holes and/or devices to be located on the distal femur 110 and/or proximal tibia 112 as alignment guides for further surgical procedures as part of providing uni or multi condylar knee replacement.

Figure 82:
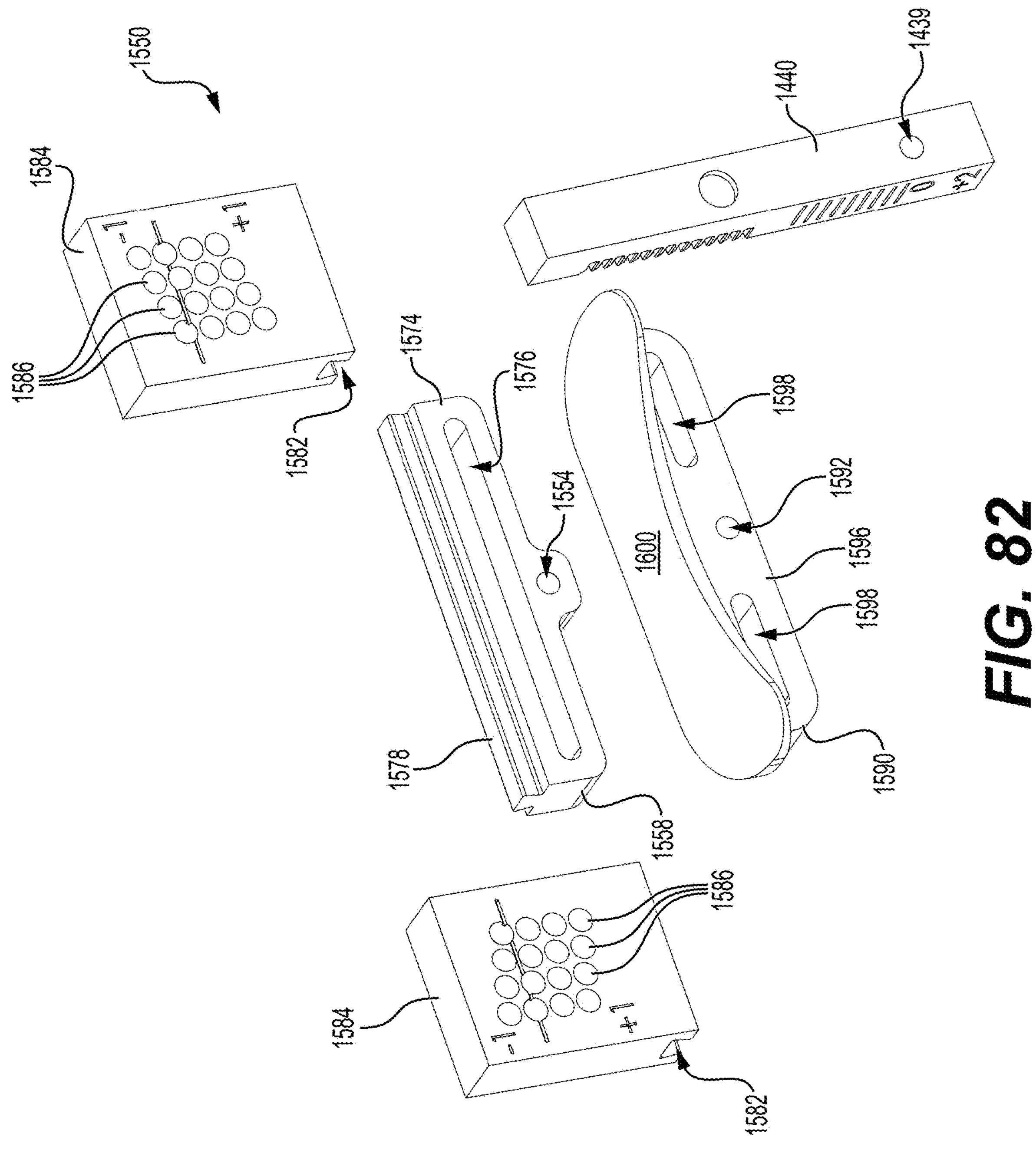
FIG. 82 is an exploded view, from the rear, of an exemplary surgical guide system in accordance with the instant disclosure.
Figure 83:
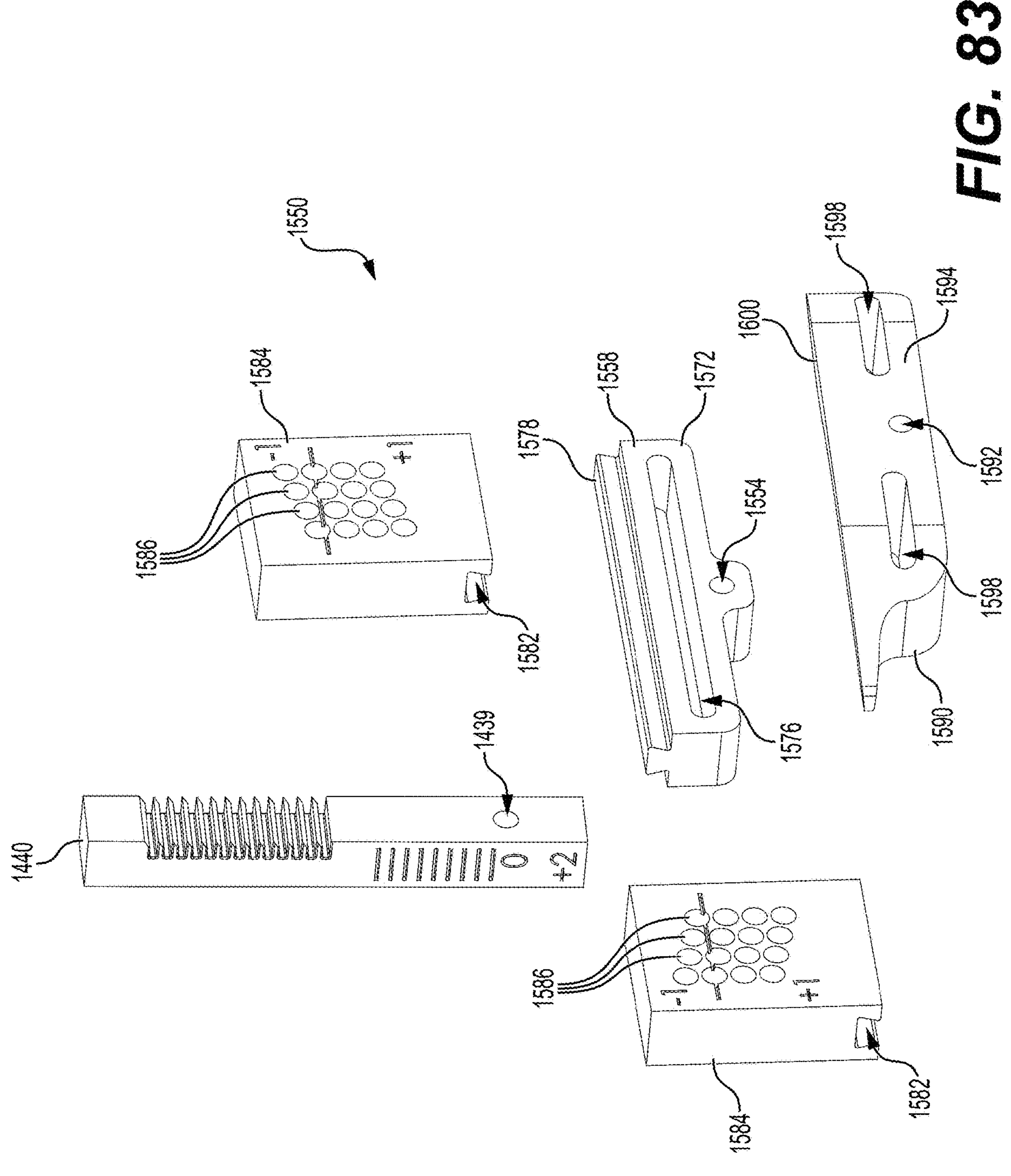
FIG. 83 is an exploded view, from the front, of the exemplary surgical guide system of FIG. 82.
Figure 84:
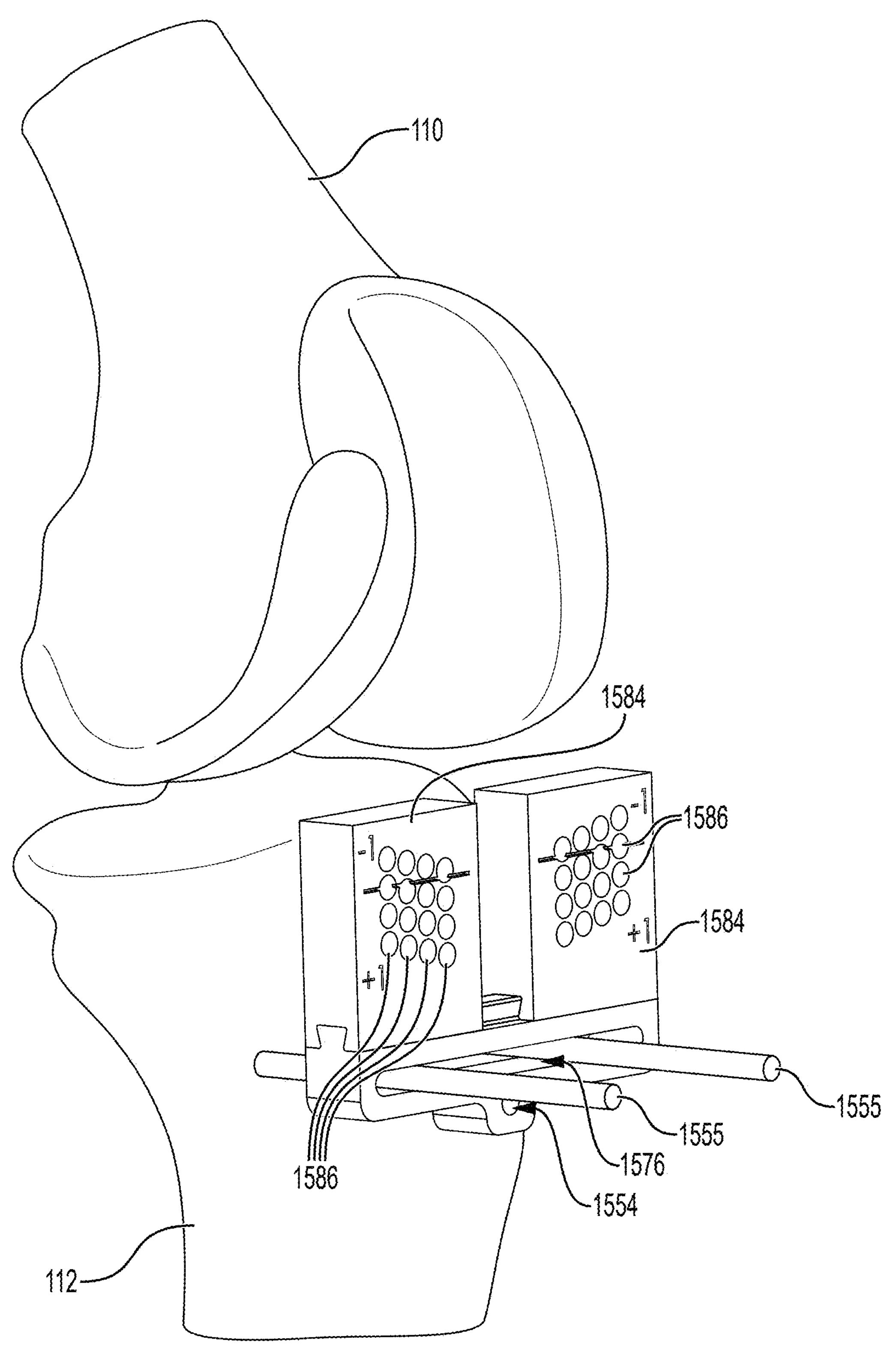
FIG. 84 is an elevated perspective view of a distal femur and a proximal tibia at or near mid-flexion with at least a portion of the exemplary surgical guide system of FIG. 82 mounted thereto.
Figure 85:
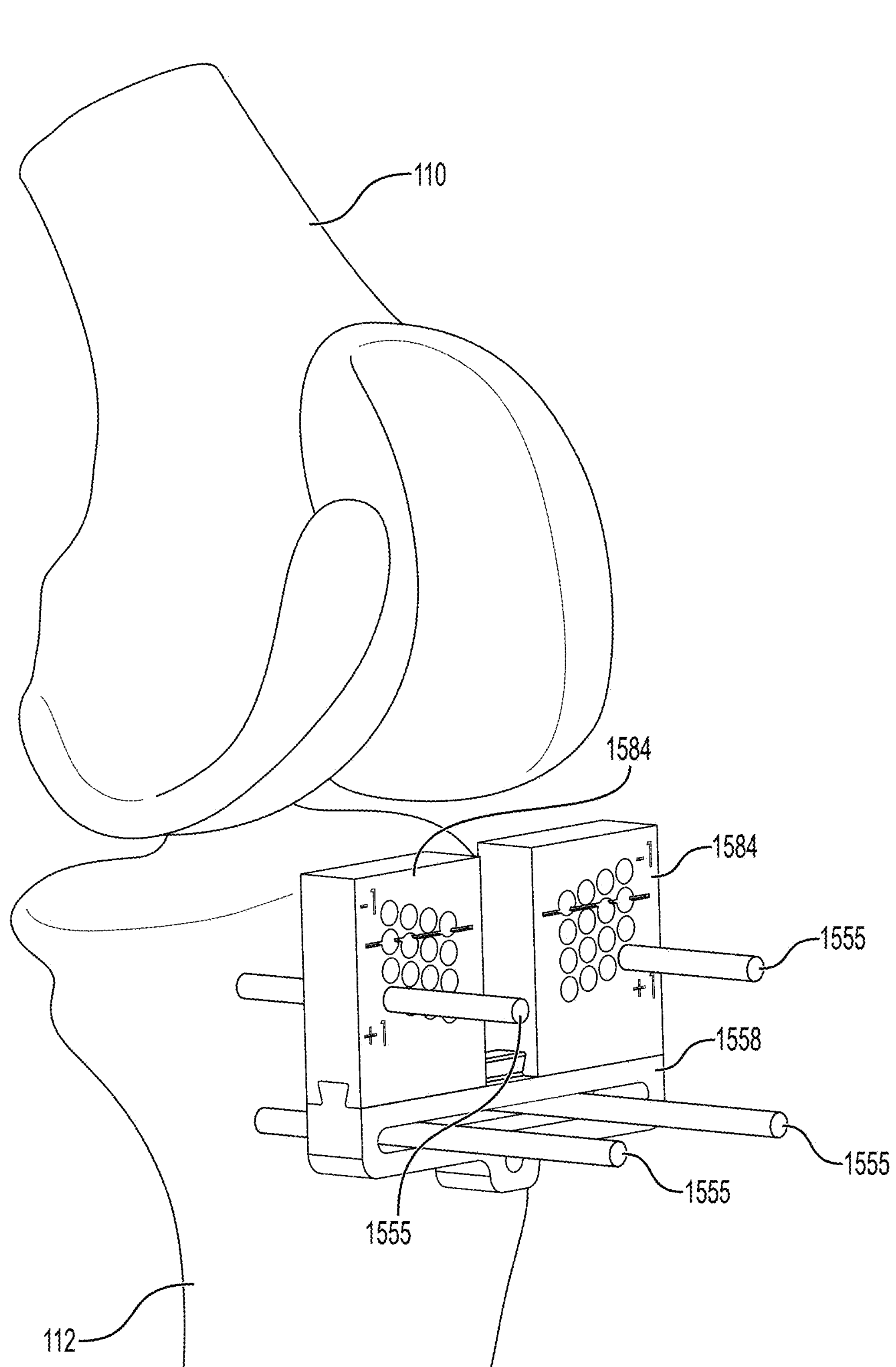
FIG. 85 is an elevated perspective view of a distal femur and a proximal tibia at or near mid-flexion with at least a portion of the exemplary surgical guide system of FIG. 82 mounted thereto, including additional surgical pins being mounted to the tibia and surgical guide system.

Turning to FIGS. 82 and 83, an exemplary surgical guide system 1550 may include a first trajectory guide 1558 comprising a frame outlining a first hole 1554. In exemplary form, the frame may include a planar proximal face 1572 that is parallel to a planar distal face 1574, with the distance between the faces attributable to a depthwise dimension that is generally uniform. Both faces 1572, 1574 include a dominant lateral dimension that is perpendicular to a lesser heightwise dimension. The frame may also outline an elongated opening 1576 delineated by parallel top and bottom walls, where the top and bottom walls are perpendicular with respect to the faces 1572, 1574. The spacing between the top and bottom walls is sufficient to accommodate one or more conventional surgical pins 1555, but not so great as to allow significant vertical play between one or more surgical pins, occupying at least a portion of the opening 1576, and the top and bottom walls. Vertically opposite the first hole 1554 is an elongated dovetail projection 1578 extending along the lateral dimension and across a top of the guide 1558. Specifically, the dovetail projection 1578 may extend from one lateral end to the opposite lateral end, though this is not required. In exemplary form, the dovetail projection 1578 includes a generally uniform cross-section and is sized to be received within a corresponding dovetail keyway 1582 formed into each of a pair of pin guides 1584.

In exemplary form, the surgical guide system 1550 may include one or more pin guides 1584 that are configured to be repositionably mounted to the first guide. For example, each pin guide 1584 may comprise a cuboid shape with a series of parallel through holes 1586, with each of the holes having a center that incrementally spaced vertically from one of the other through holes. By way of further example, the holes 1586 may be arranged in a sloped arrangement, with four holes to a sloped row, with four rows. It should be noted, however, that there is no definitive limit on the number of holes 1586 to a sloped row, or to the number of rows. Likewise, the holes 1586 need not be arranged in a sloped row. What matters is that the holes 1586 provide predetermined incremental vertical spacing options. In exemplary form, the holes 1586 may have centers that are offset in one millimeter increments. Perpendicularly oriented with respect to the holes is the dovetail keyway 1582 formed on an underside of the pin guide 1584. In exemplary form, the dimensions of the dovetail keyway 1582 are such that the keyway is configured to receive at least a portion of the dovetail projection 1578 of a pin guide 1584 so that the pin guide may engage the trajectory guide 1558 and be repositioned with respect thereto in a straight line and along a predetermined plane. As will be discussed in more detail hereafter, the pin guides 1584 may be utilized to drill respective holes into the tibia and place alignment pins therein that are used to position a cutting guide 1590 of the surgical guide system 1550.

In exemplary form, the cutting guide 1590 may comprise a frame outlining a first hole 1592. In exemplary form, the frame may include a planar proximal face 1594 that is parallel to a planar distal face 1596, with the distance between the faces attributable to a depthwise dimension that is generally uniform. Both faces 1594, 1596 include a dominant lateral dimension that is perpendicular to a lesser heightwise dimension. The frame may also outline a pair of laterally spaced apart elongated openings 1598, each delineated by parallel top and bottom walls, where the top and bottom walls are perpendicular with respect to the faces 1594, 1596. The spacing between the top and bottom walls is sufficient to accommodate one or more conventional surgical pins, but not so great as to allow significant vertical play between one or more surgical pins, occupying at least a portion of the opening 1598, and the top and bottom walls. Vertically opposite the first hole 1592 is a planar plateau 1600, optionally extending one or more of medially, laterally, anteriorly, and posteriorly beyond a footprint of the remainder of the cutting guide elements. Specifically, planar plateau 1600 may be perpendicular to the top and bottom walls delineating the openings 1598 or may be sloped in at least one of the anterior-posterior direction and the medial lateral direction. The slope of the planar plateau may be dependent upon the implant chosen by the surgeon. In any event, the planar plateau 1600 provides a planar surface upon which a surgeon may position a cutting blade and reposition the cutting place across the plateau to create a planar resection cut of the proximal tibia.

Each of the foregoing elements of the exemplary balancing assembly 1400 and the surgical guide system 1550 may be fabricated separately and thereafter assembled. Exemplary fabricating techniques for the foregoing elements may include, without limitation, one or more of machining, casting, and additive manufacturing (e.g., 3D printing). The foregoing elements may be fabricated from surgically acceptable materials that include metals, metal alloys, ceramics, plastics, and composites that are suitable to function in surgical applications.

Turning to FIGS. 75-85, an exemplary sequence for using one or two balancing assembles 1400, along with the surgical guide system 1550, will be described in the context of a total knee replacement procedure. It should be noted, however, that the exemplary sequence is applicable to uni knee replacement and knee revision joint surgeries, as well as other surgical procedures.

Referring to FIGS. 75-81, as part of carrying out a total knee replacement surgery or knee replacement revision surgery, the knee joint is exposed and partially flexed so that the femur is at mid-flexion, such as 45 degrees with respect to the tibia. It should be noted, however, that mid-flexion may range with angles between the femur and tibial of between about 30 degrees to about 70 degrees. In this fashion, at mid-flexion, the longitudinal axis of the femur may be angled approximately 45 degrees with respect to the longitudinal axis of the tibia. At this mid-flexion, the distal end of the femur and the proximal end of the tibia are exposed. Prior to utilizing the balancing assemblies 1400, as will be discussed in more detail hereafter, it should be noted that variations as to the form of the distal femur are within the scope of this disclosure. Namely, the distal femur may be native, meaning that a patient's native femur and cartilage covering the condyles may be exposed, as the case may be prior to any surgical intervention resulting in a femoral anatomical change. Conversely, the distal femur may have already been the subject of surgical intervention to perform a posterior chamfer cut on the distal femur. In this circumstance, the planar chamfer cut on the femur, when the femur is angled at approximately 45 degrees, will directly face the proximal tibia. In other alternatives, the distal femur may have already been the subject of surgical intervention to perform one or more bone cuts on the distal femur, followed by mounting a prosthetic trial onto the cut femur. In this circumstance, after the planar chamfer cut on the femur (though covered by a prosthetic trial) is made and the femur (with trial) is angled at approximately 45 degrees, the chamfer cut and part of the orthopedic trial will directly overlap with the proximal tibia. In yet another alternative, the distal femur may include exposing a permanent orthopedic implant, where the permanent femoral implant may be exposed because of a revision surgery or because the TKA procedure has progressed through fitting and attachment of the permanent femoral implant. Regardless of which of the foregoing scenarios is present as to the condition of the distal femur, it is preferred that the knee joint is positioned in partial flexion (approximately 45 degrees of flexion) in order to balance the knee joint.

Next, a pair of balancing assemblies 1400 are set so that the paddles 1402, 1404 are generally level with one another (from a medial-to-lateral perspective). In this configuration, the handle 1470 is extended, which corresponds to the springs 1416 being fully extended or partially compressed and maintained in this position by the stopper 1456 prohibiting vertical motion of the rack 1440 (see FIG. 81) and corresponding vertical motion of the paddles 1402, 1404 with respect to one another. The balancing assemblies 1400 may be repositioned individually or as a pair with respect to a patient's joint (in this case, a knee joint comprising a distal femur 110 and a proximal tibia 112) so that the paddles 1402, 1404 interpose two bones.

Figure 75:
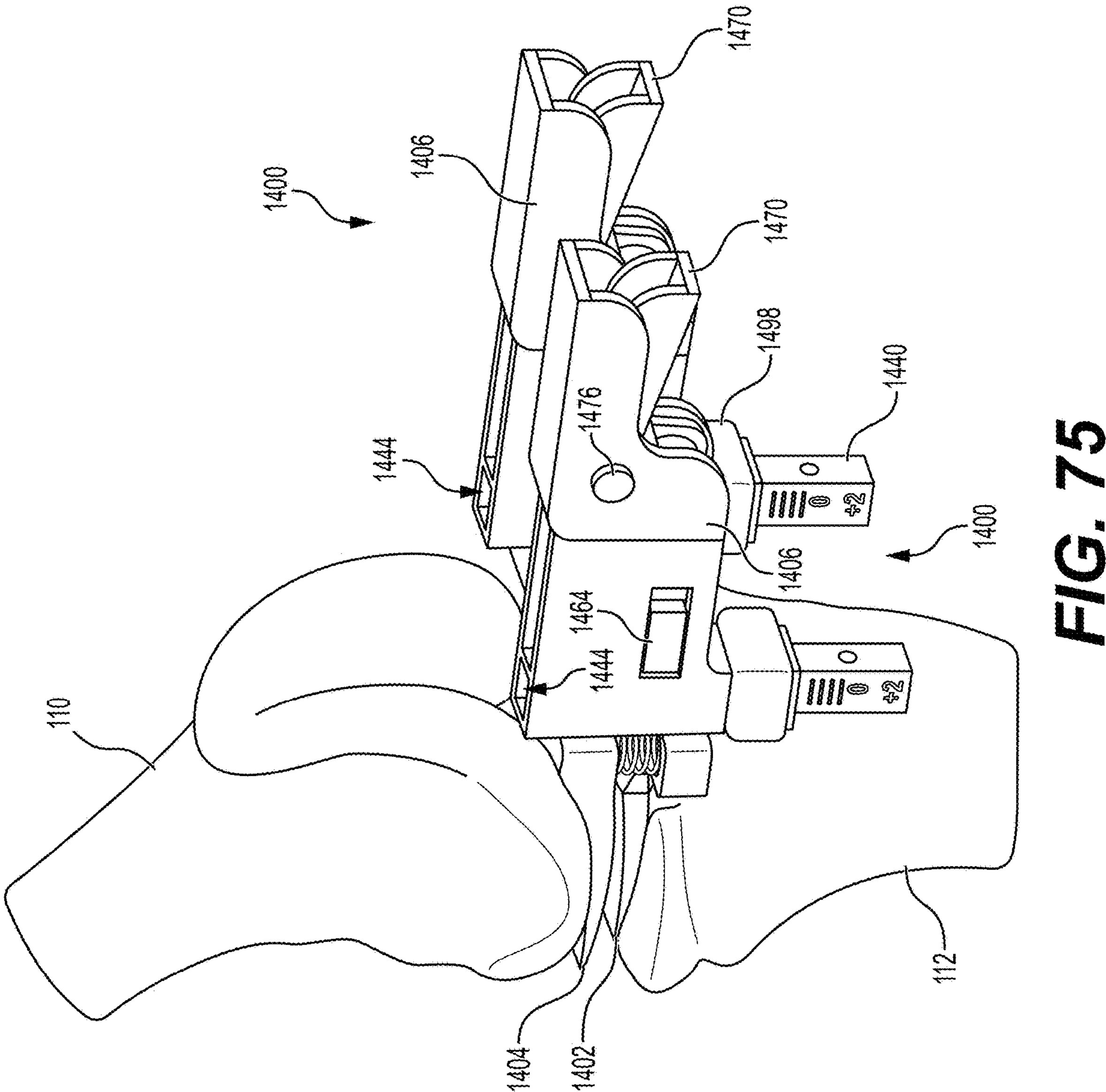
FIG. 75 is an elevated perspective view showing a tibia and a femur at approximately mid-flexion with further alternate exemplary balancing assemblies inserted therebetween.
Figure 76:
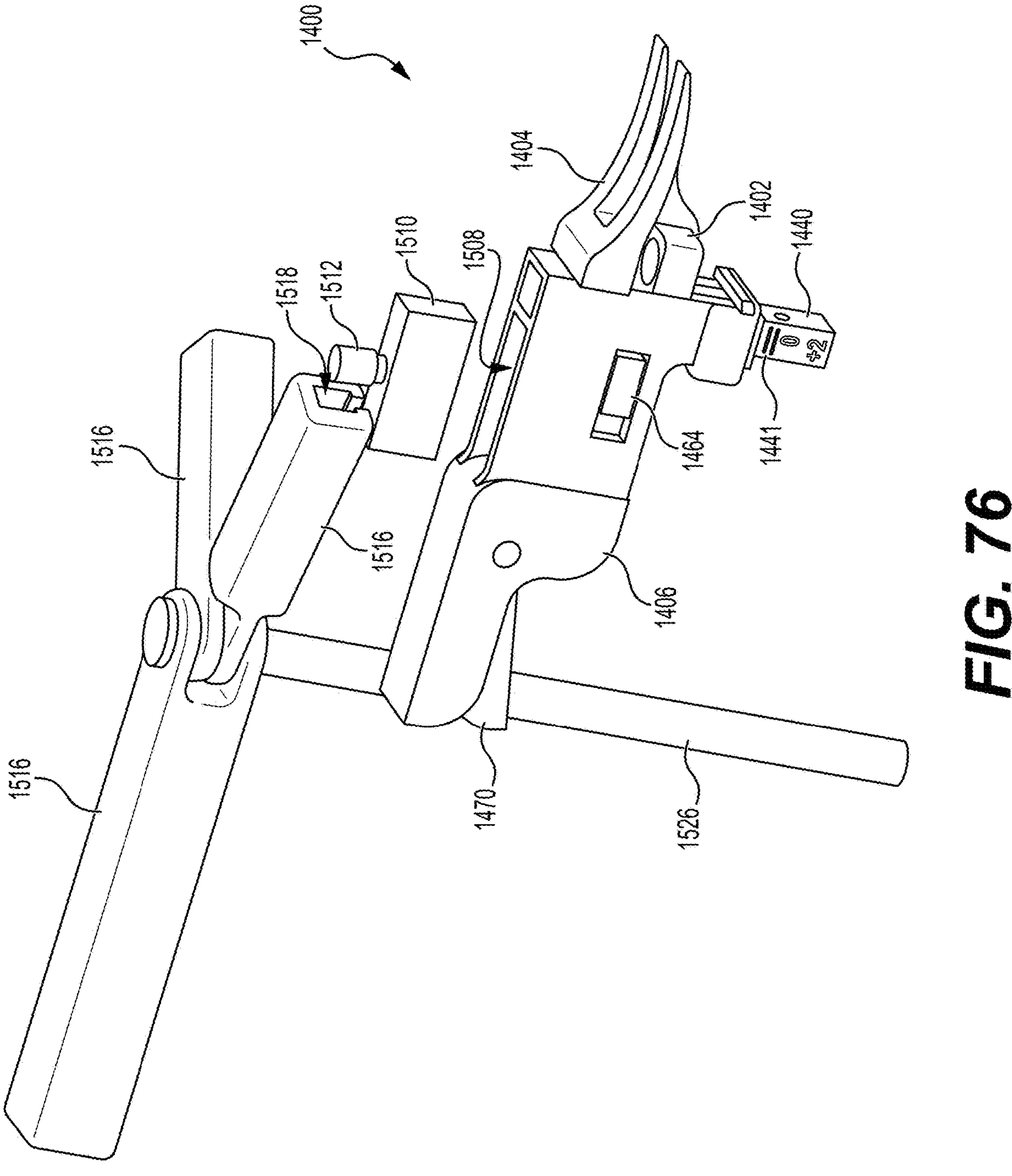
FIG. 76 is an elevated perspective view of an alternate exemplary balancing assembly of FIG. 75, along with a positioning device, all in accordance with the instant disclosure.
Figure 77:
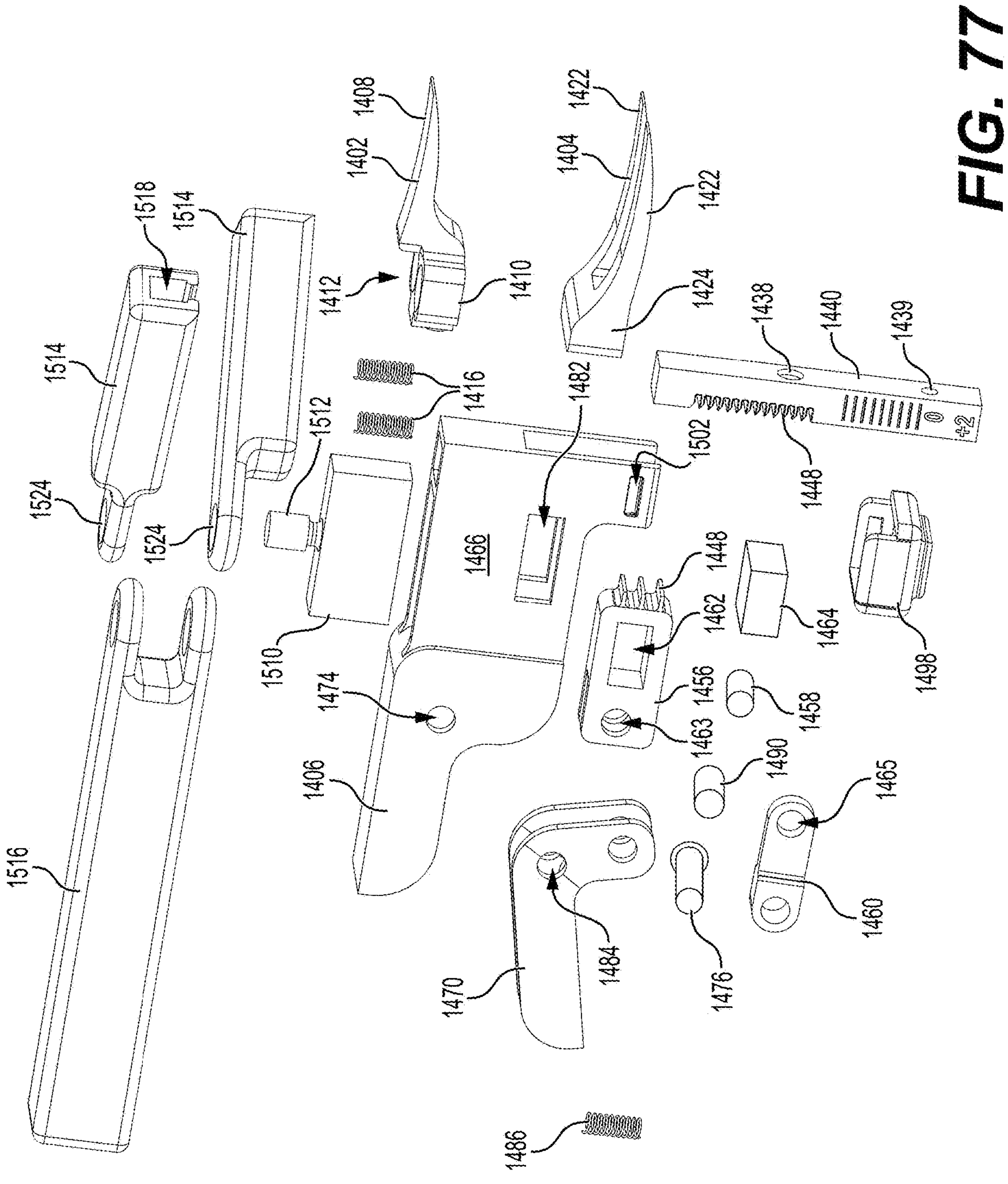
FIG. 77 is a top exploded view of the alternate exemplary balancing assembly and the positioning device of FIG. 76.
Figure 78:
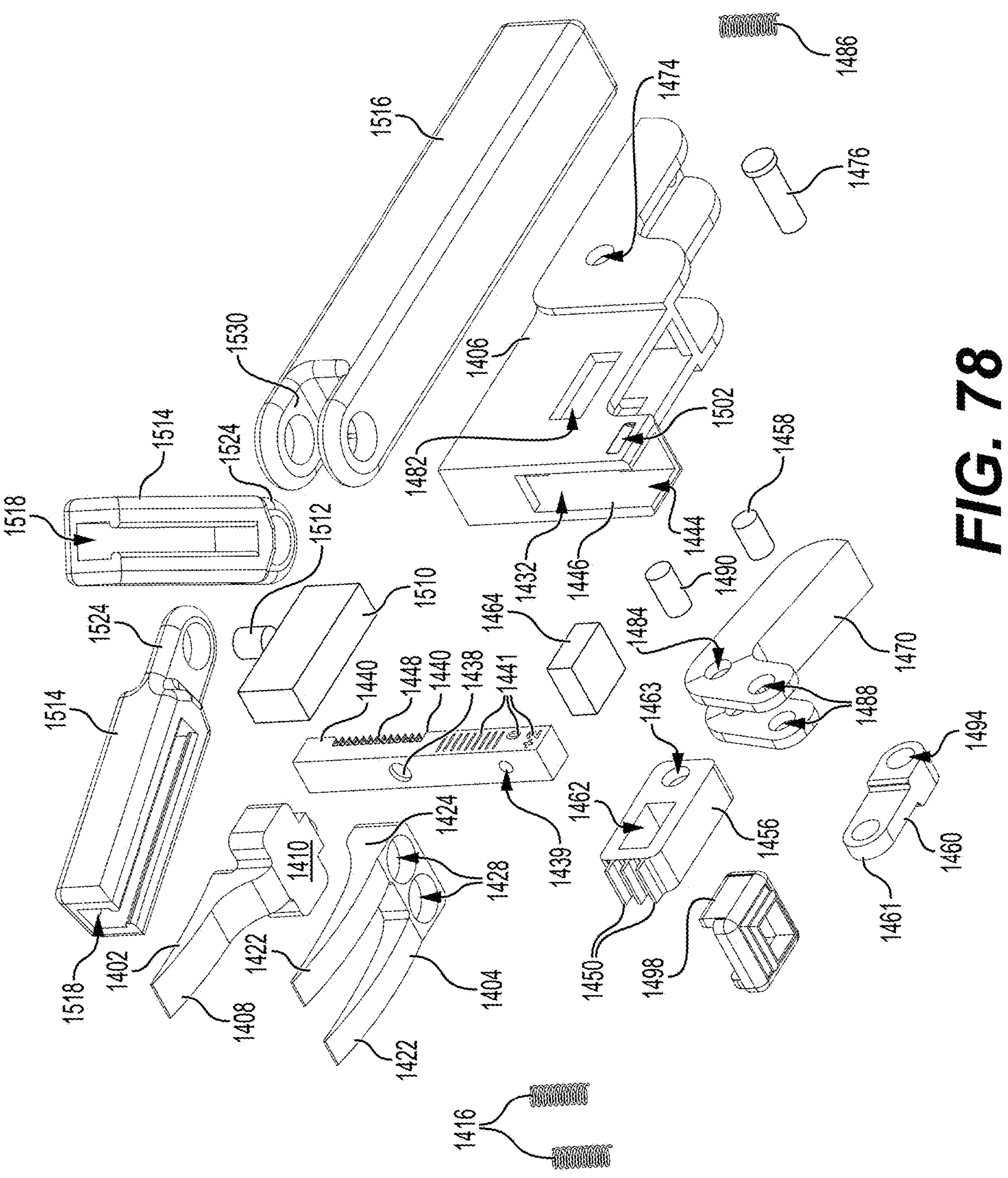
FIG. 78 is a bottom exploded view of the alternate exemplary balancing assembly and the positioning device of FIG. 76.
Figure 79:
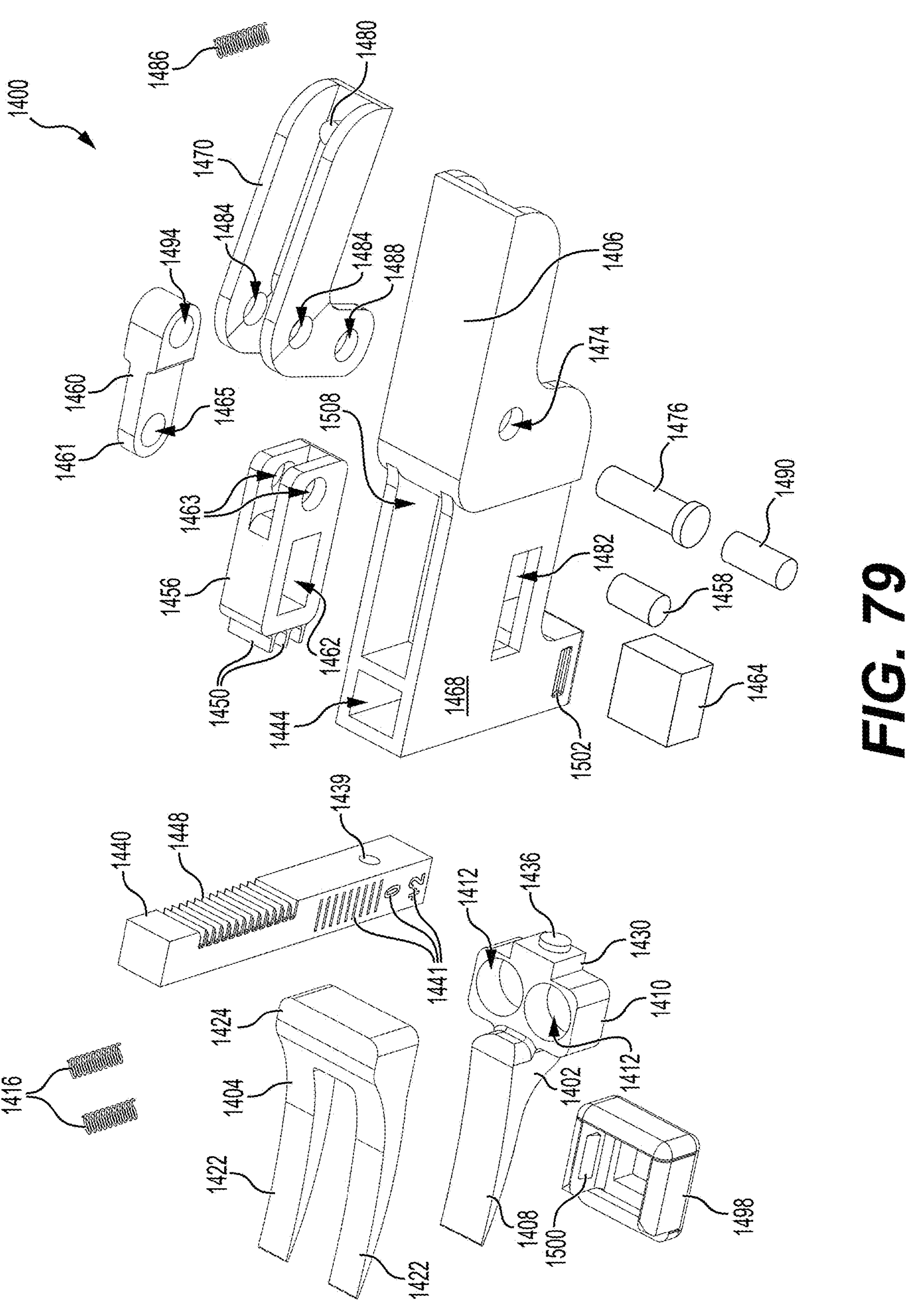
FIG. 79 is a top exploded view of the alternate exemplary balancing assembly of FIG. 76.
Figure 80:
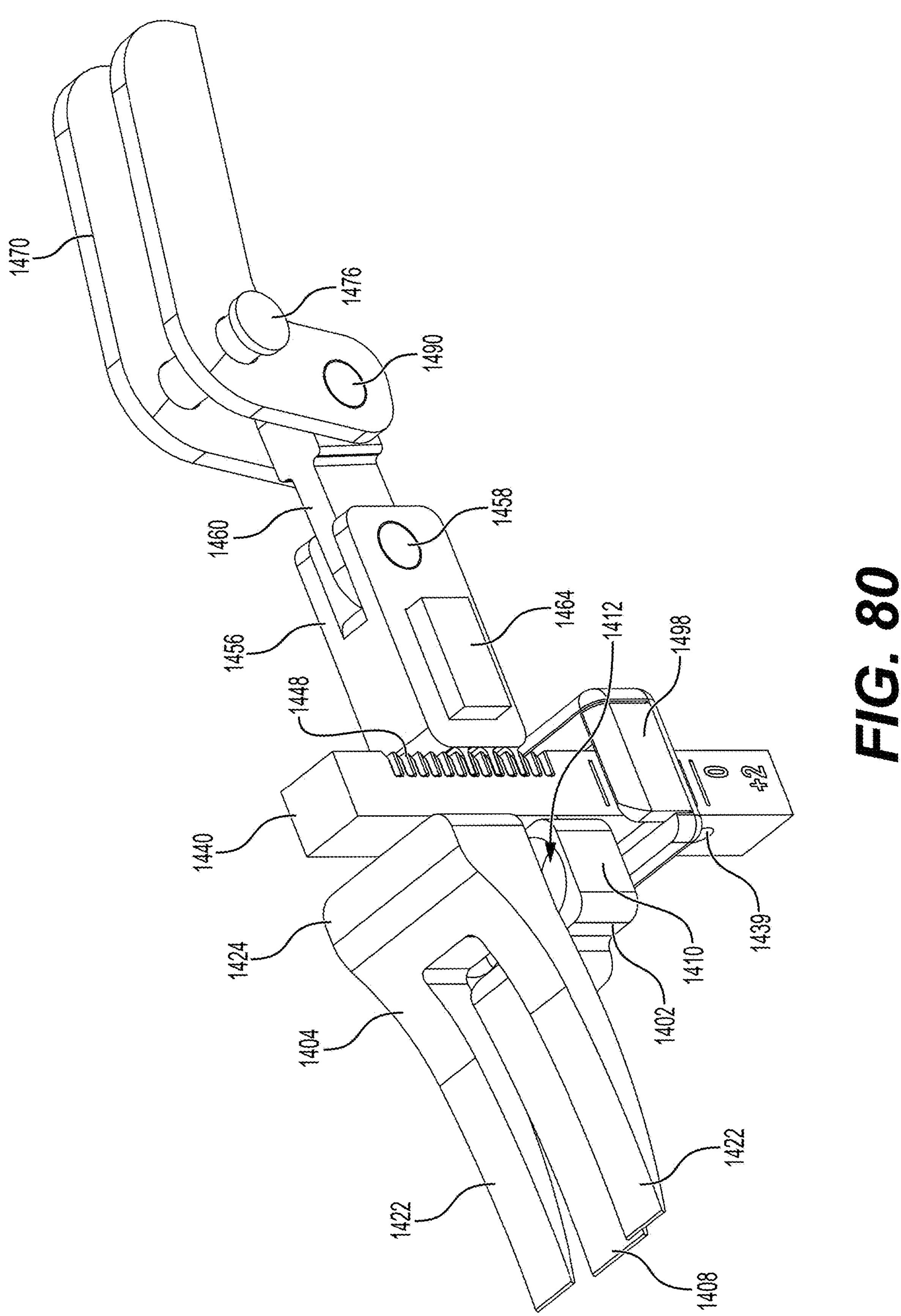
FIG. 80 is an elevated perspective view of the alternate exemplary balancing assembly of FIG. 75, with the housing removed, all in accordance with the instant disclosure.
Figure 81:
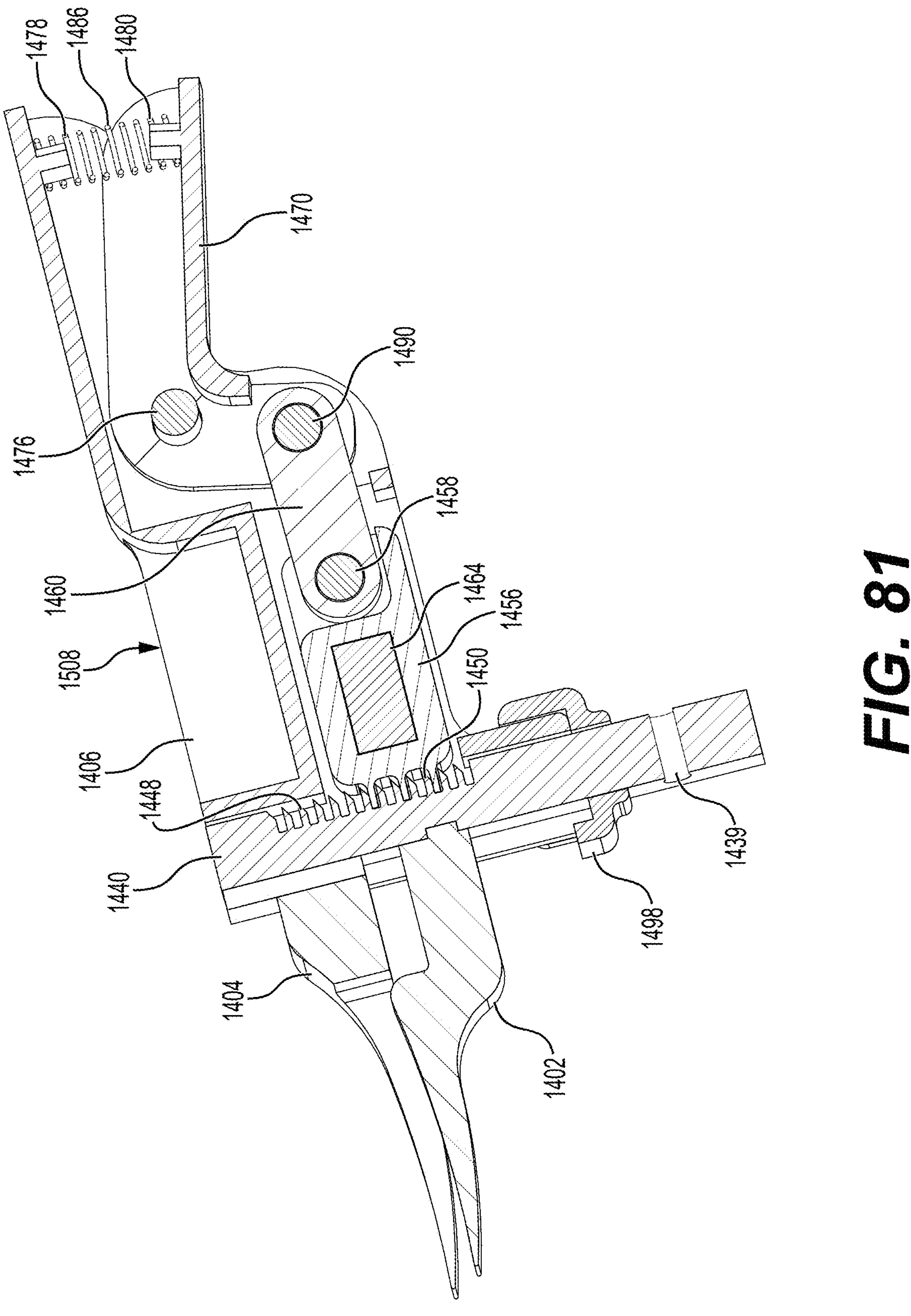
FIG. 81 is a cross-sectional view of the alternate exemplary balancing assembly of FIG. 75 taken along the dominant proximal-to-distal dimension.

By way of example, a first balancing assembly 1400 is positioned so that the paddles 1402, 1404 are positioned between the lateral condyle of the femur 110 and the lateral condyle receiver of the tibia 112. More specifically, the first balancing assembly 1400 may be repositioned so that the paddles 1402, 1404 are positioned between a lateral condyle dwell location on the femur 110 and a lateral condyle receiver dwell location on the tibia 112. And the second balancing assembly 1400 is positioned so that the paddles 1402, 1404 are positioned between the medial condyle of the femur 110 and the medial condyle receiver of the tibia 112. More specifically, the second balancing assembly 1400 may be repositioned so that the paddles 1402, 1404 are positioned between a medial condyle dwell location on the femur 110 and a medial condyle receiver dwell location on the tibia 112. It should be noted that while FIG. 75 depicts the knee joint at or near mid-flexion when the balancing assemblies are initially positioned, the balancing assemblies 1400 may be positioned between the tibia and femur in various angles of flexion including, without limitation, at or near full extension or at or near 90 degrees of flexion, or at any angle chosen between full flexion and full extension.

Referencing FIGS. 75-81, after reaching the proper position of the paddles 1402, 1404 for each balancing assembly 1400 with respect to dwell locations on the tibia 112 and femur 110 (step I), respective positioning blocks 1510 are inserted into a respective upward facing cavity 1508 of each housing 1406 so that the cylindrical projection 1512 is directed upward, away from the housing. In exemplary form, the dimensions of the upward facing cavity 1508 are such that a positioning block 1510 may be inserted therein and be allowed to freely travel in the vertical direction (akin to floating) without binding on any of the four vertical sides. But, preferably, the dimensions of the upward facing cavity 1508 are such that considerable play is not provided for between the housing 1406 and a positioning block 1510 in either the medial-to-lateral direction or the anterior-to-posterior direction.

After both positioning blocks 1510 are received within respective cavities 1508 of the housings 1506, the handgrip 1516 may be repositioned. Namely, the handgrip 1516 may be repositioned so that the positioning guides 1514 flare out and allow the elongated cavities 1518 thereof to respectively align with one of the cylindrical projections 1512 of the positioning blocks 1510. Post alignment, the handgrip 1516 is positioned toward the joint in order to cause the cylindrical projections 1512 of the positioning blocks 1510 to become recessed within the elongated cavities 1518. After being captured within the elongated cavities 1518, the handgrip 1516 is repositioned so that the tibial drop rod 1526 is parallel to the longitudinal axis of the tibia, and thereafter retained in that position. By retaining the handgrip 1516 in position, so that the tibial drop rod 1526 is parallel to the longitudinal axis of the tibia, the balancing assemblies 1400 will have the same anterior-to-posterior (AP) slope. The reason for this common AP slope is that the interface between a respective positioning block 1510 and a respective positioning guide 1514 is operative to prohibit vertical and limited lateral motion, but allowing rotational motion. And this common AP slope is also the result of the interface between a respective positioning block 1510 and a respective housing 1506 that is operative to prohibit rotational, lateral, and forward-to-rearward motions. In other words, when a respective positioning block 1510 concurrently engages a respective positioning guide 1514 and a housing 1506, and when the drop rod is parallel to the longitudinal axis of the tibia, there is no degree of freedom with respect to AP slope. Instead, the AP slope when these conditions are met is zero (i.e., completion of step II).

While the position of the handgrip 1516 is maintained so that the AP slope is zero of each balancing assembly 1400, the handle 1470 of each balancing assembly is compressed (need not occur simultaneously) with respect to the housing 1406. Doing so is operative to pivot the handle 1470 about the pivot pin 1476, which in turn is operative to reposition the link 1460 rearward (away from the paddles 1402, 1404). As the link 1460 is positioned rearward, its coupling to the stopper 1456 results in the stopper moving rearward too. This rearward motion of the stopper 1456 coincides with rearward motion of the catches 1450 with respect to the teeth 1448 of the rack 1440, eventually causing the catches to no longer engage the teeth. When the catches 1450 no longer engage the teeth 1448, the bias of the springs 1416 allows the lower paddle 1402 and rack 1440 to be repositioned vertically downward. In this manner, the lower paddle 1402 is repositioned so that a gap between the bones (on the medial or lateral side) is spanned by the paddles 1402, 1404. It should be noted that the bias of the springs 1416 can vary depending upon physician preference (i.e., whether the physician prefers a laxer joint or a tauter joint). Accordingly, the instant balancing assembly 1400 provides for the physician to tune the balancing assembly 1400 by using different springs with different spring rates depending upon physician preference and patient considerations. In summary, after the paddles 1402, 1404 are initially positioned with respect to the tibia 112 and femur 110, the handle 1470 is compressed with respect to the housing 1406, which almost instantaneously causes the lower paddle 1402 to be repositioned vertically so the vertical spacing between the paddles is such that the paddles become wedged between the femur 110 and tibia 112. Afterwards, the handle 1470 may be repositioned (i.e., released) and no longer compressed (essentially ending step III).

After the respective handles 1470 are released, the tensioned gap on the medial and lateral side of the joint may be measured in step IV. Specifically, the handle 1470 of each balancing assembly 1400 is released so the handle pivots around a respective pivot pin 1476 in the opposite direction, with the pivoting motion of each handle being operative to push a link 1460 forward (toward the paddles 1402, 1404). And the forward motion of the link 1460 pushes the stopper 1456 forward so that the catches 1450 engage the teeth 1448 and effectively lock the paddles 1402, 1404 of each balancing assembly 1400 in position. It should be noted that the teeth 1448 may include a beveled edge that works to inhibit the catches 1450 from stopping at the leading edge and not effectively being seated between corresponding teeth, which would otherwise allow free vertical motion of the rack 1440 and the lower paddle 1402. When the paddles 1402, 1404 are spaced apart from one another and locked in relative position, the surgeon may measure the vertical distance between the paddles. In this fashion, the rack 1440 may include outside indicia 1441 that corresponds to the spacing between the paddles. Namely, the indicia 1441 may be in two millimeter increments and start at zero and go up and through eight additional marks or 16 total millimeters, for example. It should be noted that increments other than two millimeters may be used and may extend longer or shorter than 16 total millimeters. When the paddles 1402, 1404 are initially positioned to overlap one another, the only portion of the indicia 1441 visible from the rack 1440, that extends from the cap 1498, is the first line that corresponds to a zero gap. Conversely, when the paddles 1402, 1404 are vertically spaced apart from one another (such as after the handle 1470 is initially depressed and the springs 1416 cause the paddles to separate from one another), additional portions of the indicia 1441 that extend from the cap 1498 are visible. In this circumstance, the user would count the number of lines showing or extending beyond the cap 1498, with four lines corresponding to a gap between the paddles 1402, 1404 of six millimeters, or two lines showing that corresponds to a gap between the paddles 1402, 1404 of two millimeters, and so on.

Before or after reading the indicia 1441 of each balancing assembly 1400 to determine the spacing between the paddles 1402, 1404, the rack 1440 may be used to drill a hole into the tibia. Specifically, while the handgrip 1516 is maintained so that the AP slope is zero and the paddles 1402, 1404 span the gap between the tibia and femur, a hole may be drilled into the tibia using the through opening 1439 of the rack 1440 as a guide. In exemplary form, a surgical drill bit (not shown) is inserted through the opening 1439 and a surgical drill is activated to cause the drill bit to contact the tibia and progressively remove bone along a predetermined path that is normal to the longitudinal axis of the tibia. The hole is drilled deep enough to accept and retain a surgical pin. This process is carried out for both the medial and lateral balancing assemblies 1400. After the holes have been drilled, the balancing assemblies 1400, the handgrip 1516, the tibial drop rod 1526, the positioning guides 1514, and the guide blocks 1464 may be removed to conclude step V. At this stage, only the two holes remain in the tibia. It is now time to utilize the surgical guide system 1550.

In step VI, two surgical pins are inserted into the two tibial holes drilled. Using the inserted pins, the surgical guide system 1550 may be utilized, specifically the trajectory guide 1558. In exemplary form, the distal face 1574 of the trajectory guide 1558 may be oriented to face the tibia, with the elongated opening 1576 oriented to receive the two surgical pins. In this fashion, the trajectory guide may be repositioned so that at least a portion of the distal face 1574 abuts the tibia, while the surgical pins extend through the elongated opening. The medial to lateral position of the trajectory guide 1558 may be adjusted so that the first hole 1554 is centered medially-to-laterally with respect to the tibia. Thereafter, the first hole 1554 may be used as a drill bit guide to guide a drill bit for creating a third hole into the tibia. After drilling this third hole, a third surgical pin may be inserted through the first hole 1554 and into the tibia, where the three surgical pins provide a triangular arrangement that operates to fix the orientation of the trajectory guide 1558 to effectively inhibit changes in slope, medial-to-lateral repositioning, and rotation. It should also be noted that this fixed orientation can be accomplished with only one surgical pin extending through the elongated opening 1576 and one surgical pin extending through the first hole 1554. With the relative position and orientation of the trajectory guide 1558 being fixed by its interaction with the surgical pins, step VI is concluded, and use of the pin guides 1584 in step VII follows.

As discussed herein, each pin guide 1584 is configured to engage the trajectory guide 1558 via the interaction of the dovetail projection 1578 and the corresponding dovetail keyway 1582. Specifically, after the position and orientation of the trajectory guide 1584 is established, respective pin guides 1584 may be slid onto the trajectory guide so that the dovetail projection 1578 is received within the dovetail keyway 1582. Using this interface, the tolerances between the dovetail projection 1578 and the dovetail keyway 1582 only allow motion of the pin guides 1584 in the medial-to-lateral direction with respect to the trajectory guide (which is effectively fixed in position). As referenced, the holes extending through each pin guide 1584 are straight and have axes in parallel with one another and perpendicular to the longitudinal axis of the dovetail keyway 1582, which means the holes each have a longitudinal axis perpendicular to the longitudinal axis of the tibia.

Dependent upon the implant, polyethylene thickness, and the surgeon's preference, a determination is made regarding how much tibia bone should be removed to account for the vertical height of the orthopedic implant. This determination takes into account the gap balancing measurement described herein where the surgeon, when the paddles 1402, 1404 span the gap between the joint bones and the ligaments are tensioned to be in balance, reads the indicia 1441 and deduces the properly tensioned gap. A couple of examples will be provided for greater understanding.

In a first example, the balancing assembly 1400 on the medial side indicated a tensioned gap of four millimeters, because when balanced and tensioned, the indicia 1441 had three marks appearing beneath the cap 1498. Similarly, the balancing assembly 1400 on the lateral side indicated a tensioned gap of four millimeters too, because when balanced and tensioned, the indicia 1441 for this balancing assembly had three marks appearing beneath the cap 1498. As a consequence, if the total height of the implant is six millimeters and the femoral dimensions will remain the same post implant fitting, then this means that two millimeters must be cut from the tibia on both sides. As a result, a lateral pin guide 1584 engages the trajectory guide 1558 using the dovetail/keyway interface and may be repositioned in the medial direction until the third hole (from left to right) in the second row (from top to bottom) is centered with respect to at least one of the lateral condyle and the lateral condyle receiver. When centered, this third hole in the second row acts as a guide for a drill bit when a surgical drill is used to create a hole in the tibia centered with respect to at least one of the lateral condyle and lateral condyle receiver. Similarly, a medial pin guide 1584 engages the trajectory guide 1558 using the dovetail/keyway interface and may be repositioned in the lateral direction until the third hole (from left to right) in the second row (from top to bottom) is centered with respect to at least one of the medial condyle and the medial condyle receiver. When centered, this third hole in the second row acts as a guide for a drill bit when a surgical drill is used to create a hole in the tibia centered with respect to at least one of the medial condyle and medial condyle receiver. After forming both the medial and lateral holes in the tibia, the trajectory guide 1558, the pin guides 1584, and the surgical pins may be removed at the end of step VII.

In a second example, the balancing assembly 1400 on the medial side indicated a tensioned gap of two millimeters, because when balanced and tensioned, the indicia 1441 had two marks appearing beneath the cap 1498. Conversely, the balancing assembly 1400 on the lateral side indicated a tensioned gap of four millimeters, because when balanced and tensioned, the indicia 1441 for this balancing assembly had three marks appearing beneath the cap 1498. As a consequence, if the total height of the implant is six millimeters and the femoral dimensions will remain the same post implant fitting, then this means that four millimeters must be cut from the tibia on the medial side and two millimeters must be cut from the tibia on the lateral side. As a result, a lateral pin guide 1584 engages the trajectory guide 1558 using the dovetail/keyway interface and may be repositioned in the medial direction until the third hole (from left to right) in the second row (from top to bottom) is centered with respect to at least one of the lateral condyle and the lateral condyle receiver. When centered, this third hole in the second row acts as a guide for a drill bit when a surgical drill is used to create a hole in the tibia centered with respect to at least one of the lateral condyle and lateral condyle receiver. Conversely, a medial pin guide 1584 engages the trajectory guide 1558 using the dovetail/keyway interface and may be repositioned in the lateral direction until the first hole (from left to right) in the third row (from top to bottom) is centered with respect to at least one of the medial condyle and the medial condyle receiver. When centered, this third hole in the second row acts as a guide for a drill bit when a surgical drill is used to create a hole in the tibia centered with respect to at least one of the medial condyle and medial condyle receiver. After forming both the medial and lateral holes in the tibia, the trajectory guide 1558, the pin guides 1584, and the surgical pins may be removed at the end of step VII.

In step VII, surgical pins are inserted into the holes in the tibia formed using the pin guides 1584. Using these two surgical pins, the cutting guide 1590 is oriented so that its proximal face 1594 abuts the tibia and the respective surgical pins extend through respective openings 1598. Given the dimensional tolerances between the surgical pins and the walls delineating the openings 1598, there is no rotational or angular degree of freedom for the cutting guide 1590. Instead, the degrees of freedom are anterior-to-posterior and medial-to-lateral, with the medial-to-lateral degree of freedom being limited by the medial-to-lateral spacing between the surgical pins. Nevertheless, to the extent that there is some freedom in the medial-to-lateral dimension, the cutting guide 1590 may be centered with respect to the tibia and another hole drilled in the tibia using the hole 1592 of the cutting guide. Post this hole being created, another surgical pin may be inserted into the tibia and concurrently extend through the first hole 1592 to form a triangular arrangement of surgical pins.

The triangular arrangement of the surgical pins operates to fix the orientation of the cutting guide 1590 to effectively inhibit changes in slope, medial-to-lateral repositioning, and rotation. It should also be noted that this fixed orientation can be accomplished with only one surgical pin extending through one elongated opening 1576 and one surgical pin extending through the first hole 1592. With the relative position and orientation of the cutting guide 1590 being fixed by its interaction with the surgical pins, and the cutting guide being pushed to abut the tibia, a surgical saw can be utilized in step IX to create a planar cut on the proximal tibia.

In exemplary form, the planar cut on the proximal tibia is intended to be formed using a surgical saw blade with a planar side that sits and rides upon the planar surface of the plateau 1600 of the cutting guide 1590. It should be noted that, to the extent a surgeon desires a sloped cut (in the AP direction), this slope is accounted for as part of the plateau 1600. In other words, it is within the scope of the disclosure to provide a series of cutting guides 1590 having incremental slopes in the AP direction that a surgeon may choose depending upon personal preference, the orthopedic implant chosen, and other relevant considerations. After creating the tibial cut, the surgical pins and cutting guide 1590 may be removed, followed by further surgical procedures in furtherance of TKA or similar procedure, or replacement of a preexisting surgical implant.

Figure 86:
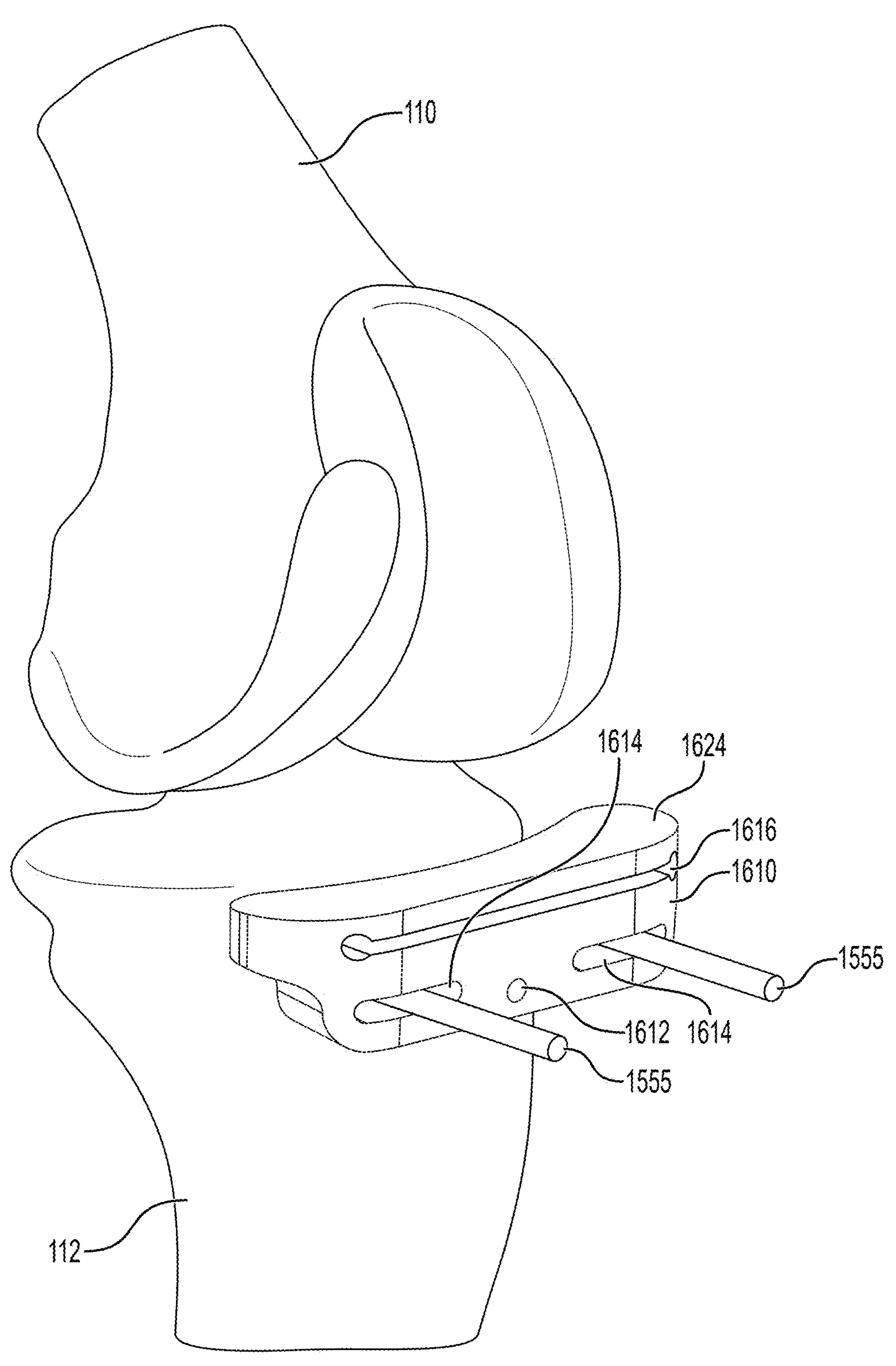
FIG. 86 is an elevated perspective view of a distal femur and a proximal tibia at or near mid-flexion with an alternate exemplary cutting guide mounted to the proximal tibia and surgical pins.
Figure 87B:
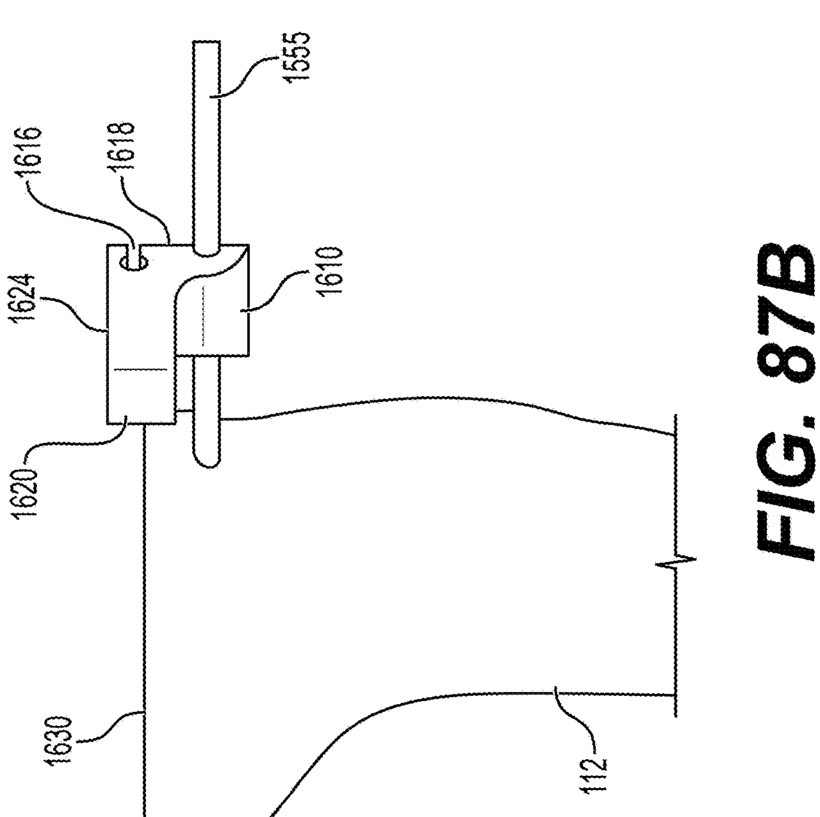
FIG. 87B is a profile view of the proximal tibia and alternate exemplary cutting guide of FIG. 86, post tibia resection.
Figure 87A:
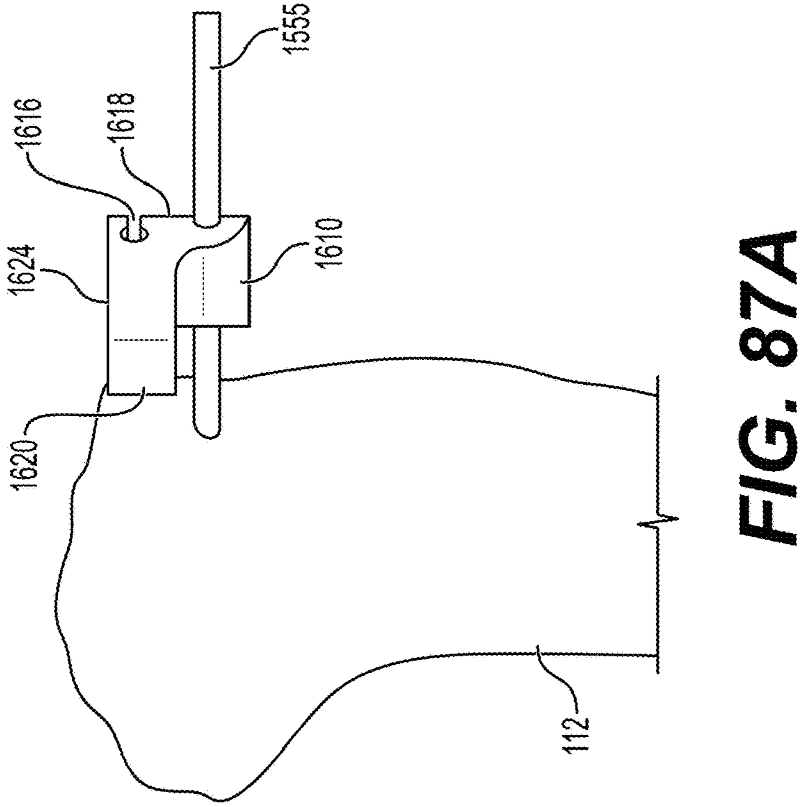
FIG. 87A is a profile view of the proximal tibia and alternate exemplary cutting guide of FIG. 86, prior to tibia resection.

As depicted in FIGS. 86-87B, an alternate exemplary cutting guide 1610 may be used in lieu of the foregoing described cutting guide 1590. Accordingly, a discussion regarding use of this alternate exemplary cutting guide 1610 is omitted in furtherance of brevity. Therefore, the foregoing discussion of using the exemplary cutting guide 1590 is equally applicable for this alternate exemplary cutting guide 1610.

This alternate exemplary cutting guide 1610 may include a frame outlining a plurality of through holes or through elongated openings 1612, 1614, 1616 extending in the proximal-to-distal direction. In exemplary form, the frame may include a planar proximal face 1618 that is parallel to a planar distal face 1620, with the distance between the faces attributable to a depthwise dimension that is generally uniform. Both faces 1618, 1620 include a dominant lateral dimension that is perpendicular to a lesser heightwise dimension. The spacing between opposed top and bottom walls of the first elongated openings 1614 is sufficient to accommodate one or more conventional surgical pins 1555, but not so great as to allow significant vertical play between one or more of the surgical pins and the top and bottom walls. Vertically opposite the first hole 1612 is a planar plateau 1624, optionally extending one or more of medially, laterally, anteriorly, and posteriorly beyond a footprint of the remainder of the cutting guide elements. Specifically, planar plateau 1624 may be perpendicular to the top and bottom walls delineating the elongated openings 1614 or may be sloped in at least one of the anterior-posterior direction and the medial lateral direction. The slope of the planar plateau 1624 may be dependent upon the implant chosen by the surgeon. In any event, the planar plateau 1624 may be used to provide a planar surface upon which a surgeon may position a cutting blade and reposition the cutting place across the plateau to create a planar resection cut of the proximal tibia. Alternatively, the surgeon may use the second elongated opening 1616, which interposes the planar plateau 1624 and the first elongated openings 1614, to insert a surgical blade and track the bounds of the opening 1616 to more precisely ensure the cutting blade is maintained within a planar range of motion, thereby ensuring the tibial resection results in a planar top surface 1630 when finished.

Following from the above description, it should be apparent to those of ordinary skill in the art that, while the methods and apparatuses herein described constitute exemplary embodiments of the present invention, the foregoing disclosure is not limited to any precise embodiment and that changes, substitutions, subtractions, revisions, or otherwise may be made to such embodiments and components of the described embodiments without departing from the scope of the disclosure. After all, it is the claims that define the invention to be patented and those skilled in the art will understand that the claims may be amended to change their scope and doing so to change their scope, whether to narrow or broaden, is not an intermediate generalization outside the scope of the disclosure and beyond what one skilled in the art should expect and understand. Moreover, it is to be understood that the invention is defined by the claims and it is not intended that any limitations or elements described as part of one or more exemplary embodiments set forth herein are not to be necessarily incorporated as part of any other claim elements, unless such limitation or element is explicitly stated as being essential. Attempting to incorporate non-essential aspects of the embodiments disclosed herein and assert the claimed invention is somehow incomplete or an intermediate generalization frustrates the intent of the disclosure because it is the claims, not the disclosure, that dictates the invention. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of performing at least one bone cut for a knee arthroplasty, the method comprising:

inserting at least a femoral portion and a tibial portion of a first distractor between a distal femur condyle and a proximal tibia condyle receiver of a knee joint comprising a proximal tibia and a distal femur;

tensioning soft tissue proximate the knee joint when in mid-flexion that includes manipulating a handle of the first distractor to reposition a catch and release a spring force applied to the femoral portion and the tibial portion of the first distractor to bias the femoral portion and the tibial portion away from one another and occupy a gap between the distal femur condyle and the proximal tibia condyle;

manipulating the handle to reposition the catch to lock a spacing between the femoral portion with respect to the tibial portion while occupying the gap;

identifying a measure of the gap between the distal femur condyle and the proximal tibia condyle receiver in mid-flexion when the soft tissue is tensioned;

establishing a cutting plane for resecting at least one of the proximal tibia and the distal femur using exclusively intraarticular references that include the identified measure of the gap; and, resecting at least one of the proximal tibia and the distal femur using the cutting plane.

2. The method of claim 1, wherein inserting the first distractor between the distal femur condyle and the proximal tibia condyle receiver includes inserting paddles of the first distractor between the distal femur condyle and the proximal tibia condyle receiver, where at least one of the paddles is repositionable with respect to a second of the paddles.

3. The method of claim 2, wherein inserting paddles of the first distractor between the distal femur condyle and the proximal tibia condyle receiver includes medially-to-laterally centering the paddles with respect to the distal femur condyle and the proximal tibia condyle receiver.

4. The method of claim 3, wherein medially-to-laterally centering the paddles with respect to the distal femur condyle and the proximal tibia condyle receiver includes orienting the paddles to overlap a dwell location on at least one of the distal femur condyle and the proximal tibia condyle receiver.

5. The method of claim 1, wherein using the first distractor to identify the gap between the distal femur condyle and the proximal tibia condyle receiver includes repositioning at least one of a plurality of paddles of the first distractor that are positioned between the distal femur condyle and the proximal tibia condyle receiver, and measuring a distance traveled by the at least one paddle.

6. The method of claim 5, wherein measuring the distance traveled by the at least one paddle includes reading a gauge associated with the first distractor.

7. The method of claim 6, wherein the gauge reflects a straight line distance traveled by the at least one paddle.

8. The method of claim 6, wherein the gauge comprises a vertical support that is operatively coupled to the at least one paddle and repositionable with respect to a housing of the first distractor.

9. The method of claim 8, wherein the vertical support is constrained by the housing to inhibit straight line motion in the medial-to-lateral direction and the proximal-to-distal direction, and rotational motion, so the only degree of freedom available to the vertical support is in the vertical direction that is perpendicular to the medial-to-lateral direction and the proximal-to-distal direction.

10. The method of claim 1, wherein tensioning the soft tissue proximate the knee joint includes monitoring rate of change in strain as a function of stress applied to the soft tissue, where tensioning is achieved when the rate of change in strain has markedly decreased, but the stress has not markedly decreased.

11. The method of claim 1, wherein using the first distractor to identify the gap between the distal femur condyle and the proximal tibia condyle receiver includes releasing a stopper of the first distractor to allow paddles of the first distractor to reposition away from one another until reaching an equilibrium.

12. The method of claim 11, wherein when the paddles reach the equilibrium, engaging the stopper to lock the relative vertical positions of the paddles with respect to one another and thereafter identifying the gap.

13. The method of claim 11, wherein the paddles are biased away from one another using at least one spring comprising part of the first distractor.

14. The method of claim 11, wherein releasing the stopper of the first distractor includes repositioning a handle repositionably mounted to a housing of the first distractor, which repositions the stopper with respect to at least one of the paddles.

15. The method of claim 1, further comprising:

operatively coupling a drill guide to at least a portion of the first distractor, where the drill guide includes a plurality of through openings facing at least one of the distal femur and the proximal tibia; and, drilling two holes into at least one of the distal femur and the proximal tibia using the drill guide.

16. The method of claim 15, wherein:

operatively coupling the drill guide to at least a portion of the first distractor includes operatively coupling a ball with respect to a receiver having a partially spherical cavity; and, where the ball is associated with one of the drill guide and the first distractor, while the receiver is associated with the other of the drill guide and the first distractor.

17. The method of claim 15, wherein:

operatively coupling the drill guide to at least a portion of the first distractor includes operatively coupling a projection with respect to a receiver having a cavity configured to receive the projection; and, where the projection is associated with one of the drill guide and the first distractor, while the receiver is associated with the other of the drill guide and the first distractor.

18. The method of claim 15, wherein operatively coupling the drill guide to at least a portion of the first distractor includes limiting at least one of vertical repositioning and lateral repositioning of the drill guide with respect to the first distractor.

19. The method of claim 15, wherein operatively coupling the drill guide to at least a portion of the first distractor includes allowing rotational repositioning of the drill guide with respect to the first distractor about an axis in parallel with a longitudinal axis of at least one of the plurality of through openings.

20. The method of claim 15, further comprising:

mounting a surgical pin to at least one of the proximal tibia and the distal femur by inserting a surgical pin into each of the two holes drilled;

wherein drilling two holes includes drilling two holes into the proximal tibia by inserting the drill bit through a first of the plurality of through openings and inserting the drill bit through a second of the plurality of through openings.

21. The method of claim 20, further comprising positioning a cutting guide with respect to the proximal tibia using the surgical pin, wherein:

mounting the surgical pin includes mounting a pair of surgical pins to the proximal tibia; and, positioning the cutting guide with respect to the proximal tibia using the surgical pin includes sliding the cutting guide over the pair of surgical pins so that a top of the cutting guide establishes a plane parallel to a plane of the eventual resected tibia.

22. The method of claim 21, further comprising:

using the cutting guide to drill a hole into the proximal tibia; and, mounting an individual surgical pin to the proximal tibia, where the individual surgical pin and the pair of surgical pins, when mounted to the proximal tibia, are orientated in a triangular arrangement;

wherein positioning the cutting guide with respect to the proximal tibia includes sliding the cutting guide over the pair of surgical pins and the individual surgical pin so that rotation of the cutting guide with respect to the proximal tibia is precluded.

23. The method of claim 20, further comprising positioning a cutting guide with respect to the proximal tibia using the surgical pin, wherein:

mounting the surgical pin includes mounting a pair of surgical pins to the proximal tibia; and, positioning the cutting guide with respect to the proximal tibia using the surgical pin includes sliding the cutting guide over the pair of surgical pins so that an elongated through slot of the cutting guide establishes a trajectory parallel to a plane of the eventual resected tibia.

24. The method of claim 23, further comprising:

using the cutting guide to drill a hole into the proximal tibia; and, mounting an individual surgical pin to the proximal tibia, where the individual surgical pin and the pair of surgical pins, when mounted to the proximal tibia, are orientated in a triangular arrangement;

wherein positioning the cutting guide with respect to the proximal tibia using the surgical pin includes sliding the cutting guide over the pair of surgical pins and the individual surgical pin so that rotation of the cutting guide with respect to the proximal tibia is precluded.

25. A method of performing at least one bone cut for a knee surgery, the method comprising:

inserting at least a femoral portion and a tibial portion of a first distractor between a distal femur condyle and a proximal tibia condyle receiver of a knee joint comprising a proximal tibia and a distal femur;

tensioning soft tissue proximate the knee joint when the knee joint is in mid-flexion including releasing a spring bias associated with the first distractor to automatically reposition at least one of the femoral portion and the tibial portion to occupy bounds of a gap between the distal femur condyle and the proximal tibia condyle receiver;

repositioning a catch of the first distractor to lock a relative position of the femoral portion with respect to the tibial portion when occupying bounds of the gap;

identifying a vertical dimension of the gap;

establishing a cutting plane for resecting at least one of the proximal tibia and the distal femur using the vertical dimension; and, resecting at least one of the proximal tibia and the distal femur using the cutting plane.

26. A method of performing at least one bone cut for a knee surgery, the method comprising:

inserting at least a portion of a first distractor in a locked position between a distal femur condyle and a proximal tibia condyle receiver of a knee joint comprising a proximal tibia and a distal femur;

tensioning soft tissue proximate the knee joint when the knee joint is in mid-flexion including unlocking and releasing a previously restrained expansion force to automatically push apart the distal femur condyle and the proximal tibia condyle receiver;

measuring a vertical distance of a gap between the distal femur condyle and the proximal tibia condyle receiver while the soft tissue proximate the knee joint is tensioned and the knee joint is in mid-flexion;

establishing a cutting plane for resecting at least one of the proximal tibia and the distal femur using the vertical distance; and, resecting at least one of the proximal tibia and the distal femur using the cutting plane.

* * * * *